United States Patent
Sheikh et al.

(10) Patent No.: US 11,117,927 B2
(45) Date of Patent: *Sep. 14, 2021

(54) 2,2-DIFLUOROPROPIONAMIDE DERIVATIVES OF BARDOXOLONE METHYL, POLYMORPHIC FORMS AND METHODS OF USE THEREOF

(71) Applicant: AbbVie Inc., North Chicago, IL (US)

(72) Inventors: Ahmad Y. Sheikh, Deerfield, IL (US); Alessandra Mattei, Chicago, IL (US); Xiu C. Wang, Green Oaks, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/186,051

(22) Filed: Nov. 9, 2018

(65) Prior Publication Data

US 2020/0062800 A1    Feb. 27, 2020

Related U.S. Application Data

(63) Continuation of application No. 15/821,508, filed on Nov. 22, 2017, now abandoned, which is a continuation of application No. 14/260,532, filed on Apr. 24, 2014, now Pat. No. 9,856,286.

(60) Provisional application No. 61/815,502, filed on Apr. 24, 2013.

(51) Int. Cl.
C07J 63/00 (2006.01)
A61P 29/00 (2006.01)

(52) U.S. Cl.
CPC ............. *C07J 63/008* (2013.01); *A61P 29/00* (2018.01); *C07B 2200/13* (2013.01)

(58) Field of Classification Search
CPC ...... C07J 63/008; C07B 2200/13; A61P 29/00
See application file for complete search history.

(56) References Cited

U.S. PATENT DOCUMENTS

| 4,395,423 A | 7/1983 | Neumann |
| 5,064,823 A | 11/1991 | Lee et al. |
| 5,443,826 A | 8/1995 | Borody |
| 5,599,795 A | 2/1997 | McCann et al. |
| 6,326,507 B1 | 12/2001 | Gribble et al. |
| 6,369,101 B1 | 4/2002 | Carlson |
| 6,552,075 B2 | 4/2003 | Gribble et al. |
| 6,642,217 B2 | 11/2003 | Krasutsky et al. |
| 6,649,654 B1 | 11/2003 | Karin et al. |
| 6,951,847 B2 | 10/2005 | Gibson et al. |
| 6,974,801 B2 | 12/2005 | Honda et al. |
| 7,053,119 B2 | 5/2006 | Karin et al. |
| 7,144,875 B2 | 12/2006 | Gibson et al. |
| 7,176,237 B2 | 2/2007 | Honda et al. |
| 7,288,568 B2 | 10/2007 | Gribble et al. |
| 7,399,606 B2 | 7/2008 | Karin et al. |
| 7,410,958 B2 | 8/2008 | Krasutsky et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,513,436 B2 | 8/2013 | Anderson et al. |
| 8,586,775 B2 | 11/2013 | Gribble et al. |
| 8,747,901 B2 | 6/2014 | Zhang et al. |
| RE45,288 E | 12/2014 | Anderson et al. |
| 8,921,419 B2 | 12/2014 | Gribble et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |

(Continued)

FOREIGN PATENT DOCUMENTS

| WO | WO 1999/065478 | 12/1999 |
| WO | WO 2002/047611 | 6/2002 |

(Continued)

OTHER PUBLICATIONS

Netdoctor, Conjunctivitis: how to treat eye inflammation. Reviewed by Dr. Roger Henderson, (Year: 2019).*
Wikipedia, Corneal endothelium. (Year: 2020).*
Gorovoy et al., Recognizing and treating corneal endothelial disease. The problem can be too few cells—or too many. Ophthalmology Management, (Year: 2010).*

(Continued)

*Primary Examiner* — Barbara P Badio
(74) *Attorney, Agent, or Firm* — Parker Highlander PLLC

(57) ABSTRACT

The present invention relates generally to the compound:

N-((4aS,6aR,6bS,8aR,12aS,14aR,14bS)-11-cyano-2,2,6a, 6b,9,9,12a-heptamethyl-10,14-dioxo-1,2,3,4,4a,5,6,6a, 6b,7,8,8a,9,10,12a,14,14a,14b-octadecahydropicen-4a-yl)-2,2-difluoropropanamide, polymorphic forms thereof, methods for preparation and use thereof, pharmaceutical compositions thereof, and kits and articles of manufacture thereof.

15 Claims, 62 Drawing Sheets

(56) References Cited

U.S. PATENT DOCUMENTS

| | | |
|---|---|---|
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,278,913 B2 | 3/2016 | Gribble et al. |
| 9,290,536 B2 | 3/2016 | Anderson et al. |
| 9,464,082 B2 | 10/2016 | Donner et al. |
| 9,512,094 B2 | 12/2016 | Jiang et al. |
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,856,286 B2 | 1/2018 | Sheikh et al. |
| 9,889,143 B2 | 2/2018 | Jiang et al. |
| 10,093,614 B2 | 10/2018 | Anderson et al. |
| 10,105,372 B2 | 10/2018 | Meyer et al. |
| 10,398,711 B2 | 9/2019 | Jiang et al. |
| 10,501,489 B2 | 12/2019 | Bender et al. |
| 10,556,858 B2 | 2/2020 | Anderson et al. |
| 2002/0042535 A1 | 4/2002 | Gribble et al. |
| 2003/0119732 A1 | 6/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Kratsutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt |
| 2007/0155742 A1 | 7/2007 | Honda et al. |
| 2007/0232577 A1 | 10/2007 | Xu et al. |
| 2007/0244081 A1 | 10/2007 | Kratsutsky et al. |
| 2007/0249561 A1 | 10/2007 | Taylor |
| 2007/0259839 A1 | 11/2007 | Kratsutsky et al. |
| 2007/0259842 A1 | 11/2007 | Kratsutsky et al. |
| 2008/0220057 A1 | 9/2008 | Gribble et al. |
| 2008/0233195 A1 | 9/2008 | Sporn et al. |
| 2008/0234368 A9 | 9/2008 | Gribble et al. |
| 2008/0254055 A1 | 10/2008 | Oblong et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0093447 A1 | 4/2009 | Konopleva et al. |
| 2009/0060873 A1 | 5/2009 | Sporn et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0250300 A1 | 10/2011 | Biswal et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0237721 A1 | 9/2013 | Gribble et al. |
| 2013/0274480 A1 | 10/2013 | Honda et al. |
| 2013/0303607 A1 | 11/2013 | Gribble et al. |
| 2013/0303797 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0073700 A1 | 3/2014 | Wagner et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0323579 A1 | 10/2014 | Sheikh et al. |
| 2015/0011627 A1 | 1/2015 | Gribble et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2015/0376121 A1 | 12/2015 | Anderson et al. |
| 2017/0165278 A1 | 6/2017 | Jiang et al. |
| 2018/0094020 A1 | 4/2018 | Sheikh et al. |
| 2018/0127380 A1 | 5/2018 | Jiang et al. |
| 2019/0153022 A1 | 5/2019 | Visnick et al. |
| 2019/0350941 A1 | 11/2019 | Meyer |

FOREIGN PATENT DOCUMENTS

| | | |
|---|---|---|
| WO | WO 2003/059339 | 7/2003 |
| WO | WO 2004/064723 | 8/2004 |
| WO | WO 2007/005879 | 1/2007 |
| WO | WO 2007/112043 | 10/2007 |
| WO | WO 2008/016095 | 2/2008 |
| WO | WO 2008/064132 | 5/2008 |
| WO | WO 2008/064133 | 5/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/089545 | 7/2009 |
| WO | WO 2010/011782 | 7/2009 |
| WO | WO 2009/129546 | 10/2009 |
| WO | WO 2009/129548 | 10/2009 |
| WO | WO 2010/053817 | 10/2009 |
| WO | WO 2009/129545 | 11/2009 |
| WO | WO 2009/146216 | 12/2009 |
| WO | WO 2009/146218 | 12/2009 |
| WO | WO 2010/127029 | 4/2010 |
| WO | WO 2010/093944 | 8/2010 |
| WO | WO 2011/130302 | 10/2011 |
| WO | WO 2012/009171 | 1/2012 |
| WO | WO 2012/083306 | 6/2012 |
| WO | WO 2012/125488 | 9/2012 |
| WO | WO 2012/154554 | 11/2012 |
| WO | WO 2013/169553 | 5/2013 |
| WO | WO 2013/163344 | 10/2013 |
| WO | WO 2013/169740 | 11/2013 |
| WO | WO 2013/188818 | 12/2013 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2015/112792 | 1/2015 |
| WO | WO 2015/027206 | 2/2015 |
| WO | WO 2017/053868 | 3/2017 |
| WO | WO 2018/089539 | 5/2018 |

OTHER PUBLICATIONS

Hylo Eye Care, Inflammation of the eye, downloaded Nov. 5, 2020 (Year: 2020).*

Abraham and Kappas, "Heme oxygenase and the cardiovascular-renal system," *Free Radic. Biol. Med.,* 39(1):1-25, 2005.

Aghajan et al., "Obesity, Autophagy, and the Pathogenesis of Liver and Pancreatic Cancers," J. Gastroenterology and Hepatology, 27(Supp. 2):10-14, 2012.

Ahmad et al., "Triterpenoid CDDO-Me blocks the NF-kappaB pathway by direct inhibition of IKKbeta on Cys-179," J. Biol. Chem., 281:35764-35769, 2006.

Ahmad et al., "Triterpenoid CDDO-methyl ester inhibits the Janus-activated kinase-1 (JAK1)àsignal transducer and activator of transcription-3 (STAT3) pathway by direct inhibition of JAK1 and STAT3," Cancer Res., 68 (8): 2920-2926, 2008.

(56) References Cited

OTHER PUBLICATIONS

Akiyama et al., "Cell mediators of inflammation in the Alzheimer disease brain," Alzheimer Dis. Assoc. Disord.,14 (1): S47-S53, 2000.
Angulo et al., "Early myeloid cells are high producers of nitric oxide upon CD40 plus IFN-gamma stimulation through a mechanism dependent on endogenous TNF-alpha and IL-1alpha," Eur. J. Immunol, 30 (5): 1263-1271, 2000.
Araujo et al., "Systemic rather than local heme oxygenase-1 overexpression improves cardiac allograft outcomes in a new transgenic mouse," J. Immunol., 171(3):1572-1580, 2003.
Arend and Dayer, "Inhibition of the production and effects of interleukin-1 and tumor necrosis factor alpha in rheumatoid arthritis," Arthritis Rheum., 38 (2): 151-160, 1995.
Arend et al., "Interleukin-1 receptor antagonist: role in biology," Annu. Rev. Immunol., 16: 27-55, 1998.
Autenrieth et al., "Immune responses to Yersinia enterocolitica in susceptible BALB/c and resistant C57BL/6 mice: an essential role for gamma interferon," Infect. Immun, 62 (6):2590-2599, 1994.
Bach, "Heme oxygenase-1 and transplantation tolerance," Hum. Immunol., 67(6):430-432, 2006.
Bagasra et al., "Activation of the inducible form of nitric oxide synthase in the brains of patients with multiple sclerosis," Proc. Natl. Acad. Sci. USA, 92:12041-12045, 1995.
Ball, "Enthesopathy of rheumatoid and ankylosing spondylitis," Ann. Rheum. Dis., 30 (3):213-223, 1971.
Beal, "Mitochondria, free radicals, and neurodegeneration," Curr. Opin. Neurobiol., 6:661-666, 1996.
Blumberg et al., "Ara nomenclature and classification of arthritis and rheumatism (tentative)," Arthritis Rheum., 7: 93-97, 1964.
Botoman et al., "Management of inflammatory bowel disease," Am. Fam. Physician, 57 (1): 57-68, 1998.
Brandt et al., "Successful treatment of active ankylosing spondylitis with the anti-tumor necrosis factor alpha monoclonal antibody infliximab," Arthritis Rheum., 43 (6): 1346-1352, 2000.
Braun et al., "Low secretion of tumor necrosis factor alpha, but no other Th1 or Th2 cytokines, by peripheral blood mononuclear cells correlates with chronicity in reactive arthritis," Arthritis Rheum., 42 (10): 2039-2044, 1999.
Brewerton et al., "Ankylosing spondylitis and HL-A 27," Lancet., 1 (7809): 904-907, 1973.
Brewerton et al., "HLA-27 and Arthropathies associated with ulcerative colitis and psoriasis," Lancet., 1: 956-957, 1973.
Bronte et al., "L-arginine metabolism in myeloid cells controls T-lymphocyte functions," Trends Immunol., 24 (6): 301-305, 2003.
Brown and DuBois, "COX-2: a molecular target for colorectal cancer prevention," J. Clin. Oncol., 23 (12): 2840-2855, 2005.
Brynskov et al., "A Placebo-Controlled, Double-Blind, Randomized Trial of Cyclosporine Therapy in Active Chronic Crohn's Disease," New Engl. J. Med., 321(13):845-850, 1989.
Burger and Dayer, "Inhibitory cytokines and cytokine inhibitors," Neurology, 45 (6S-6):S39-S43, 1995.
Cai et al., "Local and systemic insulin resistance resulting from hepatic activation of IKK-beta and NF-kappaB," Nat. Med., 11 (2): 183-190, 2005.
Cann et al., "Oral domperidone: double blind comparison with placebo in irritable bowel syndrome," Gut., 24 (12): 1135-1140, 1983.
Chauhan and Chauhan, "Oxidative stress in autism," Pathophysiology, 13(3): 171-181, 2006.
Chomarat et al., "Differential effects of interleukins 10 and 4 on the production of interleukin-6 by blood and synovium monocytes in rheumatoid arthritis," Arthritis Rheum., 38 (8): 1046-1054, 1995.
Clinicaltrial.gov Study NCT02029716, "RTA 408 Lotion in Healthy Volunteers," and associated updates, first published Jan. 8, 2014.
Clinicaltrial.gov Study NCT02029729, "RTA 408 in the Treatment of Advanced Solid Tumors (NSCLC & Melanoma)—DISCOVER," and associated updates, first published Jan. 8, 2014.

Clinicaltrial.gov Study NCT02065375, "RTA 408 Ophthalmic Suspension for the Treatment of Ocular Inflammation and Pain Following Ocular Surgery," and associated updates, first published Feb. 19, 2014.
Clinicaltrial.gov Study NCT02128113, "RTA 408 Ophthalmic Suspension for the Prevention of Corneal Endothelial Cell Loss Following Cataract Surgery—GUARD," and associated updates, first published May 1, 2014.
Clinicaltrial.gov Study NCT02142959, "RTA 408 Lotion in Patients at Risk for Radiation Dermatitis—PRIMROSE," and associated updates, first published May 20, 2014.
Clinicaltrial.gov Study NCT02255422, "RTA 408 Capsules in Patients With Mitochondrial Myopathy—MOTOR," and associated updates, first published Oct. 2, 2014.
Clinicaltrial.gov Study NCT02255435, "RTA 408 Capsules in Patients With Friedreich's Ataxia—MOXIe," and associated updates, first published Oct. 2, 2014.
Clinicaltrial.gov Study NCT02259231, "RTA 408 Capsules in Patients With Melanoma—REVEAL," and associated updates, first published Oct. 8, 2014.
Clinicaltrial.gov Study NCT03593499, "Expanded Access to Omaveloxolone for Melanoma for Patients Previously Enrolled in 408-C-1401," and associated updates, first published Jul. 20, 2018.
Clinicaltrial.gov Study NCT03664453, "A Pharmacokinetic Study of Omaveloxolone in Healthy Volunteers," and associated updates, first published Sep. 10, 2018.
Clinicaltrial.gov Study NCT03902002, "A Pharmacokinetic Study of Omaveloxolone in Subjects With Hepatic Impairment and Normal Hepatic Function," and associated updates, first published Apr. 3, 2019.
Clinicaltrial.gov Study NCT03931590, "A Human AME Study for Omaveloxolone," and associated updates, first published Apr. 30, 2019.
Clinicaltrial.gov Study NCT04008186, "A Clinical Drug-Drug Interaction (DDI) Study With Omaveloxolone," and associated updates, first published Jul. 4, 2019.
Coyle and Puttfarcken, "Oxidative stress, glutamate, and neurodegenerative disorders," Science, 262:689-695, 1993.
Crowell et al., "Is inducible nitric oxide synthase a target for chemoprevention," Mol. Cancer Ther., 2 (8): 815-823, 2003.
De Waal et al., "Interleukin-10 (IL-10) Inhibits Cytokine Synthesis by Human Monocytes: An Autoregulatory Role of IL-10 Produced by Monocyte," j. Exp. Med., 174: 1209-1220, 1991.
Dickerson et al., "Elevated serum levels of C-reactive protein are associated with mania symptoms in outpatients with bipolar disorder," Prog. Neuropschopharmacol Biol. Psychiatry, 31(4):952-955, 2007.
Dinarello, "Interleukin-1, interleukin-1 receptors and interleukin-1 receptor antagonist," Int. Rev. Immunol., 16 (5-6): 457-499, 1998.
Dinkova-Kostova et al., "Extremely potent triterpenoid inducers of the phase 2 response: correlations of protection against oxidant and inflammatory stress," Proc. Natl. Acad. Sci., 102(12): 4584-4589, 2005.
Dionne et al., "Colonic explant production of IL-1and its receptor antagonist is imbalanced in inflammatory bowel disease (IBD)," Clin. Exp. Immunol., 112 (3): 435-442, 1998.
Doran et al., "Predictors of longterm outcome in ankylosing spondylitis," J. Rheumatol., 30 (2): 316-320, 2003.
Drossman et al., "Irritable bowel syndrome: a technical review for practice guideline development," Gastroenterology, 112 (6): 2120-2137, 1997.
Drossman et al., "U.S. householder survey of functional gastrointestinal disorders. Prevalence, sociodemography, and health impact," Dig. Dis. Sci., 38 (9): 1569-1580, 1993.
Dulleman et al., "Treatment of Crohn's Disease with Anti-tumor Necrosis Factor Chimeric Monoclonal Antibody," Gastroenterology, 109(1):129-135, 1995.
Eastgate et al., "Correlation of plasma interleukin 1 levels with disease activity in rheumatoid arthritis," Lancet, 2 (8613): 706-709, 1988.
Eikelenboom et al., "Neuroinflammation in Alzheimer's disease and prion disease," Glia, 40 (2): 232-239, 2002.

(56) References Cited

OTHER PUBLICATIONS

Ettehadi et al., "Elevated tumour necrosis factor-alpha (TNF-alpha) biological activity in psoriatic skin lesions," Clin. Exp. Immunol., 96(1): 146-151, 1994.
Everhart and Renault., "Irritable bowel syndrome in office-based practice in the United States," Gastroenterol., 100 (4): 998-1005, 1991.
Fauci, Eds., In: Harrison's Principles of Internal Medicine, 1998, 14th Edition, McGraw-Hill, New York, pp. 1880-1888.
Fearon and Locksley, "The instructive role of innate immunity in the acquired immune response," Science, 272 (5258): 50-53, 1996.
Feldtkeller et al., "Age at disease onset and diagnosis delay in HLA-B27 negative vs. positive patients with ankylosing spondylitis," Rheumatolo. Int., 23 (2): 61-66, 2003.
Firestein et al., "IL-1 receptor antagonist protein production and gene expression in rheumatoid arthritis and osteoarthritis synovium," Arthritis Rheum., 37: 644-652, 1994.
Forstermann, "Janus-faced role of endothelial NO synthase in vascular disease: uncoupling of oxygen reduction from NO synthesis and its pharmacological reversal," Biol. Chem, 387: 1521-1533, 2006.
Fujikawa et al., "Interleukin-1 receptor antagonist production in cultured synovial cells from patients with rheumatoid arthritis and osteoarthritis," Ann. Rheum. Dis., 54 (4): 318-320, 1995.
Funakoshi et al., "Spectrum of cytokine gene expression in intestinal mucosal lesions of Crohn's disease and ulcerative colitis," Digestion, 59 (1): 73-78, 1998.
Galley and Webster, "The immuno-inflammatory cascade," Br. J. Anaesth., 77 (1): 11-16, 1996.
Gehrmann et al., "Amyloid precursor protein (APP) expression in multiple sclerosis lesions," Glia, 15 (2): 141-151, 1995.
Genain and Hauser, "Creation of a model for multiple sclerosis in *Callithrix jacchus* marmosets," J. Mol. Med., 75 (3): 187-197, 1997.
Gladman et al., "Psoriatic Arthritis: Recent Advances in Pathogenesis and Treatment," Rheumatic Diseases Clinics of North America, 18(1):247-256, 1992.
Gladman et al., "Clinical indicators of progression in psoriatic arthritis: multivariate relative risk model," Br. J. Rheumatol., 22 (4): 675-679, 1995.
Gladman et al., "Psoriatic arthritis (PSA)—an analysis of 220 patients," J. Med., 62 (238):127-141, 1987.
Goodman et al., "Heme oxygenase-1 protects against radiocontrast-induced acute kidney injury by regulating anti-apoptotic proteins," Kidney Int., 72 (8): 945-953, 2007.
Graeber et al., "Microglia in brain tumors," Glia, 40(2): 252-259, 2002.
Greten et al., "IKKbeta links inflammation and tumorigenesis in a mouse model of colitis-associated cancer," Cell, 118 (3): 285-296, 2004.
Griffin et al., "Brain interleukin 1 and S-100 immunoreactivity are elevated in Down syndrome and Alzheimer disease," PNAS, 86 (19): 7611-7615, 1989.
Grivennikov and Karin, "Dangerous Liaisons: STAT3 and NF-κB collaboration and crosstalk in cancer", Cytokine Growth Factor Rev., 2010, 21(1):11-19.
Guilherme et al., "Adipocyte dysfunctions linking obesity to insulin resistance and type 2 diabetes," Nat. Rev. Mol. Cell Biol., 9 (5):367-377, 2008.
Gwee et al., "The role of psychological and biological factors in postinfective gut dysfunction," Gut., 44 (3): 400-406, 1999.
Hannum et al., "Interleukin-1 receptor antagonist activity of a human interleukin-1 inhibitor," Nature, 343 (6256): 336-340, 1990.
Hanson et al., "Inflammation and atherosclerosis," Annu. Rev. Pathol: Mech. Dis., 1: 297-329, 2006.
Hanson et al., "Theories of schizophrenia: a genetic-inflammatory-vascular synthesis," BMC Medical Genetics, 6: 7, 2005.
Harrison et al., "The performance of the 1987 ARA classification criteria for rheumatoid arthritis in a population based cohort of patients with early inflammatory polyarthritis. American Rheumatism Association," J. Rheumatol., 25 (12): 2324-2330, 1998.

Hart et al., "Comparison of the suppressive effects of interleukin-10 and interleukin-4 on synovial fluid macrophages and blood monocytes from patients with inflammatory arthritis," Immunology, 84 (4): 536-542, 1995.
He and Karin, "NF-κB and STAT3—key players in liver inflammation and cancer", Cell Research, 2011, 21:159-168.
Honda et al., "A novel dicyanotriterpenoid, 2-cyano-3,12-dioxooleana-1,9(11)-dien-28-onitrile, active at picomolar concentrations for inhibition of nitric oxide production," Bioorg. Med. Chem. Lett, 12:1027-1030, 2002.
Honda et al., "Design and synthesis of 2-cyano-3,12-dioxoolean-1,9-dien-28-oic acid, a novel and highly active inhibitor of nitric oxide production in mouse macrophages," Bioorg Med Chem Lett., 8(19):2711-2714, 1998.
Honda et al., "New enone derivatives of oleanolic acid and ursolic acid as inhibitors of nitric oxide production in mouse macrophages," Bioorg. Med. Chem. Lett., 7:1623-1628, 1997.
Honda et al., "Novel synthetic oleanane and ursane triterpenoids with various enone functionalities in ring A as inhibitors of nitric oxide production in mouse macrophages," J. Med. Chem, 43:1866-1877, 2000.
Honda et al., "Novel synthetic oleanane triterpenoids: a series of highly active inhibitors of nitric oxide production in mouse macrophages," Bioorg Med Chem Lett, 9(24):3429-3434, 1999.
Honda et al., "Synthetic oleanane and ursane triterpenoids with modified rings A and C: A series of highly active inhibitors of nitric oxide production in mouse macrophages," J. Med. Chem, 43:4233-4246, 2000.
Horwitz and Fisher, "The irritable bowel syndrome," N. E. J. Med., 344 (24): 1846-1850, 2001.
Hotamisligil, "Inflammation and metabolic disorders," Nature, 444 (7121): 860-867, 2006.
International Search Report and Written Opinion for Application No. PCT/US2014/035279, dated Aug. 6, 2014, 14 pages.
Ishikawa et al., "Heme oxygenase-1 inhibits atherogenesis in Watanabe heritable hyperlipidemic rabbits," Circulation, 104 (15): 1831-1836, 2001.
Ishizawa and Dickson, "Microglial activation parallels system degeneration in progressive supranuclear palsy and corticobasal degeneration," J. Neuropathol. Exp. Neurol., 60 (6):647-657, 2001.
Jacob et al., "Heritable Major Histocompatibility Complex II-associated differences in production of tumor necrosis factor alpha: relevance to genetic predisposition to systemic lupus erythematosus," PNAS, 87(3):1233-1237, 1990.
Jailwala et al., "Pharmacologic treatment of the irritable bowel syndrome: a systematic review of randomized, controlled trials," Ann. Intern. Med., 133 (2): 136-147, 2000.
Jarvis, "Juvenile rheumatoid arthritis: a guide for pediatricians," Pediatr. Ann., 31 (7):437-446, 2002.
Jarvis, "Pathogenesis and mechanisms of inflammation in the childhood rheumatic diseases," Curr. Opin. Rheumatol., 10 (5): 459-467, 1998.
Jones et al., "Psoriatic arthritis: outcome of disease subsets and relationship of joint disease to nail and skin disease," Br. J. Rheumatol., 33 (9): 834-839, 1994.
Jonsson et al., "B-lymphocyte selection and autoimmunity," Trends Immunol., 22 (12): 653-654, 2001.
Jonsson et al., "Current issues in Sjögren's syndrome," Oral Dis., 8 (3): 130-140, 2002.
Jonsson et al., "Progression of sialadenitis in Sjögren's syndrome," Br. J. Rheumatol., 32 (7): 578-581, 1993.
Kahle et al., "Determination of cytokines in synovial fluids: correlation with diagnosis and histomorphological characteristics of synovial tissue," Ann. Rheum. Dis., 51 (6): 7 3 1-7 34, 1992.
Kaltschmidt et al.,"Transcription factor NF-kappaB is activated in primary neurons by amyloid beta peptides and in neurons surrounding early plaques from patients with Alzheimer disease," Proc. Natl. Acad. Sci. USA, 94:2642-2647, 1997.
Karin et al., "Nuclear factor-κB in cancer development and progression," Nature, 441(7092):431-436, 2006.
Kawakami et al., "A comparative study of nitric oxide, glutathione, and glutathione peroxidase activities in cerebrospinal fluid from

(56) References Cited

OTHER PUBLICATIONS children with convulsive diseases/children with aseptic meningitis," Brain Dev., 28 (4): 243-246, 2006.
Kellow and Phillips, "Altered small bowel motility in irritable bowel syndrome is correlated with symptoms," Gasteroeneterology, 92 (6): 1885-1893, 1987.
Kendall-Tackett, "Inflammation, cardiovascular disease, and metabolic syndrome as sequelae of violence against women: the role of depression, hostility, and sleep disturbance," Trauma Biolence Abuse, 8 (2): 117-126, 2007.
Khan, "Cytokine-induced accumulation of very long-chain fatty acids in rat C6 glial cells: implication for X-adrenoleukodystrophy," J. Neurochem., 71 (7): 78-87, 1998.
Khan, "Effects of hydrogen sulfide exposure on lung mitochondrial respiratory chain enzymes in rats," Toxicol. Applied Pharmacol, 103 (3): 484-490, 1990.
Kortylewski et al., "Inhibiting Stat3 signaling in the hematopoietic system elicits multicomponent antitumor immunity," Nat. Med., 11 (12): 1314-1321, 2005.
Kotake et al., "Gamma interferon and interleukin-10 gene expression in synovial tissues from patients with early stages of Chlamydia-associated arthritis and undifferentiated oligoarthritis and from healthy volunteers," Infect. Immun, 67(5): 2682-2686, 1999.
Kotzin, "Systemic lupus erythematosus," Cell, 85 (3): 303-306, 1996.
Kruger et al., "Up-regulation of heme oxygenase provides vascular protection in an animal model of diabetes through its antioxidant and antiapoptotic effects," J. Pharmacol. Exp. Ther.,319 (3): 1144-1152, 2006.
Kuboyama, "Increased circulating levels of interleukin-1 receptor antagonist in patients with inflammatory bowel disease," Kurume Med. J ., 45 (1): 33-37, 1998.
Lahesmaa et al., "Yersinia enterocolitica activates a T helper type 1-like T cell subset in reactive arthritis," J. Immunol, 148 (10): 3079-3085, 1992.
Lee et al., "Double-stranded RNA induces iNOS gene expression in Schwann cells, sensory neuronal death, and peripheral nerve demyelination," Glia, 55(7): 712-722, 2007.
Lencz et al., "Converging evidence for a pseudoautosomal cytokine receptor gene locus in schizophrenia," Mol. Psychiatry, 12 (6): 572-580, 2007.
Liby et al., "The synthetic triterpenoids, CDDO and CDDO-imidazolide, are potent inducers of heme oxygenase-1 and Nrf2/ARE signaling," Cancer Res, 65:4789-4798, 2005.
Liby et al., "Triterpenoids and rexinoids as multifunctional agents for the prevention and treatment of cancer," Nat. Rev. Cancer, 7 (5): 357-369, 2007.
Liu et al., "Heme oxygenase-1 (HO-1) inhibits postmyocardial infarct remodeling and restores ventricular function," FASEB J., 20 (2): 207-216, 2006.
Lo et al., "Mapping genes regulating lymphocyte function: correlations with autoimmunity," Curr. Dire. Autoimmun., 1: 226-246, 1999.
Lugering et al., "Current concept of the role of monocytes/macrophages in inflammatory bowel disease—balance of proinflammatory and immunosuppressive mediators," Ital. J. Gastroenterol. Hepatol., 30 (3): 338-344, 1998.
Lynn and Friedman, "Irritable bowel syndrome," N. E. J. Med., 329 (26): 1940-1945, 1993.
Macatonia et al., "Differential effect of IL-10 on dendritic cell-induced T cell proliferation and IFN-gamma production," J. Immunol., 150 (9): 3755-3765, 1993.
Marsal et al., "Clinical, radiographic and HLA associations as markers for different patterns of psoriatic arthritis," Rheumatology, 38 (4): 332-337, 1999.
Mazur et al., "Acetylsalicylic acid (ASA) blocks influenza virus propagation via its NF-kappaB-inhibiting activity," Cell Microbiol., 9 (7): 1683-1694, 2007.

Mazzoni et al., "Myeloid suppressor lines inhibit T cell responses by an NO-dependent mechanism," J. Immunol., 168 (2): 689-695, 2002.
McAlindon et al., "Expression of interleukin 1 beta and interleukin 1 beta converting enzyme by intestinal macrophages in health and inflammatory bowel disease," Gut, 42 (2)214-219, 1998.
McGeer and McGeer, "The inflammatory response system of brain: implications for therapy of Alzheimer and other neurodegenerative diseases," Brain Research Reviews, 21:195-218, 1995.
McGonagle et al., "Enthesitis in spondyloarthropathy," Curr. Opin. Rheumatol., 11 (4): 244-250, 1999.
McIver et al., "NO-mediated alterations in skeletal muscle nutritive blood flow and lactate metabolism in fibromyalgia," Pain, 120 (1-2): 161-169, 2005.
Mease et al., "Etanercept in the treatment of psoriatic arthritis and psoriasis: a randomised trial," Lancet, 356:385-390, 2000.
Merrill and Beneiste, "Cytokines in inflammatory brain lesions: helpful and harmful," Trends Neurosci, 19(8):331-338, 1996.
Mertz et al., "Regional cerebral activation in irritable bowel syndrome and control subjects with painful and nonpainful rectal distention," Gastroenetrol., 118 (5): 842-848, 2000.
Moll and Wright, "Familial occurrence of psoriatic arthritis," Ann. Rheum. Dis., 32 (3): 181-201, 1973.
Moll and Wright, "Psoriatic arthritis," Semin. Arthritis Rheum., 3 (1): 55-78, 1973.
Morris et al., "Association of a functional inducible nitric oxide synthase promoter variant with complications in type 2 diabetes," J. Mol. Med., 80(2):96-104, 2002.
Morse and Choi, "Heme oxygenase-1: from bench to bedside," Am. J. Respir. Crit. Care Med., 172 (6): 660-670, 2005.
Morse and Choi, "Heme oxygenase-1: the 'emerging molecule' has arrived," Am. J. Respir. Crit. Care Med., 27(1):8-16, 2002.
Naik et al., Role of oxidative stress in pathophysiology of peripheral neuropathy and modulation by N-acetyl-L-cysteine in rats, Eur. J. Pain, 10 (7): 573-579, 2006.
Nath et al., "Progression of progressive multifocal leukoencephalopathy despite treatment with beta-interferon," Neurology, 66(1): 149-150, 2006.
Neal et al., "Prevalence of gastrointestinal symptoms six months after bacterial gastroenteritis and risk factors for development of the irritable bowel syndrome: postal survey of patients," BMJ., 314 (7083): 779-782, 1997.
Nichols, "NF-kappaB and reperfusion injury," Drug News Perpect., 17(2): 99-104, 2004.
Nielen et al., "Specific autoantibodies precede the symptoms of rheumatoid arthritis: a study of serial measurements in blood donors," Arthritis Rheum., 50 (2): 380-386, 2004.
O'Dell et al., "Systemic Lupus Erythematous," In: Sampler's Immunological Diseases, Frank et al., Ed., p. 667-697, 1995.
Ohnishi et al., "Comparison of pathogenic and non-pathogenic murine antibodies to DNA: antigen binding and structural characteristics," Int. Immunol., 6 (6): 817-830, 1994.
Pall, "Nitric oxide synthase partial uncoupling as a key switching mechanism for the NO/ONOO-cycle," Med. Hypoth., 69 (4): 821-825, 2007.
Partsch et al., "Highly increased levels of tumor necrosis factor-alpha and other proinflammatory cytokines in psoriatic arthritis synovial fluid," Br. J. Rheumatol., 24 (3): 518-523, 1997.
Pergola et al., "Bardoxolone Methyl and Kidney Function in CKD with Type 2 Diabetes" N. Engl. J. Med., 365:327-336, 2011.
Pica et al., "Delta(12)-prostaglandin J(2) is a potent inhibitor of influenza A virus replication," Antimicrob. Agents Chemother., 44(1): 200-204, 2000.
Pimental et al., "Eradication of small intestinal bacterial overgrowth reduces symptoms of irritable bowel syndrome," Am. J. Gastroenterol., 95 (12): 3503-3506, 2000.
Place et al., "The novel synthetic triterpenoid, CDDO-imidazolide, inhibits inflammatory response and tumor growth in vivo," Clin. Cancer Res, 9:2798-2806, 2003.
Prieur et al., "Specific interleukin-1 inhibitor in serum and urine of children with systemic juvenile chronic arthritis," Lancet, 2 (8570): 1240-1242, 1987.

(56) References Cited

OTHER PUBLICATIONS

Rajakariar et al., "Hematopoietic prostaglandin D2 synthase controls the onset and resolution of acute inflammation through PGD2 and 15-deoxyDelta12 14 PGJ2," PNAS USA, 104 (52): 20979-20984, 2007.
Rantää-Dahlqvist et al., "Antibodies against cyclic citrullinated peptide and IgA rheumatoid factor predict the development of rheumatoid arthritis," Arthritis Rheum, 48 (10): 2741-2749, 2003.
Reimund et al., "Antioxidants inhibit the in vitro production of inflammatory cytokines in Crohn's disease and ulcerative colitis," Eur. J. Clin. Invest., 28 (2): 145-150, 1998.
Ribbens et al., "Increased synovial fluid levels of interleukin-12, sCD25 and sTNF-RII/sTNF-RI ratio delineate a cytokine pattern characteristic of immune arthropathies," Eur. Cytokine Netw., 1 (4)1: 669-676, 2000.
Rogers et al., "Expression of immune system-associated antigens by cells of the human central nervous system: Relationship to the pathology of Alzheimer's disease," Neurobiol. Aging, 9 (4): 339-349, 1988.
Rogler and Andus, "Cytokines in inflammatory bowel disease," World J. Surg., 22 (4): 382-389, 1998.
Rooney et al., "Interleukin 1 beta in synovial fluid is related to local disease activity in rheumatoid arthritis," Rheumatol. Int., 10 (5): 217-219, 1990.
Ross et al., "Breast cancer biomarkers and molecular medicine," Expert Rev. Mol. Diagn., 3(5): 573-585, 2003.
Ross et al., "HER-2/neu testing in breast cancer," Am. J. Clin. Pathol., 120(Suppl):S53-71, 2003.
Rostom et al., "Nonsteroidal anti-inflammatory drugs and cyclooxygenase-2 inhibitors for primary prevention of colorectal cancer: a systematic review prepared for the U.S. Preventive Services Task Force," Ann. Intern. Med., 146 (5): 376-389, 2007.
Rothstein, "Irritable bowel syndrome," Med. Clin. North Am., 84 (5): 1247-1257, 2000.
Ruster et al., "Detection of elevated N epsilon-carboxymethyllysine levels in muscular tissue and in serum of patients with fibromyalgia," Scand. J. Rheumatol., 34(6): 460-463, 2005.
Sacerdoti et al., "Heme oxygenase overexpression attenuates glucose-mediated oxidative stress in quiescent cell phase: linking heme to hyperglycemia complications," Curr. Neurovasc. Res., 2(2): 103-111, 2005.
Saha et al., "The triterpenoid 2-cyano-3,12-dioxo-oleana-19-dien-28-oic acid methyl ester has potent anti-diabetic effects in diet-induced diabetic mice and Lepr(db/db) mice," J. Biol. Chem, 285(52):40581-40592, 2010.
Saiki et al., "Detection of pro- and anti-inflammatory cytokines in stools of patients with inflammatory bowel disease," Scand. J. Gastroenterol., 33 (6): 616-622, 1998.
Salomonsson and Jonsson, "Cellular basis of ectopic germinal center formation and autoantibody production in the target organ of patients with Sjögren's syndrome," Arthritis Rheum., 48 (11): 3187-3201, 2003.
Salomonsson et al., "Expression of the B cell-attracting chemokine CXCL13 in the target organ and autoantibody production in ectopic lymphoid tissue in the chronic inflammatory disease Sjögren's syndrome," Scand. J. Immunol., 55 (4): 336-342, 2002.
Salvarani et al., "Psoriatic arthritis," Curr. Opin. Rheumatol., 10 (4): 299-305, 1998.
Salvemini et al., "Endogenous nitric oxide enhances prostaglandin production in a model of renal inflammation," J. Clin. Invest., 93(5):1940-1947, 1994.
Sandler, "Epidemiology of irritable bowel syndrome in the United States," Gastroenterology, 99 (2): 409-415, 1990.
Sarchielli et al., "NF-kappaB activity and iNOS expression in monocytes from internal jugular blood of migraine without aura patients during attacks," Cephalalgia, 26 (9): 1071-1079, 2006.
Satoh et al., "Activation of the Keap1/Nrf2 pathway for neuroprotection by electrophillic phase II inducers," PNAS, 103 (3): 768-773, 2006.

Schlaak et al., "Different cytokine profiles in the synovial fluid of patients with osteoarthritis, rheumatoid arthritis and seronegative spondylarthropathies," Clin. Exp. Rheumatol., 14 (2): 155-162, 1996.
Schlaak et al., "Predominance of Th1-type T cells in synovial fluid of patients with Yersinia-induced reactive arthritis," Eur. J. Immunol., 22 (11): 2771-2776, 1992.
Schlosstein et al., "High association of an HL-A antigen, W27, with ankylosing spondylitis," N.E.J. Medicine, 288 (14): 704-706, 1973.
Schreiber, "Experimental immunomodulatory therapy of inflammatory bowel disease," Neth. J. Med., 53 (6): S24-S31, 1998.
Schulz et al., "Nitric oxide, tetrahydrobiopterin, oxidative stress, and endothelial dysfunction in hypertension," Antioxid. Redox. Sig., 10 (6):1115-1126, 2008.
Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," Clin. Cancer Res, 12: 1828-1838, 2006.
Sieper and Braun, "Pathogenesis of spondylarthropathies. Persistent bacterial antigen, autoimmunity, or both," Arthritis Rheum., 38 (11):1547-1554, 1995.
Simon et al., "Analysis of cytokine profiles in synovial T cell clones from chlamydial reactive arthritis patients: predominance of the Th1 subset," Clin. Exp. Immunol, 94 (1):122-126, 1993.
Simon et al., "Divergent T-cell cytokine patterns in inflammatory arthritis," PNAS., 91(18):8562-85666, 1994.
Simonian and Coyle, "Oxidative stress in neurodegenerative diseases," Annu. Rev. Pharmacol. Toxicol., 36:83-106, 1996.
Sinha et al., "Prostaglandin E2 promotes tumor progression by inducing myeloid-derived suppressor cells," Cancer Res, 67 (9):4507-4513, 2007.
Smith, et al., March's Advanced Organic Chemistry: Reactions, Mechanisms, and Structure, 2007, 6th Edition, Wiley-Interscience, A John Wiley and Sons, Inc., Publication, Table of Contents.
Stack et al., "Randomised controlled trial of CDP571 antibody to tumour necrosis factor-alpha in Crohn's disease," Lancet, 349(9051):521-524, 1997.
Stahl et al., eds., Handbook of Pharmaceutical Salts: Properties, Selection, and Use, Verlag Helvetica Chimica Acta, Wiley-VCH, 2002.
Stewart et al., "Risk of Alzheimer's disease and duration of NSAID use" Neurology, 48:626-632, 1997.
Strejan et al., "Suppression of chronic-relapsing experimental allergic encephalomyelitis in strain-13 guinea pigs by administration of liposome-associated myelin basic protein," J. Neuroimmunol., 7 (1): 27, 1984.
Suh et al., "A novel synthetic oleanane triterpenoid, 2-cyano-3,12-dioxoolean-1,9-dien-28-oic acid, with potent differentiating, antiproliferative, and anti-inflammatory activity," Cancer Res., 59(2):336-341, 1999.
Suh et al., "Novel triterpenoids suppress inducible nitric oxide synthase (iNOS) and inducible cyclooxygenase (COX-2) in mouse macrophages," Cancer Res, 58:717-723, 1998.
Szabo et al., "Peroxynitrite: biochemistry, pathophysiology and development of therapeutics," Nature Rev. Drug Disc., 6:662-680, 2007.
Takahashi et al., "Increased expression of inducible and endothelial constitutive nitric oxide synthases in rat colon tumors induced by azoxymethane," Cancer Res, 57: 1233-1237, 1997.
Talley et al., "Medical costs in community subjects with irritable bowel syndrome," Gastroenterol., 109 (6): 1736-1741, 1995.
Tamir and Tannebaum, "The role of nitric oxide (NO) in the carcinogenic process," Biochim. Biophys. Acta, 1288:F31-F36, 1996.
Targan et al., "A short-term study of chimeric monoclonal antibody cA2 to tumor necrosis factor alpha for Crohn's disease. Crohn's Disease cA2 Study Group," N. Engl. J. Med., 337(15):1029-1035, 1997.
Touzani et al., "Potential mechanisms of interleukin-1 involvement in cerebral ischaemia," J. Neuroimmunol., 100 (1-2): 203-215, 1999.

(56) References Cited

OTHER PUBLICATIONS

Tumlin et al., "Pathophysiology of contrast-induced nephropathy," Am. J. Cardiol., 98 (6A): 14K-20K, 2006.
Van den Berg, "Uncoupling of inflammatory and destructive mechanisms in arthritis," Semin. Arthritis Rheum, 30 (5S-2): 7-16, 2001.
Van Hogezand and Verspaget, "The future role of anti-tumour necrosis factor-alpha products in the treatment of Crohn's disease," Drugs, 56(3):299-305, 1998.
Vazquez et al., "Human immunodeficiency virus type 1-induced macrophage gene expression includes the p21 gene, a target for viral regulation," J. Virol., 7 9:4479-4491, 2005.
Wardle, "Nuclear factor kappaB for the nephrologist," Nephrol. Dial. Transplant., 16(9):1764-8, 2001.
Warrington et al., "CD4+,CD28− T cells in rheumatoid arthritis patients combine features of the innate and adaptive immune systems," Arthritis and Rheumatism, 44 (1):13-20, 2001.
Weyand and Goronzy, "Ectopic germinal center formation in rheumatoid synovitis," Ann. NY Acad. Sci., 987:140-149, 2003.
Whitehead et al., "Tolerance for rectosigmoid distention in irritable bowel syndrome," Gastroenterol., 98(5 Pt 1):1187-1192, 1990.
Williams et al., "Immunology of multiple sclerosis," Clin. Neurosci., 2(3-4):229-245, 1994.
Wordsworth, "Genes and arthritis," Bri. Medical Bulletin, 51: 249-266, 1995.
Wright, "A unifying concept for the spondyloarthropathies," Clin. Orthop. Related Res., 143:8-14, 1979.
Wright, "Psoriasis and arthritis," Ann. Rheum. Dis., 15 (4): 348-356, 1956.
Xanthou et al., "'Lymphoid' chemokine messenger RNA expression by epithelial cells in the chronic inflammatory lesion of the salivary glands of Sjögren's syndrome patients: possible participation in lymphoid structure formation," Arthritis Rheum, 44(2):408-418, 2001.
Yin et al., "Crucial role of interleukin-10/interleukin-12 balance in the regulation of the type 2 T helper cytokine response in reactive arthritis," Arthritis Rheum., 40 (10):1788-1797, 1997.
Yin et al., "The elevated ratio of interferon gamma-/interleukin-4-positive T cells found in synovial fluid and synovial membrane of rheumatoid arthritis patients can be changed by interleukin-4 but not by interleukin-10 or transforming growth factor beta", Rheumatology, 38(11):1058-1067, 1999.
Yoh et al., "Nrf2-deficient female mice develop lupus-like autoimmune nephritis," Kidney Int., 60(4): 1343-1353, 2001.
Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," Mol. Cancer Ther., 5(12):3232-3239, 2006.
Yu et al., "Crosstalk between cancer and immune cells: role of STAT3 in the tumour microenvironment," Nat. Rev. Immunol., 7 (1):41-51, 2007.
Zhou et al., "Carbon monoxide suppresses bleomycin-induced lung fibrosis," Am. J. Pathol., 166 (1): 27-37, 2005.
Zhou et al., "Myeloid suppressor cell-associated immune dysfunction in CSA1M fibrosarcoma tumor-bearing mice," Cancer Sci., 98 (6): 882-889, 2007.
Zingarelli et al., "Peroxisome proliferator activator receptor-gamma ligands, 15-deoxy-Delta(12,14)-prostaglandin J2 and ciglitazone, reduce systemic inflammation in polymicrobial sepsis by modulation of signal transduction pathways," J. Immunol., 171(12):6827-6837, 2003.
Hayashi, Ryuhei, et al. "The role of the Nrf2-mediated defense system in corneal epithelial wound healing." *Free Radical Biology and Medicine* 61 (2013): 333-342.
Himori, Noriko, et al. "Critical role of Nrf2 in oxidative stress-induced retinal ganglion cell death." *Journal of neurochemistry* 127.5 (2013): 669-680.
Liu, Xiaobin, et al. "The novel triterpenoid RTA 408 protects human retinal pigment epithelial cells against H2O2-induced cell injury via NF-E2-related factor 2 (Nrf2) activation." *Redox biology* 8 (2016): 98-109.
Nagai, Norihiro, et al. "Nrf2 is a critical modulator of the innate immune response in a model of uveitis." *Free Radical Biology and Medicine* 47.3 (2009): 300-306.
Pitha-Rowe, Ian, et al. "Synthetic triterpenoids attenuate cytotoxic retinal injury: cross-talk between Nrf2 and PI3K/AKT signaling through inhibition of the lipid phosphatase PTEN." *Investigative ophthalmology & visual science* 50.11 (2009): 5339-5347.
Wei, Yanhong, et al. "Nrf2 has a protective role against neuronal and capillary degeneration in retinal ischemia—reperfusion injury." *Free Radical Biology and Medicine* 51.1 (2011): 216-224.
Goldman et al., "The Triterpenoid RTA 408 is a Robust Mitigator of Hematopoietic Acute Radiation Syndrome in Mice", Radiat. Res., 183(3):338-344, 2015.
Liu et al., "The novel triterpenoid RTA 408 protects human retinal pigment epithelial cells against H2O2-induced cell injury Via NF-E2-related factor 2 (Nrf2) activation," Redox Biol., 8:98-109, 2016.
Probst et al., "RTA 408, a novel synthetic triterpenoid with broad anti-cancer and anti-inflammatory activity," PLoS One, 10(4):e0122942, 2015.
Reisman et al., "Topical Application of the Synthetic Triterpenoid RTA 408 Protects Mice from Radiation-Induced Dermatitis," Radiat. Res. Soc., 2014.
Reisman et al., "Topical application of the synthetic triterpenoid RTA 408 activates Nrf2 and induces cytoprotective genes in rat skin," Archives of Dermatological Research, 306(5):447-454, 2014.

\* cited by examiner

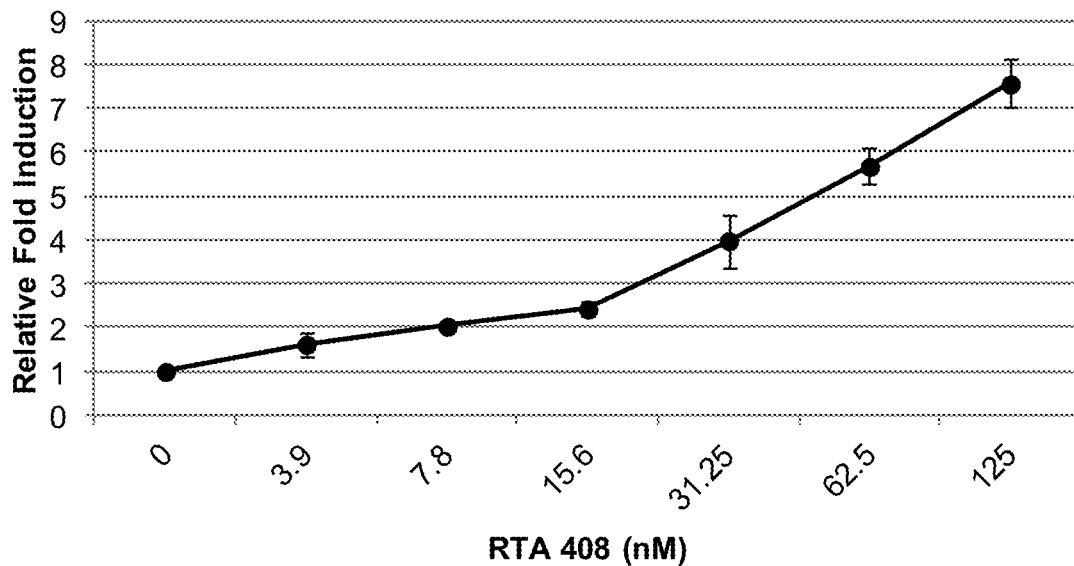
(a)
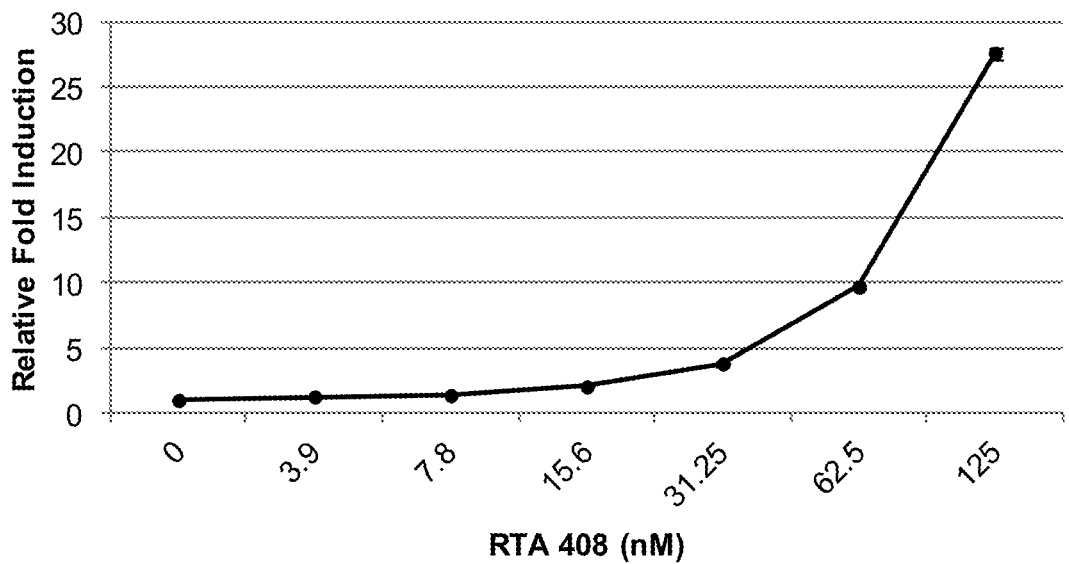
(b)
FIGS. 2a & b

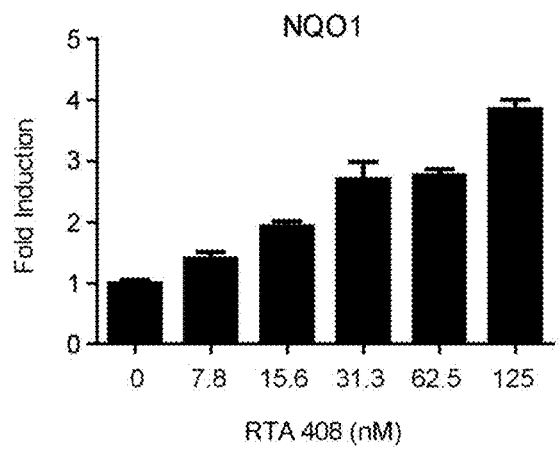
(a)
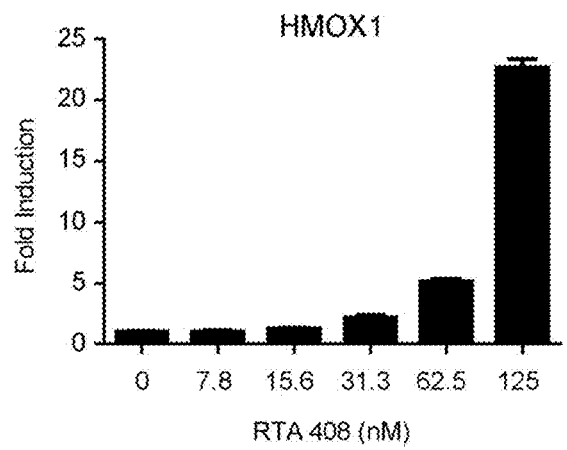
(b)
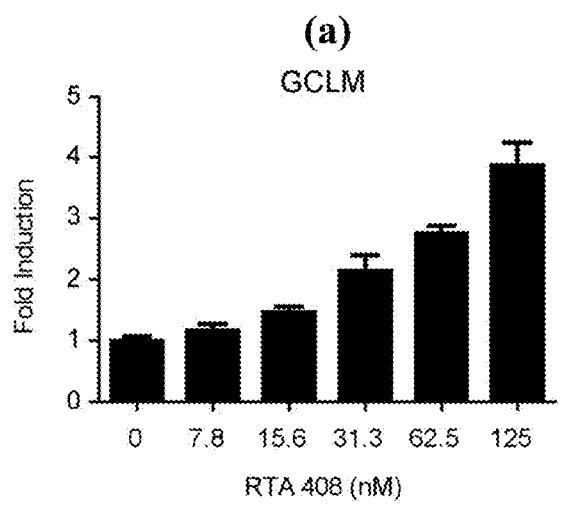
(c)
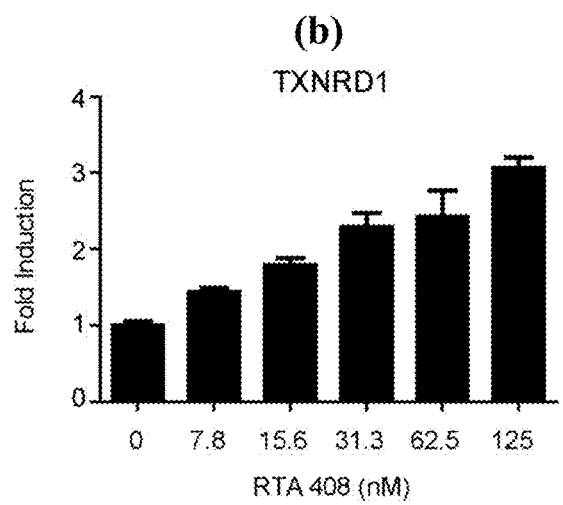
(d)
FIGS. 3a – d

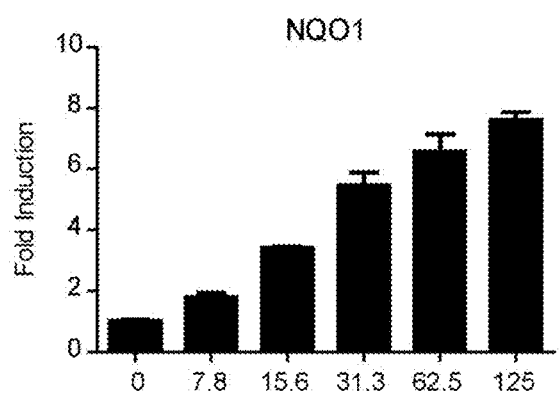
(a)
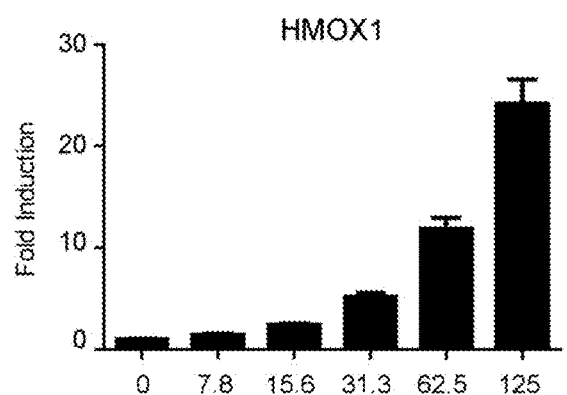
(b)
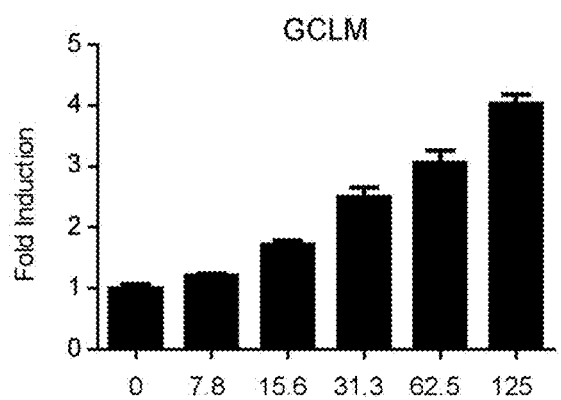
(c)
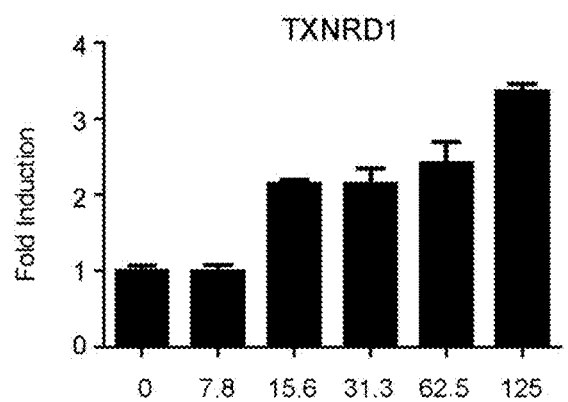
(d)
FIGS. 4a – d

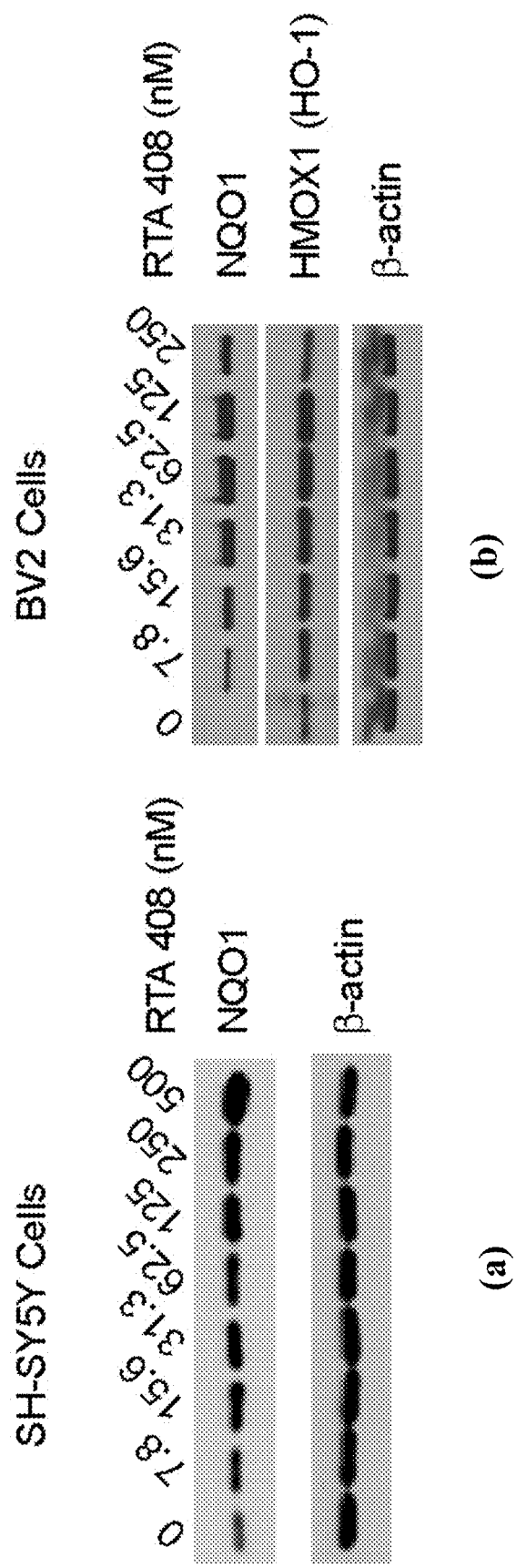
FIGS. 5a & b

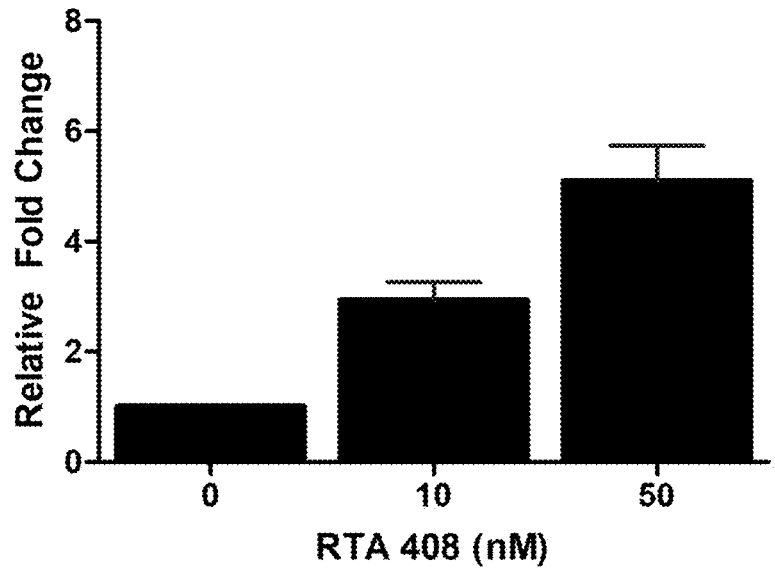
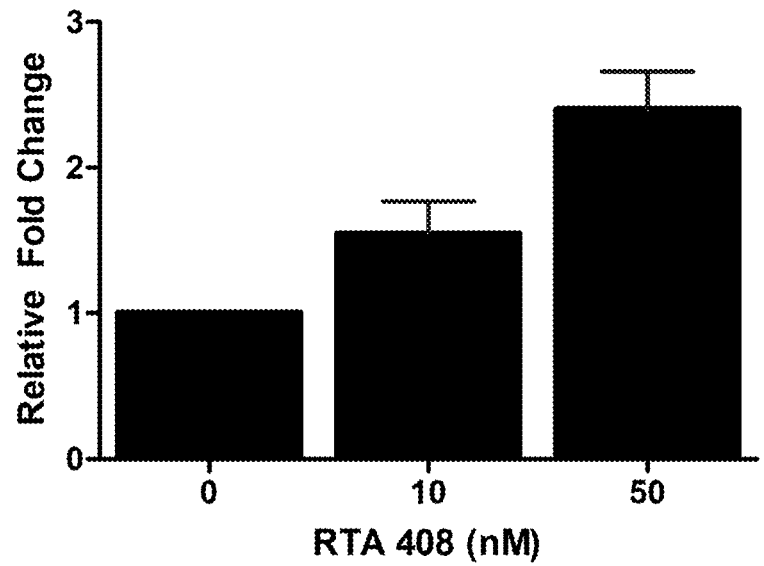
FIGS. 9a & b

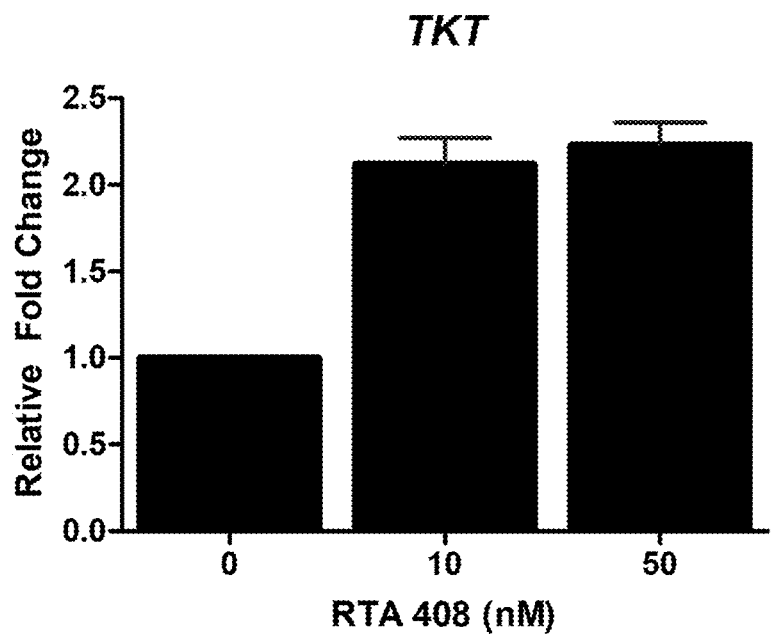
(c)
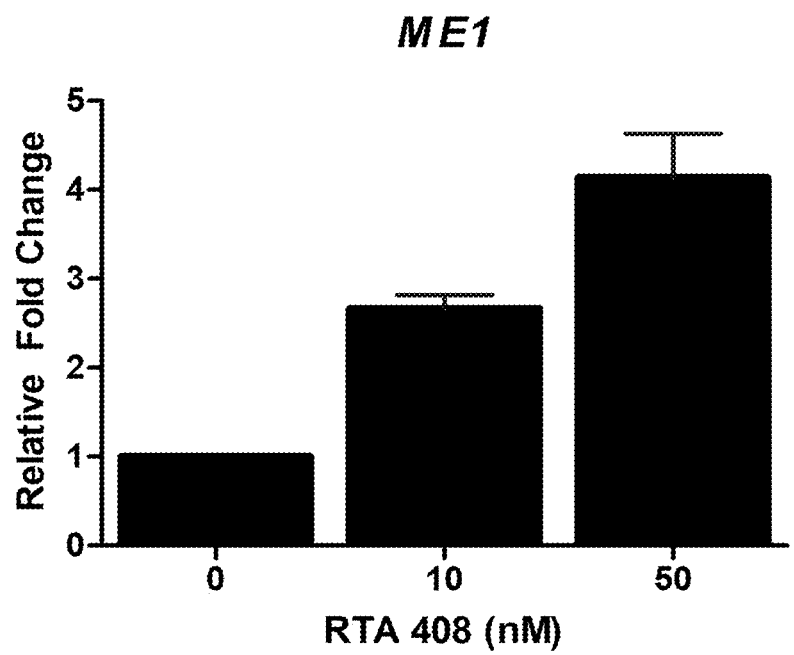
(d)
FIGS. 9c & d

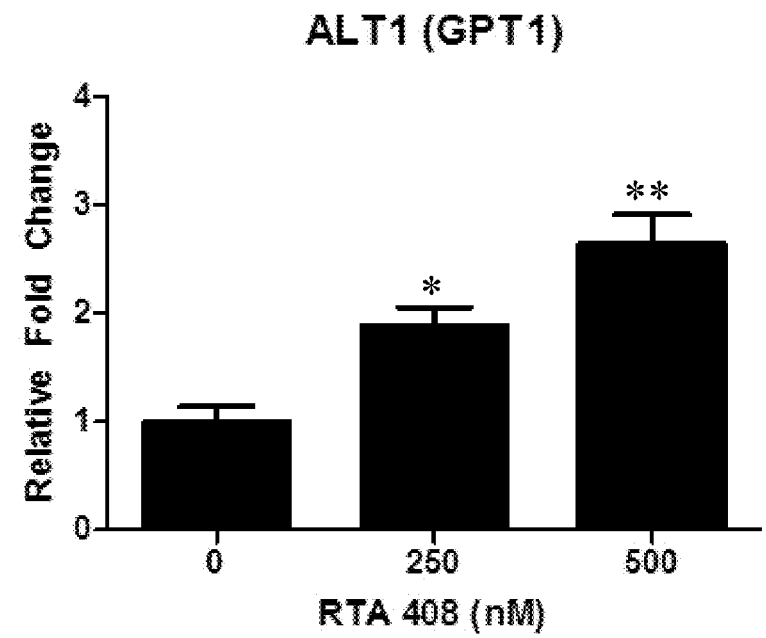
(a)
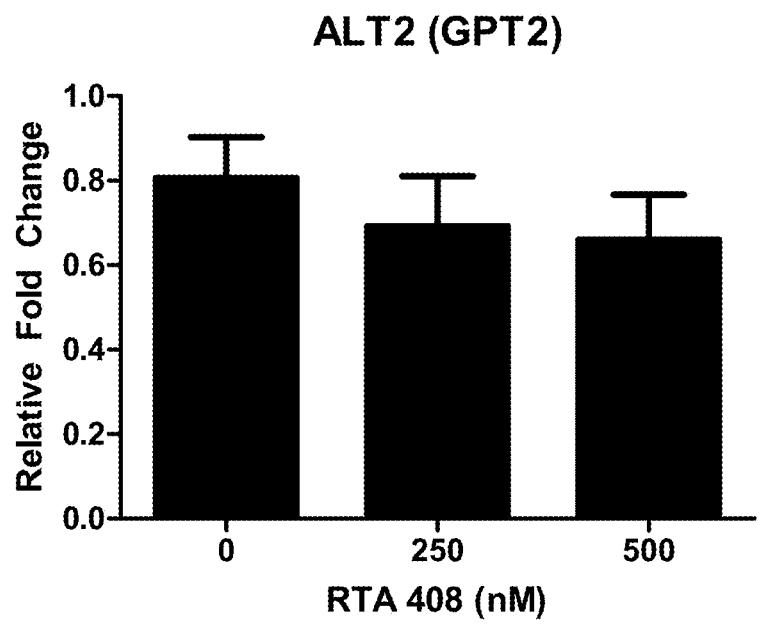
(b)
FIGS. 12a & b

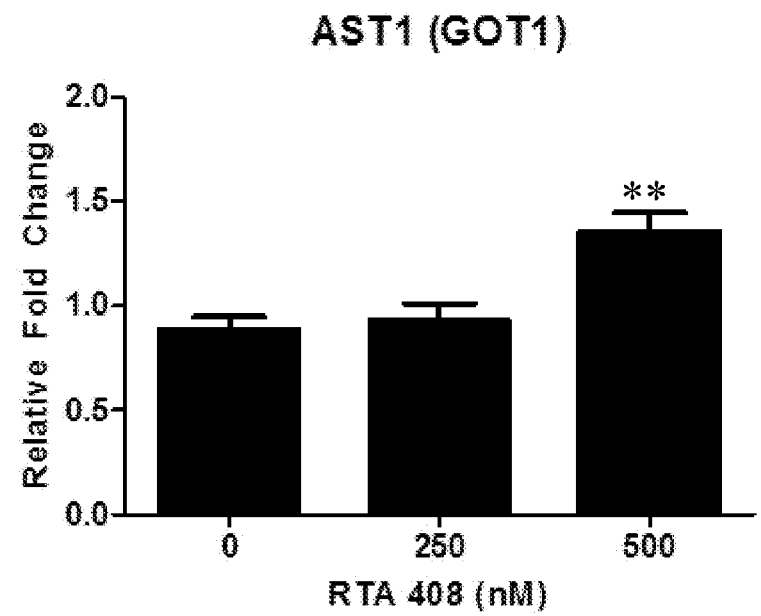
(c)
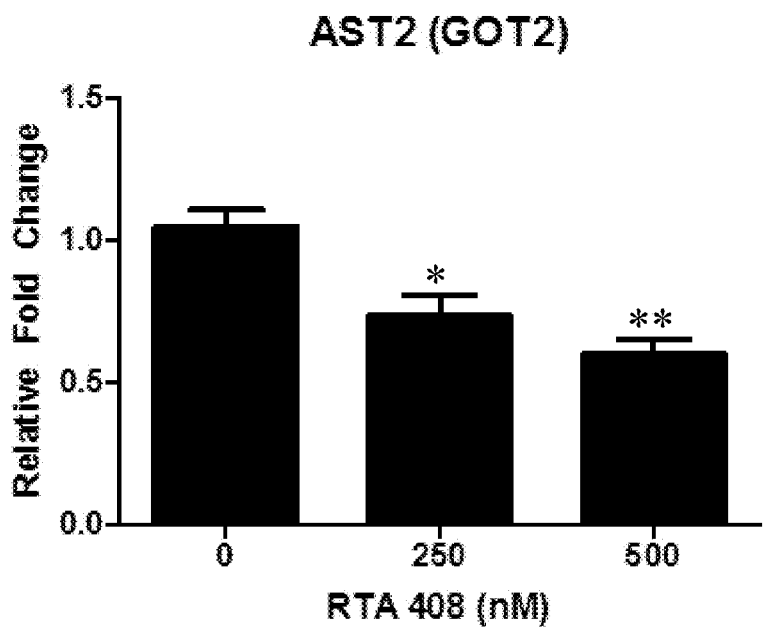
(d)
FIGS. 12c & d

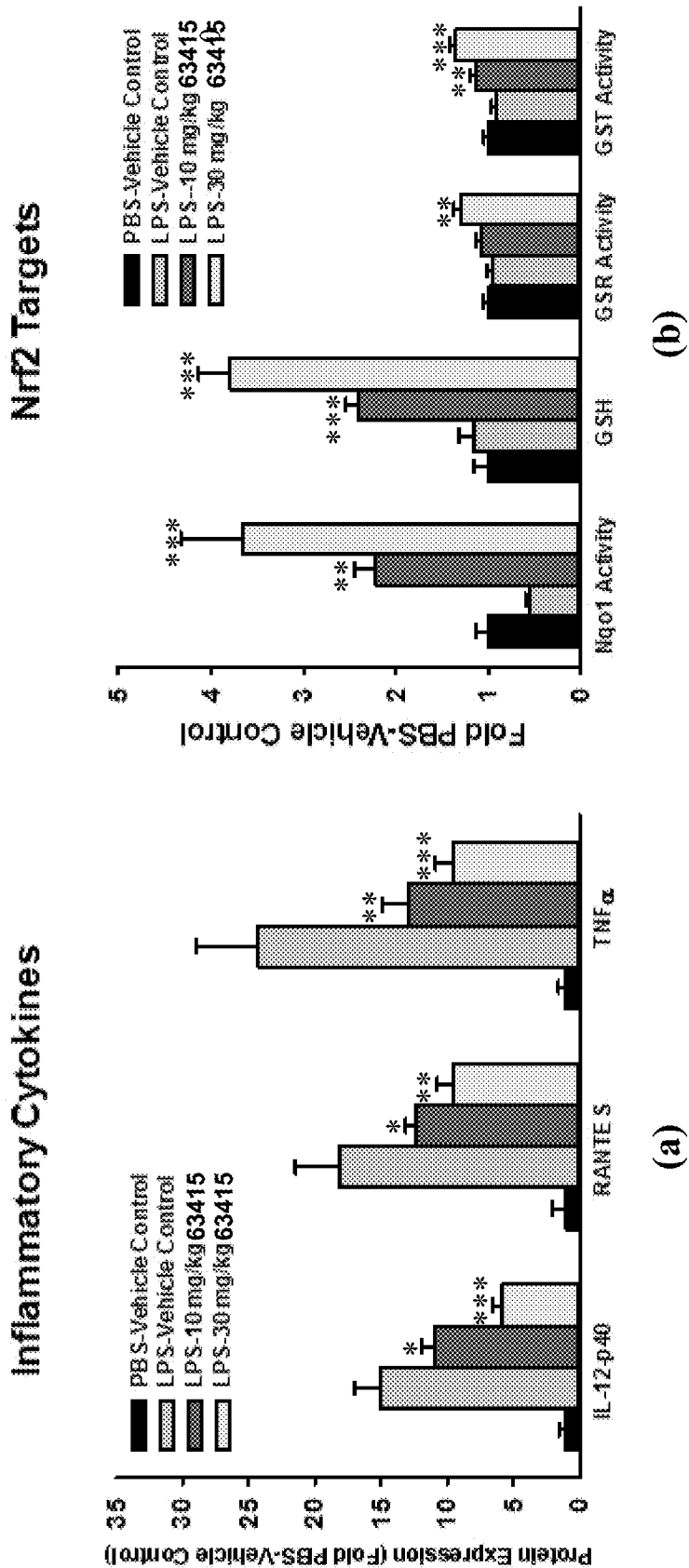
FIGS. 15a & b

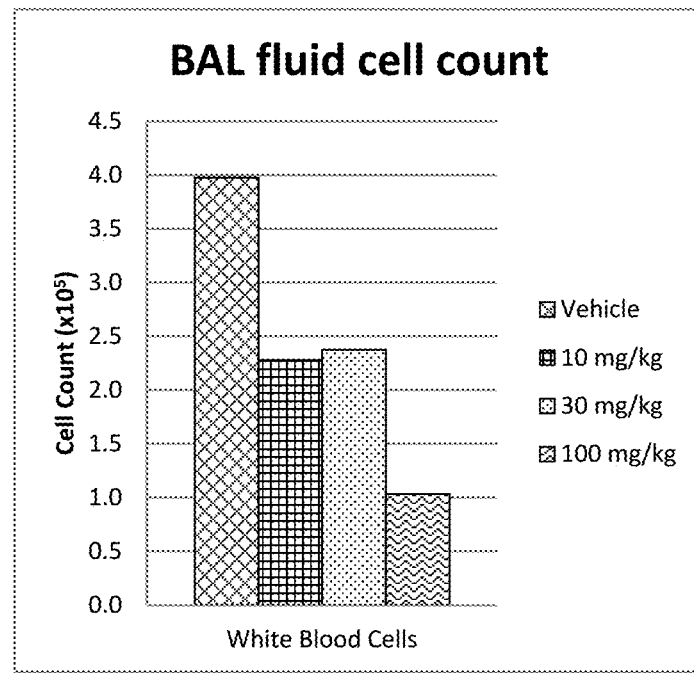
(a)
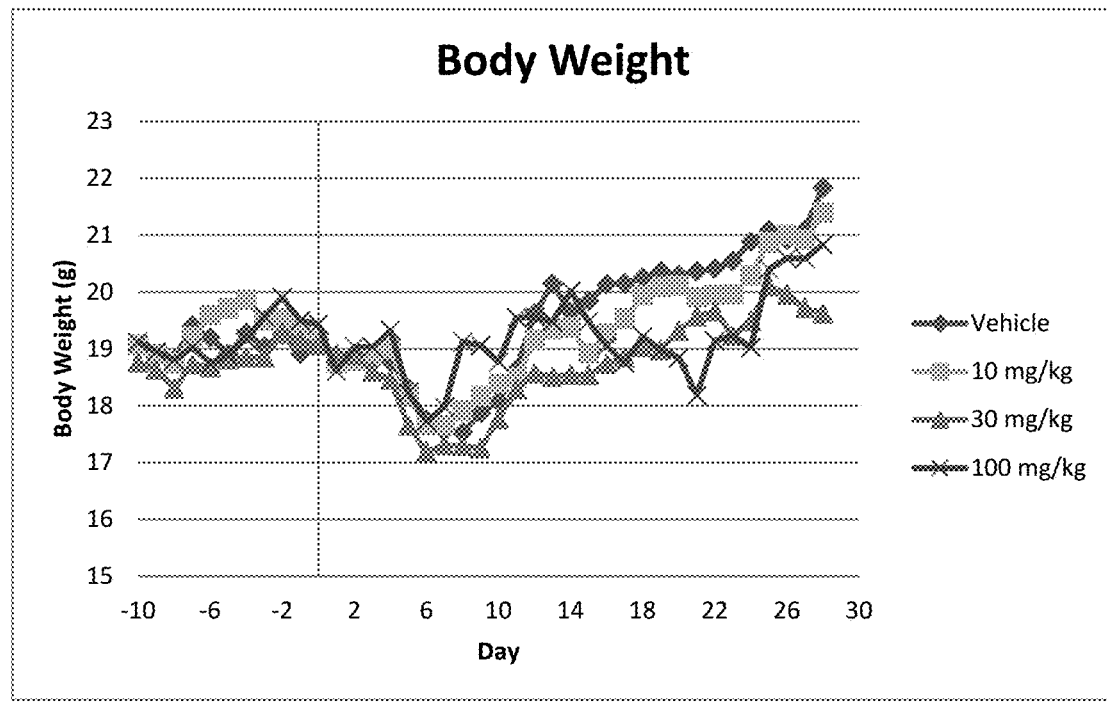
(b)
FIGS. 16a & b

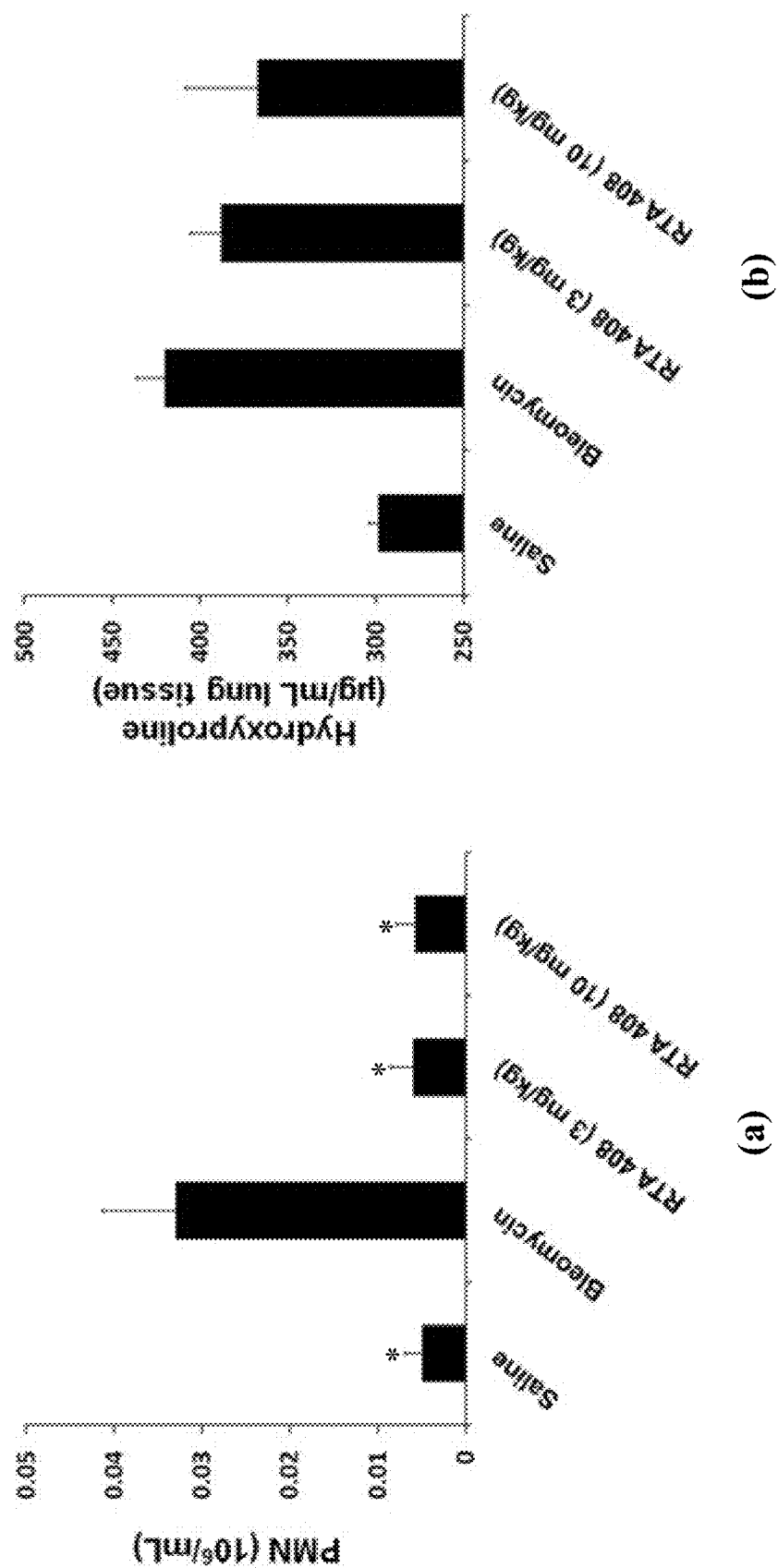
FIGS. 17a & b

FIGS. 19a – e

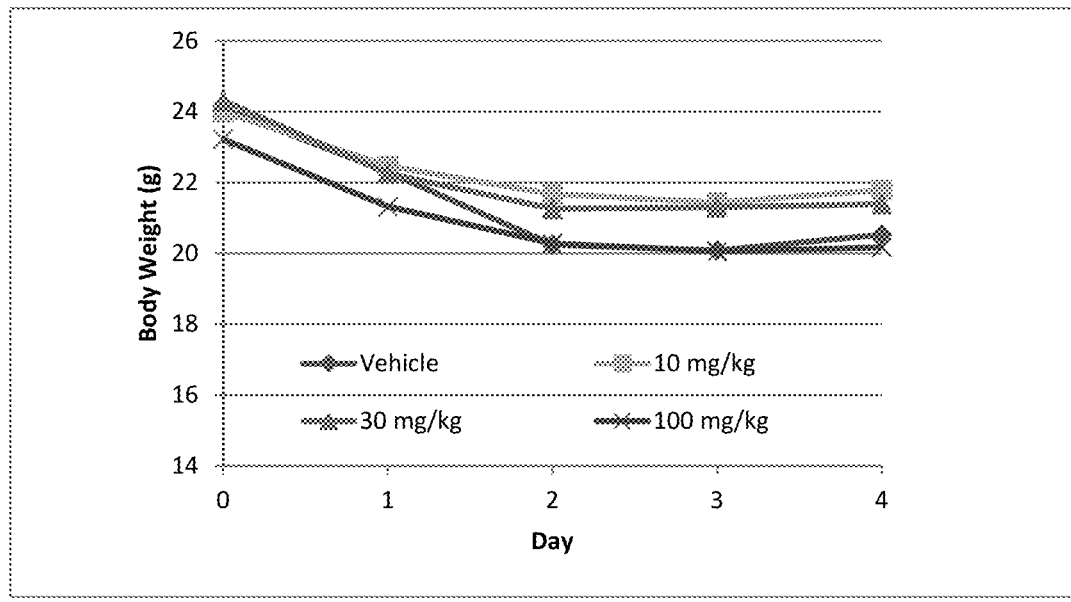
(a)
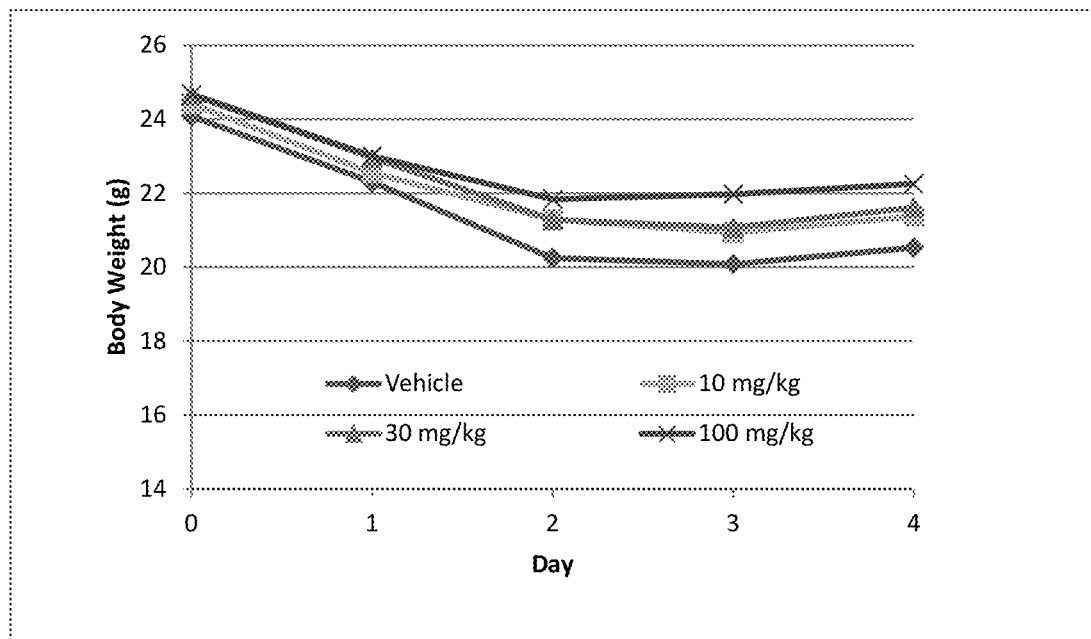
(b)
FIGS. 21a & b

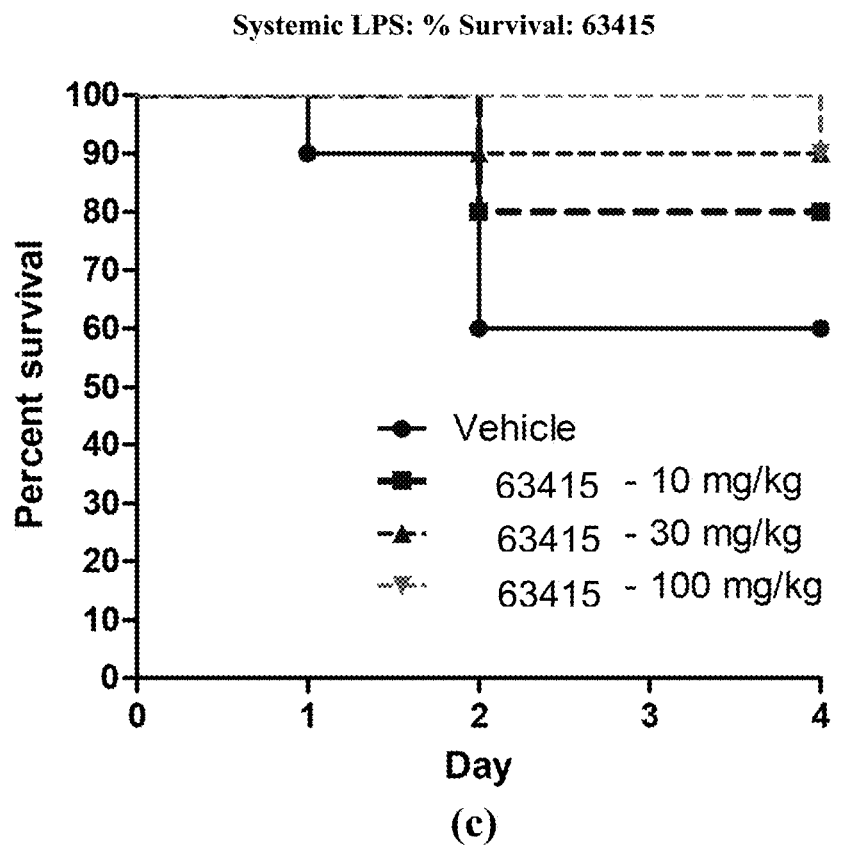
(c)
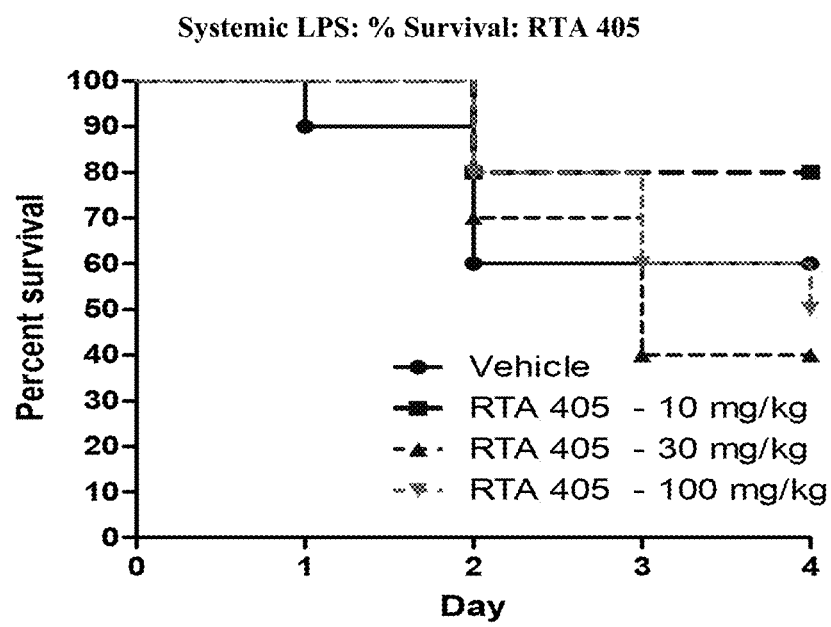
(d)
FIGS. 21c & d

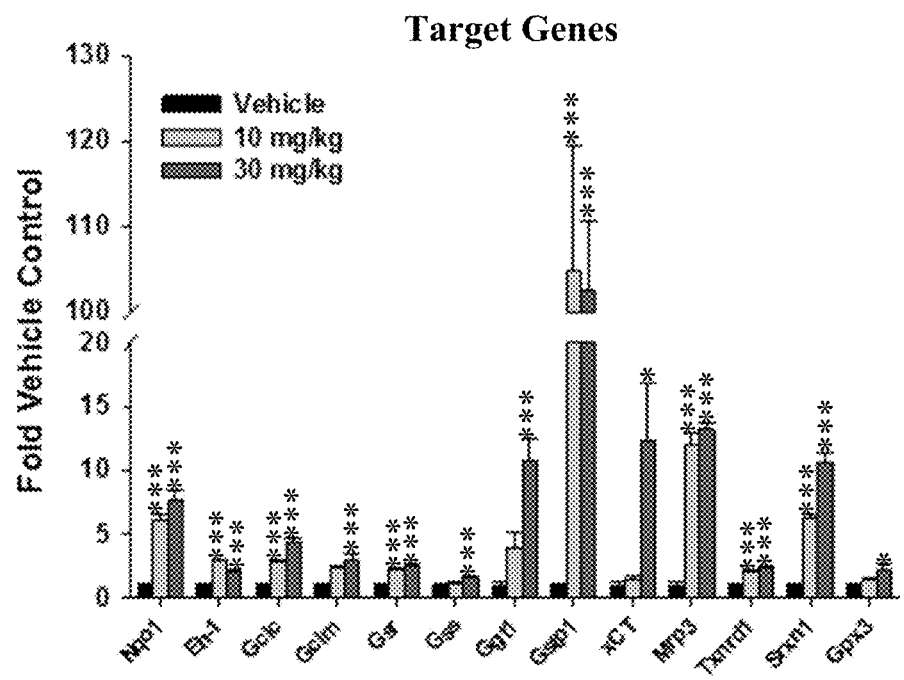
(a)
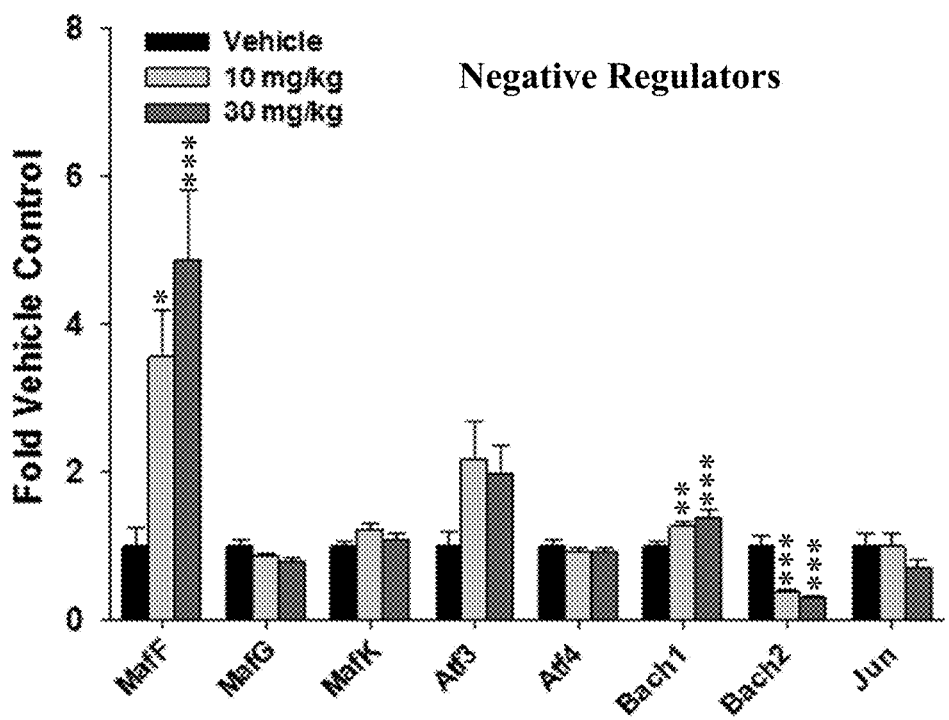
(b)
FIGS. 24a & b

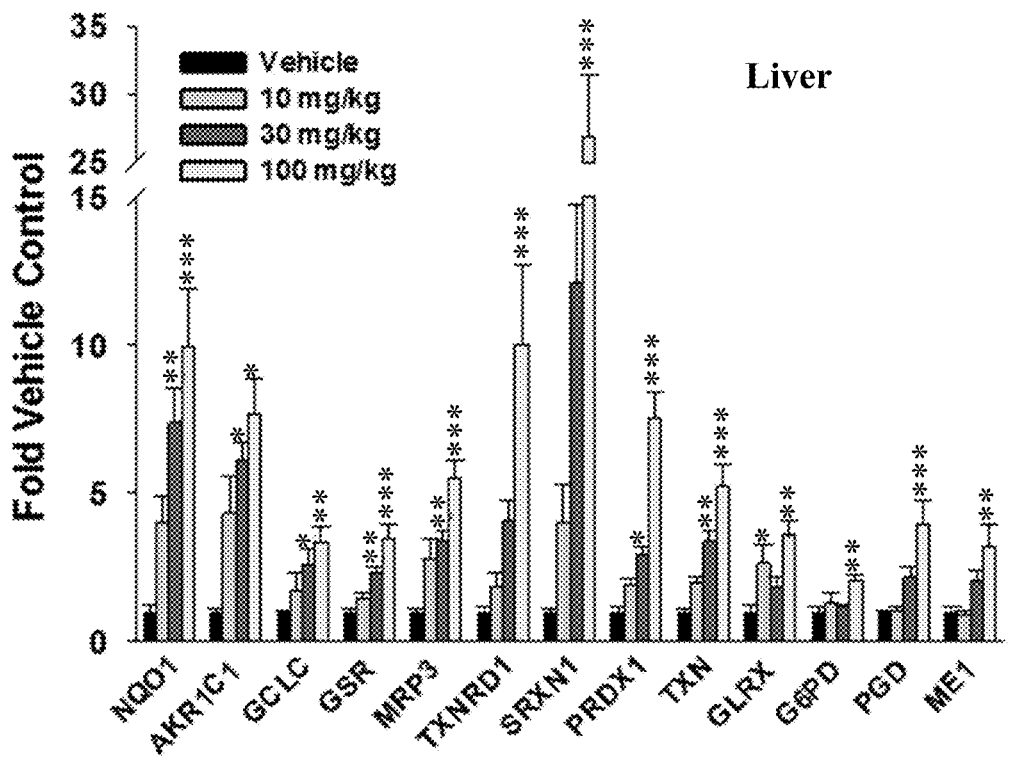
(a)
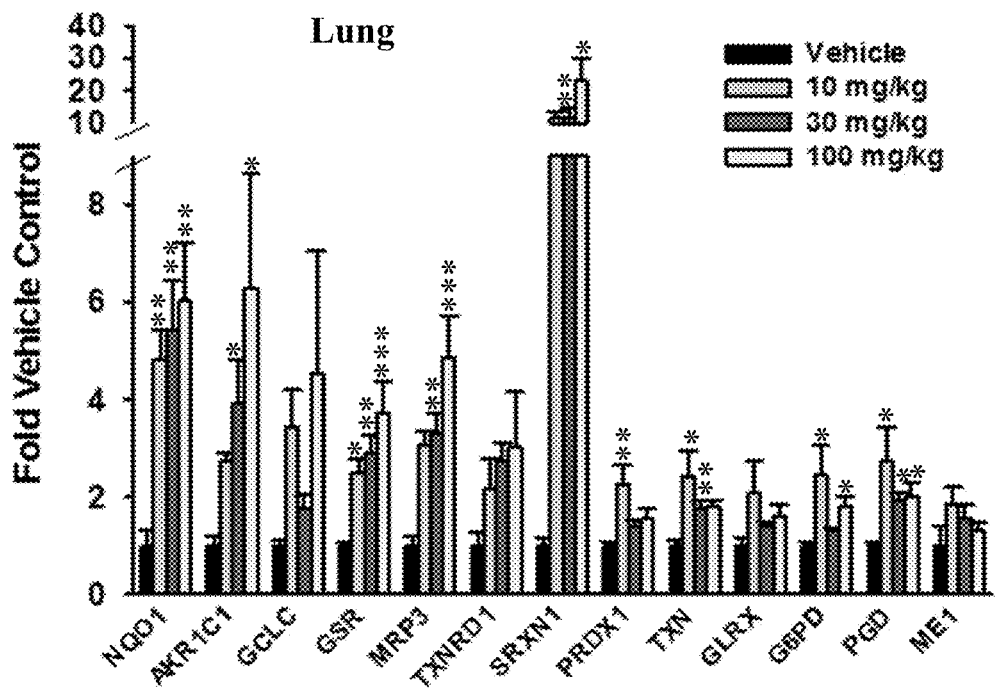
(b)
FIGS. 25a & b

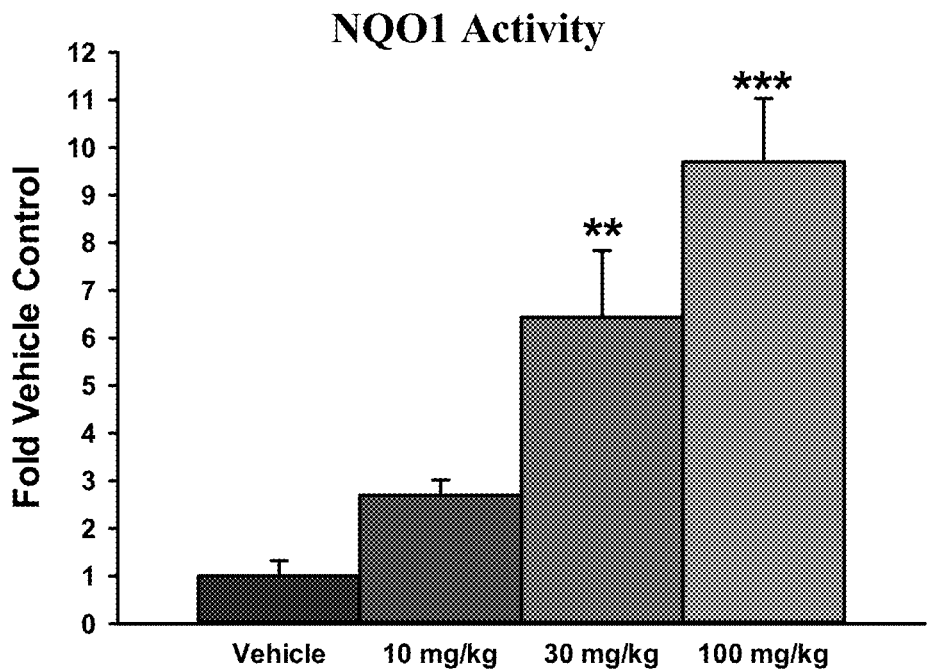
(a)
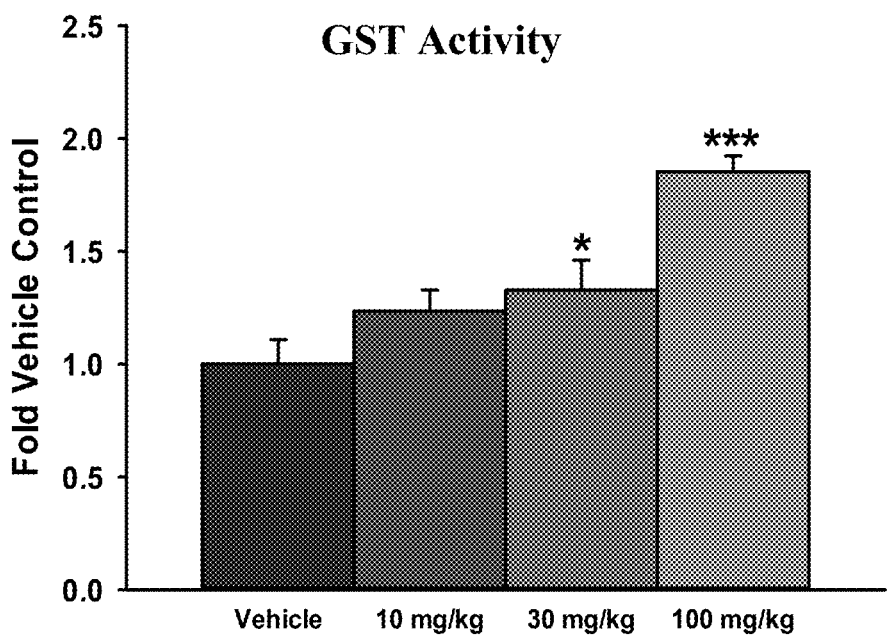
(b)
FIGS. 26a & b

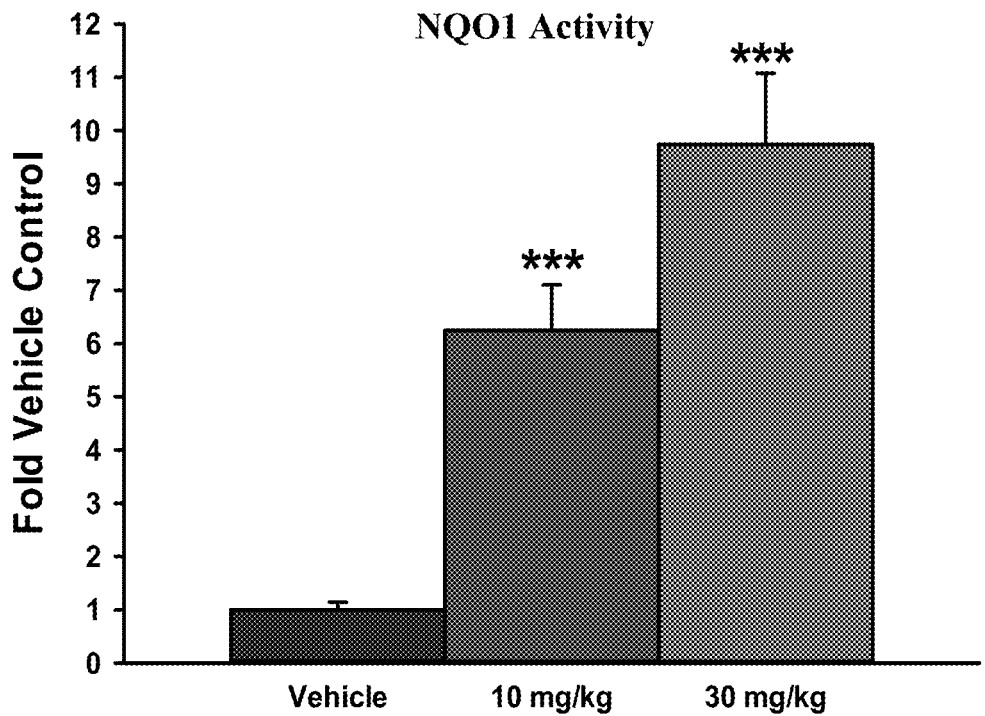
(a)
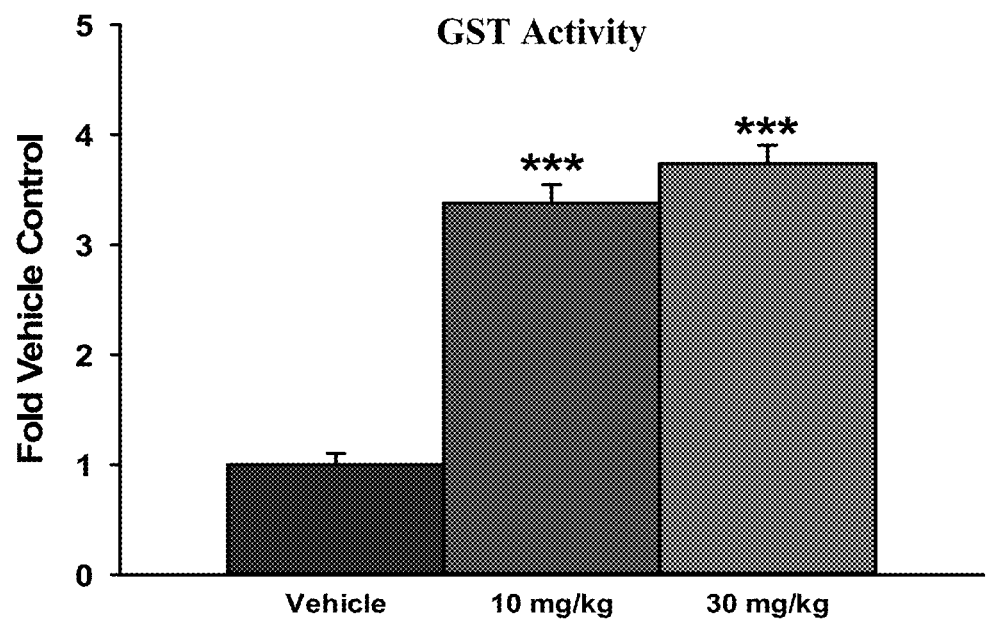
(b)
FIGS. 27a & b

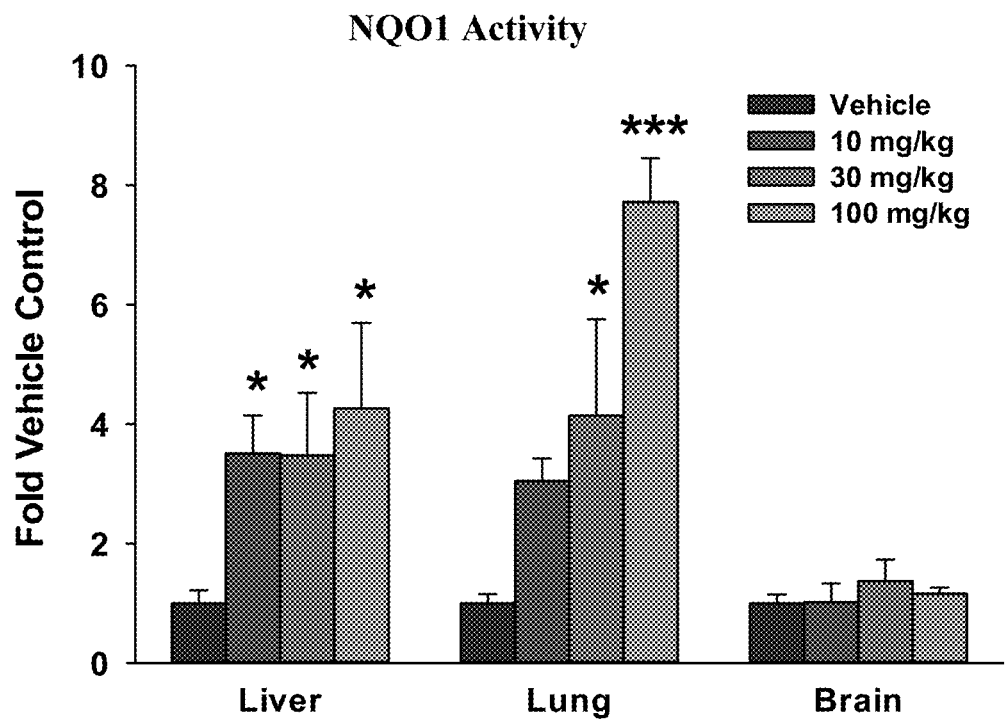
(a)
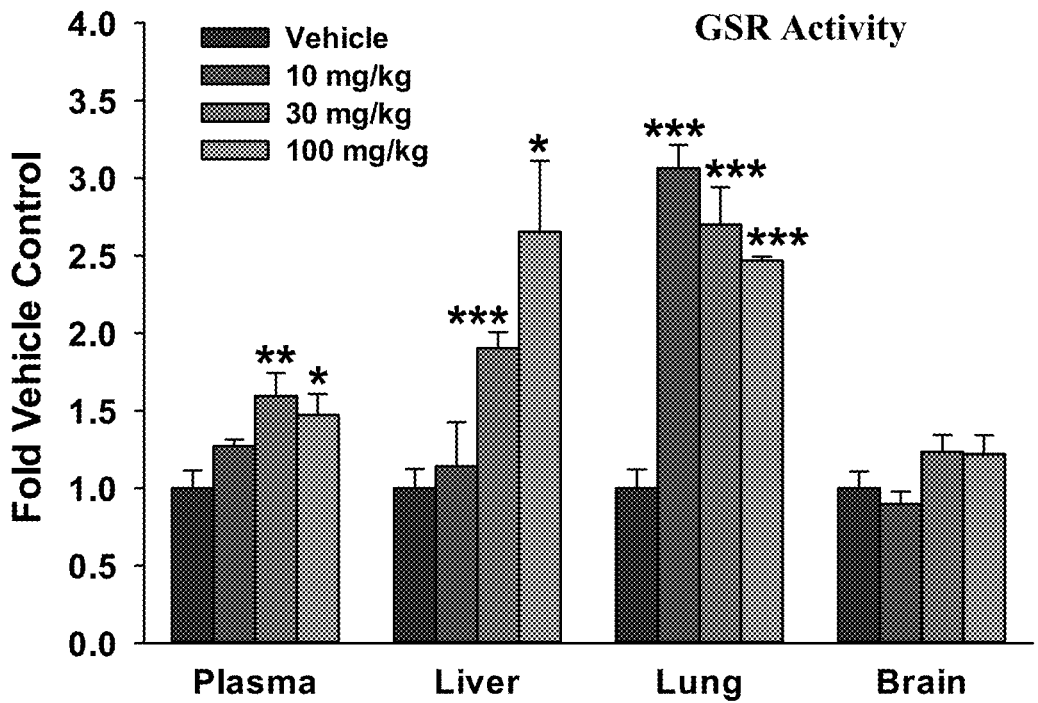
(b)
FIGS. 28a & b

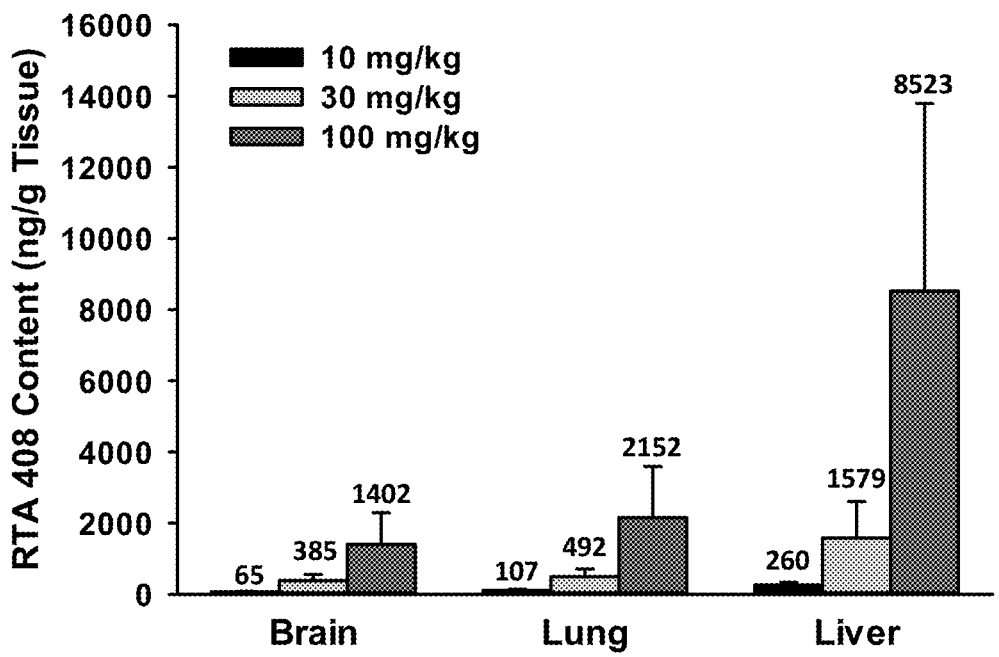
(a)
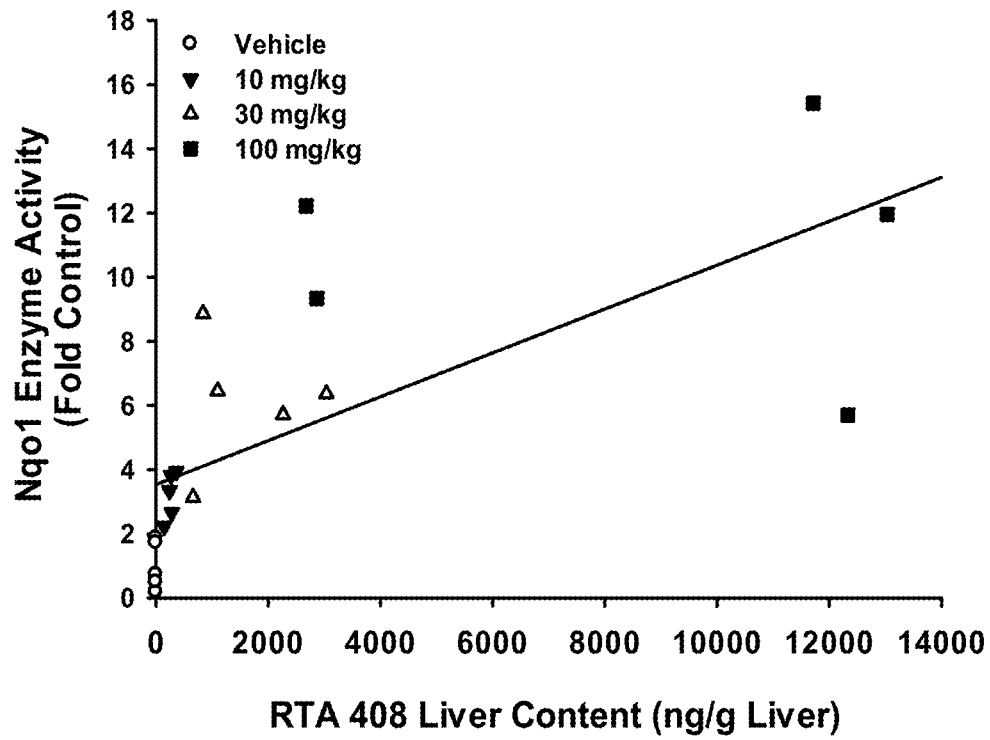
(b)
FIGS. 29a & b

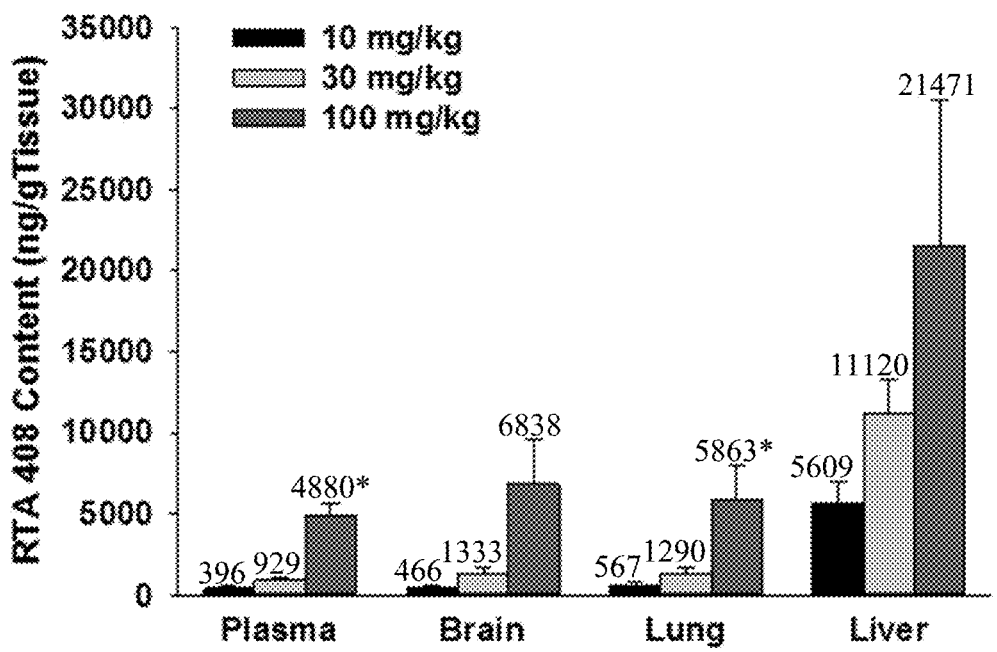
(a)
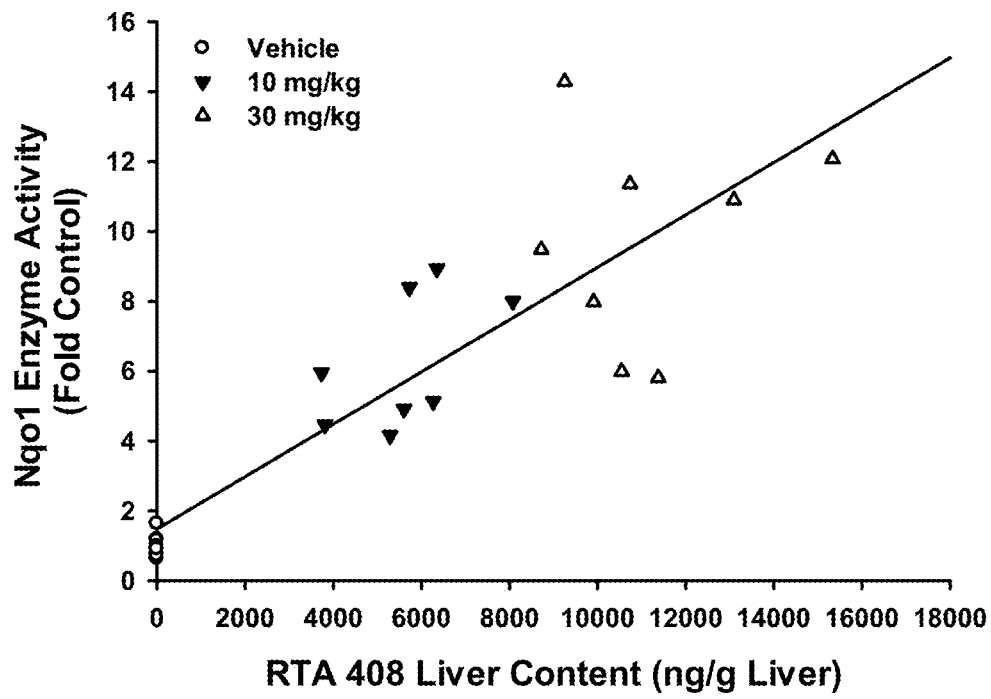
(b)
FIGS. 30a & b

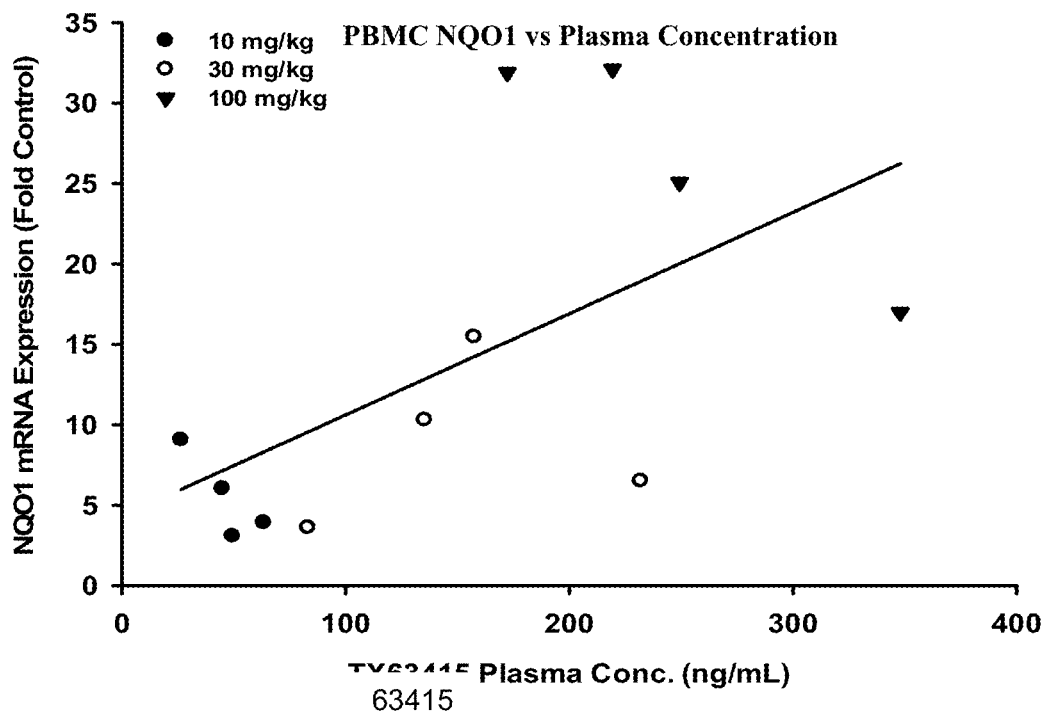
(a)
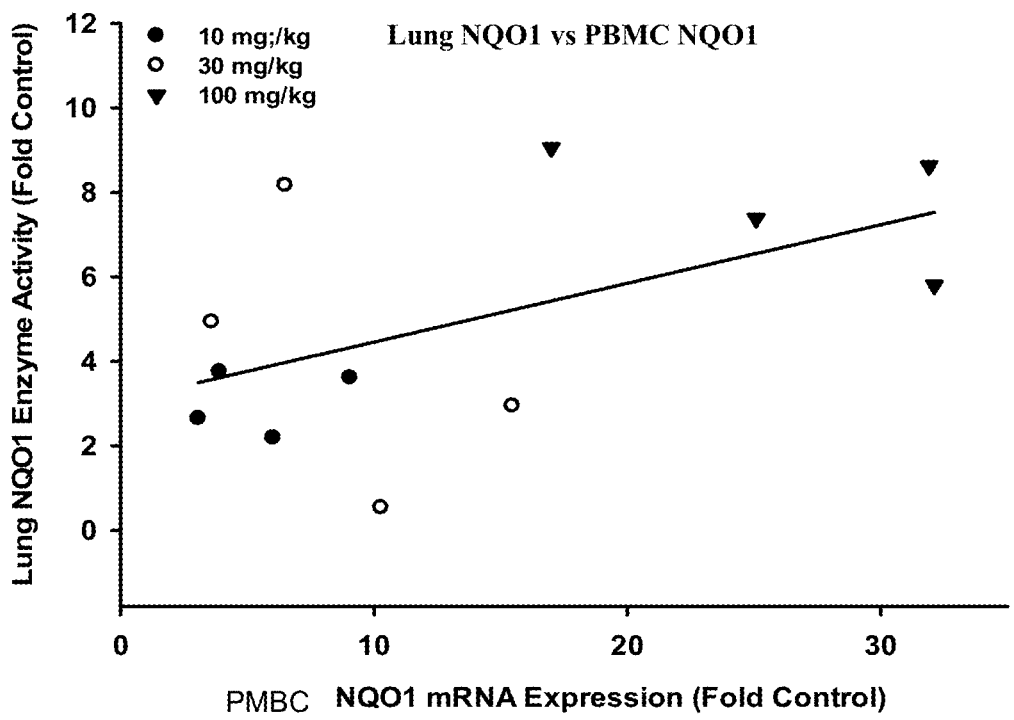
(b)
FIGS. 31a & b

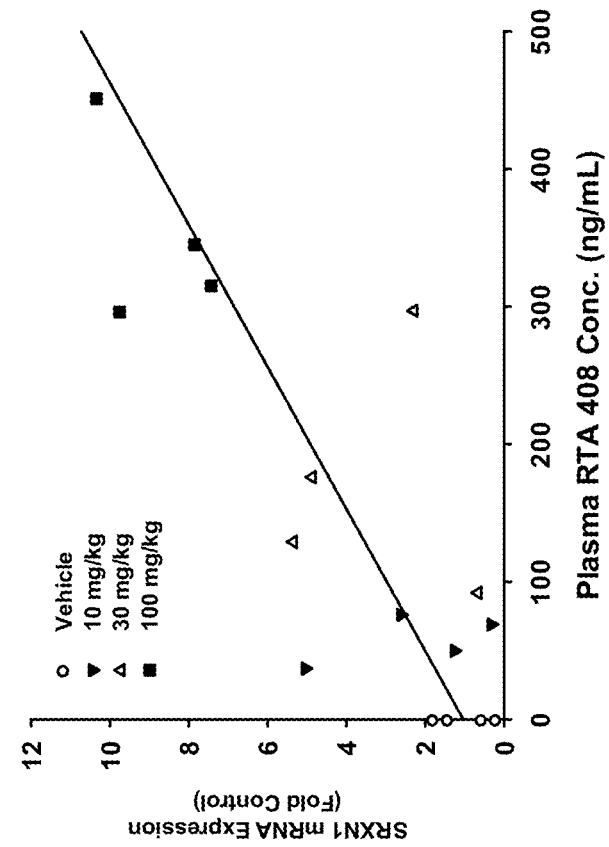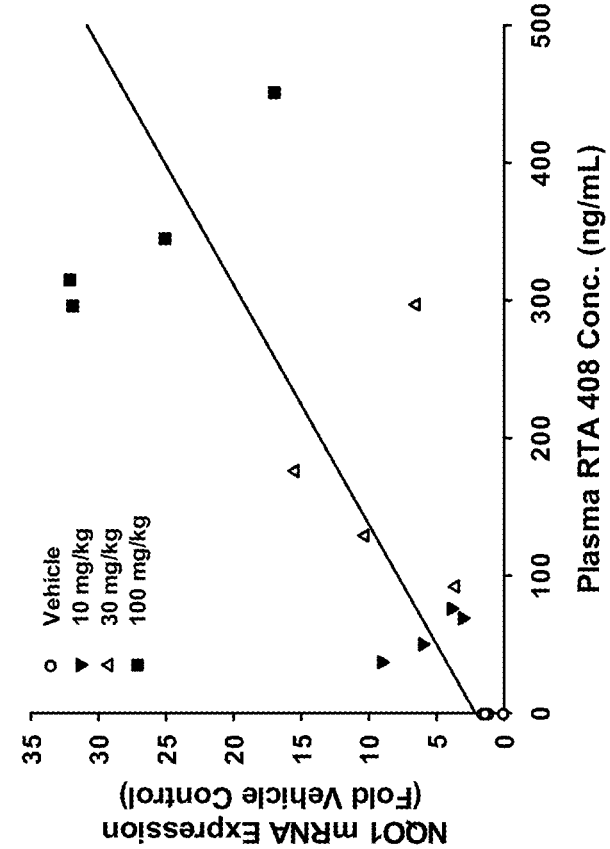
FIGS. 34a & b

DSC of RTA 408 Form A

TGA-MS of RTA 408 Form A

DSC of RTA 408 Form A

TGA-MS of RTA 408 Form B

2,2-DIFLUOROPROPIONAMIDE DERIVATIVES OF BARDOXOLONE METHYL, POLYMORPHIC FORMS AND METHODS OF USE THEREOF

This application is a continuation of U.S. patent application Ser. No. 15/821,508, filed Nov. 22, 2017, which is a continuation of U.S. patent application Ser. No. 14/260,532, filed Apr. 24, 2014, now U.S. Pat. No. 9,856,286, issued on Jan. 2, 2018, which claims priority to U.S. Provisional Application Ser. No. 61/815,502 filed Apr. 24, 2013, the entirety of each of which is incorporated herein by reference.

BACKGROUND OF THE INVENTION

I. Field of the Invention

The present invention relates generally to the compound: N-((4aS,6aR,6bS,8aR,12aS,14aR,14bS)-11-cyano-2,2,6a, 6b,9,9,12a-heptamethyl-10,14-dioxo-1,2,3,4,4a,5,6,6a, 6b,7,8,8a,9,10,12a,14,14a,14b-octadecahydropicen-4a-yl)-2,2-difluoropropanamide, also referred to herein as RTA 408, 63415, or PP415. The present invention also relates to polymorphic forms thereof, methods for preparation and use thereof, pharmaceutical compositions thereof, and kits and articles of manufacture thereof.

II. Description of Related Art

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed. See Honda et al., 1997; Honda et al., 1998; Honda et al., 1999; Honda et al., 2000a; Honda et al., 2000b; Honda et al., 2002; Suh et al., 1998; Suh et al., 1999; Place et al., 2003; Liby et al., 2005; and U.S. Pat. Nos. 8,129,429, 7,915,402, 8,124,799, and 7,943,778, all of which are incorporated herein by reference. The methyl ester, bardoxolone methyl (CDDO-Me), has been evaluated in phase II and III clinical trials for the treatment and prevention of diabetic nephropathy and chronic kidney disease. See Pergola et al., 2011, which is incorporated herein by reference.

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al, (2000a), Honda et al. (2000b), Honda et al. (2002), and U.S. Pat. Nos. 8,129,429, 7,915, 402, 8,124,799, and 7,943,778, which are all incorporated herein by reference. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007, and U.S. Pat. Nos. 8,129,429, 7,915,402, 8,124, 799, and 7,943,778).

Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with different biological activity profiles for the treatment or prevention of one or more indications.

SUMMARY OF THE INVENTION

In some aspects of the present invention, there is provided a compound of the formula (also referred to as RTA 408, 63415, or PP415):

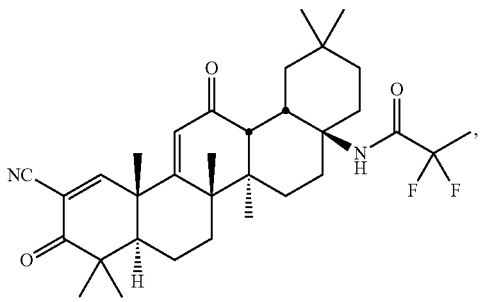

or a pharmaceutically acceptable salt thereof.

In some embodiments, the compound is in the form of a pharmaceutically acceptable salt. In some embodiments, the compound is not in the form of a salt.

In another aspect of the present invention, there are provided polymorphic forms of the above compound.

In some embodiments, the polymorphic form is crystalline, having an X-ray powder diffraction pattern (CuKα) comprising peaks at about 10.601, 11.638, 12.121, 13.021, 13,435, 15.418, 15.760, 17.830, 18.753, and 19.671 °2θ. In some embodiments, the X-ray powder diffraction pattern (CuKα) is substantially as shown in FIG. 53.

In some embodiments, the polymorphic form is crystalline, having an X-ray powder diffraction pattern (CuKα) comprising peaks at about 7.552, 10.339, 11.159, 12.107, 14.729, 15.329, 15.857, 16.824, 17.994, 18.344, 19.444, 19.764, 20.801, and 22.414 °2θ. In some embodiments, the X-ray diffraction pattern (CuKα) is substantially as shown in FIG. 56.

In another aspect of the present invention, there are provided pharmaceutical compositions comprising an active ingredient consisting of the above compound or polymorphic forms thereof (such as, e.g., any one of the polymorphic forms described herein above or below), and a pharmaceutically acceptable carrier. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularily, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral, intraarterial, intravenous, or topical administration. In some embodiments, the pharmaceutical composition is formulated for oral administration.

In some embodiments, the pharmaceutical composition is formulated as a hard or soft capsule, a tablet, a syrup, a suspension, a solid dispersion, a wafer, or an elixir. In some embodiments, the pharmaceutical composition according to the invention further comprises an agent that enhances solubility and dispersibility. In some embodiments, the compound or polymorphic form is suspended in sesame oil.

In other embodiments, the pharmaceutical composition is formulated for topical administration. In other embodiments, the pharmaceutical composition is formulated as a lotion, a cream, a gel, an oil, an ointment, a salve, or a suspension. In some embodiments, the pharmaceutical composition is formulated as a lotion, as a cream, or as a gel. In some embodiments, the amount of the active ingredient is from about 0.01% to about 5% by weight, about 0.01% to about 3% by weight, or 0.01%, 0.1%, 1%, or 3% by weight.

In another aspect of the present invention there are provided methods of treating or preventing a condition associated with inflammation or oxidative stress in a patient in need thereof, comprising administering to the patient a therapeutically effective amount of the pharmaceutical composition as described above or below. The invention likewise relates to the compound N-((4aS,6aR,6bS,8aR,12aS,14aR,14bS)-11-cyano-2,2,6a,6b,9,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide (or RTA 408, 63415, or PP415) or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described above), for use in treating or preventing a condition associated with inflammation or oxidative stress. The invention also relates to the use of the aforementioned compound, polymorphic form or pharmaceutical composition for the preparation of a medicament for the treatment or prevention of a condition associated with inflammation or oxidative stress. In some embodiments, the condition is associated with inflammation. In other embodiments, the condition is associated with oxidative stress. In some embodiments, the condition is a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease or diabetes.

The present invention furthermore relates to the compound N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide (or RTA 408) or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described above), for use in treating or preventing a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes. Accordingly, the invention relates to the use of the aforementioned compound, polymorphic form or pharmaceutical composition for the preparation of a medicament for the treatment or prevention of a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes. The invention also relates to a method of treating or preventing a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes in a patient in need thereof, the method comprising administering to the patient a therapeutically effective amount of the aforementioned compound, polymorphic form or pharmaceutical composition.

In some embodiments, the condition is a skin disease or disorder such as dermatitis, a thermal or chemical burn, a chronic wound, acne, alopecia, other disorders of the hair follicle, epidermolysis bullosa, sunburn, complications of sunburn, disorders of skin pigmentation, an aging-related skin condition; a post-surgical wound, a scar from a skin injury or burn, psoriasis, a dermatological manifestation of an autoimmune diseases or a graft-versus host disease, skin cancer; or a disorder involving hyperproliferation of skin cells. In some embodiments, the skin disease or disorder is dermatitis. In some embodiments, the dermatitis is allergic dermatitis, atopic dermatitis, dermatitis due to chemical exposure, or radiation-induced dermatitis. In other embodiments, the skin disease or disorder is a chronic wound. In some embodiments, the chronic wound is a diabetic ulcer, a pressure sore, or a venous ulcer. In other embodiments, the skin disease or disorder is alopecia. In some embodiments, the alopecia is selected from baldness or drug-induced alopecia. In other embodiments, the skin disease or disorder is a disorder of skin pigmentation. In some embodiments, the disorder of skin pigmentation is vitiligo. In other embodiments, the skin disease or disorder is a disorder involving hyperproliferation of skin cells. In some embodiments, the disorder involving hyperproliferation of skin cells is hyperkeratosis.

In other embodiments, the condition is an autoimmune disease, such as rheumatoid arthritis, lupus, Crohn's disease, or psoriasis. In other embodiments, the condition is liver disease, such as fatty liver disease or hepatitis.

In other embodiments, the condition is an eye disorder, such as uveitis, macular degeneration, glaucoma, diabetic macular edema, blepharitis, diabetic retinopathy, a disease or disorder of the corneal endothelium, post-surgical inflammation, dry eye, allergic conjunctivitis or a form of conjunctivitis. In some embodiments, the eye disorder is macular degeneration. In some embodiments, the macular degeneration is the dry form. In other embodiments, the macular degeneration is the wet form. In some embodiments, the disease or disorder of the corneal endothelium is Fuchs endothelial corneal dystrophy.

In other embodiments, the condition is a lung disease, such as pulmonary inflammation, pulmonary fibrosis, COPD, asthma, cystic fibrosis, or idiopathic pulmonary fibrosis. In some embodiments, the COPD is induced by cigarette smoke.

In other embodiments, the condition is sepsis. In other embodiments, the condition is mucositis resulting from radiation therapy or chemotherapy. In some embodiments, the mucositis presents orally. In other embodiments, the condition is associated with exposure to radiation. In some embodiments, the radiation exposure leads to dermatitis. In some embodiments, the radiation exposure is acute. In other embodiments, the radiation exposure is fractionated.

In other embodiments, the condition is cancer. In some non-limiting embodiments, the cancer is leukemia, lymphoma, multiple myeloma, or cancer of the breast, skin, lung, pancreas, liver, stomach, small intestine, large intestine or colon, gall bladder, esophagus, ovary, endometrium, cervix, oral or nasal mucosa, brain, prostate, bladder, urogenital tract, testicle, kidney, genitalia, thyroid, or muscle tissue. In some embodiments, the cancer is a carcinoma or sarcoma.

In some embodiments, the compound or composition of the invention is administered before or immediately after a subject is treated with radiation therapy, chemotherapy, or both. In some embodiments, the compound or composition of the invention is administered both before and after the subject is treated with radiation therapy, chemotherapy or both. In some embodiments, the effect of the composition of the invention is to reduce side effects of radiation therapy, chemotherapy, or combined radio- and chemo-therapy, including mucositis and dermatitis. In some embodiments, the effect of the composition of the invention is to enhance the efficacy of the radiation therapy, chemotherapy, or combined radio- and chemo-therapy. In some embodiments, the effect of the composition of the invention is to reduce the side effects of, and enhance the efficacy of, the radiation therapy, chemotherapy, or combined radio- and chemo-therapy.

Combination treatment therapy is also contemplated by the present disclosure. For example, regarding methods of treating cancer in a subject, comprising administering to the subject a pharmaceutically effective amount of a compound of the present disclosure, the method may further comprise a treatment selected from the group consisting of administering a pharmaceutically effective amount of a second drug, radiotherapy, gene therapy, and surgery. Such methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. The second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

Methods of treating or preventing a disease with an inflammatory component in a subject, comprising administering to the subject a pharmaceutically effective amount of a compound of the present disclosure are also contemplated. The disease may be, for example, lupus or rheumatoid arthritis. The disease may be an inflammatory bowel disease, such as Crohn's disease or ulcerative colitis. The disease with an inflammatory component may be a cardiovascular disease. The disease with an inflammatory component may be diabetes, such as type 1 or type 2 diabetes. RTA 408 may also be used to treat complications associated with diabetes. Such complications are well-known in the art and include, for example, obesity, hypertension, atherosclerosis, coronary heart disease, stroke, peripheral vascular disease, hypertension, nephropathy, neuropathy, myonecrosis, retinopathy and metabolic syndrome (syndrome X). The disease with an inflammatory component may be a skin disease, such as psoriasis, acne, or atopic dermatitis. Administration of a RTA 408 in treatment methods of such skin diseases may be, for example, topical or oral.

The disease with an inflammatory component may be metabolic syndrome (syndrome X). A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670, incorporated herein by reference. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Another general method of the present disclosure entails a method of treating or preventing a cardiovascular disease in a subject, comprising administering to the subject a pharmaceutically effective amount of a compound of the present disclosure. The cardiovascular disease may be, for example, atherosclerosis, cardiomyopathy, congenital heart disease, congestive heart failure, myocarditis, rheumatic heart disease, valve disease, coronary artery disease, endocarditis, or myocardial infarction. Combination therapy is also contemplated for such methods. For example, such methods may further comprise administering a pharmaceutically effective amount of a second drug. The second drug may be, for example, a cholesterol lowering drug, an anti-hyperlipidemic, a calcium channel blocker, an anti-hypertensive, or an HMG-CoA reductase inhibitor. Non-limiting examples of second drugs include amlodipine, aspirin, ezetimibe, felodipine, lacidipine, lercanidipine, nicardipine, nifedipine, nimodipine, nisoldipine or nitrendipine. Other non-limiting examples of second drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. The second drug may be, for example, a statin, such as atorvastatin, cerivastatin, fluvastatin, lovastatin, mevastatin, pitavastatin, pravastatin, rosuvastatin or simvastatin.

Methods of treating or preventing a neurodegenerative disease in a subject, comprising administering to the subject a pharmaceutically effective amount of a compound of the present disclosure are also contemplated. The neurodegenerative disease may, for example, be selected from the group consisting of Parkinson's disease, Alzheimer's disease, multiple sclerosis (MS), Huntington's disease and amyotrophic lateral sclerosis. In particular embodiments, the neurodegenerative disease is Alzheimer's disease. In particular embodiments, the neurodegenerative disease is MS, such as primary progressive, relapsing-remitting secondary progressive or progressive relapsing MS. The subject may be, for example, a primate. The subject may be a human.

In particular embodiments of methods of treating or preventing a neurodegenerative disease in a subject, comprising administering to the subject a pharmaceutically effective amount of a compound of the present disclosure, the treatment suppresses the demyelination of neurons in the subject's brain or spinal cord. In certain embodiments, the treatment suppresses inflammatory demyelination. In certain embodiments, the treatment suppresses the transection of neuron axons in the subject's brain or spinal cord. In certain embodiments, the treatment suppresses the transection of neurites in the subject's brain or spinal cord. In certain embodiments, the treatment suppresses neuronal apoptosis in the subject's brain or spinal cord. In certain embodiments, the treatment stimulates the remyelination of neuron axons in the subject's brain or spinal cord. In certain embodiments, the treatment restores lost function after an MS attack. In certain embodiments, the treatment prevents a new MS attack. In certain embodiments, the treatment prevents a disability resulting from an MS attack.

One general aspect of the present disclosure contemplates a method of treating or preventing a disorder characterized by overexpression of iNOS genes in a subject, comprising administering to the subject a pharmaceutically effective amount of a compound of the present disclosure.

Another general aspect of the present disclosure contemplates a method of inhibiting IFN-γ-induced nitric oxide production in cells of a subject, comprising administering to said subject a pharmaceutically effective amount of a compound of the present disclosure.

Yet another general method of the present disclosure contemplates a method of treating or preventing a disorder characterized by overexpression of COX-2 genes in a subject, comprising administering to the subject a pharmaceutically effective amount of compound of the present disclosure.

Methods of treating renal/kidney disease (RKD) in a subject, comprising administering to the subject a pharmaceutically effective amount of a compound of the present disclosure are also contemplated. See U.S. patent application Ser. No. 12/352,473, which is incorporated by reference herein in its entirety. The RKD may result from, for example, a toxic insult. The toxic insult may result from, for example, an imaging agent or a drug. The drug may be a chemotherapeutic, for example. The RKD may result from ischemia/reperfusion injury, in certain embodiments. In certain embodiments, the RKD results from diabetes or hypertension. The RKD may result from an autoimmune disease. The RKD may be further defined as chronic RKD, or acute RKD.

In certain methods of treating renal/kidney disease (RKD) in a subject, comprising administering to the subject a pharmaceutically effective amount of a compound of the present disclosure, the subject has undergone or is undergoing dialysis. In certain embodiments, the subject has undergone or is a candidate to undergo kidney transplant. The subject may be a primate. The primate may be a human. The subject in this or any other method may be, for example, a cow, horse, dog, cat, pig, mouse, rat or guinea pig.

Also contemplated by the present disclosure is a method for improving glomerular filtration rate or creatinine clearance in a subject, comprising administering to the subject a pharmaceutically effective amount of a compound of the present disclosure.

In some embodiments, the pharmaceutical composition is administered in a single dose per day. In other embodiments, the pharmaceutical composition is administered in more than one dose per day. In some embodiments, the pharmaceutical composition is administered in a pharmaceutically effective amount.

In some embodiments, the active ingredient is administered in a dose from about 1 mg/kg to about 2000 mg/kg. In other embodiments, the dose is from about 3 mg/kg to about 100 mg/kg. In other embodiments, the dose is about 3, 10, 30, or 100 mg/kg.

In other embodiments, the pharmaceutical composition is administered topically. In some embodiments, the topical administration is administered to the skin. In other embodiments, the topical administration is administered to the eye.

In other embodiments, the pharmaceutical composition is administered orally. In other embodiments, the pharmaceutical composition is administered intraocularly.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIGS. 2a & b—Effect of RTA 408 on antioxidant response element activation: (a) NQO1-ARE luciferase activity; (b) GSTA2-ARE luciferase activity.

FIGS. 3a-d—Effect of RTA 408 on Nrf2 target gene expression in HFL1 lung fibroblasts: (a) NQO1; (b) HMOX1; (c) GCLM; (d) TXNRD1.

FIGS. 4a-d—Effect of RTA 408 on Nrf2 target gene expression in BEAS-2B bronchial epithelial cells: (a) NQO1; (b) HMOX1; (c) GCLM; (d) TXNRD1.

FIGS. 5a & b—Effect of RTA 408 on Nrf2 target protein levels: (a) SH-SY5Y cells; (b) BV2 cells.

FIGS. 9a-d—Effect of RTA 408 on expression of genes involved in NADPH synthesis: (a) H6PD; (b) PGD; (c) TKT; (d) ME1.

FIGS. 12a-d—Effect of RTA 408 on transaminase gene expression: (a) ALT1 (GPT1); (b) ALT2 (GPT2); (c) AST1 (GOT1); (d) AST1 (GOT2). Asterisks indicate a statistically-significant difference from the control group (*P<0.05; **P<0.01).

FIGS. 15a & b—Effect of RTA 408 on LPS-induced pulmonary inflammation in mice: (a) inflammatory cytokines; (b) Nrf2 targets. Methods: RTA 408 administered to female BALB/c mice (n=10) QD×6 at Time 0, 24, 48, 72, 96, and 120 hours followed by LPS at 121 hours with animals sacrificed at 141 hours. Pro-inflammatory cytokine protein expression assayed in BALF; Nrf2 biomarkers assayed in lung. Asterisks indicate a statistically significant difference from the saline control group (*P<0.05; P<0.01; *P<0.001).

FIGS. 16a & b—RTA 408 reduces BALF infiltrates in bleomycin-induced pulmonary inflammation: (a) BAL fluid cell count; (b) body weight. RTA 408 was administered QD×39 on Days −10 to 28 in C57BL/6 mice. Bleomycin was given on Day 0. Daily weights were measured. BAL fluid cell counts were obtained at sacrifice. A notable reduction in inflammatory infiltrate was observed. No significant improvement in chronic inflammation score, interstitial fibrosis, or number of fibrotic foci was observed.

FIGS. 17a & b—Effect of RTA 408 on bleomycin-induced pulmonary fibrosis in rats: (a) PMN; (b) Hydroxyproline. Asterisks indicate a statistically significant difference from the bleomycin control group (*P<0.05).

FIGS. 21a-d—show body weight as a function of time of 63415-treated BALB/c mice that serves as a model of sepsis. LPS was administered to all animals on Day 0. (a) Body Weight: 63415, (b) Body Weight: RTA 405, (c) Systemic LPS: % Survival: 63415, (d) Systemic LPS: % Survival: RTA 405. Both RTA 408 and 63415 was administered QD×5 on Days −2 to 2. 63415 improved survival.

FIGS. 24a & b—Induction of Nrf2 target genes in the rat liver by RTA 408 (63415): (a) Target genes; (b) Negative regulators. mRNA of Nrf2 target genes was assessed in livers of rats treated PO QDx14.

FIGS. 25a & b—RTA 408 (63415) induces Nrf2 target genes in monkey tissues: (a) Liver; (b) Lung. mRNAs of Nrf2 target genes were assessed in monkeys treated PO QDx14 using Panomics QUANTIGENE® 2.0 Plex technology.

FIGS. 26a & b—RTA 408 (63415) induces Nrf2 target enzyme activity in the mouse liver: (a) NQO1 activity; (b) GST activity. Nrf2 target enzyme activity was assessed in livers of mice treated PO QD×14. NQO1 and GST enzyme activities were induced in a dose dependent manner.

FIGS. 27a & b—Induction of target enzyme activity in the rat liver by RTA 408 (63415): (a) NQO1; (b) GST. Nrf2 target enzyme activity was assessed in livers of rats treated PO QD×14. NQO1 and GST enzyme activities were induced dose-dependently.

FIGS. 28a & b—RTA 408 (63415) induces Nrf2 target enzyme activity in various tissues of cynomolgus monkeys: (a) NQO1 activity; (b) GSR activity.

FIGS. 29a & b—RTA 408 concentration in mouse liver, lung, and brain, and NQO1 activity in mouse liver after 14 days of daily oral administration. (a) Tissue distribution of RTA 408 in mice after 14 days of daily oral administration. Data represent mean±SD RTA 408 concentrations in tissue collected 4 hours after the final dose of the study. Numbers above the error bars are representative of the mean. (b) Correlation of mouse liver RTA 408 content with NQO1 enzyme activity. Individual mouse liver RTA 408 liver content was plotted against individual enzyme activity from this report.

FIGS. 30a & b—RTA 408 concentration in rat plasma, liver, lung, and brain, and NQO1 activity in rat liver after 14 days of daily oral administration. (a) Tissue distribution of RTA 408 in rats after 14 days of daily oral administration. Data represent mean±SD RTA 408 concentrations in tissue collected 4 hours after the final dose of the study. Numbers above the error bars are representative of the mean. *Two values were excluded from the mean calculation due to being outliers, defined as values causing the set of data to fail the Shapiro-Wilk normality test. (b) Correlation of rat liver RTA 408 content with NQO1 enzyme activity. Individual rat liver RTA 408 liver content was plotted against individual enzyme activity from this report. The tissues from the 100 mg/kg RTA 408 dose group were collected on Day 6, and the observed toxicities in this group precluded liver NQO1 enzyme activity evaluations.

FIGS. 31a & b—RTA 408 (63415) treatment of monkeys activated Nrf2 in PBMC cells: (a) PBMC NQO1 vs. Plasma Concentration; (b) Lung NQO1 vs. PBMC NQO1.

FIGS. 34a & b—Correlation of exposure to RTA 408 in monkey plasma with NQO1 and SRXN1 mRNA expression in PBMCs: (a) NQO1; (b) SRXN1.

DESCRIPTION OF ILLUSTRATIVE EMBODIMENTS

Figure 1:
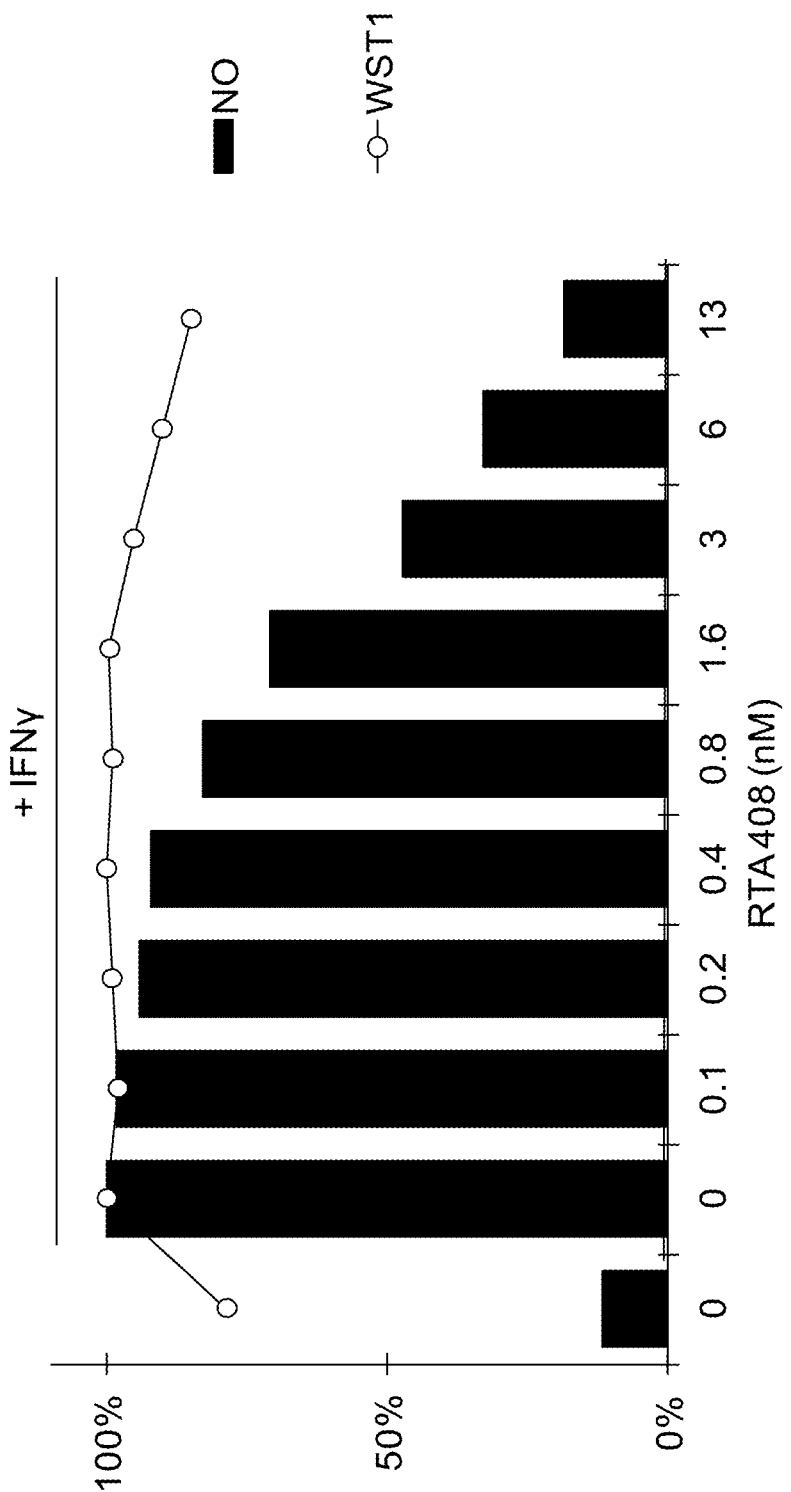
FIG. 1—Effect of RTA 408 on IFNγ-induced nitric oxide production and cell viability in RAW264.7 cells.

The present invention provides in one aspect the compound:
N-((4aS,6aR,6bS,8aR,12aS,14aR,14bS)-11-cyano-2,2,6a,
 6b,9,9,12a-heptamethyl-10,14-dioxo-1,2,3,4,4a,5,6,6a,
 6b,7,8,8a,9,10,12a,14,14a,14b-octadecahydropicen-4a-
 yl)-2,2-difluoropropanamide,
which is also referred to herein as RTA 408. In other non-limiting aspects, the present invention also provides polymorphic forms thereof, including solvates thereof. In other non-limiting aspects, the invention also provides pharmaceutically acceptable salts thereof. In other non-limiting aspects, there are also provided methods for preparation, pharmaceutical compositions, and kits and articles of manufacture of these compounds and polymorphic forms thereof.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "cyano" means —CN; "isocyanate" means —N=C=O; "azido" means —N$_3$; in a monovalent context "phosphate" means —OP(OXOH)$_2$ or a deprotonated form thereof; in a divalent context "phosphate" means —OP(OXOH)O— or a deprotonated form thereof; "thio" means =S; and "sulfonyl" means —S(O)$_2$—. Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. When used in the context of X-ray powder diffraction, the term "about" is used to indicate a value of ±0.2 °2θ from the reported value, preferably a value of ±0.1 °2θ from the reported value. When used in the context of differential scanning calorimetry or glass transition temperatures, the term "about" is used to indicate a value of ±10° C. relative to the maximum of the peak, preferably a value of ±2° C. relative to the maximum of the peak. When used in another context, the term "about" is used to indicate a value of ±10% of the reported value, preferably a value of ±5% of the reported value. It is to be understood that, whenever the term "about" is used, a specific reference to the exact numerical value indicated is also included.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a non-human mammal. In certain embodiments, the patient or subject is a primate. In certain embodiments, the patient or subject is a human. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

In the context of this disclosure, the formulas:

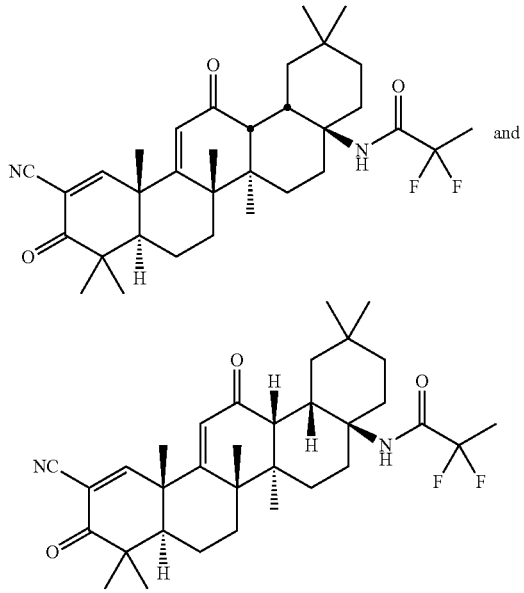

represent the same structures. When a dot is drawn on a carbon, the dot indicates that the hydrogen atom attached to that carbon is coming out of the plane of the page.

The above definitions supersede any conflicting definition in any of the references that are incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. RTA 408 and Synthetic Methods

RTA 408 can be prepared according to the methods described in the section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

RTA 408 may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

RTA 408 may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. RTA 408 may occur as racemates and racemic mixtures, single enantiomers, diastereomeric mixtures and individual diastereomers. In some embodiments, a single diastereomer is obtained. The chiral centers of RTA 408 according to the present invention can have the S or the R configuration.

In addition, atoms making up RTA 408 of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of RTA 408 may be replaced by a sulfur or selenium atom(s).

RTA 408 and polymorphic form thereof may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

III. Polymorphic Forms of RTA 408

Figure 58:
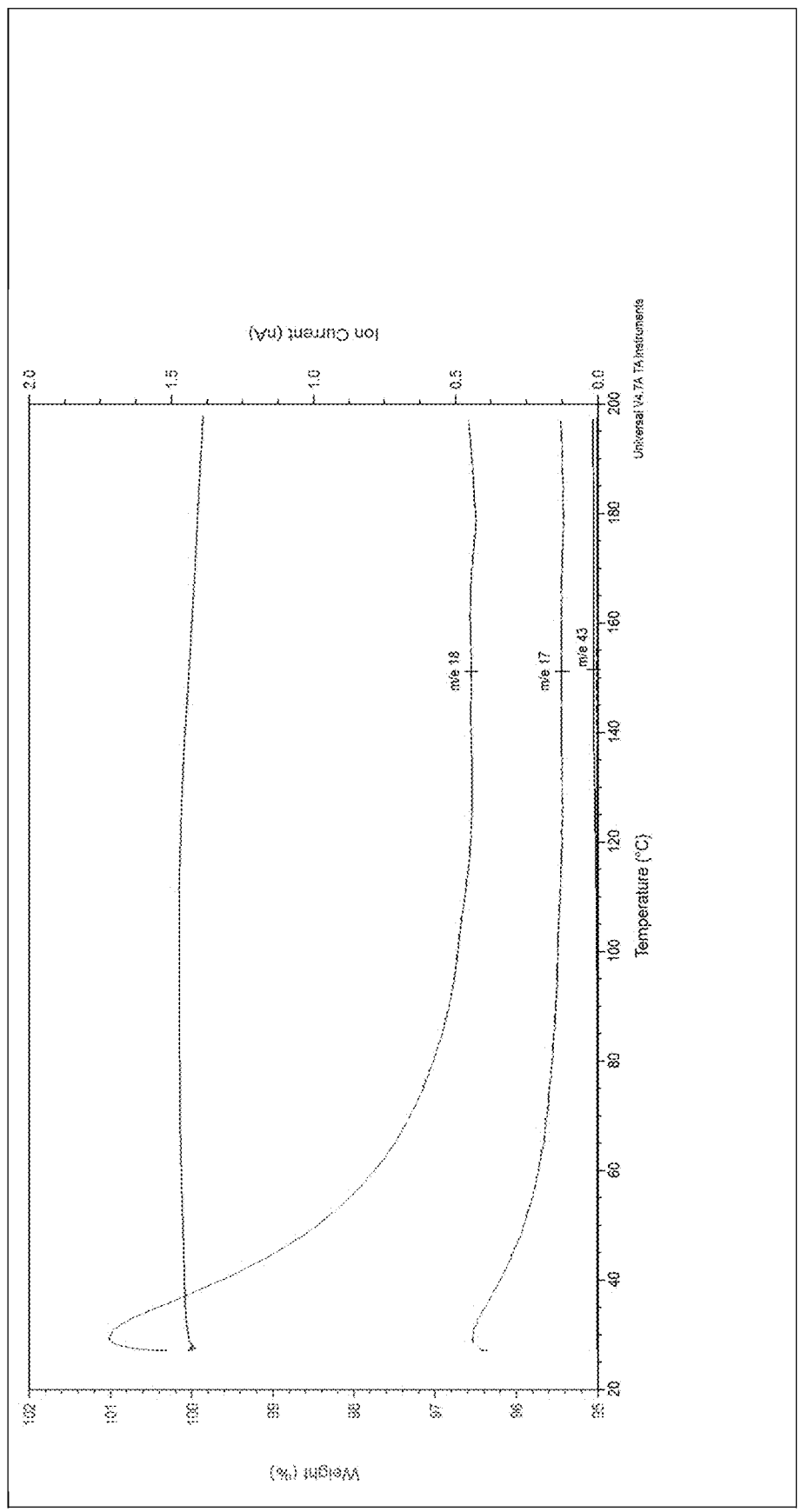
FIG. 58—TGA-MS thermogram (25-200° C.) of RTA 408 Form B.

In some embodiments, the present invention provides different solid forms of RTA 408, including solvates thereof. A polymorphism study was performed, and RTA 408 was found in two, essentially solvent-free, crystalline forms (Form A and Form B). For a description of the classes, see Table 1 below. Crystalline Form A is metastable and has a melting point at 181.98° C. and ΔH fusion=42.01 J/g. This form may have utility for obtaining amorphous forms of RTA 408 or in extrusion formulations. Crystalline Form A may be slightly hygroscopic (mass loss of ~0.5 wt. % in TGA-MS, FIG. 55). Crystalline Form B has greater thermodynamic stability than Form A as indicated by a higher melting point (250.10° C.) and greater enthalpy of fusion (ΔH fusion=47.85 J/g). Greater chemical and physical stability is expected for Form B compared to Form A both at ambient and elevated temperatures. A minimal amount of surface water may exist on Form B as indicated by TGA-MS (FIG. 58).

The new forms were characterized by PXRD (Table 8 and Table 9).

TABLE 1

| Summary of Solid Forms | | |
|---|---|---|
| Form | Melting Point | Enthalpy of Fusion |
| A | 181.98° C. | 42.01 J/g |
| B | 250.10° C. | 47.85 J/g |

IV. Diseases Associated With Inflammation And/Or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines, such as TNF-α and IL-1, and production of reactive oxygen or nitrogen species, such as hydrogen peroxide, superoxide, and peroxynitrite. In later stages of inflammation, tissue remodeling, angiogenesis, and scar formation (fibrosis) may occur as part of the wound healing process. Under normal circumstances, the inflammatory response is regulated, temporary, and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented herein, RTA 408 can be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species, such as superoxide, hydrogen peroxide, nitric oxide, and peroxynitrite, is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins, such as inducible nitric oxide synthase (iNOS). Chronic organ failure, such as renal failure, heart failure, liver failure, and chronic obstructive pulmonary disease, is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases, including degenerative diseases of the central nervous system and the retina.

Many other disorders involve oxidative stress and inflammation in affected tissues, including inflammatory bowel disease; inflammatory skin diseases; mucositis and dermatitis related to radiation therapy and chemotherapy; eye diseases, such as uveitis, glaucoma, macular degeneration, and various forms of retinopathy; transplant failure and rejection; ischemia-reperfusion injury; chronic pain; degenerative conditions of the bones and joints, including osteoarthritis and osteoporosis; asthma and cystic fibrosis; seizure disorders; and neuropsychiatric conditions, including schizophrenia, depression, bipolar disorder, post-traumatic stress disorder, attention deficit disorders, autism-spectrum disorders, and eating disorders, such as anorexia nervosa. Dysregulation of inflammatory signaling pathways is believed to be a major factor in the pathology of muscle wasting diseases, including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines, such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a), Honda et al. (2000b), and Honda et al. (2002), which are all incorporated herein by reference.

In one aspect, RTA 408 disclosed herein is in part characterized by its ability to inhibit the production of nitric oxide in macrophage-derived RAW 264.7 cells induced by exposure to γ-interferon. RTA 408 is further characterized by the ability to induce the expression of antioxidant proteins, such as NQO1, and reduce the expression of pro-inflammatory proteins, such as COX-2 and inducible nitric oxide synthase (iNOS). These properties are relevant to the treatment of a wide array of diseases and disorders involving oxidative stress and dysregulation of inflammatory processes, including cancer, complications from localized or total-body exposure to ionizing radiation, mucositis and dermatitis resulting from radiation therapy or chemotherapy, autoimmune diseases, cardiovascular diseases, including atherosclerosis, ischemia-reperfusion injury, acute and chronic organ failure, including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases, including osteoarthritis and osteoporosis, inflammatory bowel diseases, dermatitis and other skin diseases, sepsis, burns, seizure disorders, and neuropsychiatric disorders.

In another aspect, RTA 408 may be used for treating a subject having a condition such as eye diseases. For example, uveitis, macular degeneration (both the dry form and wet form), glaucoma, diabetic macular edema, blepharitis, diabetic retinopathy, diseases and disorders of the corneal endothelium such as Fuchs endothelial corneal dystrophy, post-surgical inflammation, dry eye, allergic conjunctivitis and other forms of conjunctivitis are non-limiting examples of eye diseases that could be treated with RTA 408.

In another aspect, RTA 408 may be used for treating a subject having a condition such as skin diseases or disorders. For example, dermatitis, including allergic dermatitis, atopic dermatitis, dermatitis due to chemical exposure, and radiation-induced dermatitis; thermal or chemical burns; chronic wounds including diabetic ulcers, pressure sores, and venous ulcers; acne; alopecia including baldness and drug-induced alopecia; other disorders of the hair follicle; epidermolysis bullosa; sunburn and its complications; disorders of skin pigmentation including vitiligo; aging-related skin conditions; post-surgical wound healing; prevention or reduction of scarring from skin injury, surgery, or burns; psoriasis; dermatological manifestations of autoimmune diseases or graft-versus host disease; prevention or treatment of skin cancer; disorders involving hyperproliferation of skin cells such as hyperkeratosis is a non-limiting example of skin diseases that could be treated with RTA 408.

Without being bound by theory, the activation of the antioxidant/anti-inflammatory Keap1/Nrf2/ARE pathway is believed to be implicated in both the anti-inflammatory and anti-carcinogenic properties of the compound disclosed herein.

In another aspect, RTA 408 may be used for treating a subject having a condition caused by elevated levels of oxidative stress in one or more tissues. Oxidative stress results from abnormally high or prolonged levels of reactive oxygen species, such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells, such as macrophages and neutrophils, by acute exposure to an external agent, such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states, such as hyperglycemia or hypoglycemia.

In animal models of many such conditions, stimulating expression of inducible heme oxygenase (HO-1), a target gene of the Nrf2 pathway, has been shown to have a significant therapeutic effect including in models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, RTA 408 may be used in preventing or treating tissue damage or organ failure, acute and chronic, resulting from oxidative stress exacerbated by inflammation. Examples of diseases that fall in this category include heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders, such as psychosis, major depression, and bipolar disorder; seizure disorders, such as epilepsy; pain and sensory syndromes, such as migraine, neuropathic pain, or tinnitus; and behavioral syndromes, such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation. In some instances, such as a cancer patient receiving radiation therapy or chemotherapy (or both), the compound of the invention may be administered both before and after the radiation or chemotherapy, or may be administered in combination with the other therapies. Depending on the nature of the radiation therapy or chemotherapy, various combinations of pre-treatment, post-treatment, or simultaneous administration of the compound of the invention may be used. The compound of the invention may prevent or reduce the severity of side effects associated with the radiation therapy or chemotherapy. Because such side effects may be dose-limiting, their reduction or prevention may allow higher or more frequent dosing of the radiation therapy or chemotherapy, resulting in greater efficacy. Alternatively, as shown herein, use of the compound of the invention in combination with the radiation therapy or chemotherapy may enhance the efficacy of a given dose of radiation or chemotherapy. In part, this combinatorial efficacy may result from inhibition of the activity of the pro-inflammatory transcription factor NF-κB by the compound of the invention. NF-κB is often chronically activated in cancer cells, and such activation is associated with resistance to therapy and promotion of tumor progression (e.g., Karin M, Nature. 2006 May 25; 441(7092):431-6; Aghajan et al., J Gastroenterol Hepatol. 2012 March; 27 Suppl 2:10-4). Other transcription factors that promote inflammation and cancer, such as STAT3 (e.g., He G and Karin M, Cell Res. 2011 January; 21(1): 159-68; Grivennikov SI and Karin M, Cytokine Growth Factor Rev. 2010 February; 21(1): 11-9), may also be inhibited by the compound of the invention.

RTA 408 may be used to treat or prevent inflammatory conditions, such as sepsis, dermatitis, autoimmune disease, and osteoarthritis. RTA 408 may also be used to treat or prevent inflammatory pain and/or neuropathic pain, for example, by inducing Nrf2 and/or inhibiting NF-κB.

RTA 408 may also be used to treat or prevent diseases, such as cancer, inflammation, Alzheimer's disease, Parkinson's disease, multiple sclerosis, autism, amyotrophic lateral sclerosis, Huntington's disease, autoimmune diseases, such as rheumatoid arthritis, lupus, Crohn's disease, and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins, such as prostaglandin E. RTA 408 may be used to promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. It has been demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, RTA 408 may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, RTA 408 may be used to increase the production of antioxidant and reductive molecules (NQO1, HO-1, SOD1, γ-GCS) and decrease oxidative stress and the production of pro-oxidant and pro-inflammatory molecules (iNOS, COX-2, TNF-α). In some embodiments, RTA 408 may be used to cause the cells that host the inflammatory event to revert to a non-inflammatory state by promoting the resolution of inflammation and limiting excessive tissue damage to the host.

A. Cancer

Further, RTA 408 may be used to induce apoptosis in tumor cells, to induce cell differentiation, to inhibit cancer cell proliferation, to inhibit an inflammatory response, and/or to function in a chemopreventative capacity. For example, RTA 408 has one or more of the following properties: (1) an ability to induce apoptosis and differentiate both malignant and non-malignant cells, (2) an activity at sub-micromolar or nanomolar levels as an inhibitor of proliferation of many malignant or premalignant cells, (3) an ability to suppress the de novo synthesis of the inflammatory enzyme inducible nitric oxide synthase (iNOS), (4) an ability to inhibit NF-κB activation, and (5) an ability to induce the expression of heme oxygenase-1 (HO-1).

The levels of iNOS and COX-2 are elevated in certain cancers and have been implicated in carcinogenesis and COX-2 inhibitors have been shown to reduce the incidence of primary colonic adenomas in humans (Rostom et al., 2007; Brown and DuBois, 2005; Crowel et al., 2003). iNOS is expressed in myeloid-derived suppressor cells (MDSCs) (Angulo et al., 2000) and COX-2 activity in cancer cells has been shown to result in the production of prostaglandin E2 (PGE2), which has been shown to induce the expression of arginase in MDSCs (Sinha et al., 2007). Arginase and iNOS are enzymes that utilize L-arginine as a substrate and produce L-ornithine and urea, and L-citrulline and NO, respectively. The depletion of arginine from the tumor microenvironment by MDSCs, combined with the production of NO and peroxynitrite has been shown to inhibit proliferation and induce apoptosis of T cells (Bronte et al., 2003). Inhibition of COX-2 and iNOS has been shown to reduce the accumulation of MDSCs, restore cytotoxic activity of tumor-associated T cells, and delay tumor growth (Sinha et al., 2007; Mazzoni et al., 2002; Zhou et al., 2007).

Inhibition of the NF-κB and JAK/STAT signaling pathways has been implicated as a strategy to inhibit proliferation of cancer epithelial cells and induce their apoptosis. Activation of STAT3 and NF-κB has been shown to result in suppression of apoptosis in cancer cells, and promotion of proliferation, invasion, and metastasis. Many of the target genes involved in these processes have been shown to be transcriptionally regulated by both NF-κB and STAT3 (Yu et al., 2007).

In addition to their direct roles in cancer epithelial cells, NF-κB and STAT3 also have important roles in other cells found within the tumor microenvironment. Experiments in animal models have demonstrated that NF-κB is required in both cancer cells and hematopoeitic cells to propagate the effects of inflammation on cancer initiation and progression (Greten et al., 2004). NF-κB inhibition in cancer and myeloid cells reduces the number and size, respectively, of the resultant tumors. Activation of STAT3 in cancer cells results in the production of several cytokines (IL-6, IL-10) which suppress the maturation of tumor-associated dendritic cells (DC). Furthermore, STAT3 is activated by these cytokines in the dendritic cells themselves. Inhibition of STAT3 in mouse models of cancer restores DC maturation, promotes antitumor immunity, and inhibits tumor growth (Kortylewski et al., 2005).

B. Treatment of Multiple Sclerosis and Other Neurodegenerative Conditions

The compound and methods of this invention may be used for treating patients for multiple sclerosis (MS). MS is known to be an inflammatory condition of the central nervous system (Williams et al., 1994; Merrill and Benvenist, 1996; Genain and Nauser, 1997). Based on several investigations, there is evidence suggesting that inflammatory, oxidative, and/or immune mechanisms are involved in the pathogenesis of Alzheimer's disease (AD), Parkinson's disease (PD), amyotrophic lateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD. Successful therapeutic candidates for treating such a disease typically require an ability to penetrate the blood-brain barrier. See, for example, U.S. Patent Publication 2009/0060873, which is incorporated by reference herein in its entirety.

C. Neuroinflammation

The compound and methods of this invention may be used for treating patients with neuroinflammation. Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin et al., 1989; Rogers et al., 1988), where it has revolutionized our understanding of this disease (Akiyama et al., 2000). These ideas have been extended to other neurodegenerative diseases (Eikelenboom et al., 2002; Ishizawa and Dickson, 2001), to ischemic/toxic diseases (Gehrmann et al., 1995; Touzani et al., 1999), to tumor biology (Graeber et al., 2002) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

D. Treatment of Renal Failure

The compound and methods of this invention may be used for treating patients with renal failure. See U.S. patent application Ser. No. 12/352,473, which is incorporated by reference herein in its entirety. Another aspect of the present disclosure concerns new methods and compounds for the treatment and prevention of renal disease. Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001). Furthermore, several studies have demonstrated that HO-1 expression is induced in response to renal damage and inflammation and that this enzyme and its products-bilirubin and carbon monoxide-play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

E. Cardiovascular Disease

The compound and methods of this invention may be used for treating patients with cardiovascular disease. See U.S. patent application Ser. No. 12/352,473, which is incorporated by reference herein in its entirety. Cardiovascular (CV) disease is among the most important causes of mortality worldwide, and is the leading cause of death in many developed nations. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel. Such thrombosis is the principal cause of heart attacks, in which one or more of the coronary arteries is blocked and blood flow to the heart itself is disrupted. The resulting ischemia is highly damaging to cardiac tissue, both from lack of oxygen during the ischemic event and from excessive formation of free radicals after blood flow is restored (a phenomenon known as ischemia-reperfusion injury). Similar damage occurs in the brain during a thrombotic stroke, when a cerebral artery or other major vessel is blocked by thrombosis. Hemorrhagic strokes, in contrast, involve rupture of a blood vessel and bleeding into the surrounding brain tissue. This creates oxidative stress in the immediate area of the hemorrhage, due to the presence of large amounts of free heme and other reactive species, and ischemia in other parts of the brain due to compromised blood flow. Subarachnoid hemorrhage, which is frequently accompanied by cerebral vasospasm, also causes ischemia/reperfusion injury in the brain.

Alternatively, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials (e.g., Hansson et al., 2006).

Pharmaceutical treatments for cardiovascular disease include preventive treatments, such as the use of drugs intended to lower blood pressure or circulating levels of cholesterol and lipoproteins, as well as treatments designed to reduce the adherent tendencies of platelets and other blood cells (thereby reducing the rate of plaque progression and the risk of thrombus formation). More recently, drugs such as streptokinase and tissue plasminogen activator have been introduced and are used to dissolve the thrombus and restore blood flow. Surgical treatments include coronary artery bypass grafting to create an alternative blood supply, balloon angioplasty to compress plaque tissue and increase the diameter of the arterial lumen, and carotid endarterectomy to remove plaque tissue in the carotid artery. Such treatments, especially balloon angioplasty, may be accompanied by the use of stents, expandable mesh tubes designed to support the artery walls in the affected area and keep the vessel open. Recently, the use of drug-eluting stents has become common in order to prevent post-surgical restenosis (renarrowing of the artery) in the affected area. These devices are wire stents coated with a biocompatible polymer matrix containing a drug that inhibits cell proliferation (e.g., paclitaxel or rapamycin). The polymer allows a slow, localized release of the drug in the affected area with minimal exposure of non-target tissues. Despite the significant benefits offered by such treatments, mortality from cardiovascular disease remains high and significant unmet needs in the treatment of cardiovascular disease remain.

As noted above, induction of HO-1 has been shown to be beneficial in a variety of models of cardiovascular disease, and low levels of HO-1 expression have been clinically correlated with elevated risk of CV disease. Compounds of the invention, therefore, may be used in treating or preventing a variety of cardiovascular disorders including but not limited to atherosclerosis, hypertension, myocardial infarction, chronic heart failure, stroke, subarachnoid hemorrhage, and restenosis.

F. Diabetes

The compound and methods of this invention may be used for treating patients with diabetes. See U.S. patent application Ser. No. 12/352,473, which is incorporated by reference herein in its entirety. Diabetes is a complex disease characterized by the body's failure to regulate circulating levels of glucose. This failure may result from a lack of insulin, a peptide hormone that regulates both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as Type 2 diabetes. Type 2 diabetes, the most common type, is highly associated with obesity and hypertension. Obesity is associated with an inflammatory state of adipose tissue that is thought to play a major role in the development of insulin resistance (e.g., Hotamisligil, 2006; Guilherme et al., 2008).

Diabetes is associated with damage to many tissues, largely because hyperglycemia (and hypoglycemia, which can result from excessive or poorly timed doses of insulin) is a significant source of oxidative stress. Chronic kidney failure, retinopathy, peripheral neuropathy, peripheral vasculitis, and the development of dermal ulcers that heal slowly or not at all are among the common complications of diabetes. Because of their ability to protect against oxidative stress, particularly by the induction of HO-1 expression, compounds of the invention may be used in treatments for many complications of diabetes. As noted above (Cai et al., 2005), chronic inflammation and oxidative stress in the liver are suspected to be primary contributing factors in the development of Type 2 diabetes. Furthermore, PPARγ agonists such as thiazolidinediones are capable of reducing insulin resistance and are known to be effective treatments for Type 2 diabetes.

The effect of treatment of diabetes may be evaluated as follows. Both the biological efficacy of the treatment modality as well as the clinical efficacy are evaluated, if possible. For example, because the disease manifests itself by increased blood sugar, the biological efficacy of the treatment therefore can be evaluated, for example, by observation of return of the evaluated blood glucose towards normal. Measurement of glycosylated hemoglobin, also called A1c or HbA1c, is another commonly used parameter of blood glucose control. Measuring a clinical endpoint which can give an indication of b-cell regeneration after, for example, a six-month period of time, can give an indication of the clinical efficacy of the treatment regimen.

G. Rheumatoid Arthritis

The compound and methods of this invention may be used for treating patients with RA. Typically the first signs of rheumatoid arthritis (RA) appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-α), which plays a role in inflammation (Dinarello, 1998; Arend and Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

In normal joints, the effects of these and other proinflammatory cytokines are balanced by a variety of anti-inflammatory cytokines and regulatory factors (Burger and Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

H. Psoriatic Arthritis

The compound and methods of this invention may be used for treating patients with psoriatic arthritis. Psoriasis is an inflammatory and proliferative skin disorder with a prevalence of 1.5-3%. Approximately 20% of patients with psoriasis develop a characteristic form of arthritis that has several patterns (Gladman, 1992; Jones et al., 1994; Gladman et al., 1995). Some individuals present with joint symptoms first but in the majority, skin psoriasis presents first. About one-third of patients have simultaneous exacerbations of their skin and joint disease (Gladman et al., 1987) and there is a topographic relationship between nail and distal interphalangeal joint disease (Jones et al., 1994; Wright, 1956). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg et al., 1964). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in the, including PsA but not RA (McGonagle et al., 1999; McGonagle et al., 1998). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal et al., 1999; Salvarani et al., 1998). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll and Wright, 1973). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed.

Increased amounts of TNF-α have been reported in both psoriatic skin (Ettehadi et al., 1994) and synovial fluid (Partsch et al., 1997). Recent trials have shown a positive benefit of anti-TNF treatment in both PsA (Mease et al., 2000) and ankylosing spondylitis (Brandt et al., 2000).

I. Reactive Arthritis

The compound and methods of this invention may be used for treating patients with reactive arthritis. In reactive arthritis (ReA) the mechanism of joint damage is unclear, but it is likely that cytokines play critical roles. A more prevalent Th1 profile high levels of interferon gamma (IFN-γ) and low levels of interleukin 4 (IL-4) has been reported (Lahesmaa et al., 1992; Schlaak et al., 1992; Simon et al., 1993; Schlaak et al., 1996; Kotake et al., 1999; Ribbens et al., 2000), but several studies have shown relative predominance of IL-4 and 1-10 and relative lack of IFN-γ and tumor necrosis factor alpha (TNF-α) in the synovial membrane (Simon et al., 1994; Yin et al., 1999) and fluid (SF) (Yin et al., 1999; Yin et al., 1997) of reactive arthritis patients compared with rheumatoid arthritis (RA) patients. A lower level of TNF-α secretion in reactive arthritis than in RA patients has also been reported after ex vivo stimulation of peripheral blood mononuclear cells (PBMC) (Braun et al., 1999).

It has been argued that clearance of reactive arthritis-associated bacteria requires the production of appropriate levels of IFN-γ and TNF-α, while IL-10 acts by suppressing these responses (Autenrieth et al., 1994; Sieper and Braun, 1995). IL-10 is a regulatory cytokine that inhibits the synthesis of IL-12 and TNF-γ by activated macrophages (de Waal et al., 1991; Hart et al., 1995; Chomarat et al., 1995) and of IFN-γ by T cells (Macatonia et al., 1993).

J. Enteropathic Arthritis

The compound and methods of this invention may be used for treating patients with enteropathic arthritis. Typically enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles. It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies comprise a collection of rheumatologic conditions that share a link to GI pathology. These conditions include reactive (i.e., infection-related) arthritis due to bacteria (e.g., *Shigella, Salmonella, Campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

K. Juvenile Rheumatoid Arthritis

The compound and methods of this invention may be used for treating patients with JRA. Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Both innate and adaptive immune systems use multiple cell types, a vast array of cell surface and secreted proteins, and interconnected networks of positive and negative feedback (Lo et al., 1999). Furthermore, while separable in thought, the innate and adaptive wings of the immune system are functionally intersected (Fearon and Locksley, 1996), and pathologic events occurring at these intersecting points are likely to be highly relevant to our understanding of pathogenesis of adult and childhood forms of chronic arthritis (Warrington, et al., 2001).

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

L. Early Inflammatory Arthritis

The compound and methods of this invention may be used for treating patients with early inflammatory arthritis. The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen et al., 2004; Rantapaa-Dahlqvist et al., 2003).

M. Ankylosing Spondylitis

The compound and methods of this invention may be used for treating patients with ankylosing spondylitis. AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years (Khan, 1998). These same studies suggest that the spondyloarthropathies may have prevalence close to that of rheumatoid arthritis (Feldtkeller et al., 2003; Doran et al., 2003).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood (Wordsworth, 1995; Calin and Taurog, 1998). It is strongly associated with the major histocompatibility class I (MHC I) HLA-B27 allele (Calin and Taurog, 1998). AS affects individuals in the prime of their life and is feared because of its potential to cause chronic pain and irreversible damage of tendons, ligaments, joints, and bones (Brewerton et al., 1973a; Brewerton et al., 1973b; Schlosstein et al., 1973). AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease (Calin and Taurog, 1998). The site of enthesitis is known to be infiltrated by plasma cells, lymphocytes, and polymorphonuclear cells. The inflammatory process frequently results in gradual fibrous and bony ankylosis, (Ball, 1971; Khan, 1990).

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip. Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement.

The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

N. Ulcerative Colitis

The compound and methods of this invention may be used for treating patients with ulcerative colitis. Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x-ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions-periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

O. Crohn's Disease

The compound and methods of this invention may be used for treating patients with Crohn's disease. Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989).

Efforts to develop diagnostic and treatment tools against Crohn's disease have focused on the central role of cytokines (Schreiber, 1998; van Hogezand and Verspaget, 1998). Cytokines are small secreted proteins or factors (5 to 20 kD) that have specific effects on cell-to-cell interactions, intercellular communication, or the behavior of other cells. Cytokines are produced by lymphocytes, especially TH1 and TH2 lymphocytes, monocytes, intestinal macrophages, granulocytes, epithelial cells, and fibroblasts (reviewed in Rogler and Andus, 1998; Galley and Webster, 1996). Some cytokines are pro-inflammatory (e.g., TNF-$\alpha$, IL-1($\alpha$ and $\beta$), IL-6, IL-8, IL-12, or leukemia inhibitory factor [LIF]); others are anti-inflammatory (e.g., IL-1 receptor antagonist, IL-4, IL-10, IL-11, and TGF-$\beta$). However, there may be overlap and functional redundancy in their effects under certain inflammatory conditions.

In active cases of Crohn's disease, elevated concentrations of TNF-$\alpha$ and 1-6 are secreted into the blood circulation, and TNF-$\alpha$, IL-1, 1-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1$\beta$/IL-1ra ratio, in favor of pro-inflammatory IL-1$\beta$, has been observed in patients with Crohn's disease (Rogler and Andus, 1998; Saiki et al., 1998; Dionne et al., 1998; but see Kuboyama, 1998). One study suggested that cytokine profiles in stool samples could be a useful diagnostic tool for Crohn's disease (Saiki et al., 1998).

Treatments that have been proposed for Crohn's disease include the use of various cytokine antagonists (e.g., IL-1ra), inhibitors (e.g., of IL-10 converting enzyme and antioxidants) and anti-cytokine antibodies (Rogler and Andus, 1998; van Hogezand and Verspaget, 1998; Reimund et al., 1998; Lugering et al., 1998; McAlindon et al., 1998). In particular, monoclonal antibodies against TNF-α have been tried with some success in the treatment of Crohn's disease (Targan et al., 1997; Stack et al., 1997; van Dullemen et al., 1995). These compounds may be used in combination therapy with compounds of the present disclosure.

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (U.S. Pat. No. 5,443,826).

P. Systemic Lupus Erythematosus

The compound and methods of this invention may be used for treating patients with SLE. There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (reviewed by Kotzin and O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (G N) (Hahn and Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

Q. Irritable Bowel Syndrome

The compound and methods of this invention may be used for treating patients with Irritable bowel syndrome (IBS). IBS is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom-diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala et al., 2000).

IBS accounts for between 2.4 million and 3.5 million visits to physicians each year. It not only is the most common condition seen by gastroenterologists but also is one of the most common gastrointestinal conditions seen by primary care physicians (Everhart et al., 1991; Sandler, 1990).

IBS is also a costly disorder. Compared with persons who do not have bowel symptoms, persons with IBS miss three times as many workdays and are more likely to report being too sick to work (Drossman et al., 1993; Drossman et al., 1997). Moreover, those with IBS incur hundreds of dollars more in medical charges than persons without bowel disorders (Talley et al., 1995).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann et al., 1983).

In studies of the small intestine during fasting, the presence of both discrete, clustered contractions and prolonged, propagated contractions has been reported in patients with IBS (Kellow and Phillips, 1987). They also experience pain with irregular contractions more often than healthy persons (Kellow and Phillips, 1987; Horwitz and Fisher, 2001)

These motility findings do not account for the entire symptom complex in patients with IBS; in fact, most of these patients do not have demonstrable abnormalities (Rothstein, 2000). Patients with IBS have increased sensitivity to visceral pain. Studies involving balloon distention of the rectosigmoid colon have shown that patients with IBS experience pain and bloating at pressures and volumes much lower than control subjects (Whitehead et al., 1990). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman et al., 1997). Functional magnetic resonance imaging studies have recently shown that compared with control subjects, patients with IBS have increased activation of the anterior cingulate cortex, an important pain center, in response to a painful rectal stimulus (Mertz et al., 2000).

Increasingly, evidence suggests a relationship between infectious enteritis and subsequent development of IBS.

Inflammatory cytokines may play a role. In a survey of patients with a history of confirmed bacterial gastroenteritis (Neal et al., 1997), 25% reported persistent alteration of bowel habits. Persistence of symptoms may be due to psychological stress at the time of acute infection (Gwee et al., 1999).

Recent data suggest that bacterial overgrowth in the small intestine may have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn and Friedman, 1993).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

R. Sjögren's Syndrome

The compound and methods of this invention may be used for treating patients with Sjögren's syndrome. Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson et al., 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou et al., 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson and Jonsson, 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand and Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson et al., 2002).

S. Psoriasis

The compound and methods of this invention may be used for treating patients with psoriasis. Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flareups include infections, stress, and changes in climate that dry the skin. Also, certain medicines, including lithium and beta blockers, which are prescribed for high blood pressure, may trigger an outbreak or worsen the disease.

T. Infectious Diseases

Compound of the present disclosure may be useful in the treatment of infectious diseases, including viral and bacterial infections. As noted above, such infections may be associated with severe localized or systemic inflammatory responses. For example, influenza may cause severe inflammation of the lung and bacterial infection can cause the systemic hyperinflammatory response, including the excessive production of multiple inflammatory cytokines, that is the hallmark of sepsis. In addition, compounds of the invention may be useful in directly inhibiting the replication of viral pathogens. Previous studies have demonstrated that related compounds such as CDDO can inhibit the replication of HIV in macrophages (Vazquez et al., 2005). Other studies have indicated that inhibition of NF-kappa B signaling may inhibit influenza virus replication, and that cyclopentenone prostaglandins may inhibit viral replication (e.g., Mazur et al., 2007; Pica et al., 2000).

The present invention relates to the treatment or prevention of each of the diseases/disorders/conditions referred to above in section IV using the compound RTA 408 or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described herein above or below).

V. Pharmaceutical Formulations and Routes of Administration

RTA 408 may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer RTA 408 by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

RTA 408 may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Sterile injectable solutions can be prepared by incorporating RTA 408 in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient (i.e., the therapeutic compound) plus any additional desired ingredient from a previously sterile-filtered solution thereof.

RTA 408 may be rendered fully amorphous using a direct spray drying procedure. RTA 408 can be orally administered, for example, with an inert diluent or an assimilable edible carrier. The therapeutic compound and other ingredients may also be enclosed in a hard or soft shell gelatin capsule, compressed into tablets, or incorporated directly into the patient's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the patients to be treated, each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

RTA 408 may also be administered topically to the skin, eye, or mucosa. Alternatively, if local delivery to the lungs is desired the therapeutic compound may be administered by inhalation in a dry-powder or aerosol formulation.

RTA 408 will typically be administered at a therapeutically effective dosage sufficient to treat a condition associated with a given patient. For example, the efficacy of a compound can be evaluated in an animal model system that may be predictive of efficacy in treating the disease in humans, such as the model systems shown in the examples and drawings.

The actual dosage amount of RTA 408 or composition comprising RTA 408 administered to a patient may be determined by physical and physiological factors, such as age, sex, body weight, severity of condition, the type of disease being treated, previous or concurrent therapeutic interventions, idiopathy of the patient, and the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, or less than 10 mg/kg/day. It may alternatively be in the range of 1 mg/kg/day to 200 mg/kg/day. In some embodiments, the amount could be 10, 30, 100, or 150 mg/kg formulated as a suspension in sesame oil. In some embodiments, the amount could be 3, 10, 30 or 100 mg/kg administered daily via oral gavage. In some embodiments, the amount could be 10, 30, or 100 mg/kg administered orally. For example, regarding treatment of diabetic patients, the unit dosage may be an amount that reduces blood glucose by at least 40% as compared to an untreated patient. In another embodiment, the unit dosage is an amount that reduces blood glucose to a level that is ±10% of the blood glucose level of a non-diabetic patient.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/ kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.01% of RTA 408. In other embodiments, RTA 408 may comprise between about 0.01% to about 75% of the weight of the unit, or between about 0.01% to about 5%, for example, and any range derivable therein. In some embodiments, RTA 408 may be used in a formulation such as a suspension in sesame oil of 0.01, 0.1, or 1%.

Single or multiple doses of the agent comprising RTA 408 are contemplated. Desired time intervals for delivery of multiple doses can be determined by one of ordinary skill in the art employing no more than routine experimentation. As an example, patients may be administered two doses daily at approximately 12 hour intervals. In some embodiments, the agent is administered once a day. The agent(s) may be administered on a routine schedule. As used herein a routine schedule refers to a predetermined designated period of time. The routine schedule may encompass periods of time that are identical or that differ in length, as long as the schedule is predetermined. For instance, the routine schedule may involve administration twice a day, every day, every two days, every three days, every four days, every five days, every six days, a weekly basis, a monthly basis, or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Synthesis of RTA 408 (63415)

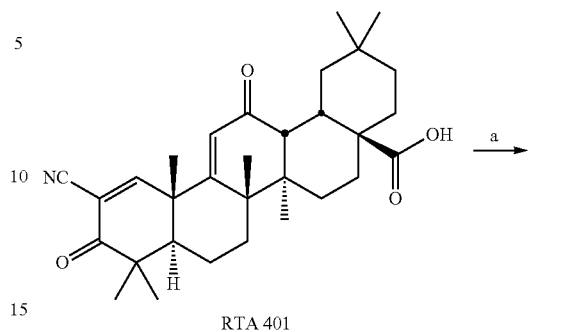

RTA 401

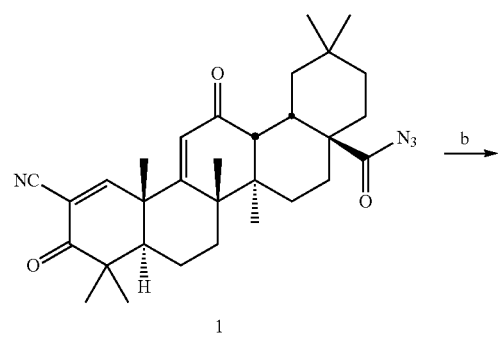

1

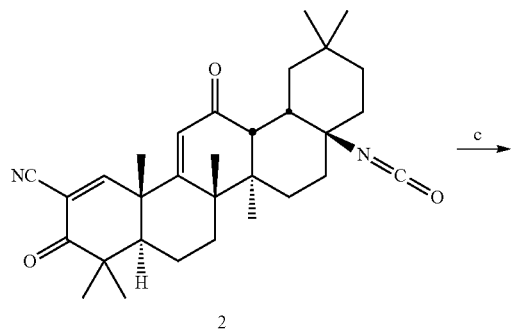

2

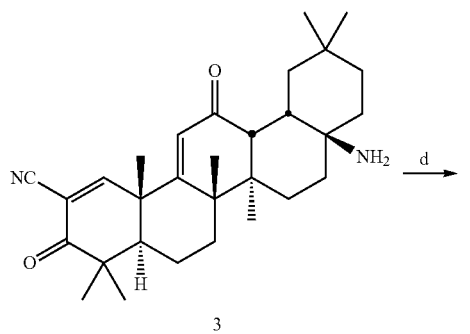

3

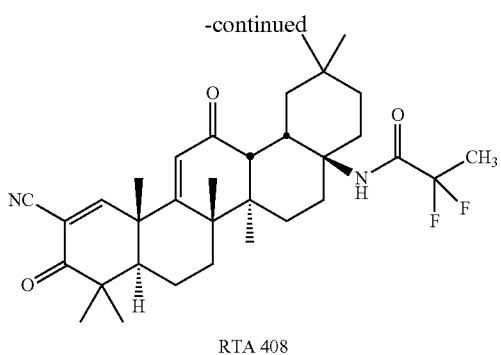

RTA 408

Reagents and conditions:
(a) (PHO)$_2$PON$_3$ (DPPA), triethylamine, toluene, 0° C. for 5 minutes, then ambient temperature overnight, ~94%;
(b) benzene, 80° C. for 2 hours;
(c) HCl, CH$_3$CN, ambient temperature for 1 hour;
(d) CH$_3$CF$_2$CO$_2$H, dicyclohexylcarbodiimide, 4-(dimethylamino)pyridine, CH$_2$Cl$_2$, ambient temperature overnight, 73% from RTA 401 (4 steps).

Compound 1:

RTA 401 (20.0 g, 40.6 mmol), triethylamine (17.0 mL, 122.0 mmol), and toluene (400 mL) were added into a reactor and cooled to 0° C. with stirring. Diphenyl phosphoryl azide (DPPA) (13.2 mL, 61.0 mmol) was added with stirring at 0° C. over 5 minutes, and the mixture was continually stirred at room temperature overnight (HPLC-MS check shows no RTA 401 left). The reaction mixture was directly loaded on a silica gel column and purified by column chromatography (silica gel, 0% to 5% ethyl acetate in CH$_2$Cl$_2$) to give compound 1 (19.7 g, ~94%, partially converted into compound 2) as a white foam.

Compound 2:

Compound 1 (19.7 g, ~38.1 mmol) and benzene (250 mL) were added into a reactor and heated to 80° C. with stirring for 2 hours (HPLC-MS check shows no compound 1 left). The reaction mixture was concentrated at reduced pressure to afford crude compound 2 as a solid residue, which was used for the next step without purification.

Compound 3:

Crude compound 2 (≤38.1 mmol) and CH$_3$CN (200 mL) were added into a reactor and cooled to 0° C. with stirring. HCl (12 N, 90 mL) was added at 0° C. over 1 minute, and the mixture was continually stirred at room temperature for 1 hour (HPLC-MS check shows no compound 2 left). The reaction mixture was cooled to 0° C. and 10% NaOH (~500 mL) was added with stirring. Then, saturated NaHCO$_3$ (1 L) was added with stirring. The aqueous phase was extracted by ethyl acetate (2×500 mL). The combined organic phase was washed by H$_2$O (200 mL), saturated NaCl (200 mL), dried over Na$_2$SO$_4$, and concentrated to afford crude compound 3 (16.62 g) as a light yellow foam, which was used for the next step without purification.

RTA 408:

Crude amine 3 (16.62 g, 35.9 mmol), CH$_3$CF$_2$CO$_2$H (4.7388 g, 43.1 mmol), and CH$_2$Cl$_2$ (360 mL) were added into a reactor with stirring at room temperature. Then, dicyclohexylcarbodiimide (DCC) (11.129 g, 53.9 mmol) and 4-(dimethylamino)pyridine (DMAP) (1.65 g, 13.64 mmol) were added and the mixture was continually stirred at room temperature overnight (HPLC-MS check shows no compound 3 left). The reaction mixture was filtered to remove solid by-products, and the filtrate was directly loaded on a silica gel column and purified by column chromatography (silica gel, 0% to 20% ethyl acetate in hexanes) twice to give compound RTA 408 (16.347 g, 73% from RTA 401 over 4 steps) as a white foam: $^1$H NMR (400 MHz, CD$_3$Cl) δ ppm 8.04 (s, 1H), 6.00 (s, 1H), 5.94 (s, br, 1H), 3.01 (d, 1H, J=4.8 Hz), 2.75-2.82 (m, 1H), 1.92-2.18 (m, 4H), 1.69-1.85 (m, 7H), 1.53-1.64 (m, 1H), 1.60 (s, 3H), 1.50 (s, 3H), 1.42 (s, 3H), 1.11-1.38 (m, 3H), 1.27 (s, 3H), 1.18 (s, 3H), 1.06 (s, 3H), 1.04 (s, 3H), 0.92 (s, 3H); m/z 555 (M+1).

B. Pharmacodynamics

A summary of the in vitro and in vivo studies to evaluate the primary pharmacodynamic effects of RTA 408 is provided below.

1. Effects of RTA 408 on Keap1-Nrf2 and NF-κB In Vitro

Inhibition of IFNγ-induced NO production by AIMs is Nrf2-dependent (Dinkova-Kostova, 2005). RAW264.7 mouse macrophages were pre-treated with dimethyl sulfoxide (vehicle) or RTA 408 for 2 hours, followed by treatment with 20 ng/mL of mouse IFNγ for 24 hours. Nitrite (NO$_2^-$) levels in the media were measured as a surrogate for nitric oxide using the Griess reagent assay. Cell viability was assessed using the WST-1 assay. Treatment with RTA 408 resulted in a dose-dependent suppression of IFNγ-induced NO production, with an average IC$_{50}$ value of 3.8±1.2 nM. Results from a representative experiment are shown in FIG. 1. The IC$_{50}$ value for RTA 408 was found 45%-65% lower than the IC$_{50}$ values for compounds 63170 (8±3 nM), 63171 (6.9±0.6 nM), 63179 (11±2 nm), and 63189 (7±2 nM). 63170, 63171, 63179, and 63189 are compounds of the formulas:

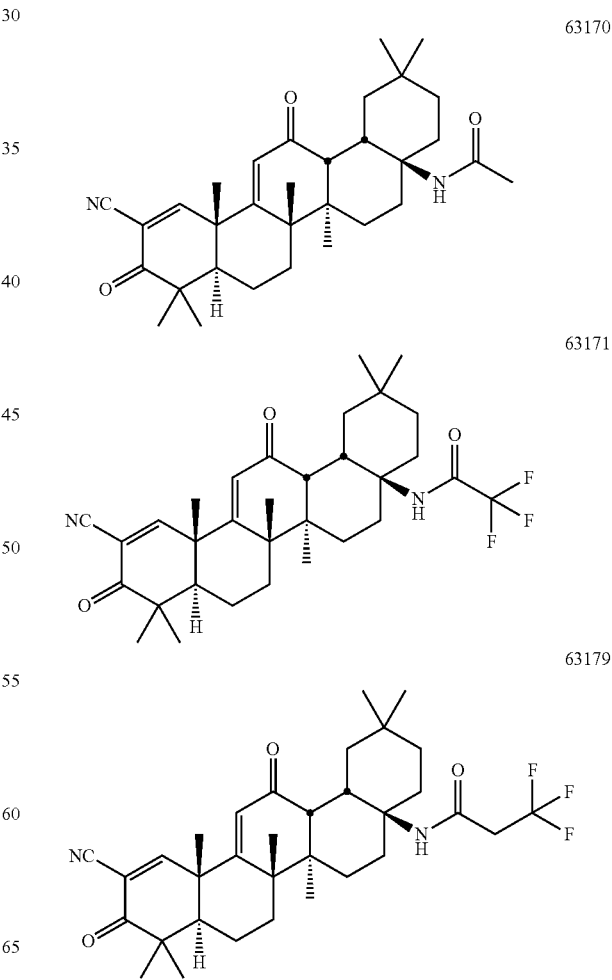

-continued

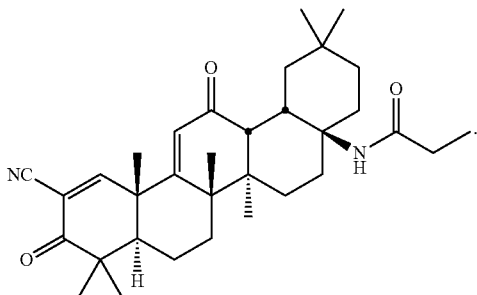

63189

2. Effect of RTA 408 on Nrf2 Target Genes

RTA 408 was tested in two different reporter assays to assess activation of the antioxidant response element (ARE). The first reporter tested was controlled by an ARE derived from the human NQO1 gene. The HuH-7 human hepatoma cell line was transiently transfected with an NQO1-ARE luciferase reporter plasmid, and cells were treated with RTA 408 for 18 hours. FIG. 2a shows a dose-dependent induction of luciferase activity by RTA 408 in this cell line. Values represent the average of three independent experiments. Twenty percent less RTA 408 (12 nM) than 63189 (14.9 nM) was required to increase transcription from the NQO1 ARE in HuH-7 cells by 2-fold. Likewise, 2.1-2.4 fold less RTA 408 than 63170 (25.2 nM) and 63179 (29.1 nM), respectively, was required to increase transcription from the NQO1 ARE in HuH-7 cells by 2-fold. The effect of RTA 408 on luciferase reporter activation was also assessed in the AREc32 reporter cell line. This cell line is derived from human breast carcinoma MCF-7 cells and is stably transfected with a luciferase reporter gene under the transcriptional control of eight copies of the rat GSTA2 ARE sequence. Following treatment with RTA 408 for 18 hours, a similar dose-dependent response was observed in the AREc32 reporter cell line (FIG. 2b). An ~2-fold induction of luciferase activity was evident following treatment with 15.6 nM RTA 408 in both reporter assays.

RTA 408 was also shown to increase transcript levels of known Nrf2 target genes in the HFL1 human lung fibroblast and BEAS-2B human bronchial epithelial cell lines. Treatment of HFL1 lung fibroblasts with RTA 408 for 18 hours resulted in increased expression of several Nrf2 target genes, including NQO1, HMOX1, GCLM, and TXNRD1, as measured by quantitative PCR (FIGS. 3a-d). For all genes tested, induction by RTA 408 was dose-dependent and evident at concentrations as low as 15.6 nM. Treatment of BEAS-2B bronchial epithelial cells with RTA 408 for 18 hours resulted in a similar dose-dependent increase of all Nrf2 target genes evaluated (FIGS. 4a-d). RTA 408 also increased expression of Nrf2 target genes in normal human mesangial cells (nHMC), the mouse BV2 microglial cell line, and the human SH-SY5Y neuroblastoma cell line at similar concentrations.

Treatment with RTA 408 also increased NQO1 protein levels in SH-SY5Y cells in a dose-dependent manner (FIG. 5a). HMOX1 protein was not detected in untreated or RTA 408-treated SH-SY5Y cells. In BV2 cells, treatment with RTA 408 increased NQO1 and HMOX1 protein levels at concentrations up to 125 nM (FIG. 5b). The $EC_{50}$ value for induction of Nrf2 protein expression in SK—N—SH cells by RTA 408 (56.4 nM) was 45%-65% lower than the $EC_{50}$ values for 63171 (122 nM), 63189 (102 nM), and 63179 (126 nM). The same amount of 63170 (54.6 nM) was required.

The $EC_{50}$ was measured using an in-cell western NQO1 assay where the cells were incubated with the compound under evaluation for 3 days. After incubation with the compound of interest, the cells were reacted with mouse NQO1 antibody and then the next day the cells were reacted with IRDye-800CW-anti-mouse IgG antibody. The target signals were visualized and then analyzed.

Figure 6:
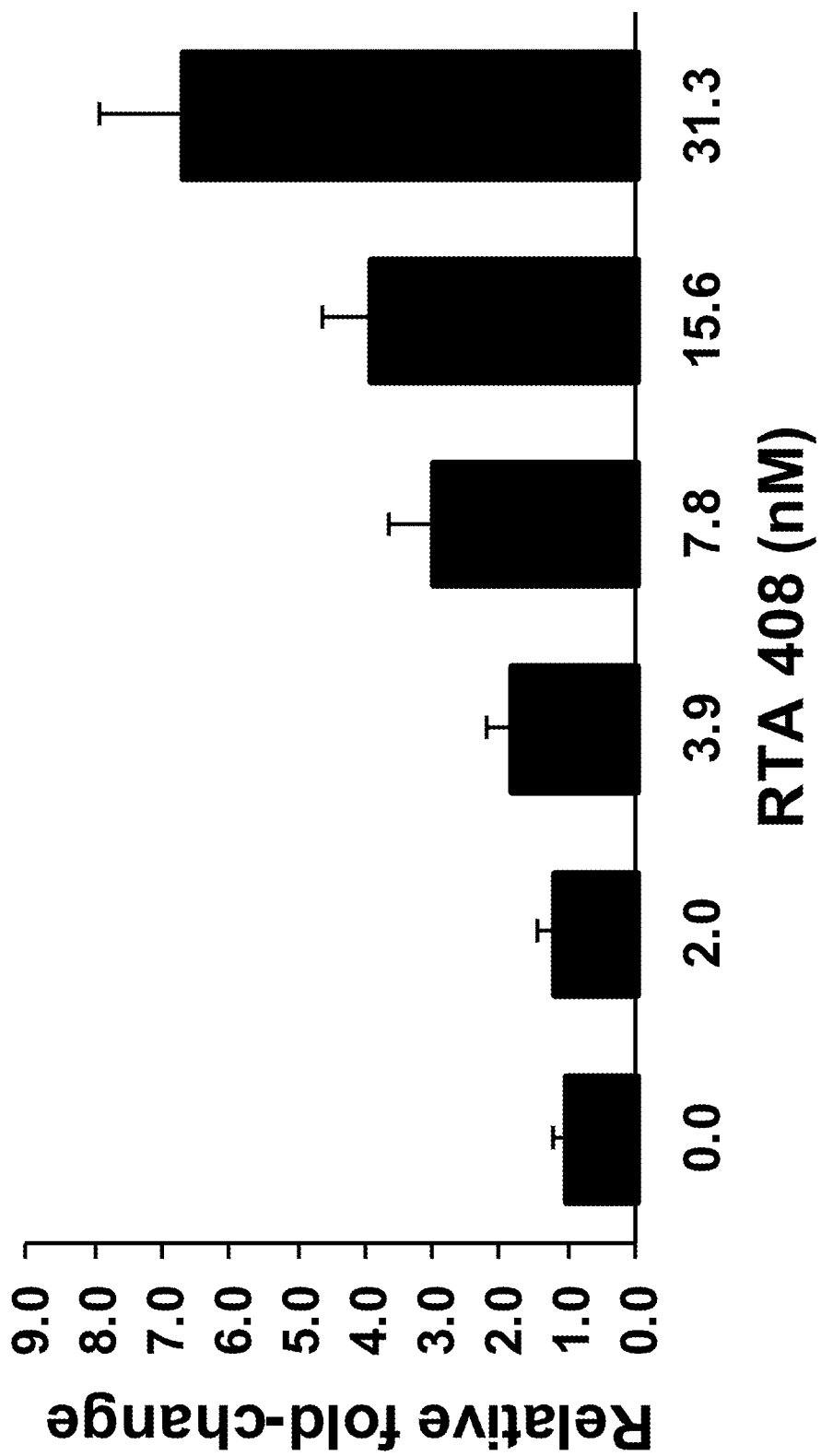
FIG. 6—Effect of RTA 408 on NQO1 enzymatic activity in RAW264.7 cells.

Consistent with induction of Nrf2 target genes and corresponding protein products, treatment of RAW264.7 mouse macrophage cells for 24 hours increased NQO1 enzymatic activity in a dose-dependent manner, with increases evident at 7.8 nM (FIG. 6).

Taken together, these data from multiple cell lines demonstrate that treatment with RTA 408 increases transcriptional activity controlled by antioxidant response elements, increases expression of Nrf2 target genes, and increases the activity of NQO1, an Nrf2 target gene product.

3. Effect of RTA 408 on Markers of Cellular Redox Capacity

Figure 7:
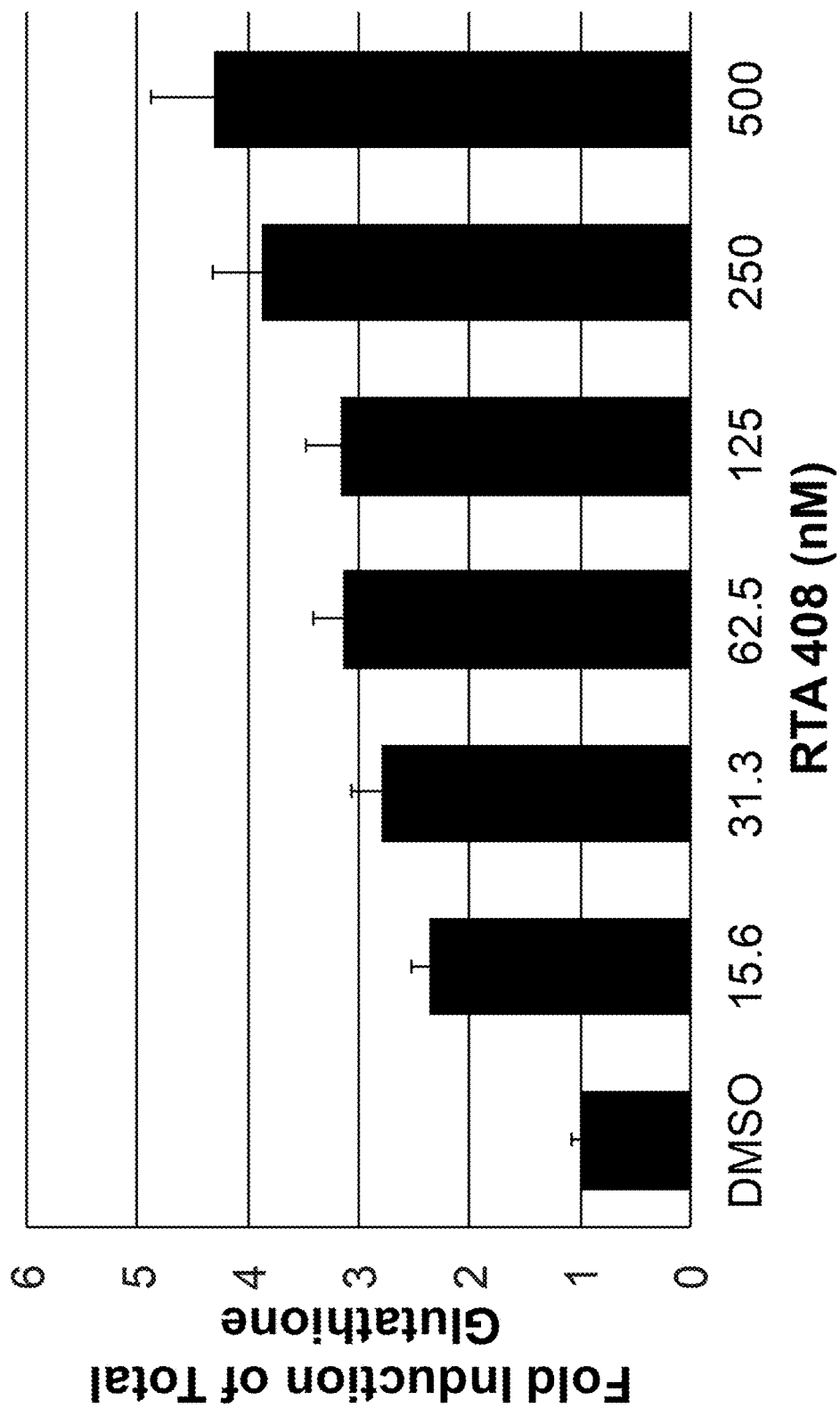
FIG. 7—Effect of RTA 408 on total glutathione levels in the AML-12 hepatocyte cell line.

Glutathione and NADPH are critical factors required for the maintenance of cellular redox capacity. Several genes involved in the synthesis of glutathione (e.g., GCLC and GLCM) and NADPH [e.g., hexose-6-phosphate dehydrogenase (H6PD) and malic enzyme 1 (ME1)] have been demonstrated to be regulated by Nrf2 (Wu, 2011). The effect of RTA 408 treatment on total glutathione levels was evaluated in the mouse AML-12 hepatocyte cell line. Treatment of AML-12 cells for 24 hours with RTA 408 increased total cellular glutathione levels in a dose-dependent manner (FIG. 7). Data shown are representative of two independent experiments. A >2-fold increase in total glutathione was observed at RTA 408 concentrations as low as 15.6 nM. The $EC_{50}$ value using a RAW264.7 mouse model for induction of glutathione levels by RTA 408 (9.9 nM) was 22%-57% lower than the $EC_{50}$ values for 63170 (12.1 nM), 63171 (23.2 nM), and 63189 (16 nM).

Figure 8:
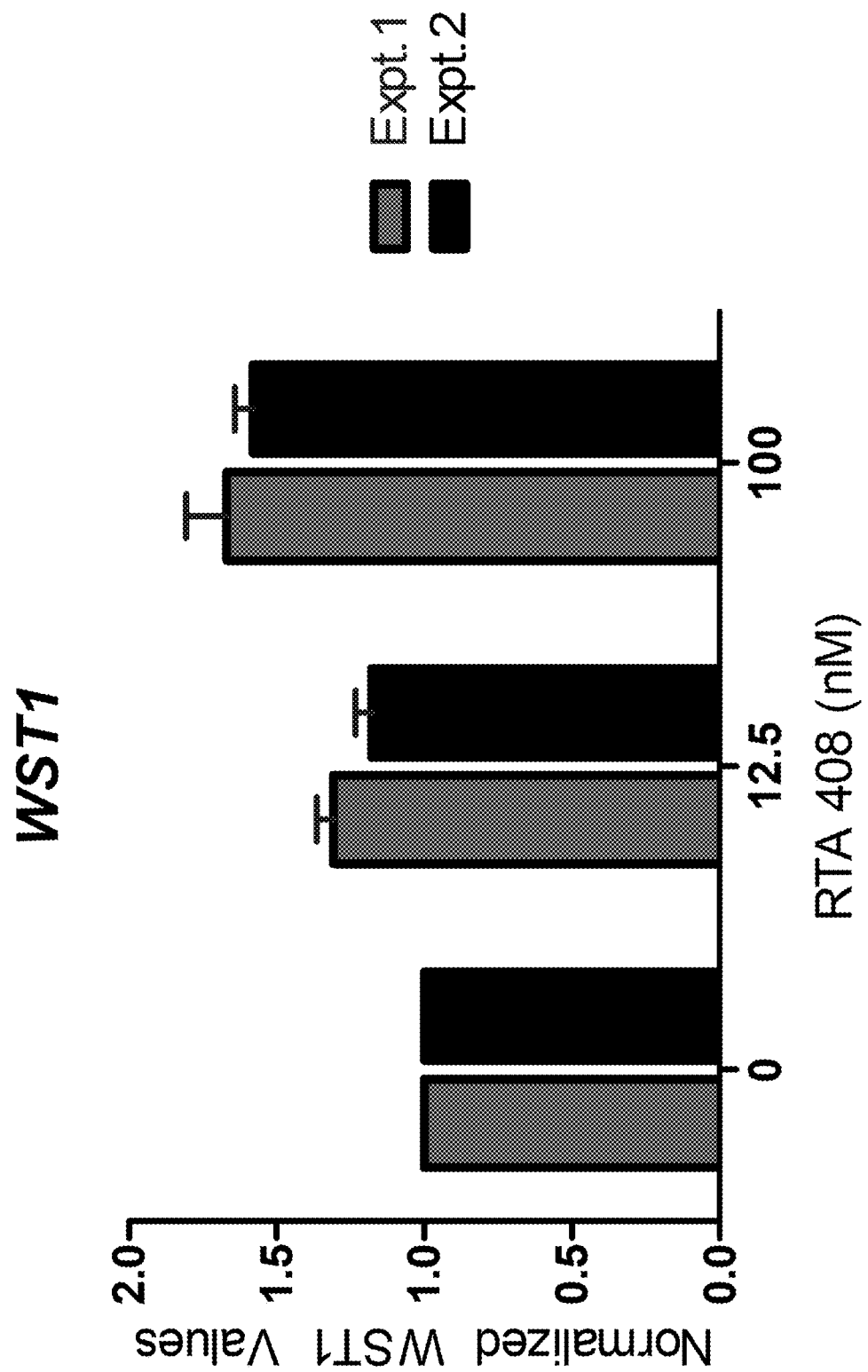
FIG. 8—Effect of RTA 408 on WST-1 absorbance as a marker of NADPH.

The effect of RTA 408 treatment on the levels of NADPH, as measured by the absorbance of a redox-sensitive dye, WST-1, was evaluated in HCT-16 cells. RTA 408 treatment for 24 hours increased WST-1 absorbance in a dose-dependent manner (FIG. 8), suggesting that NADPH levels were increased.

The effect of RTA 408 on the expression of genes involved in NADPH synthesis pathways was also evaluated in this study. HCT-116 cells were treated with RTA 408 for 24 hours, and mRNA levels of H6PD, phosphogluconate dehydrogenase (PGD), transketolase (TKT), and ME1 were measured using quantitative PCR. Treatment with RTA 408 resulted in a dose-dependent increase in expression of genes involved in NADPH synthesis (FIGS. 9a-d).

In summary, treatment with RTA 408 increased total glutathione levels in AML-12 hepatocytes and increased WST-1 absorbance, a marker of NADPH production, in HCT-116 cells. This observation correlated with an increase in the expression of several key genes encoding enzymes involved in NADPH synthesis.

4. Effect of RTA 408 on TNFα-Induced NF-κB Signaling

Figure 10:
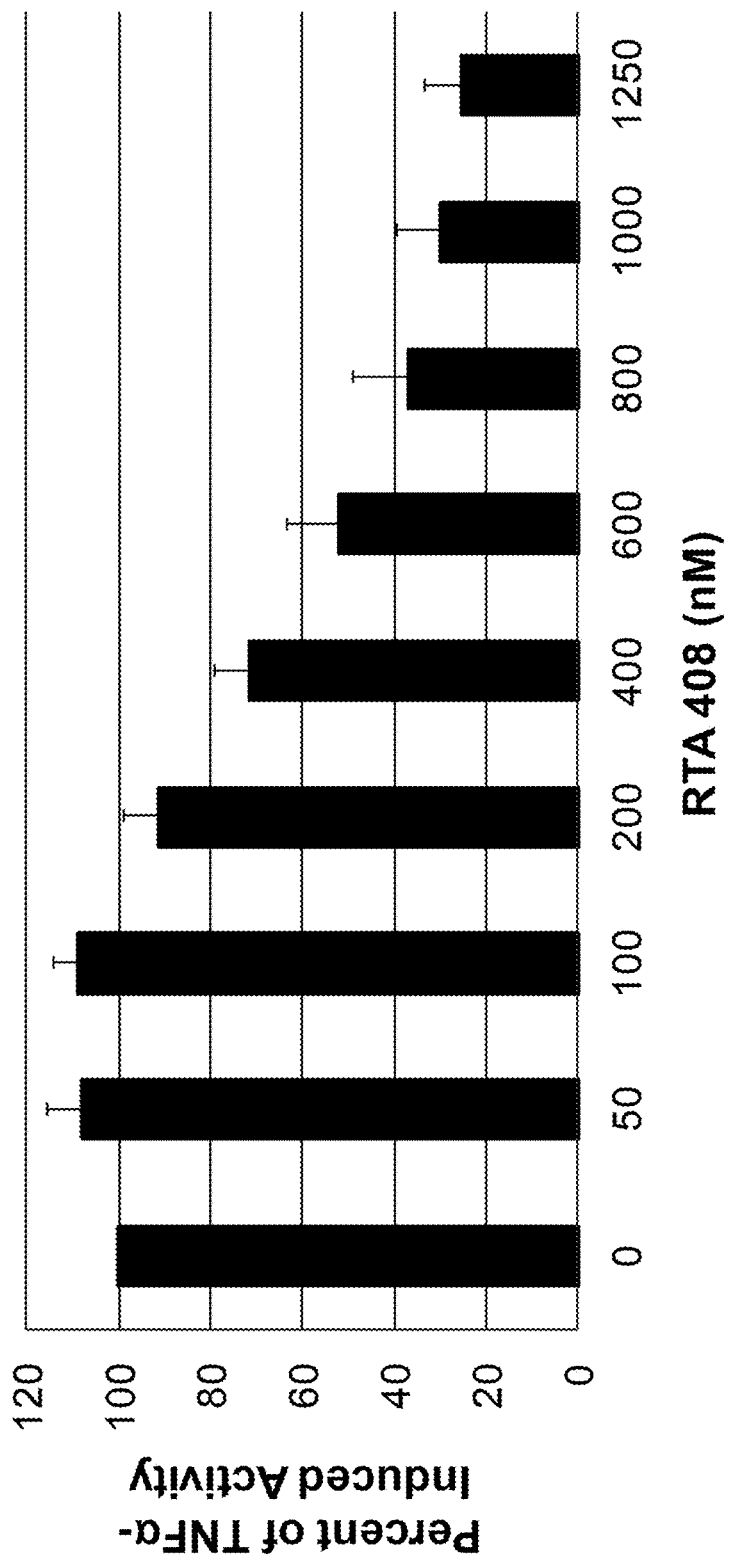
FIG. 10—Effect of RTA 408 on TNFα-induced activation of a NF-κB luciferase reporter construct.

NF-κB is a transcription factor that plays a central role in the regulation of many immune and inflammatory responses. RTA 402 and other AIMs have been shown to inhibit pro-inflammatory NF-κB signaling in a variety of cell lines (Shishodia, 2006; Ahmad, 2006; Yore, 2006). The effect of RTA 408 on TNFα-induced NF-κB signaling was evaluated in HeLa/NF-κB-Luc cells, a human cervical adenocarcinoma cell line stably transfected with a luciferase reporter construct under the control of multiple NF-κB transcriptional response elements. HeLa/NF-κB-Luc cells were pretreated for 1 hour with RTA 408, followed by treatment with TNFα (10 ng/mL) for an additional 5 hours. After treatment, luminescence was measured, and the effect of RTA 408 pretreatment on TNFα-induced luciferase activity was determined. The average results and standard deviations from three independent experiments are shown in FIG. 10. RTA 408 dose-dependently inhibited TNFα-induced NF-κB activation with an $IC_{50}$ value of 517±83 nM. Similar results were observed in another NF-κB reporter cell line (A549/NF-κB-Luc) where RTA 408 inhibited TNFα-induced NF-κB activation with an $IC_{50}$ value of 627 nM (range 614-649 nM). RTA 408 was 1.6-1.8 fold more efficient at reducing expression from the NF-κB promoter reporter in HeLa/NF-κB-Luc cells than 63189 (854 nM) and 63170 (953 nM), respectively.

Figure 11:
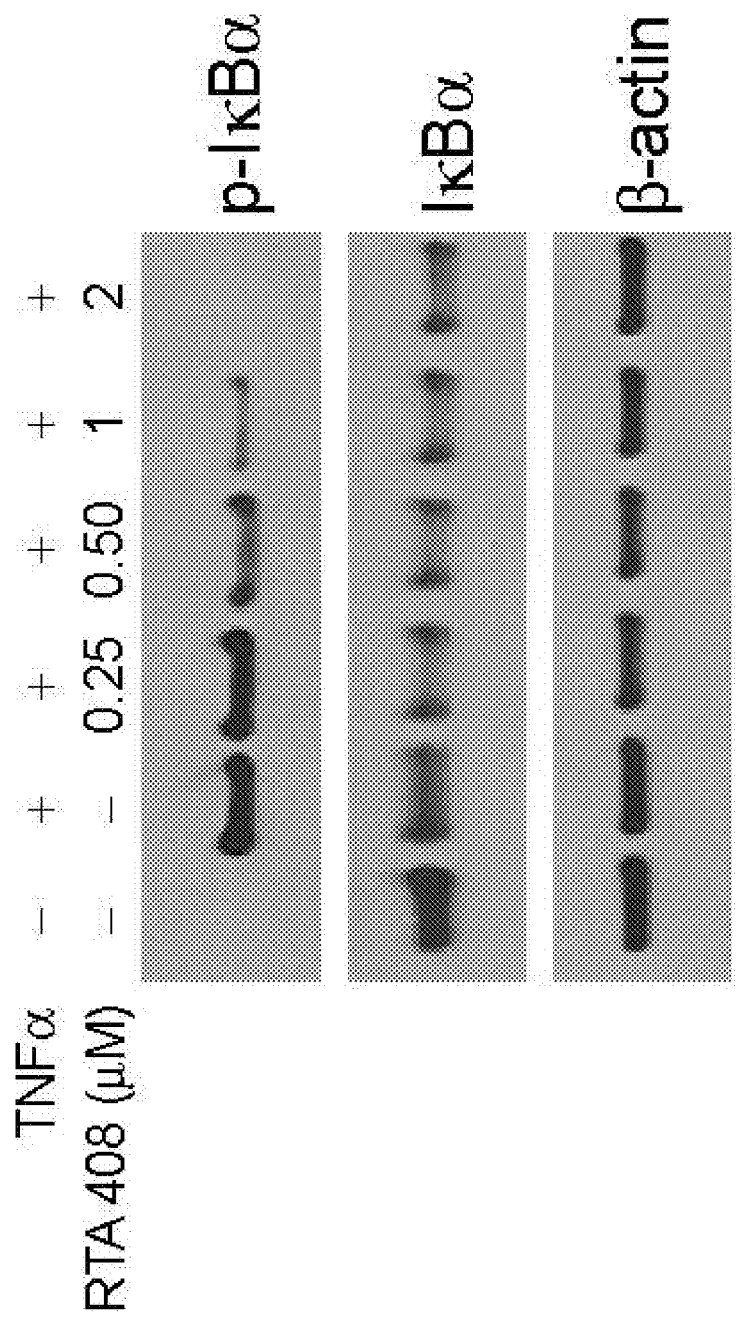
FIG. 11—Effect of RTA 408 on TNFα-induced phosphorylation of IκBα.

The effect of RTA 408 on TNFα-induced phosphorylation of IκBα, a key step in activation of the NF-κB pathway, was also evaluated in HeLa cells. HeLa cells were pretreated with RTA 408 for 6 hours, followed by treatment with TNFα (20 ng/mL) for 5 min. Total and phosphorylated levels of IκBα were evaluated by Western blot. Consistent with the results from the luciferase reporter assay, RTA 408 inhibited TNFα-induced phosphorylation of IκBα in a dose-dependent manner (FIG. 11).

RTA 408 has also been demonstrated to inhibit other pro-inflammatory signaling pathways, such as IL-6-induced signal transducer and activator of transcription 3 (STAT3) phosphorylation and receptor activator of NF-κB ligand (RANKL)-induced osteoclastogenesis. In HeLa cells, pretreatment with 1 μM RTA 408 for 6 hours inhibited phosphorylation of STAT3 induced by IL-6. Osteoclastogenesis is a multi-step differentiation process that results from the binding of RANKL to its receptor, RANK, on cells of hematopoietic origin. This results in the activation of NF-κB and MAPK, which in turn increase transcription of osteoclast-specific target genes, including tartrate-resistant acid phosphatase (TRAP). The effect of RTA 408 on RANKL-induced osteoclastogenesis was evaluated in the mouse macrophage cell line RAW264.7. RAW264.7 cells were pretreated for 2 hours with RTA 408 and then treated with 50 ng/mL recombinant mouse RANKL. RTA 408 dose-dependently inhibited RANKL-induced TRAP activity and the formation of osteoclasts, with an $IC_{50}$ of ~5-10 nM.

5. Effect of RTA 408 on Expression of Genes Encoding Transaminase Enzymes

Transaminase elevations were observed in the 28-day toxicity studies with RTA 408 in rats and, to a much lower extent, in monkeys. Similar findings have been observed following oral administration of a related AIM (bardoxolone methyl) in humans (Pergola, 2011). One hypothesis for this effect is that AIMs directly or indirectly increase transaminase gene expression in the absence of cellular toxicity. To assess whether treatment with RTA 408 affects transaminase mRNA levels, mouse AML-12 hepatocytes were treated with RTA 408 for 18 hours, and the mRNA levels of genes encoding transaminases were measured using quantitative PCR. Treatment with RTA 408 increased mRNA levels of alanine transaminase 1 (Alt1 or Gpt1) and aspartate transaminase 1 (Ast1 or Got1) (FIGS. 12a,c). RTA 408 had no effect on alanine transaminase 2 (Alt2 or Gpt2) mRNA levels and reduced mRNA levels of aspartate transaminase 2 (Ast2 or Got2) (FIGS. 12b,d). These results demonstrate that RTA 408, at the concentrations tested (250 nM or 500 nM), affects transaminase gene expression in vitro in a manner consistent with the effects of other compounds in the AIM class. However, it is unclear how the results from this in vitro system at the RTA 408 concentrations tested relate to the potential effects on transaminases at clinically-relevant dose levels in humans.

6. Effect of RTA 408 on Levels of Glycolytic Intermediates

Studies in diabetic mice have demonstrated that bardoxolone methyl increases muscle-specific insulin-stimulated glucose uptake (Saha, 2010). In humans, a higher percentage of patients receiving bardoxolone methyl reported experiencing muscle cramps compared with patients receiving placebo (Pergola, 2011). Muscle spasms have also been reported in diabetic patients following insulin administration, suggesting a possible association with muscle glucose metabolism. The effect of RTA 408 on glycolytic metabolism was evaluated through the assessment of lactate and pyruvate levels in cultured rodent C2C12 muscle cells. Similar to treatment with insulin, treatment of differentiated C2C12 myotubes with 1 μM or 2 μM RTA 408 for 3 hours significantly increased intracellular and extracellular lactate levels in a dose-dependent manner.

Figure 13:
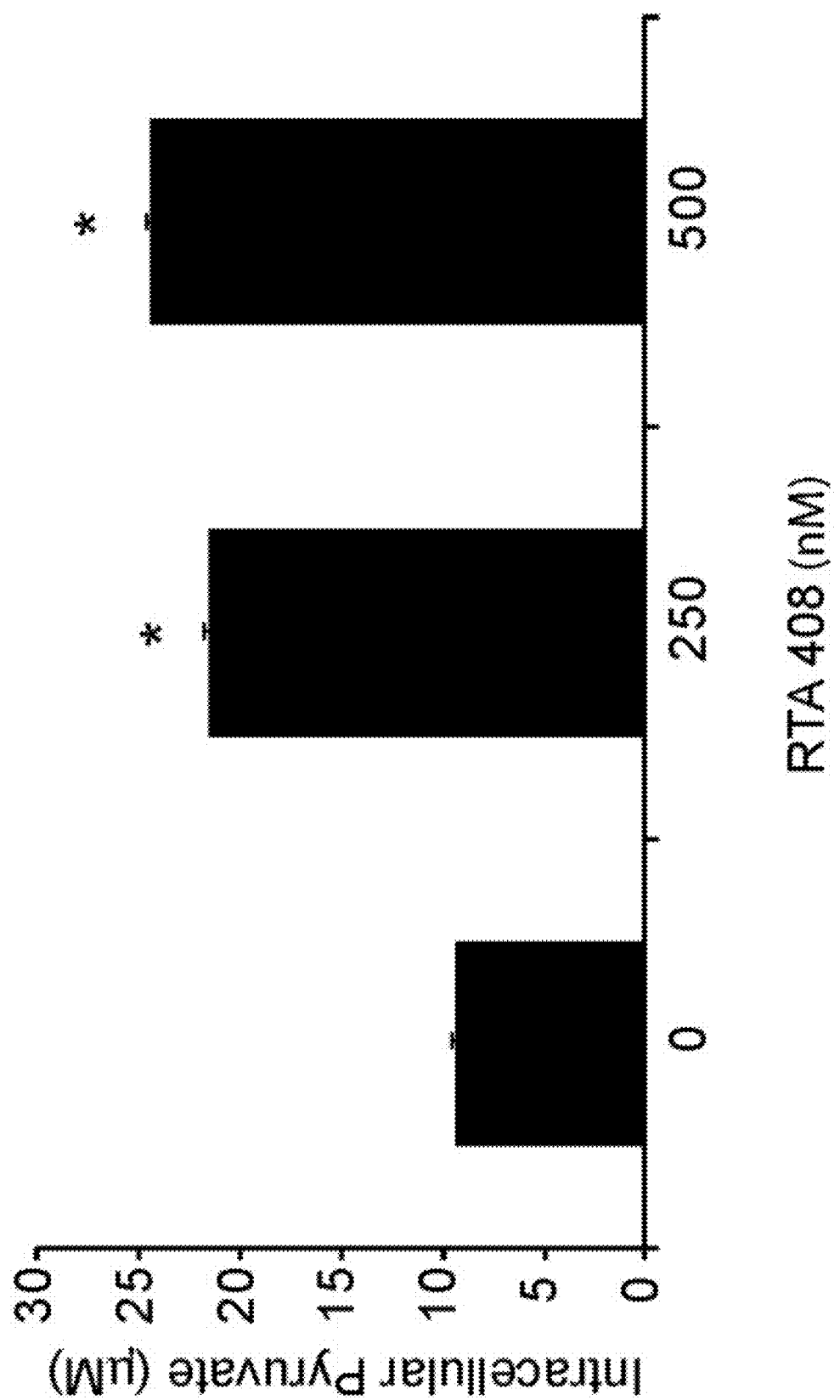
FIG. 13—Effect of RTA 408 on pyruvate levels in cultured muscle cells (*P<0.05).

Treatment of C2C12 differentiated myotubes with 250 nM or 500 nM RTA 408 for 18 hours also significantly ($P<0.0001$, noted by asterisks) increased intracellular pyruvate levels in a dose-dependent manner (FIG. 13). Together, these results demonstrate that RTA 408, at the concentrations tested, can affect muscle glycolytic intermediates in vitro; however, it is unclear how the results from this in vitro system at the RTA 408 concentrations tested relate to the potential effects on glucose metabolism at clinically-relevant dose levels in humans.

7. In Vitro Evaluation of RTA 408 Efflux by MRP-1

The efflux ratio MRP-1 for RTA 408 (1.3) was experimentally determined to be approximately ten-fold lower than 63170 (10) and 63171 (11.2) and over 40-fold lower than 63189 (57.1). The value determined for RTA 408 indicates that it is not a substrate of MRP-1, whereas the other compounds are.

C. Protective Effects of RTA 408 in Animal Models of Lung Disease

RTA 408 was tested in several animal models of pulmonary disease to evaluate its potential efficacy in the lung. For all studies, RTA 408 was orally administered daily in sesame oil at dose levels in the range of 3 to 150 mg/kg. In most cases, RTA 408 was administered starting several days prior to the induction of the lung injury response.

1. LPS-Induced Pulmonary Inflammation in Mice

Figure 14:
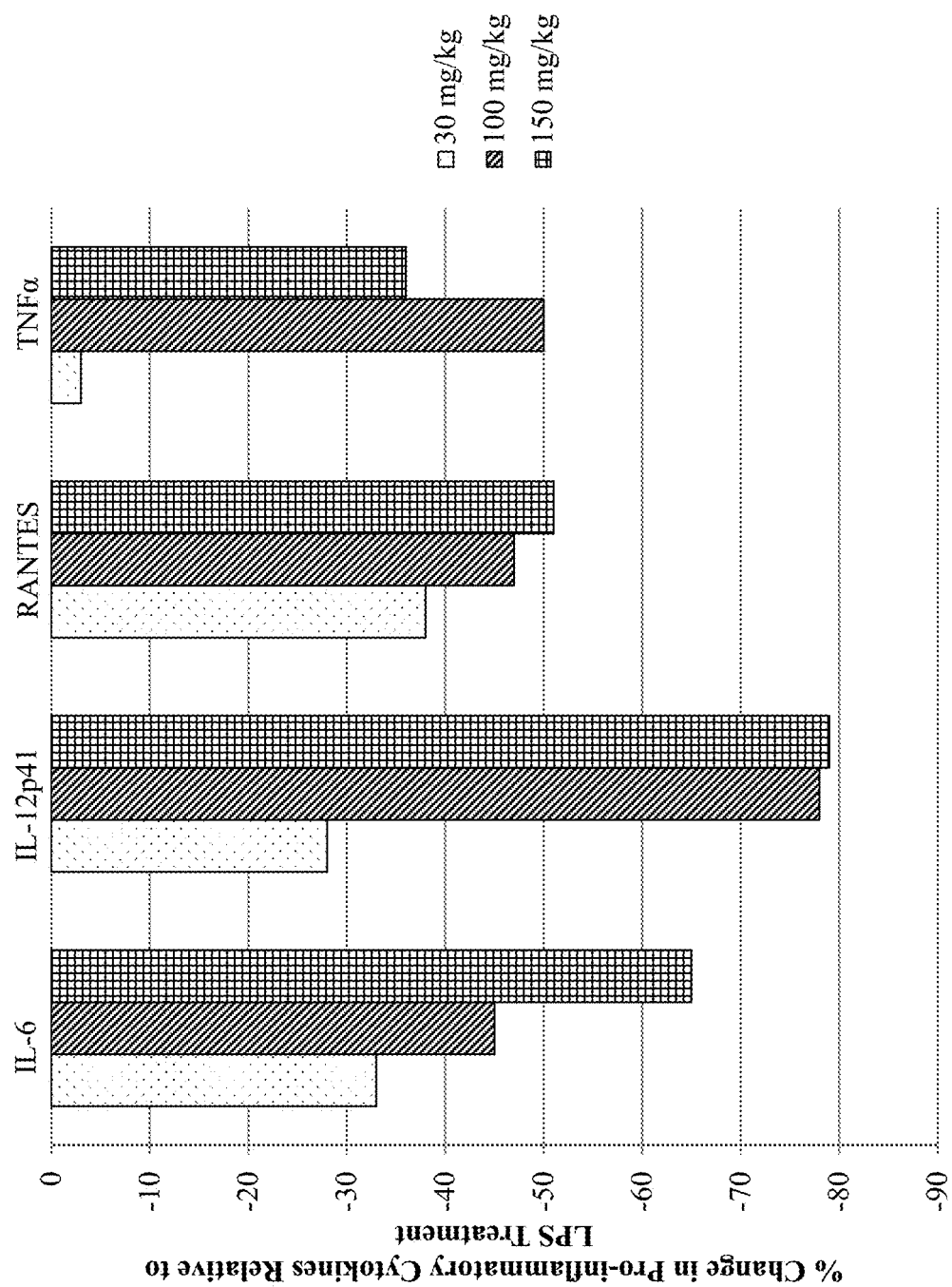
FIG. 14—RTA 408 activity in a model of pulmonary LPS-mediated inflammation (% change in pro-inflammatory cytokines relative to LPS treatment). RTA 408 was administered QD×3 at Time 0, 24, and 48 hours followed by LPS one hour after the last dose of RTA 408 in female BALB/c mice. Animals were sacrificed 20 hours after LPS administration. BALF was examined for pro-inflammatory cytokine expression. RTA 408 reduced pro-inflammatory cytokines: Dose-dependent reductions were observed, with peak reductions ranging from 50%-80% in TNF, IL-6, and IL-12.

RTA 408 was tested in two studies of LPS-induced pulmonary inflammation in mice. In the first study, intended to be a preliminary dose-range finder, RTA 408 (30, 100, or 150 mg/kg) was administered once daily for 3 days, followed by LPS administration 1 hour after the final dose. Bronchoalveolar lavage fluid (BALF) was collected 20 hours after LPS administration (21 hours after the final dose of RTA 408) and evaluated for levels of pro-inflammatory markers (i.e., IL-6, IL-12p40, TNF-α, and RANTES). RTA 408 treatment resulted in a significant reduction in IL-12p40 at all doses and in TNFα at the 100 and 150 mg/kg doses (FIG. 14). In the second study, RTA 408 (10, 30, or 100 mg/kg) was administered daily for 6 days, followed by LPS administration 1 hour after the final dose. In this study, significant decreases in body weight were observed at the 100 mg/kg dose level starting on Day 3. Significant reductions in TNFα were observed at the 10 mg/kg dose, and significant reductions in IL-12p40, TNFα, and RANTES were observed at the 30 mg/kg dose (FIG. 15a). Further evaluation of lungs from mice in this study revealed meaningful engagement of relevant Nrf2 target genes, including significant induction of NQO1 enzyme activity and increases in total GSH at 10 and 30 mg/kg (FIG. 15b).

8. Bleomycin-Induced Pulmonary Fibrosis

The effect of RTA 408 was also evaluated in models of bleomycin-induced pulmonary fibrosis in mice and rats. In the first preliminary study, RTA 408 (10, 30, or 100 mg/kg) was administered to mice daily via oral gavage for 39 days, with bleomycin challenge (intranasal) on day 10. On the last day of dosing, lung tissue was collected and histology was performed to evaluate the extent of inflammation and interstitial fibrosis. In this model, no statistically significant effects were observed at the RTA 408 doses tested (FIGS. 16a & b). Additional evaluation was performed using a rat model of pulmonary fibrosis that has been extensively characterized at the Lovelace Respiratory Research Institute. In this study, rats were challenged with bleomycin or saline by intratracheal administration on day 0. Following the challenge, animals received RTA 408 (3, 10, or 30 mg/kg) daily via oral gavage for 28 days. Administration of the 30-mg/kg dose was stopped on day 14 due to excessive dehydration and diarrhea in the animals. For the remaining animals, bronchoalveolar lavage fluid was collected on day 28 for assessment of pro-inflammatory infiltrates, and lung tissue was analyzed for hydroxyproline levels and histopathology. Challenge with bleomycin sulfate induced a substantial release of neutrophils and an increase in soluble collagen in the BALF, as well as an increase in hydroxyproline in the lung. Treatment with 3 and 10 mg/kg RTA 408 significantly suppressed polymorphonuclear (PMN) cell infiltration into the lungs and also produced a meaningful reduction (~10%-20%) in hydroxyproline deposition (FIGS. 17a & b).

Importantly, histopathological evaluation revealed a significant decrease in collagen deposition, as assessed by trichrsome staining, in rats treated with RTA 408. Whereas bleomycin control animals primarily exhibited moderate staining, animals treated with 10 mg/kg RTA 408 had predominantly minimal to mild staining (Table 2).

TABLE 2

Effect of RTA 408 on collagen deposition in rat lung as assessed by intensity of trichrome staining

| Staining Intensity[a] | Bleomycin Control | RTA 408 (3 mg/kg) | RTA 408 (10 mg/kg) |
|---|---|---|---|
| Minimal | 0 | 0 | 3 |
| Mild | 1 | 0 | 4 |
| Moderate | 7 | 7 | 1 |

[a]Values represent intensity of staining in animals with interstitial trichrome staining in areas of bleomycin-induced lung alterations.

Figure 18:
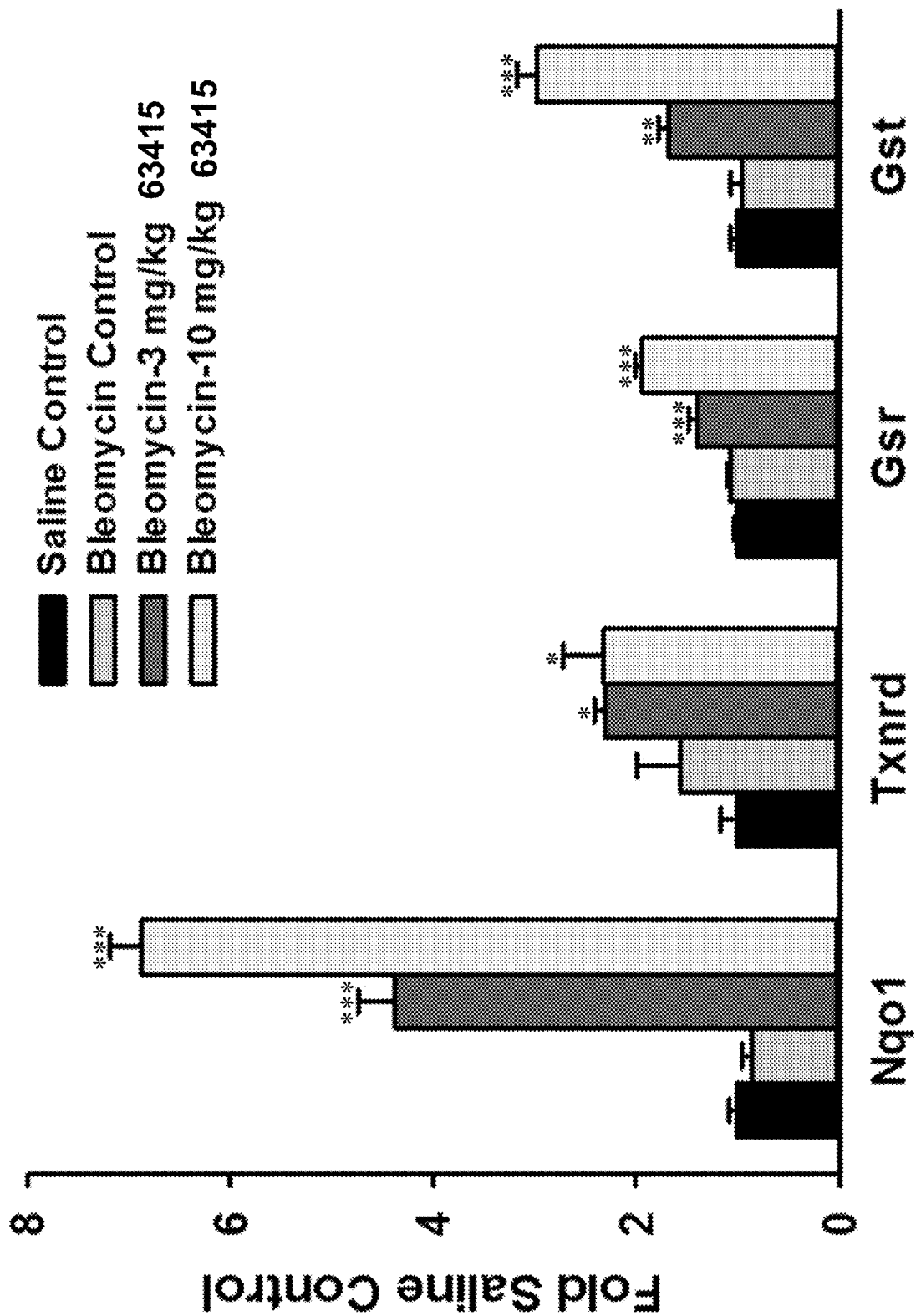
FIG. 18—Effect of RTA 408 on Nrf2 target enzymes in lungs from rats with bleomycin-induced pulmonary fibrosis. Asterisks indicate a statistically significant difference from the saline control group (*P<0.05; P<0.01; *P<0.001).
Figure 19:
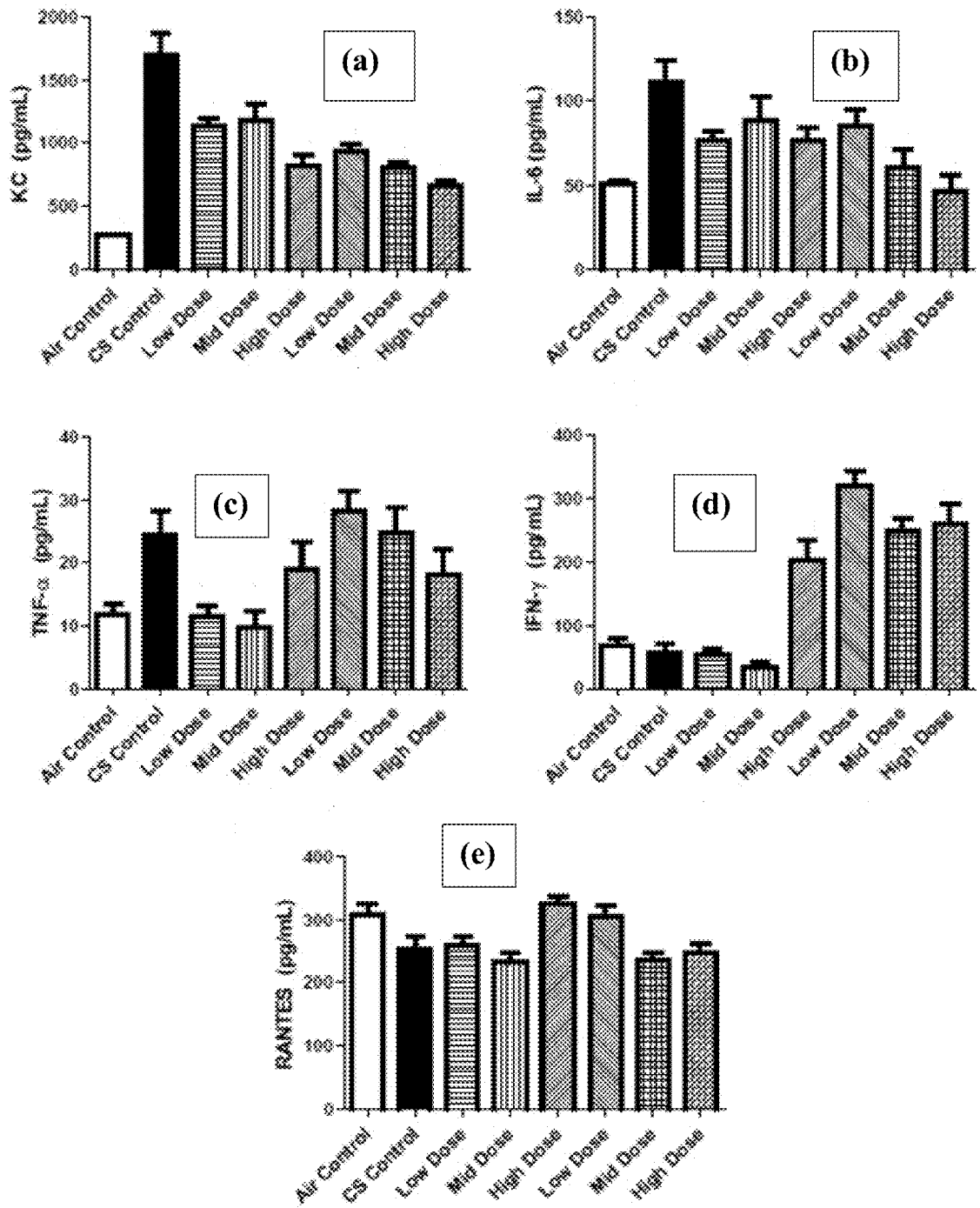
FIGS. 19a-e—Effect of RTA 408 on cigarette smoke-induced COPD in mice: (a) KC; (b) IL-6; (c) TNF-α; (d) IFN-γ; (e) RANTES. RTA 408 (63415) was tested at dose levels of 3 mg/kg (low), 10 mg/kg (mid), and 30 mg/kg (high). An AIM analog (63355) was tested in the same study for comparison. Asterisks indicate a statistically significant difference form the CS control group.

Further evaluation of lungs from rats in this study also revealed meaningful engagement of relevant Nrf2 target genes (FIG. 18). RTA 408 significantly and dose-dependently increased NQO1, Txnrd, Gsr, and Gst enzyme activity in the lungs of rats exposed to bleomycin, demonstrating Nrf2 activation by RTA 408 in this disease setting.

9. Cigarette Smoke-Induced COPD in Mice

RTA 408 was also tested in a mouse model of cigarette smoke-induced COPD. Mice received RTA 408 (3, 10, or 30 mg/kg) daily via oral gavage for two weeks and were exposed to cigarette smoke five days per week during the RTA 408 dosing period. At the end of the study, lung tissue and BALF were collected for analysis of inflammatory infiltrates and cytokines. In this experiment, multiple-dose administration of RTA 408 at doses as low as 3 mg/kg RTA 408 resulted in significant suppression of pro-inflammatory cytokines, including KC (functional mouse homolog of human IL-8) and TNFα. A summary of results from this study is presented in FIGS. 19a-e. An AIM analog (63355) was tested in the same study for comparison. 63355 is a compound of the formula:

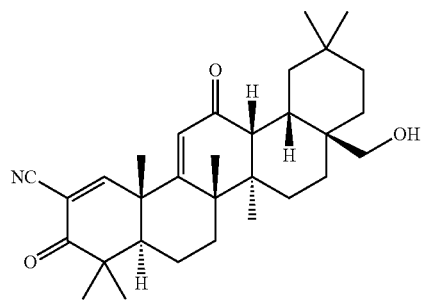

Figure 20:
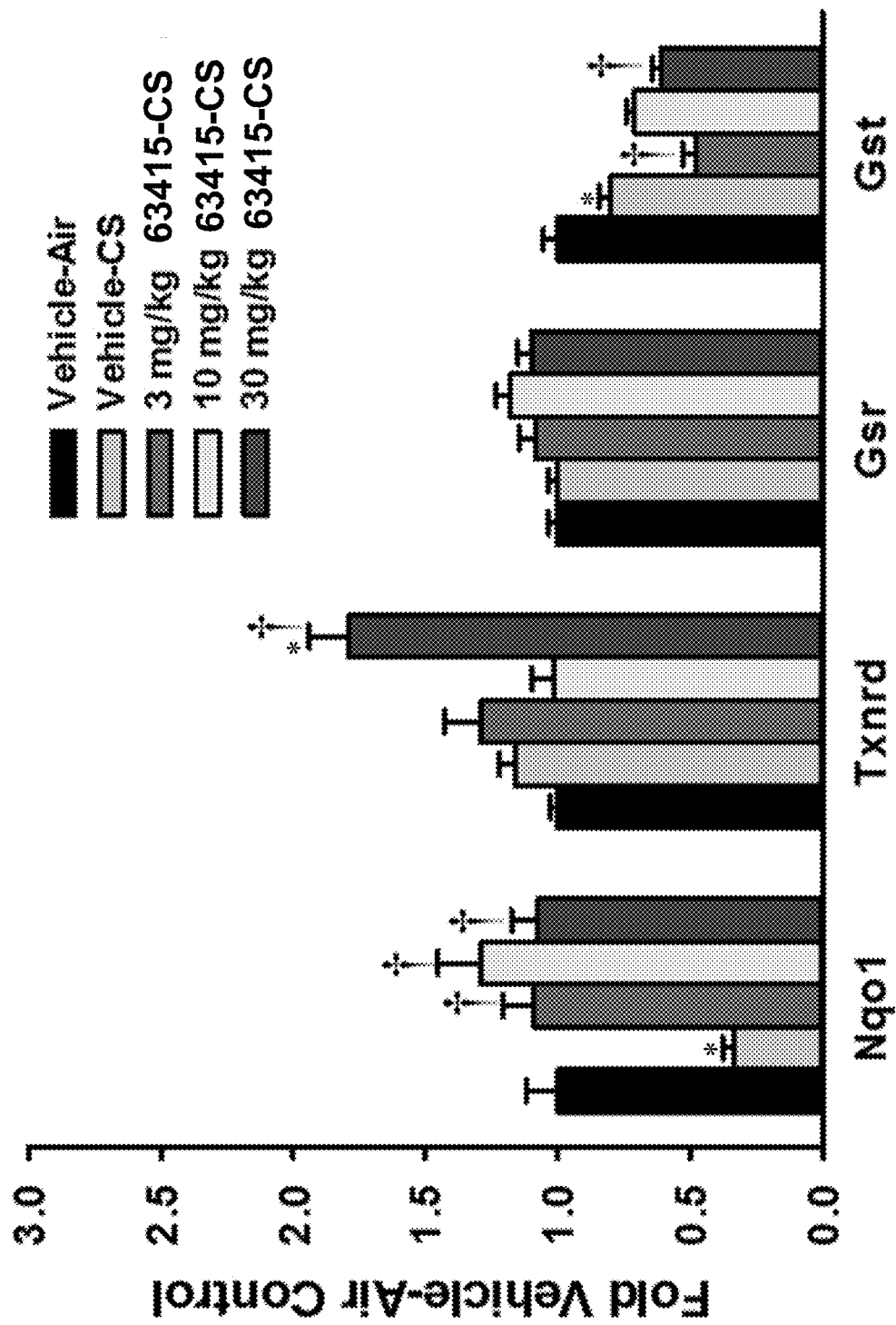
FIG. 20—Effect of RTA 408 on Nrf2 target enzymes in lungs from mice with cigarette smoke-induced COPD. Asterisks indicate a statistically significant difference from the saline control group (*P<0.05; P<0.01; *P<0.001). Daggers represent a statistically significant difference from mice expose to cigarette smoke and administered vehicle (†P<0.05).

Further evaluation of lungs from mice in this study also revealed meaningful engagement of relevant Nrf2 target genes (FIG. 20). NQO1 enzyme activity in the lung was significantly decreased by cigarette smoke exposure; administration of RTA 408 rescued this loss. Txnrd enzyme activity was also induced by the 30 mg/kg dose of RTA 408. In general Gsr enzyme activity was not altered, and Gst enzyme activity was decreased with treatment—both of which were likely the consequence of a temporal response for these enzymes.

10. Ovalbumin-Induced Asthma in Mice

The potential activity of RTA 408 was also evaluated in a pilot study in a mouse model of ovalbumin-induced asthma. Mice were sensitized with an IP injection of ovalbumin and aluminum hydroxide on Day 0 and Day 14 and challenged intranasally with ovalbumin in saline on Days 14, 25, 26, and 27. Mice received RTA 408 (3, 10, or 30 mg/kg) daily via oral gavage on Days 1-13 and 15-27. Following sensitization and challenge with ovalbumin, vehicle-treated mice had a significant increase in the total number of leukocytes compared with positive control (dexamethasone)-treated mice. An increase in the number of T cells and B cells was also observed in the vehicle-treated mice. Treatment with RTA 408 at 30 mg/kg significantly reduced the number and percentage of B cells within the airways. RTA 408 (3 and 30 mg/kg) also significantly reduced the number of macrophages, but not the mean percentage of macrophages, detected in the airways. These observations are suggestive of potential efficacy in this model.

11. Effects of RTA 408 on LPS-Induced Sepsis in Mice

Sepsis was induced on Day 0 with an IP injection of LPS (21 mg/kg), and survival was followed until Day 4. RTA 408 (10, 30, or 100 mg/kg) was administered daily via oral gavage from Day −2 to Day 2. In the vehicle control group, 60% of the animals survived until Day 4 (higher than the ~40% survival rate expected in this model). In the RTA 408 treatment groups, 80% of the animals in the 10 mg/kg dose group and 90% of the animals in the 30 mg/kg dose group survived until Day 4 (FIGS. 21c & d). For the 100 mg/kg dose group, 90% of the animals survived until Day 4, with only a single death occurring on Day 4. Although these RTA 408-induced effects are indicative of profound efficacy in this model, the relatively high survival rate in the vehicle control group precluded a statistically-significant difference between the control and RTA 408-treated groups. Results obtained using the compound RTA 405 are also presented (FIGS. 21a & b). RTA 405 is a compound of the formula:

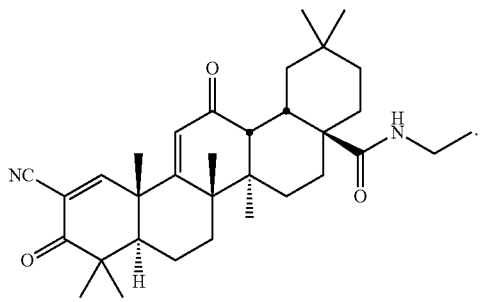

12. Effects of RTA 408 Against Radiation-Induced Oral Mucositis

Figure 22:
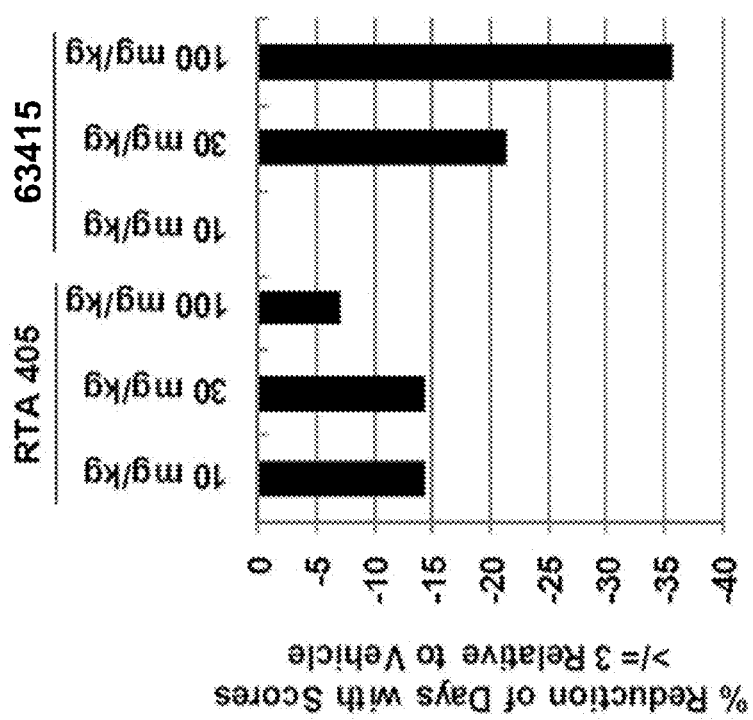
FIG. 22—RTA 408 activity in a model of radiation-induced oral mucositis. RTA 405 or RTA 408 (63415) was administered BID×20 on Days −5 to −1 and Days 1 to 15 to male Syrian Golden Hamsters. Radiation occurred on Day 0. Mucositis scores range from 0 to 5 based on clinical manifestations (0: completely healthy; 1-2: light to severe erythema; 3-5: varying degrees of ulceration). RTA 408 (63415) meaningfully improved mucositis at 30 mg/kg and 100 mg/kg with up to a 36% reduction in ulceration.

Exposure to acute radiation directed to the buccal cheek pouch of hamsters produces effects similar to those observed in oral ulcerative mucositis in humans. These effects include moderate to severe mucositis characterized by severe erythema and vasodilation, erosion of the superficial mucosa, and formation of ulcers. A single study was conducted to evaluate the effects of RTA 408 in this model. On Day 0, each hamster was given an acute radiation dose of 40 Gy directed to the left buccal cheek pouch. RTA 408 (10, 30, or 100 mg/kg) was orally administered twice daily from Day −5 to Day −1, and Day 1 to Day 15. Beginning on Day 6 and continuing until Day 28 on alternate days, oral mucositis was evaluated using a standard 6-point scoring scale. Both the 30 and 100 mg/kg doses of RTA 408 caused a significant reduction in the duration of ulcerative mucositis (FIG. 22). Furthermore, a dose-dependent decrease in the percentage of animals with mucositis scores ≥3 was also observed. However, administration of RTA 408 at 30 or 100 mg/kg caused significant dose-dependent reductions in weight gain in irradiated hamsters. Due to weight loss in excess of 20%, two out of eight hamsters in the 100 mg/kg dose group were euthanized on Day 2.

13. Effect of RTA 408 on the Induction of Nrf2 Biomarkers In Vivo

As described above, a key molecular target of RTA 408 is Nrf2, a central transcriptional regulator of antioxidative cellular protection. Activation of Nrf2 induces upregulation of a battery of cytoprotective genes, including NQO1, enzymes involved in GSH synthesis [i.e., glutamate-cysteine ligase catalytic and modifier subunits (Gclc and Gclm)], enzymes involved in detoxification (i.e., glutathione S-transferases [Gsts]), and efflux transporters [i.e., multidrug resistance-associated proteins (Mrps)]. Induction of these genes results in a coordinated cellular effort to protect against oxidative insult, highlighted by increased antioxidative capacity, induction of glutathione synthesis, and conjugation and export of potentially harmful molecules from the cell. In addition to the efficacy endpoints and Nrf2 target gene expression evaluated in the various animal models described above, the ability of RTA 408 to induce expression of Nrf2 target genes was also assessed using tissues collected from healthy RTA 408-treated mice, rats, and monkeys.

As part of the non-GLP 14-day toxicity studies of RTA 408 in mice, rats, and monkeys, tissues were collected for the purposes of measuring mRNA and enzyme activity levels of selected Nrf2 target genes. For mice and rats, liver samples were collected 4 hours after the final dose on Day 14. For monkeys, blood (for PBMC isolation), liver, lung, and brain tissue were collected 24 hours after the final dose on Day 14. Enzyme activity for NQO1, Gst, and glutathione reductase (Gsr) were measured in tissue homogenates. Levels of mRNA were determined using QUANTIGENE® Plex 2.0 technology, which involves a hybridization-based assay using XMAP® LUMINEX® magnetic beads for direct quantification of mRNA targets. In addition, RTA 408 concentrations were measured in plasma and tissues by LC/MS/MS methods.

Figure 23:
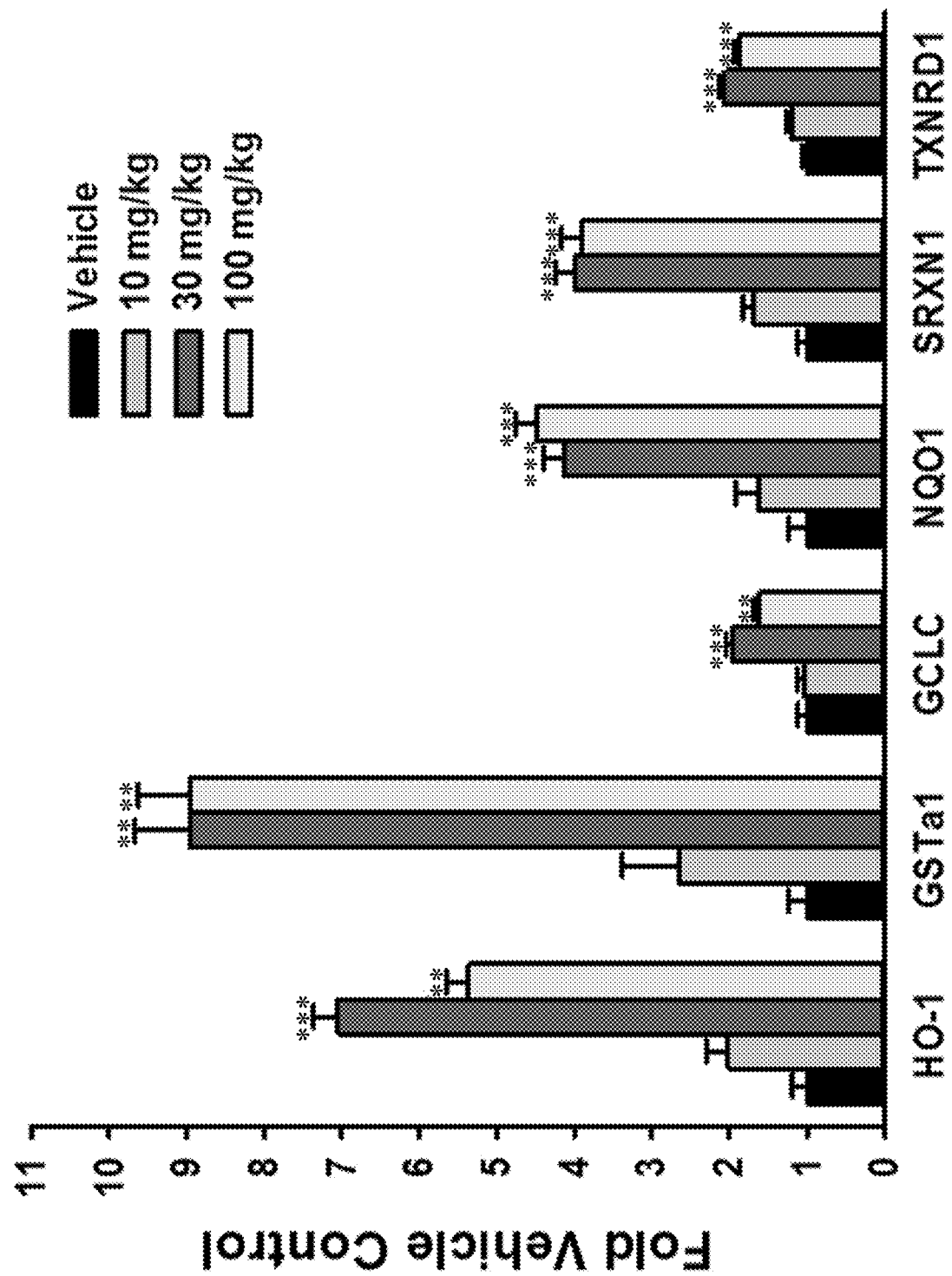
FIG. 23—Nrf2 target gene induction consistent from RTA 408 (63415) 14-day mouse toxicity study in C57BL/6 mice. mRNA of Nrf2 target genes assessed in livers of mice treated PO QD×14. Substantial increases in mRNA expression for multiple Nrf2 target genes were observed and were consistent with tissue exposure.

RTA 408 generally increased the expression of various Nrf2 target genes in a dose-dependent manner at doses of 10, 30, and 100 mg/kg (FIG. 23, FIG. 24a, FIGS. 25a & b). Transcriptional upregulation of Nrf2 target genes by RTA 408 also resulted in functional increases in the antioxidant response, as manifested by dose-dependent increases in NQO1, Gst, and Gsr enzyme activity in rodent liver, as well as monkey liver and lung (FIGS. 26a & b, FIGS. 27a & b, FIGS. 28a & b). Furthermore, in rodents liver exposure of RTA 408 correlated with the level of enzyme activity of NQO1, the prototypical target gene for Nrf2 (FIG. 29b, FIG. 30b). In monkeys, the level of mRNA expression in PBMCs of both NQO1 and sulfiredoxin 1 (SRXN1) correlated with plasma exposure to RTA 408 (FIGS. 34a & b). Overall, RTA 408 increased mRNA levels and activity of Nrf2 targets, and such increases generally correlated with tissue and plasma exposures, suggesting Nrf2 targets may serve as feasible biomarkers for Nrf2 activation (FIGS. 31a & b) and may be useful for assessing pharmacological activity of RTA 408 in healthy human subjects.

D. Safety Pharmacology

A GLP-compliant safety pharmacology program was completed using RTA 408. This included in vitro and in vivo (monkey) studies on the cardiovascular system, as well as studies on the respiratory system and central nervous system in rats.

2. Evaluation of the Effects of RTA 408 on Cloned hERG Channels Expressed in HEK293 Cells This study was conducted to assess the effects of RTA 408 on the rapidly activating inward rectifying potassium current ($I_{Kr}$) conducted by hERG (human ether-a-go-go-related gene) channels stably expressed in the human embryonic kidney (HEK293) cell line. The effects of RTA 408 on the hERG-related potassium current were assessed using whole-cell patch clamp electrophysiology methods. RTA 408 was determined to have $IC_{50}$ value of 12.4 CpM in a hERG QPatch_Kv11.1 assay. This value was 2.5-3 fold higher than the values for 63170 (4.9 μM) and 63189 (3.8 μM), respectively. The RTA 408 $IC_{50}$ value was similar to the 63171 value (15.7 μM).

3. Cardiovascular Evaluation of RTA 408 in the Cynomolgus Monkey

A single study was conducted to evaluate the potential cardiovascular effects of RTA 408 in conscious freely moving cynomolgus monkeys. The same four male and four female cynomolgus monkeys were administered the vehicle (sesame oil) and RTA 408 at dose levels of 10, 30, and 100 mg/kg according to a Latin square design, with one animal/sex/treatment dosed each week followed by a 14-day washout period between administrations, until each animal received all treatments. Vehicle and RTA 408 were administered to all animals via oral gavage at a dose volume of 5 mL/kg.

Animals were instrumented with telemetry transmitters for measurement of body temperature, blood pressure, heart rate, and electrocardiogram (ECG) evaluation. Body temperature, systolic, diastolic, and mean arterial blood pressure, heart rate, and ECG parameters (QRS duration and RR, PR, and QT intervals) were monitored continuously from at least 2 hours pre-dose until at least 24 hours post-dose. ECG tracings were printed at designated time points from the cardiovascular monitoring data and were qualitatively evaluated by a board-certified veterinary cardiologist. Prior to the first administration on study, untreated animals were continuously monitored for cardiovascular endpoints for at least 24 hours, and these data were used in the calculation of the corrected QT interval throughout the study.

Observations for morbidity, mortality, injury, and availability of food and water were conducted at least twice daily for all animals. Clinical observations were conducted pre-dose, approximately 4 hours post-dose, and following completion of the cardiovascular monitoring period. Body weights were measured and recorded on the day prior to each treatment administration.

RTA 408 at dose levels of 10, 30, and 100 mg/kg did not produce mortality, adverse clinical signs, or result in meaningful changes in body weight (FIG. 32), body temperature, blood pressure, or qualitative or quantitative (PR, RR, QRS, QT intervals) ECG parameters. In the 100 mg/kg dose group, a small (1.6% on average) but statistically significant increase in the corrected QT interval was observed; however, individual animal data did not show consistent increases in QTc that would indicate a test article related effect. Consequently, due to the small magnitude of change and lack of a consistent response in individual animals, these slight increases in QTc were not considered to be related to RTA 408 treatment. Therefore, oral administration of RTA 408 produced no effects on cardiovascular function in cynomolgus monkeys at doses up to and including 100 mg/kg.

4. Neurobehavioral Evaluation of RTA 408 in Rats

The potential acute neurobehavioral toxicity of RTA 408 was evaluated in rats. Three treatment groups of 10 male and 10 female CD® [CRL:CD® (SD)] rats received RTA 408 at dose levels of 3, 10, or 30 mg/kg. One additional group of 10 animals/sex served as the control and received vehicle (sesame oil). Vehicle or RTA 408 was administered to all groups via oral gavage once on Day 1 at a dose volume of 10 mL/kg.

Observations for morbidity, mortality, injury, and availability of food and water were conducted twice daily for all animals. Observations for clinical signs were conducted prior to dosing on Day 1 and following each functional observational battery (FOB) evaluation. FOB evaluations were conducted pre-dose (Day −1) and at approximately 4 and 24 hours post-dose. Body weights were measured and recorded pre-dose on Day 1.

RTA 408 at doses of 3, 10, and 30 mg/kg did not produce mortality, adverse clinical observations, or effects on any of the neurobehavioral measures tested. Slight decreases in body weight gain were observed approximately 24 hours after dosing in the 30 mg/kg group that may potentially be test article-related. With respect to the basic neurobehavioral endpoints evaluated in this study, RTA 408 did not produce any adverse effects in rats at doses up to and including 30 mg/kg.

5. Pulmonary Evaluation of RTA 408 in Rats

The potential effect of RTA 408 on pulmonary function was evaluated in rats. Three treatment groups of eight male and eight female CD® [CRL:CD® (SD)] rats received RTA 408 at dose levels of 3, 10, or 30 mg/kg. One additional group of eight animals/sex served as the control and received vehicle (sesame oil). Vehicle or RTA 408 was administered to all groups via oral gavage once on Day 1 at a dose volume of 10 mL/kg.

Observations for mortality, morbidity, injury, and availability of food and water were conducted twice daily for all animals. Clinical observations were conducted prior to dosing, approximately 4 hours post-dose, and following completion of the 8-hour pulmonary monitoring period. Body weights were measured and recorded on the day of RTA 408 administration. Pulmonary function (respiratory rate, tidal volume, and minute volume) was monitored for at least 1 hour prior to dosing to establish a baseline and for at least 8 hours post-dose.

RTA 408 at doses of 3, 10, and 30 mg/kg did not produce mortality, adverse clinical observations, or effects on any of the pulmonary parameters evaluated. Therefore, with respect to the basic pulmonary endpoints evaluated in this study, RTA 408 did not produce any adverse effects in rats at doses up to and including 30 mg/kg.

E. Nonclinical Overview

1. Pharmacokinetics

RTA 408 has been investigated both in vitro and in vivo to assess its PK and metabolism properties. In vitro studies have been conducted to determine RTA 408 plasma protein binding and blood/plasma partitioning, cytochrome P450 (CYP450) inhibition and induction, and to identify metabolites formed by liver microsomes of mice, rats, monkeys, and humans. Data pertaining to the in vivo absorption and distribution following repeated administration of RTA 408 has been obtained primarily through monitoring of drug levels in plasma and select tissues from toxicology studies. Sensitive and selective liquid chromatography-mass spectrometry-based bioanalytical methods (LC/MS/MS) have been used to measure concentrations of RTA 408 in plasma, blood, and tissues with appropriate accuracy and precision.

a. Absorption

The absorption and systemic pharmacokinetic behavior of RTA 408 was studied in mice, rats, and monkeys following single and repeated (daily) oral administration. Following oral administration of a suspension formulation at doses of 10 to 100 mg/kg, maximal concentrations were observed within 1 to 2 hours in mice, and within 1 to 24 hours in rats and monkeys. Systemic exposure to RTA 408 tended to be highest in rats, with lower levels observed in mice and monkeys. Estimates of the apparent terminal half-life of RTA 408 observed after oral administration were generally in the 6- to 26-hour range, though the apparent prolonged absorption phase in some instances precluded calculation of a definitive half-life estimate.

Systemic exposure to RTA 408 was generally similar in males and females. Exposure to RTA 408 following repeated daily oral administration tended to be slightly higher (≤2-fold) than the exposure observed after a single dose. Administration of RTA 408 over a dose range from 3 to 100 mg/kg in a suspension formulation generally resulted in dose-proportional increases in systemic exposure. However, administration of higher doses (100 to 800 mg/kg in monkeys; 500 to 2000 mg/kg in rats) did not result in similar increases in exposure, suggesting saturation of absorption at doses above 100 mg/kg. Following oral administration of an unoptimized (loose-filled) capsule formulation of RTA 408 (3 mg/kg) to monkeys, dose-normalized systemic exposure tended to be somewhat lower than that observed with a suspension formulation.

The absorption and systemic pharmacokinetic behavior of RTA 408 was studied in rats using single and repeated topical administration. The administration of RTA 408 over a range of 0.01 to 3% showed lower plasma concentrations relative to similar oral dosing. The systemic exposure to RTA 408 generally increased in a dose dependent manner.

The topical administration was formulated as a suspension in sesame oil.

Figure 33:
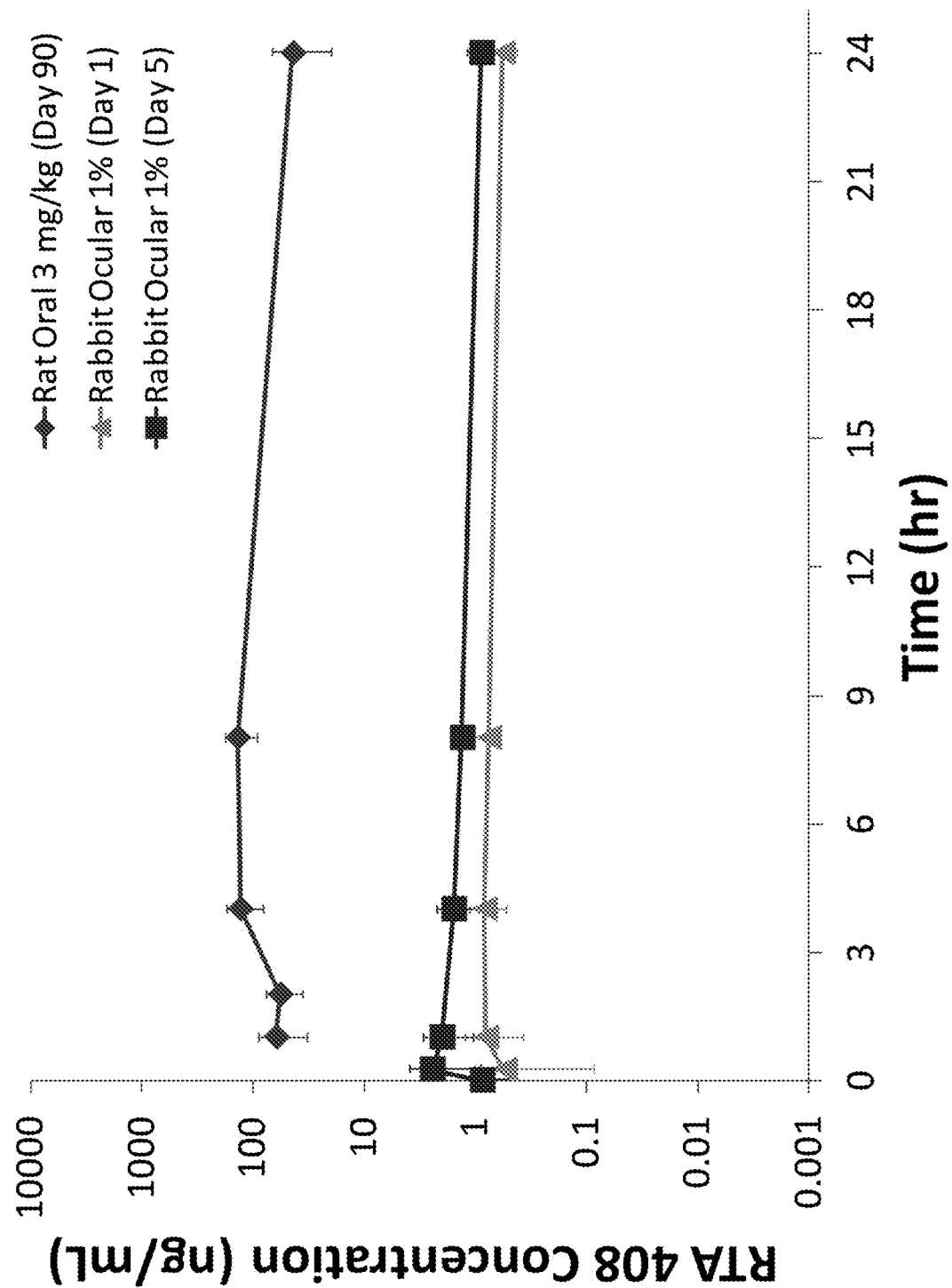
FIG. 33—Plasma concentration of RTA 408 after topical ocular and oral administrations at different times after dosing. The plasma concentration of RTA 408 was also measured after 5 days of daily topical ocular administration of RTA 408 and determined to remain relatively consistent from the measurements taken after the first day.

Using rabbits, the ocular absorption and systemic pharmacokinetic behavior of RTA 408 was evaluated. RTA 408 was administered topically to the eye once per day for 5 days. The ocular administration showed lower plasma concentration of RTA 408 relative to when RTA 408 is administered orally (FIG. 33). The amount of RTA 408 in the plasma even after five consecutive days showed only a small change compared to the concentration after the first dose relative to when RTA 408 was administered orally, where plasma concentrations were almost 100 fold higher (FIG. 33).

b. Distribution

Plasma protein binding of RTA 408 was evaluated in mouse, rat, rabbit, dog, minipig, monkey, and human plasma at RTA 408 concentrations of 10-2000 ng/mL using ultracentrifugation methodology. RTA 408 was extensively bound to plasma proteins. Plasma protein binding in the nonclinical species ranged from 93% (mouse) to >99% (minipig), with binding of 95% in the toxicology species (rat and monkey) and 97% in human. There was no evidence of concentration-dependent protein binding in any species tested. Results from blood-to-plasma partitioning experiments indicate that RTA 408 tended to distribute primarily in the plasma fraction of blood in a linear manner, with blood:plasma ratios <1.0 for all species and all concentrations tested.

The distribution of RTA 408 into tissues has been investigated after oral administration to mice, rats, and monkeys. In the 14-day non-GLP toxicity studies, select tissues (liver, lung, and brain) were collected at a single time point (4 hours for rat and mouse; 24 hours for monkey) after the final dose of the study was administered and were analyzed for RTA 408 content using LC/MS/MS. RTA 408 readily distributes into lung, liver, and brain. In lung, RTA 408 concentrations at 4 hours in mice and rats were similar to or slightly higher (<2-fold) than concentrations in plasma, while at 24 hours in monkeys, RTA 408 concentrations in lung were 6- to 16-fold higher than plasma concentrations. A similar pattern was observed for brain. In contrast, RTA 408 concentrations in liver were 5- to 17-fold higher than plasma for mice and rats at 4 hours, and 2- to 5-fold higher than plasma at 24 hours in monkeys.

The pharmacodynamic effects of RTA 408 in tissues were assessed in mice, rats, and monkeys, by monitoring the induction of Nrf2 target genes in the same tissues collected for drug exposure from the 14-day toxicity studies. Induction of Nrf2 target genes by RTA 408 resulted in increases in the antioxidant response as manifested by dose-dependent increases in NQO1, glutathione S-transferase (Gst), and glutathione reductase (Gsr) enzyme activity in the examined tissues. Furthermore, in rodents, RTA 408 liver content correlated with the level of enzyme activity for NQO1, the prototypical target gene for Nrf2. In monkeys, the level of mRNA expression in peripheral blood mononuclear cells (PBMCs) for both NQO1 and sulfiredoxin 1 (SRXN1) correlated with plasma exposure of RTA 408 (FIGS. 34a & b). Overall, RTA 408 induced biomarkers of Nrf2 in rodents and monkeys, and such inductions generally correlated well with tissue and plasma exposure to RTA 408.

Figure 35:
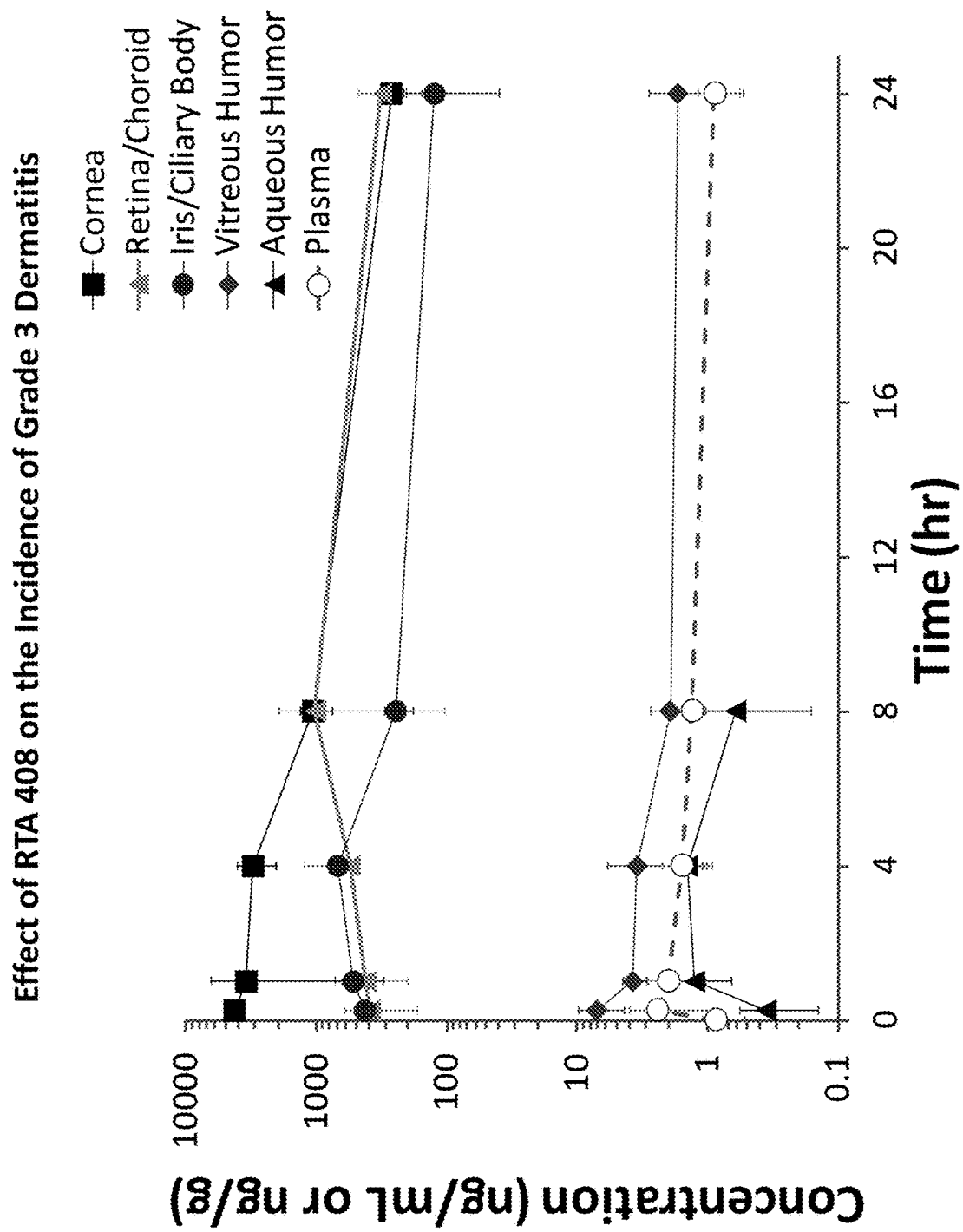
FIG. 35—Concentration of RTA 408 in various different tissues or fluids within the eye as a function of time after 5 days of topical ocular dosing. RTA 408 concentration in plasma was also measured after topical ocular administration.
Figure 36:
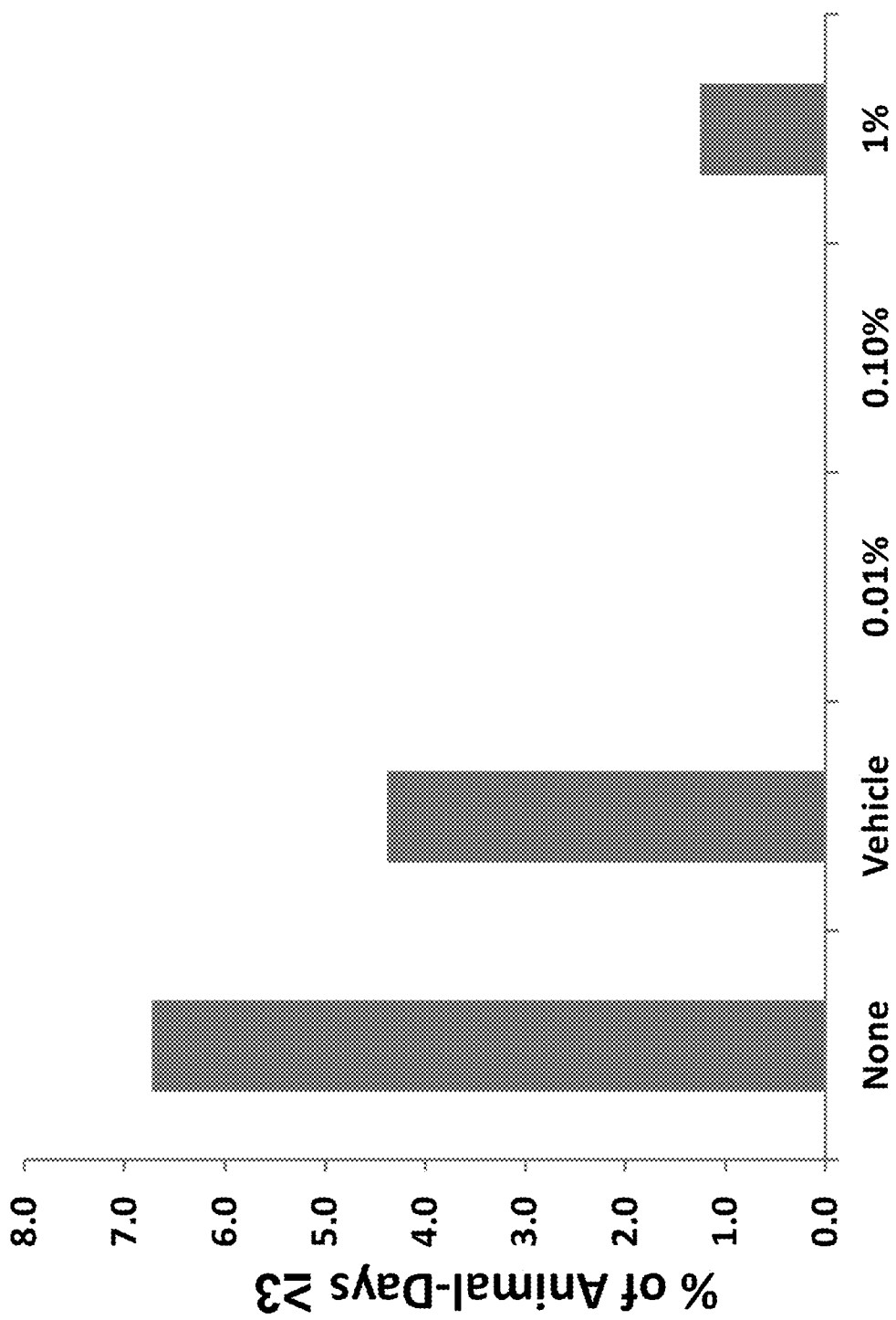
FIG. 36—Effect of RTA 408 on the incidence of grade 3 dermatitis caused by acute radiation exposure for different concentrations of RTA administered topically.
Figure 37:
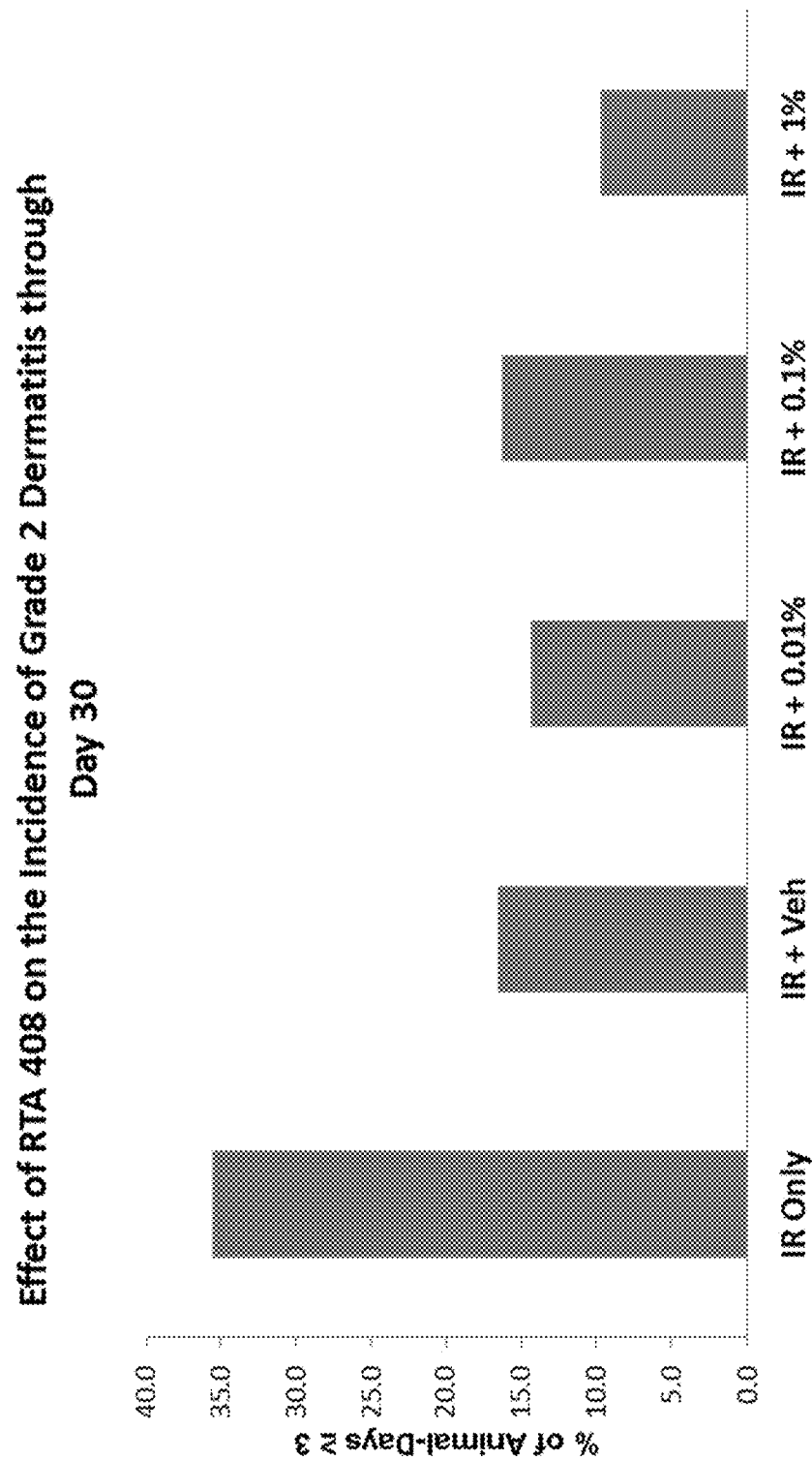
FIG. 37—Effect of RTA 408 on the incidence of grade 2 dermatitis over the course of 30 days caused by acute radiation exposure for different concentrations of RTA administered topically.
Figure 38:
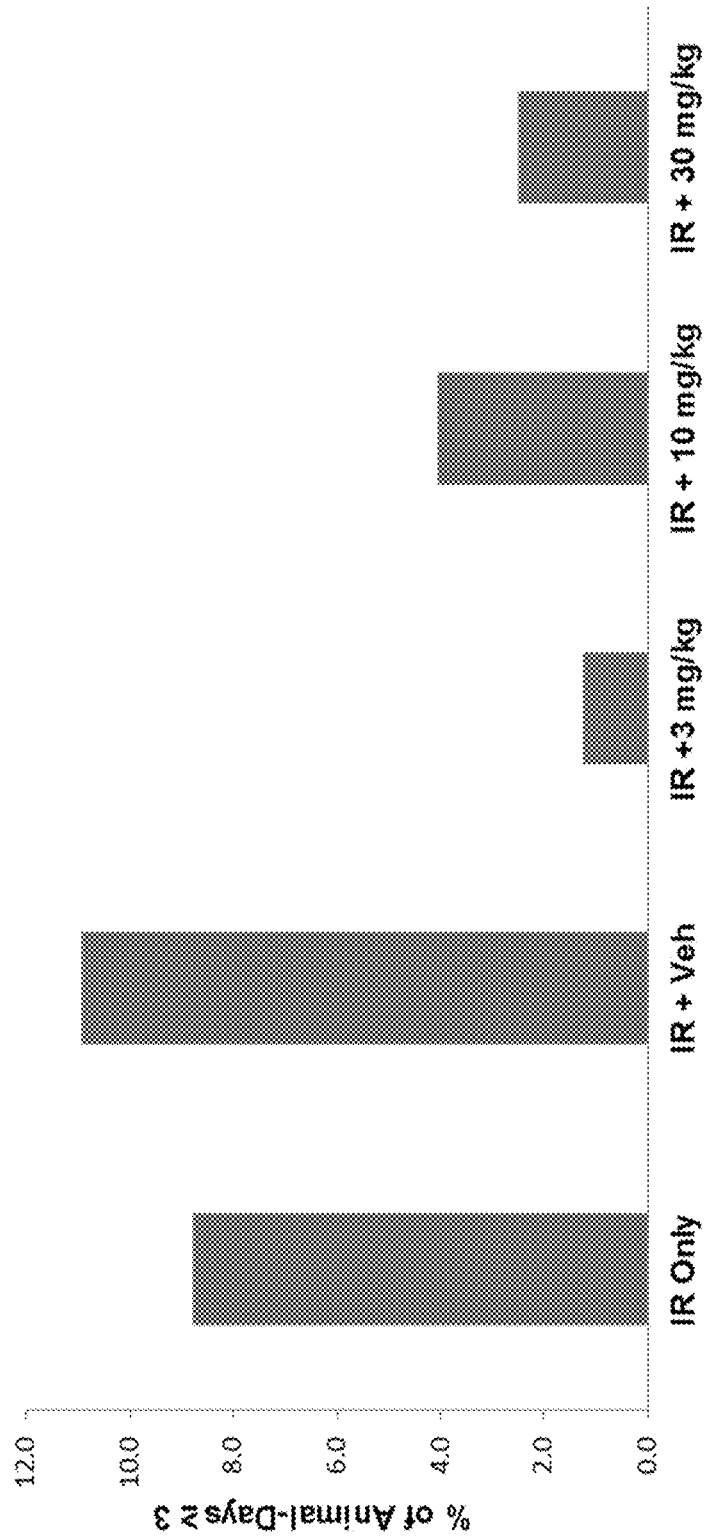
FIG. 38—Effect of RTA 408 on the incidence of grade 3 dermatitis over the course of 28 days caused by acute radiation exposure for different concentrations of RTA administered orally.
Figure 39A:
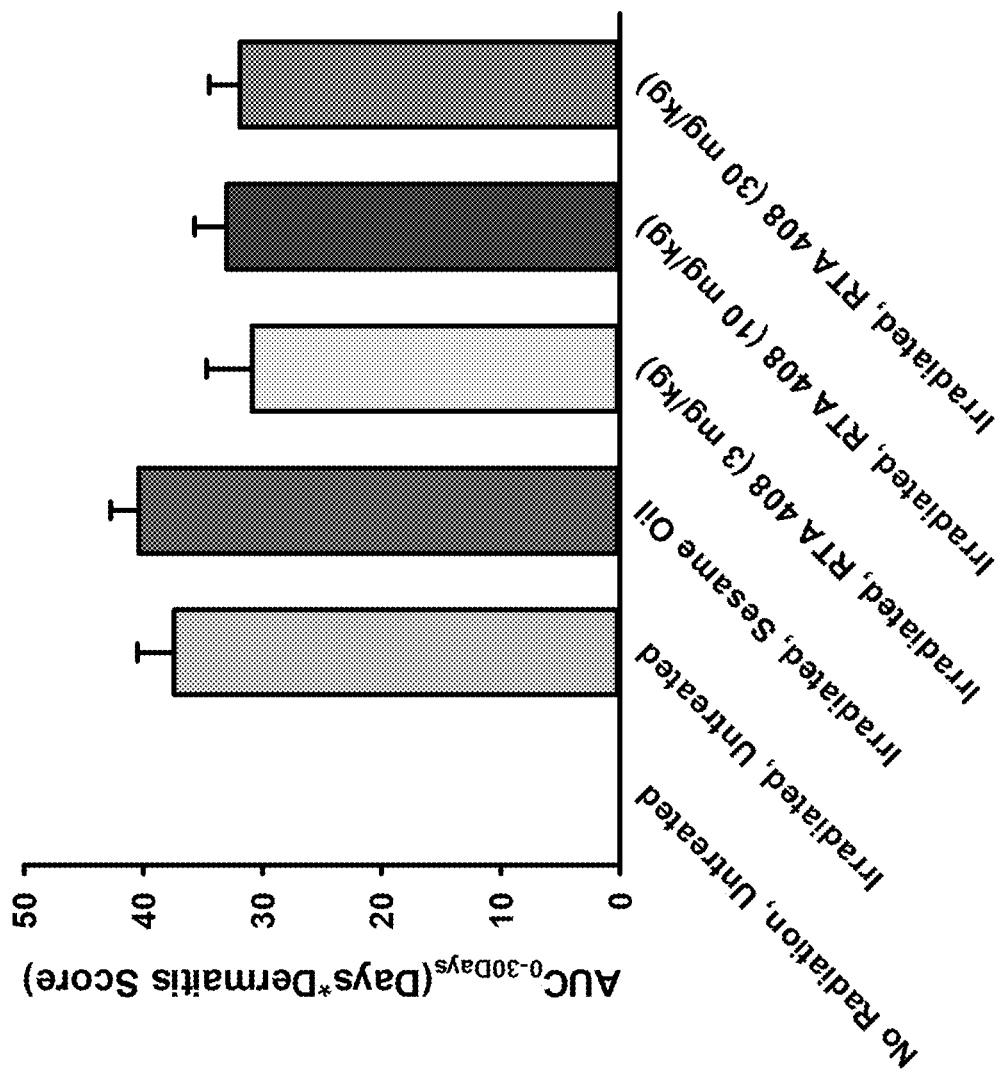
FIGS. 39a & b—a) An area under the curve analysis of clinical score of the dermatitis as a function of time for each of the different control groups including all of the animals used in the test. b) An area under the curve analysis of the clinical score of the dermatitis as a function of the duration of that score for each of the different control groups including only animals that completed the entire 30 days in the trial.
Figure 39B:
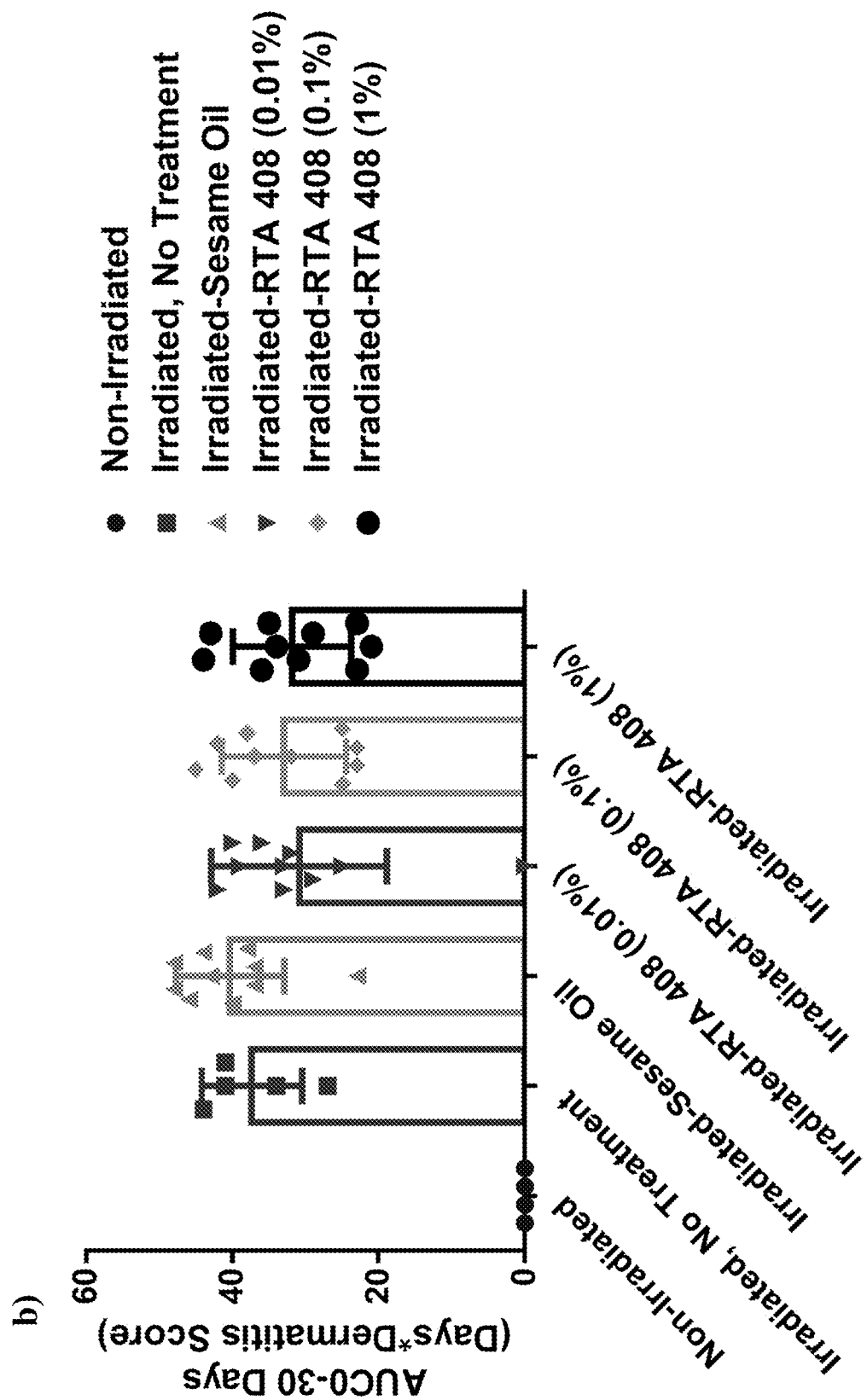

When RTA 408 was administered to rabbits via ocular topical administration, the highest concentrations of the compound were found in the cornea, retina, or iris while the vitreous humor, aqueous humor, and plasma showed significantly lower concentrations of RTA 408 (FIG. 35).

c. Metabolism

The metabolism of RTA 408 has been investigated after in vitro incubation of RTA 408 for 60 minutes with liver microsomes from mice, rats, monkeys, and humans in the presence of a nicotinamide adenine dinucleotide phosphate (NADPH)-regenerating system and a uridine diphosphate glucuronosyltransferase (UGT) reaction mixture. Extensive turnover of RTA 408 was observed with primate microsomes, with <10% of the parent molecule remaining at the end of the 60-minute incubation in both monkey and human microsomes. In contrast, the extent of metabolism was lower in rodent microsomes, with >65% of the parent molecule remaining at the end of the incubation. The lack of available authentic standards for the various potential metabolites of RTA 408 precluded quantitative evaluation of the observed metabolites. From a qualitative perspective, a similar pattern of RTA 408 metabolites was observed across species, and included peaks with masses consistent with reduction and hydroxylation of RTA 408 as well as glucuronidation of RTA 408 or of its reduction/hydroxylation metabolites. No unique human metabolites were observed, with all peaks in the human microsome incubations also being observed in one or more of the preclinical species. In particular, based on in vitro microsome data, all human metabolites were present in rat or monkey, the selected rodent and non-rodent toxicity species.

d. Pharmacokinetic Drug Interactions

The potential for RTA 408 to inhibit cytochrome P450 (CYP450)-mediated metabolism was evaluated using pooled human liver microsomes and standard substrates for specific CYP450 enzymes. RTA 408 directly inhibited CYP2C8 and CYP3A4/5 with $K_i$ values of approximately 0.5 µM for each enzyme. No meaningful inhibition was observed for the other enzymes tested (CYP1A2, CYP2B6, CYP2C9, CYP2C19, or CYP2D6), with inhibition <50% at the highest concentration tested (3 µM). In addition, there was little or no evidence of metabolism-dependent inhibition of any of the enzymes tested. Future studies investigating the potential for CYP3A4/5-mediated drug-drug interactions may be warranted based on these data, and the potentially high concentrations that may be achieved locally in the gastrointestinal (GI) tract after oral administration.

The potential for RTA 408 to induce CYP450 enzyme expression was evaluated using cultured human hepatocytes. Under conditions where prototypical inducers caused the expected increases in CYP activity, RTA 408 (up to 3 µM) was not an inducer of CYP1A2, CYP2B6, or CYP3A4 enzyme activity in cultured human hepatocytes.

F. Effects of RTA 408 on Acute Radiation Dermatitis

The effects of RTA 408 as a topical or oral preventative for acute radiation dermatitis have been examined. Using male BALB/c mice, a 30 Gy dose of radiation was administered on day 0 (Table 3). The sesame oil vehicle or RTA 408 was administered to the rats on day −5 to −1 and days 1 to 30. RTA 408 was administered both orally in 3, 10, and 30 mg/kg in sesame oil and topically in percentage composition of 0.01, 0.1, and 1% in sesame oil. The dermatitis was blindly evaluated every other day from day 4 to day 30. On day 12, the typical peak of dermatitis was observed and 4 mice were sacrificed 4 hours after administration of the dose. The remaining mice were sacrificed on day 30 at 4 hours postdose. Plasma was collected on days 12 and 30 as well as irradiated skin samples for mRNA and histological examination.

TABLE 3

Study Design for Acute Radiation Dermatitis Model

| Group | Number of Animals | Radiation (Day 0) | Treatment | Treatment Schedule |
|---|---|---|---|---|
| 1 | 9 males | — | Untreated | — |
| 2 | 10 males | 30 Gy | Untreated | — |
| 3 | 14 males | 30 Gy | Vehicle Control (sesame oil) | Day −5 to −1 & Day 1 to 30 |
| 4 | 14 males | 30 Gy | RTA 408 - 0.01% or 3 mg/kg | Day −5 to −1 & Day 1 to 30 |
| 5 | 14 males | 30 Gy | RTA 408 - 0.1% or 10 mg/kg | Day −5 to −1 & Day 1 to 30 |
| 6 | 14 males | 30 Gy | RTA 408 - 1% or 30 mg/kg | Day −5 to −1 & Day 1 to 30 |

Figure 40:
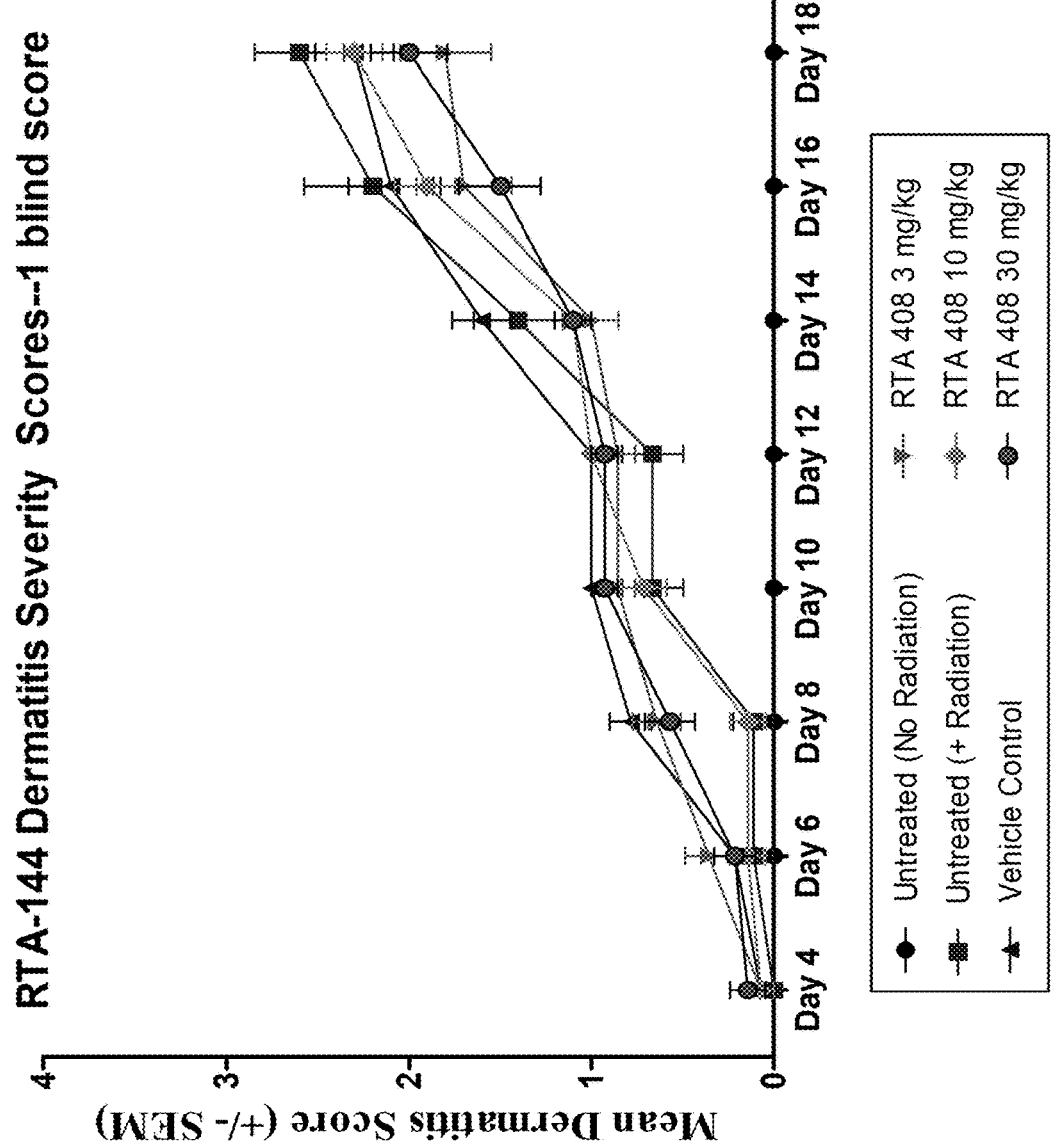
FIG. 40—Average $1^{st}$ blind score of the acute radiation dermatitis as a function of time for untreated, untreated with no radiation exposure, vehicle only and three oral amounts of RTA 408 at 3, 10 and 30 mg/kg. The dermatitis score is based upon the scale that 0 is completely healthy, 1-2 exhibits mild to moderate erythema with minimal to slight desquamation, 3-4 exhibits moderate to severe erythema and desquamation, and 5 exhibits a frank ulcer.
Figure 41:
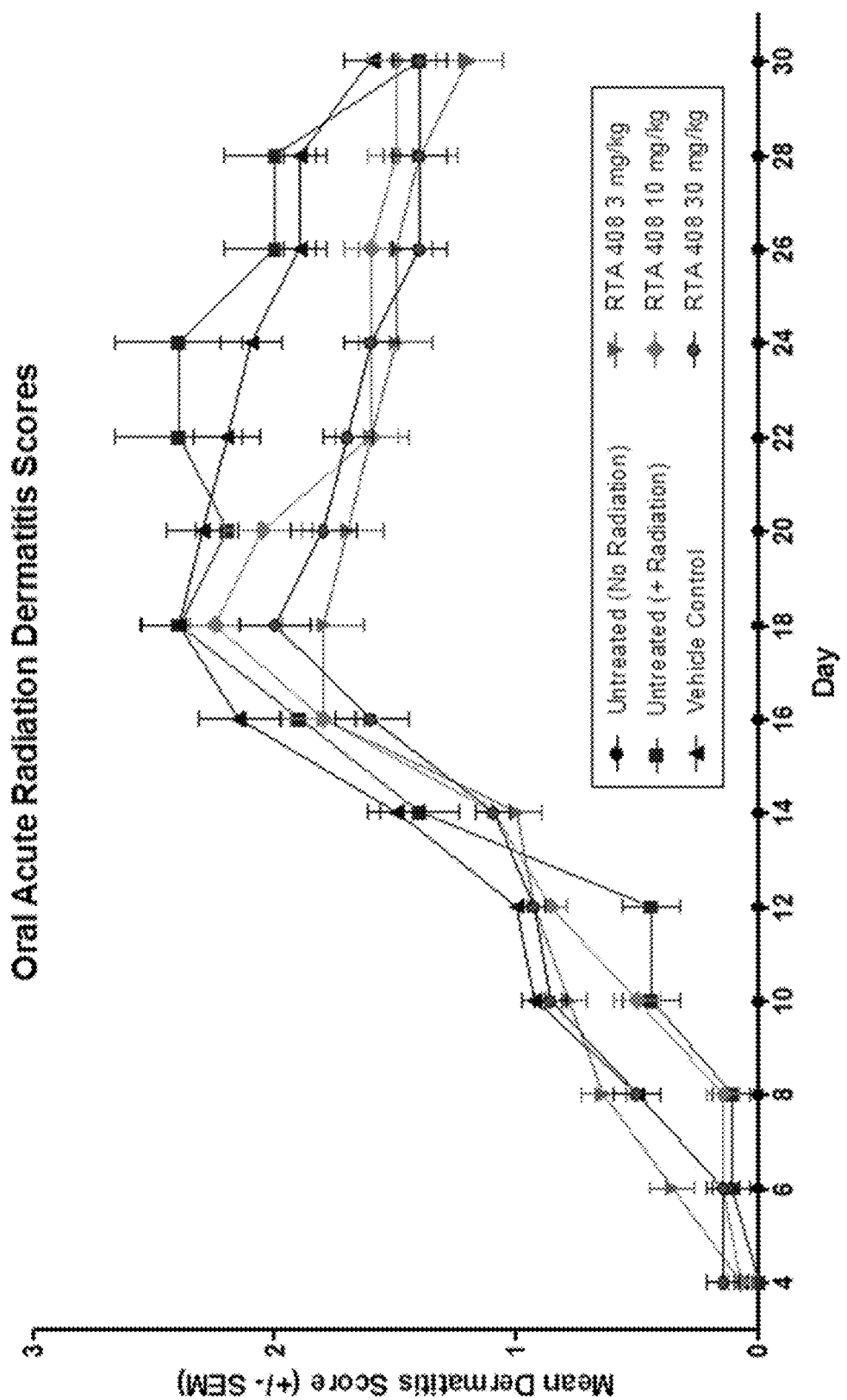
FIG. 41—Mean score of the acute radiation dermatitis as a function of time for untreated, untreated with no radiation exposure, vehicle only and three oral amounts of RTA 408 at 3, 10 and 30 mg/kg measured every other day from day 4 to day 30. The dermatitis score is based upon the scale that 0 is completely healthy, 1-2 exhibits mild to moderate erythema with minimal to slight desquamation, 3-4 exhibits moderate to severe erythema and desquamation, and 5 exhibits a frank ulcer.
Figure 42:
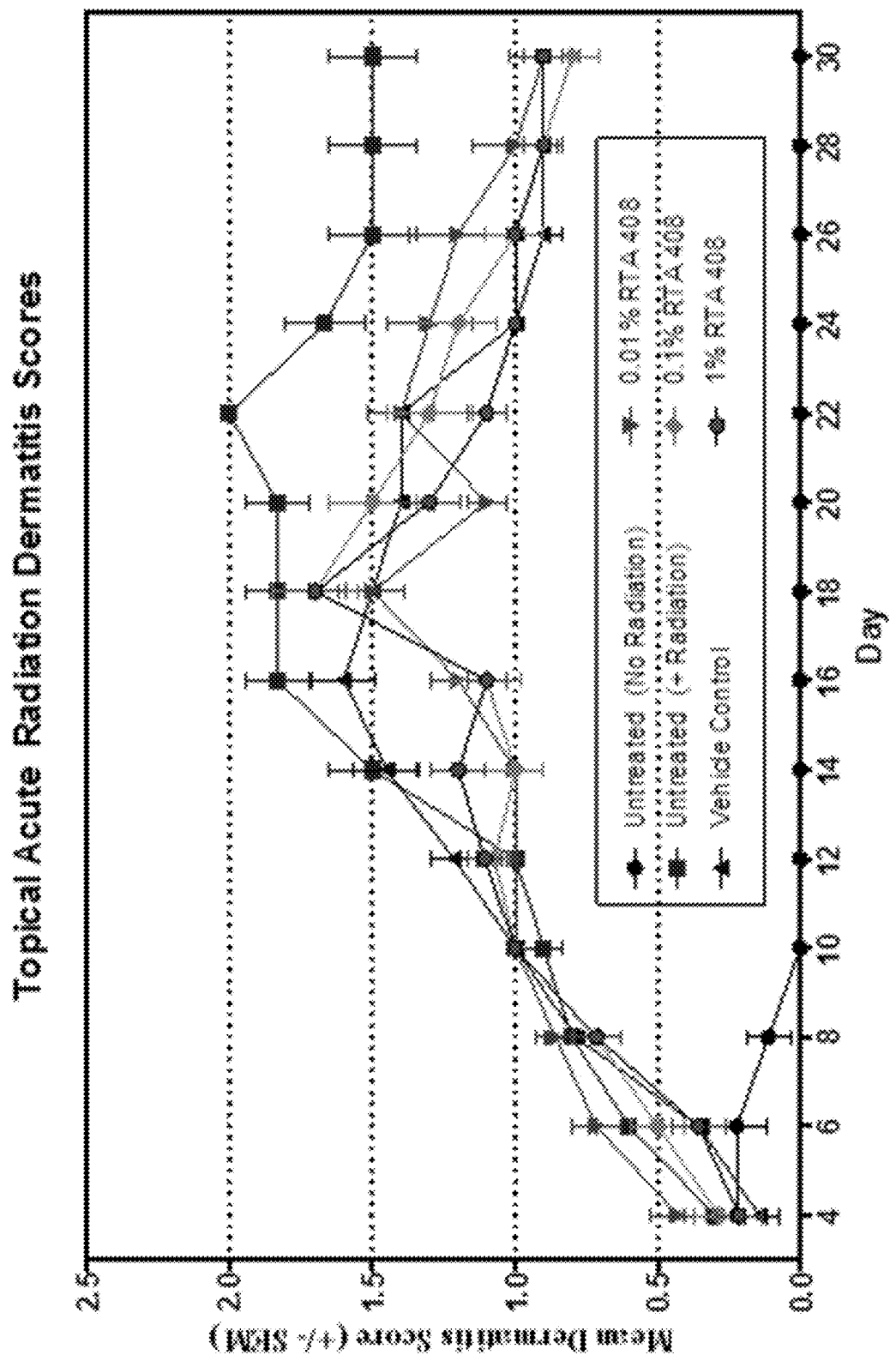
FIG. 42—Mean score of the acute radiation dermatitis as a function of time for untreated, untreated with no radiation exposure, vehicle only and three topical amounts of RTA 408 at 0.01, 0.1 and 1% measured every other day from day 4 to day 30. The dermatitis score is based upon the scale that 0 is completely healthy, 1-2 exhibits mild to moderate erythema with minimal to slight desquamation, 3-4 exhibits moderate to severe erythema and desquamation, and 5 exhibits a frank ulcer.

In the test groups where the mice were treated with RTA 408, the incidence of dermatitis appeared to be slightly diminished in severity when RTA 408 was given in either an oral or topical administration (FIGS. 36-39). Furthermore, curves plotting the average dermatitis clinic score for the test groups as a function of time show some change with the administration of RTA 408 either in oral or topical form from the untreated test groups (FIGS. 40-42) particularly in the case where RTA 408 was given through an oral administration. Furthermore, as can be seen in Tables 4 and 5 below, the percentage of mice suffering from dermatitis with a clinical score above 3 was significantly lower for mice treated with RTA 408 through an oral administration while the percentage of mice suffering from dermatitis with a clinical score above 2 was slightly lower for test groups who were given a topical administration of RTA 408.

TABLE 4

Percentage of mice per testing group which scored above 2 in their clinical dermatitis exam and given a topical treatment containing RTA 408

| | Day 12 | Day 14 | Day 16 | Day 18 | Day 20 | Day 22 | Day 24 | Day 26 | Day 28 | Day 30 | % animal-days >= 2 | % animal-days >= 3 |
|---|---|---|---|---|---|---|---|---|---|---|---|---|
| 1 no radiation, untreated | 0.0 | 0.0 | 0.0 | 0.0 | 0.0 | 0.0 | 0.0 | 0.0 | 0.0 | 0.0 | 0.0 | 0.0 |
| 2 irradiated, untreated | 0.0 | 50.0 | 83.3 | 83.3 | 83.3 | 100.0 | 66.7 | 50.0 | 50.0 | 50.0 | 35.6 | 0.0 |
| 3 irradiated, sesame oil | 21.4 | 45.0 | 60.0 | 50.0 | 40.0 | 40.0 | 0.0 | 0.0 | 0.0 | 0.0 | 16.6 | 0.0 |
| 4 irradiated, RTA 408- 0.01% | 0.0 | 0.0 | 20.0 | 50.0 | 10.0 | 40.0 | 40.0 | 40.0 | 20.0 | 10.0 | 14.4 | 0.0 |
| 5 irradiated, RTA 408-0.1% | 7.1 | 10.0 | 20.0 | 80.0 | 60.0 | 40.0 | 30.0 | 10.0 | 0.0 | 0.0 | 16.3 | 0.0 |
| 6 irradiated, RTA 408-1.0% | 10.7 | 20.0 | 10.0 | 70.0 | 30.0 | 10.0 | 0.0 | 0.0 | 0.0 | 0.0 | 9.7 | 0.0 |

TABLE 5

Percentage of mice per testing group which scored above 3 in their clinical dermatitis exam and given an oral treatment containing RTA 408

| | Day 16 | Day 18 | Day 20 | Day 22 | Day 24 | Day 26 | Day 28 | % animal-days >= 2 | % animal-days >= 3 |
|---|---|---|---|---|---|---|---|---|---|
| 1 no radiation, untreated | 0 | 0 | 0 | 0 | 0 | 0 | 0 | 0.0 | 0.0 |
| 2 irradiated, untreated | 20 | 40 | 20 | 20 | 20 | 20 | 20 | 39.0 | 8.8 |
| 3 irradiated, sesame oil | 35 | 50 | 40 | 30 | 20 | 0 | 0 | 45.6 | 10.9 |
| 4 irradiated, RTA 408-3 mg/kg | 10 | 10 | 0 | 0 | 0 | 0 | 0 | 32.5 | 1.3 |
| 5 irradiated, RTA 408-10 mg/kg | 10 | 25 | 30 | 0 | 0 | 0 | 0 | 33.8 | 4.1 |
| 6 irradiated, RTA 408-30 mg/kg | 10 | 20 | 10 | 0 | 0 | 0 | 0 | 28.8 | 2.5 |

G. Effects of RTA 408 on Fractionated Radiation Dermatitis

Figure 43:
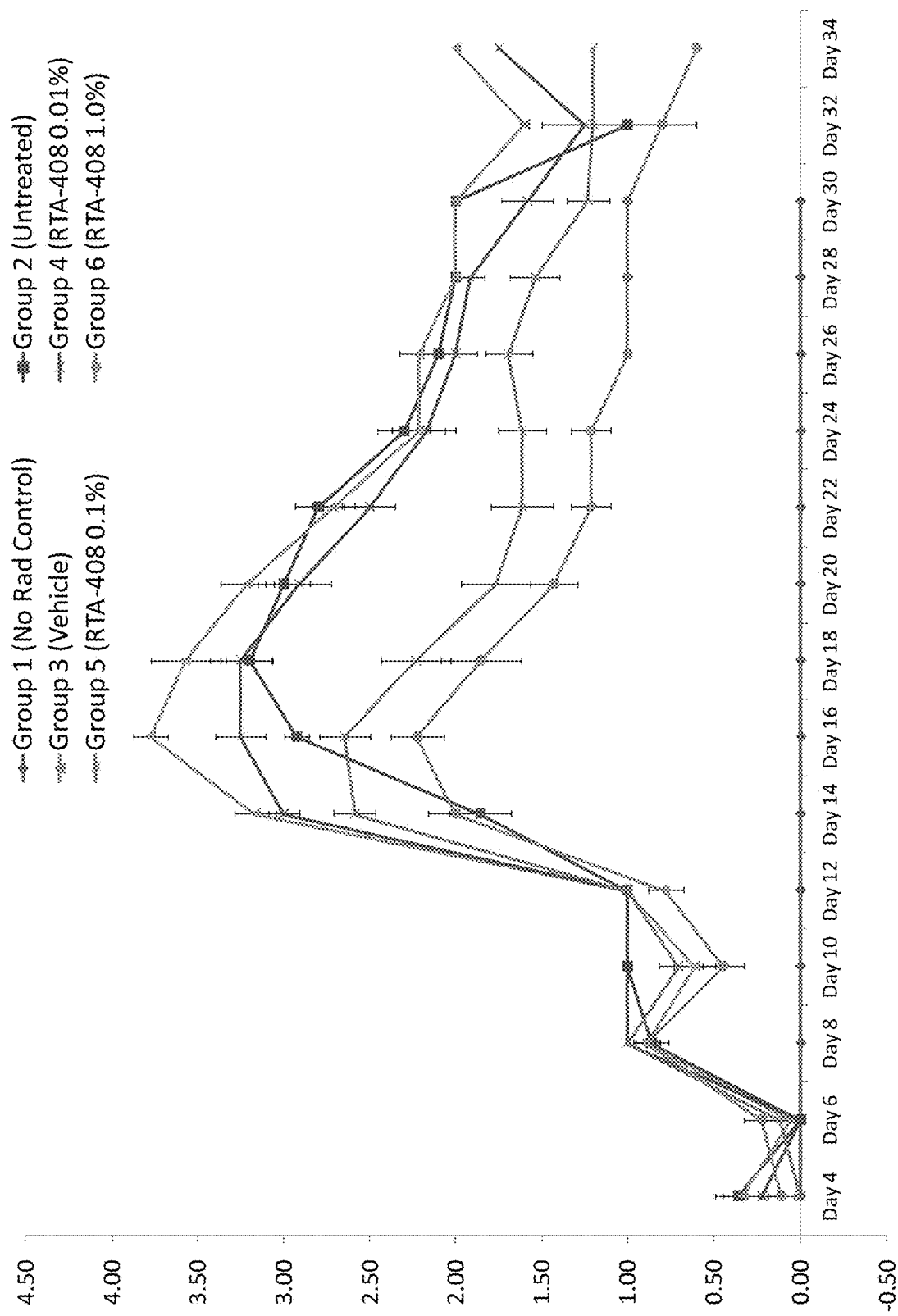
FIG. 43—Clinical scores of fractional radiation dermatitis plotted versus time and shows the change in dermatitis score for each testing group. The scale includes a dermatitis score from 0 to 5 where 0 is completely healthy, 1-2 indicates mild to moderate erythema with minimal to slight desquamation, 3-4 indicates moderate to severe erythema and desquamation, and 5 is a frank ulcer.

Utilizing RTA 408 through topical administration, the effects of RTA 408 towards ameliorating the effects of fractionated radiation dermatitis were measured. Using Balb/c mice, RTA 408 in a topical preparation was administered to the mice daily from day −5 to day 30 in three doses ranging from 0.01 to 1%. The mice were irradiated on days 0-2 and 5-7 with six 10-Gy doses per day. Clinical dermatitis scores for the mice were evaluated blindly every two days from day 4 until the end of the study. In FIG. 43, the graph shows the change in the average clinical score for each group were plotted as a function of time. The graph shows a statistically significant improvement in the scores for mice treated with 0.1 to 1% topical formulations of RTA 408. Study and treatment parameters can be found in Table 6.

TABLE 6

Study Conditions for Fractionated Radiation-Induced Dermatitis

| Group | Number of Animals | Radiation (Days 0-2, 5-7) | Treatment | Treatment Schedule |
|---|---|---|---|---|
| 1 | 9 males | — | Untreated | — |
| 2 | 14 males | 6x 10 Gy | Untreated | — |
| 3 | 18 males | 6x 10 Gy | Vehicle Control (sesame oil) | QD Days −5 to 30 |
| 4 | 18 males | 6x 10 Gy | RTA 408 - 0.01% | QD Days −5 to 30 |
| 5 | 18 males | 6x 10 Gy | RTA 408 - 0.1% | QD Days −5 to 30 |
| 6 | 18 males | 6x 10 Gy | RTA 408 - 1% | QD Days −5 to 30 |

Figure 44:
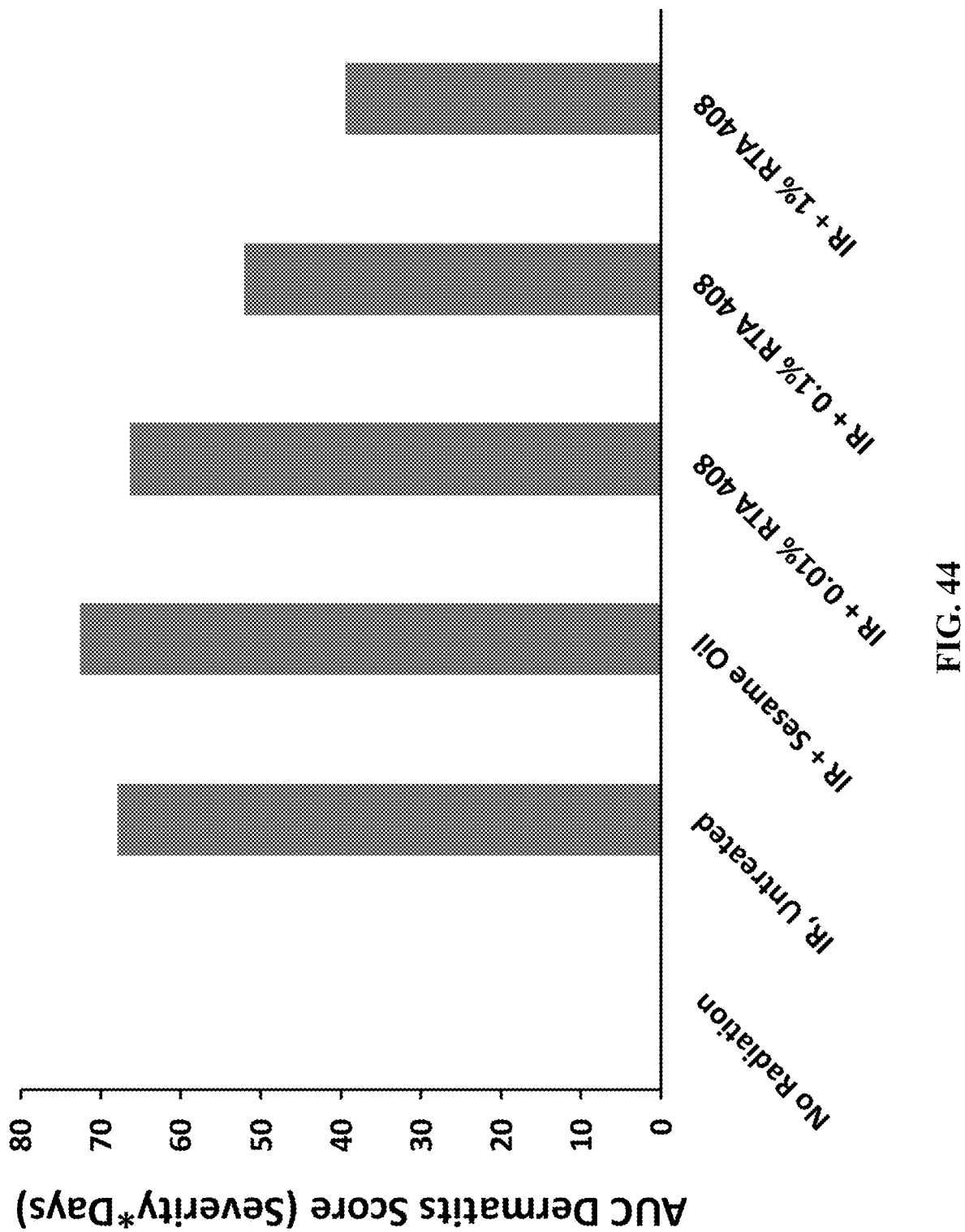
FIG. 44—Graph of the AUC analysis showing the dermatitis score (severity*days) for each of the testing groups over the entire observation period. The dermatitis scores were assessed every two days from day 4 to day 30 of the study.

By analyzing the average clinical scores that were shown in FIG. 43, an area under the curve (AUC) analysis was performed, which yielded the severity of the dermatitis relative to how long the dermatitis persisted. This AUC analysis allowed for direct comparison between the different groups of mice and the effect of the different percentage compositions of RTA 408 (FIG. 44 and Table 7). Administration of topical RTA 408 formulations reduced Grade 2 and Grade 3 lesions from 60% and 33% when the mice were only exposed to the vehicle to 21% and 6% with RTA 408 at 1%, concentration respectively. The other RTA composition showed some activity but was not as significant as that shown by the 1% formulation.

TABLE 7

Percentage of Dermatitis Score for Each Treatment Group

| Group | % Days ≥ 2 | % Days ≥ 3 |
|---|---|---|
| No Rad, No Tx | 0% | 0% |
| Rad, No Tx | 66% | 31% |
| Rad, Sesame Oil | 60% | 33% |
| Rad, RTA 408 (0.01%) | 54% | 29% |
| Rad, RTA 408 (0.1%) | 40% | 13% |
| Rad, RTA 408 (1%) | 21% | 6% |

H. Effects of RTA 408 on a Model of Ocular Inflammation

Figure 45:
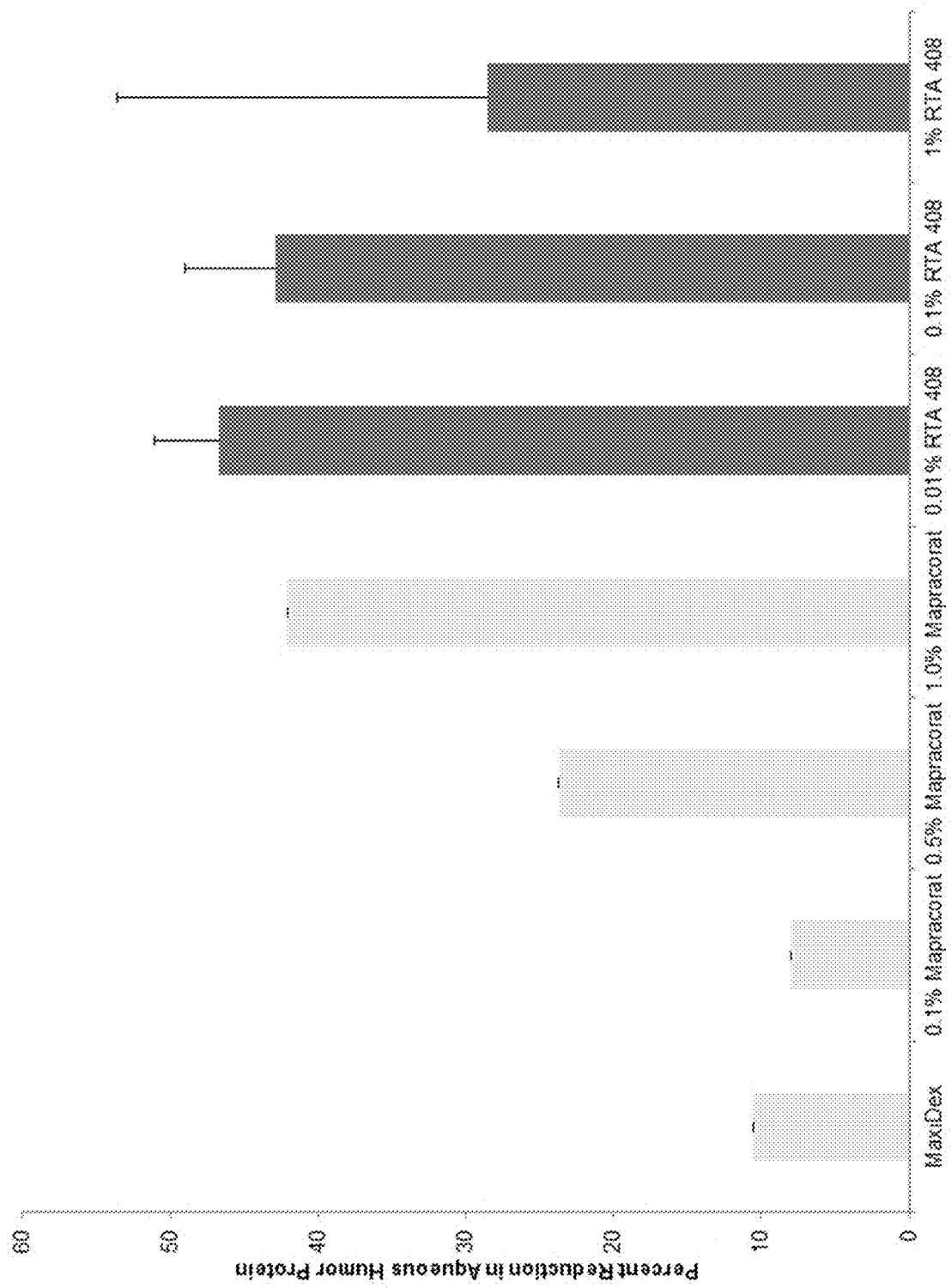
FIG. 45—Reduction of aqueous humor protein concentrations for different formulations of RTA 408 (dark bars) compared to literature values for MAXIDEX® (0.1% dexamethasone) and mapracorat (light bars) after induction of paracentesis.

A study of the effects of RTA 408 on ocular inflammation was carried out using rabbits of the New Zealand albino strain. The rabbits were divided into 5 groups of 12 rabbits which were given three different concentrations of RTA 408 (0.01, 0.1, and 1%), VOLTARENE© collyre at 0.1% and the vehicle (sesame oil). Each rabbit was given three instillations within 60 minutes before induction of paracentesis and two instillations within 30 minutes after induction of paracentesis. Each instillation was 50 μL and given in both eyes. Aqueous humor for 6 animals per time-point was collected 30 minutes and again 2 hours after induction of paracentesis. The amount of inflammation was determined by protein concentration in the aqueous humor. As shown in FIG. 45, RTA 408 showed a reduction in aqueous humor protein similar to that of the highest concentration of any of the other reference compounds (MAXIDEX® or mapracorat) at only 0.01% RTA 408 in the formulation. The effects of increasing concentration of RTA 408 appeared to be negligible as all concentrations of RTA 408 appeared to show relatively similar effects within error in reducing aqueous humor protein concentration.

I. Polymorphs of RTA 408

RTA 408 Polymorphic Form A

Example 1

17 g of RTA 408 was dissolved in 68 g of acetone. 620 g of de-ionized water was added to a 500 mL jacketed reactor and cooled to 2° C. When the water was below 7° C., the RTA 408 solution was added to the reactor via an addition funnel. A slurry of solids formed. The slurry was stirred in the reactor with nitrogen purge. Solids were isolated using vacuum filtration and dried under vacuum at room temperature to give Form A.

Example 2

300 mg of RTA 408 was dissolved in 1 mL of ethyl acetate. To the clear solution, 2 mL of heptane was added. Crystallization occurred within 30 minutes. The slurry was stirred overnight and the solids were isolated by vacuum filtration and dried at ambient temperature for 1 hour. The solids were then dried in a vacuum oven at 50° C. overnight to give Form A.

Figure 53:
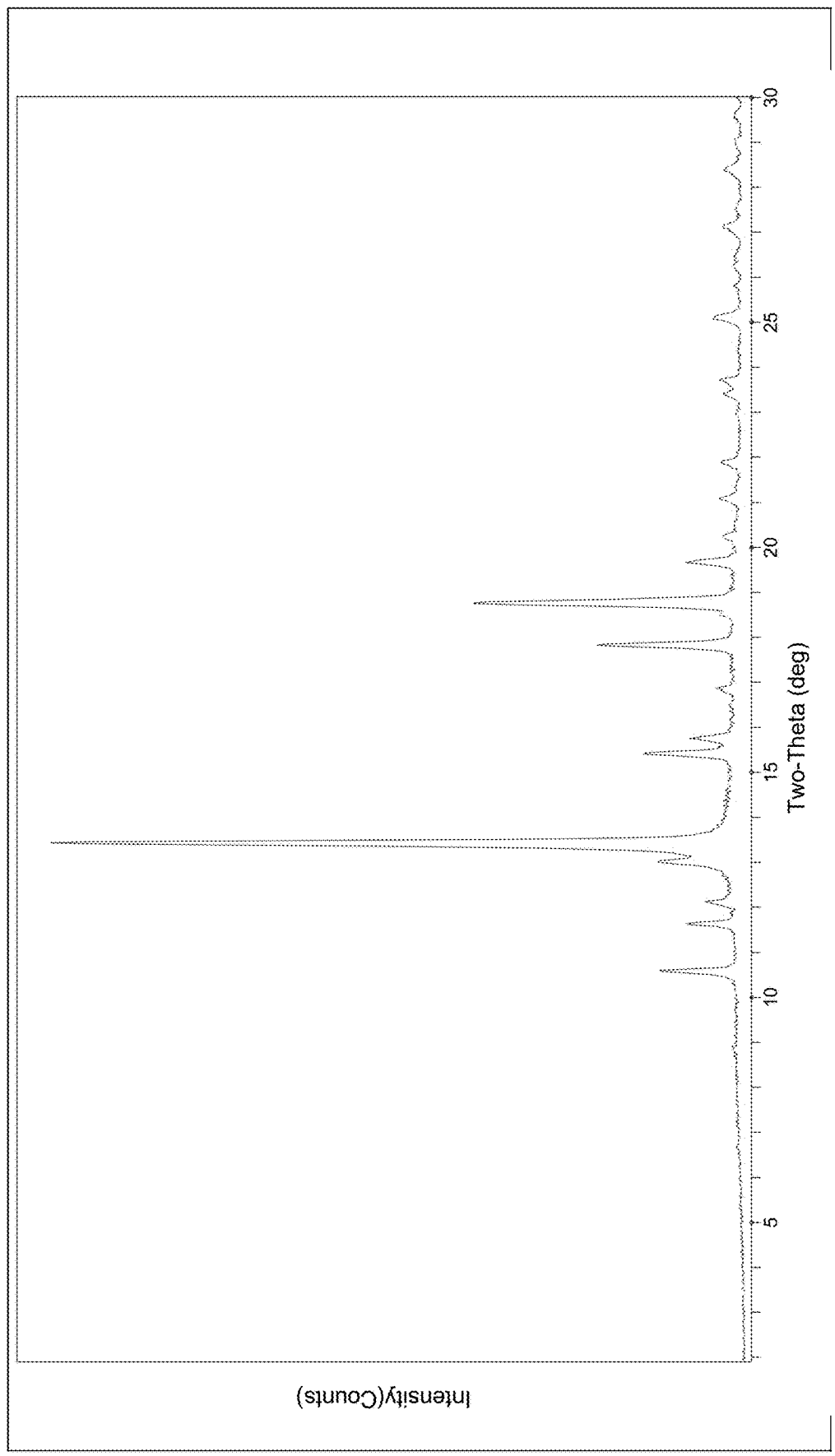
FIG. 53—PXRD patterns (2-30 °2θ) of RTA 408 Form A.
Figure 54:
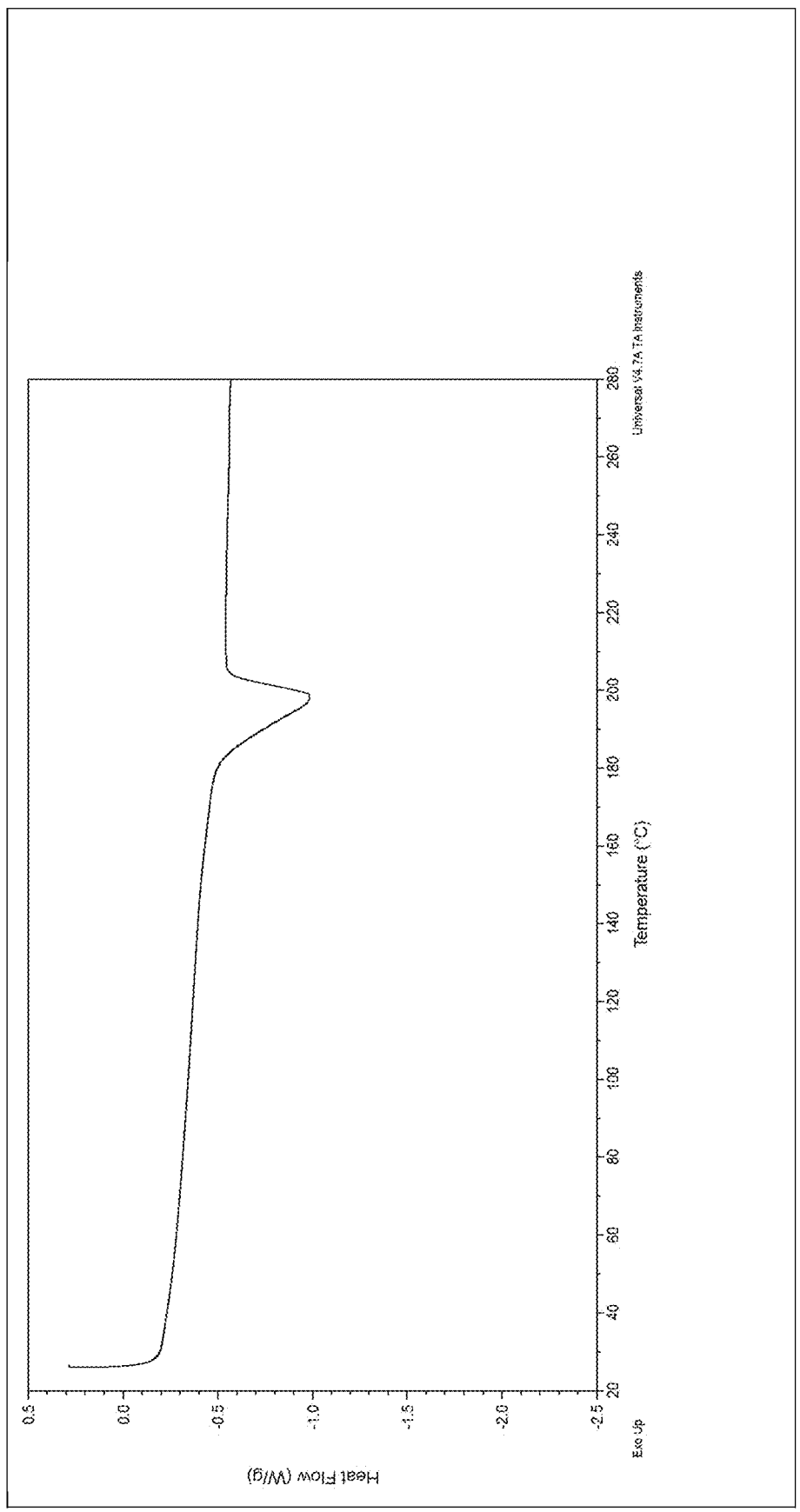
FIG. 54—DSC thermogram (25-280° C.) of RTA 408 Form A.
Figure 55:
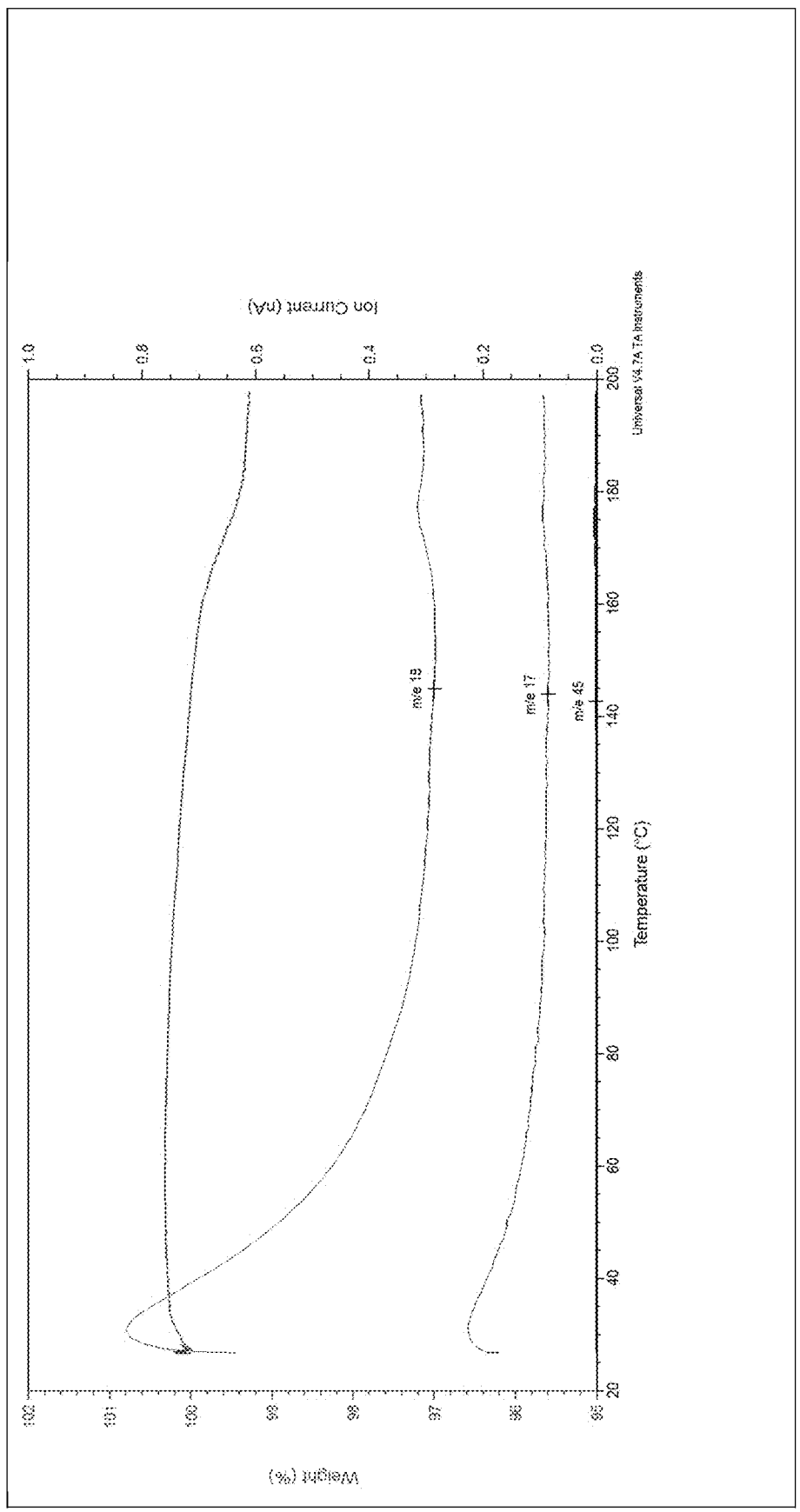
FIG. 55—TGA-MS thermogram (25-200° C.) of RTA 408 Form A.

Powder X-ray diffraction (PXRD) pattern and peak listing with relative intensities are shown in FIG. 53 and Table 8, respectively. Differential scanning calorimetry (DSC) and thermogravimetric analysis with mass spectroscopy (TGA-MS) are shown in FIGS. 54 and 55, respectively.

The DSC of Form A indicated an essentially solvent free form with a melting point of 181.98° C. and enthalpy of fusion of 42.01 J/g. The TGA-MS of Form A shows the loss of ~0.5 wt.-% with traces of $H_2O$ between 25 and 200° C., predominantly above 160° C., indicating that RTA 408 Polymorphic Form A may be slightly hygroscopic.

TABLE 8

Peak Listing of RTA 408 Form A

| Peak Position (°2θ) | Relative Intensity |
|---|---|
| 10.601 | 11.0 |
| 11.638 | 7.1 |
| 12.121 | 4.6 |
| 13.021 | 10.9 |
| 13.435 | 100.0 |
| 15.418 | 12.7 |
| 15.760 | 5.9 |
| 17.830 | 19.7 |
| 18.753 | 38.3 |
| 19.671 | 7.5 |

RTA 408 Polymorphic Form B

Example 3

1.0 g of RTA 408 was dissolved in 1.5 mL of acetone. In a scintillation vial, 10 mL of de-ionized water was heated to 50° C. and the RTA 408 solution was added to the vial dropwise. Upon stirring for 2 hours, a slurry of solids formed. The slurry was then cooled to room temperature. The resulting solids were isolated by filtration and dried in a vacuum oven at 50° C. overnight to give Form B.

Example 4

2.9 g of RTA 408 was dissolved in 20 mL of isopropyl alcohol at reflux. 20 mL of heptane was added to the solution at reflux. The solution was cooled to room temperature and mixed for 1 hour. A slurry of solids formed. The solids were isolated by vacuum filtration and dried under vacuum at ambient temperature to give Form B.

Figure 56:
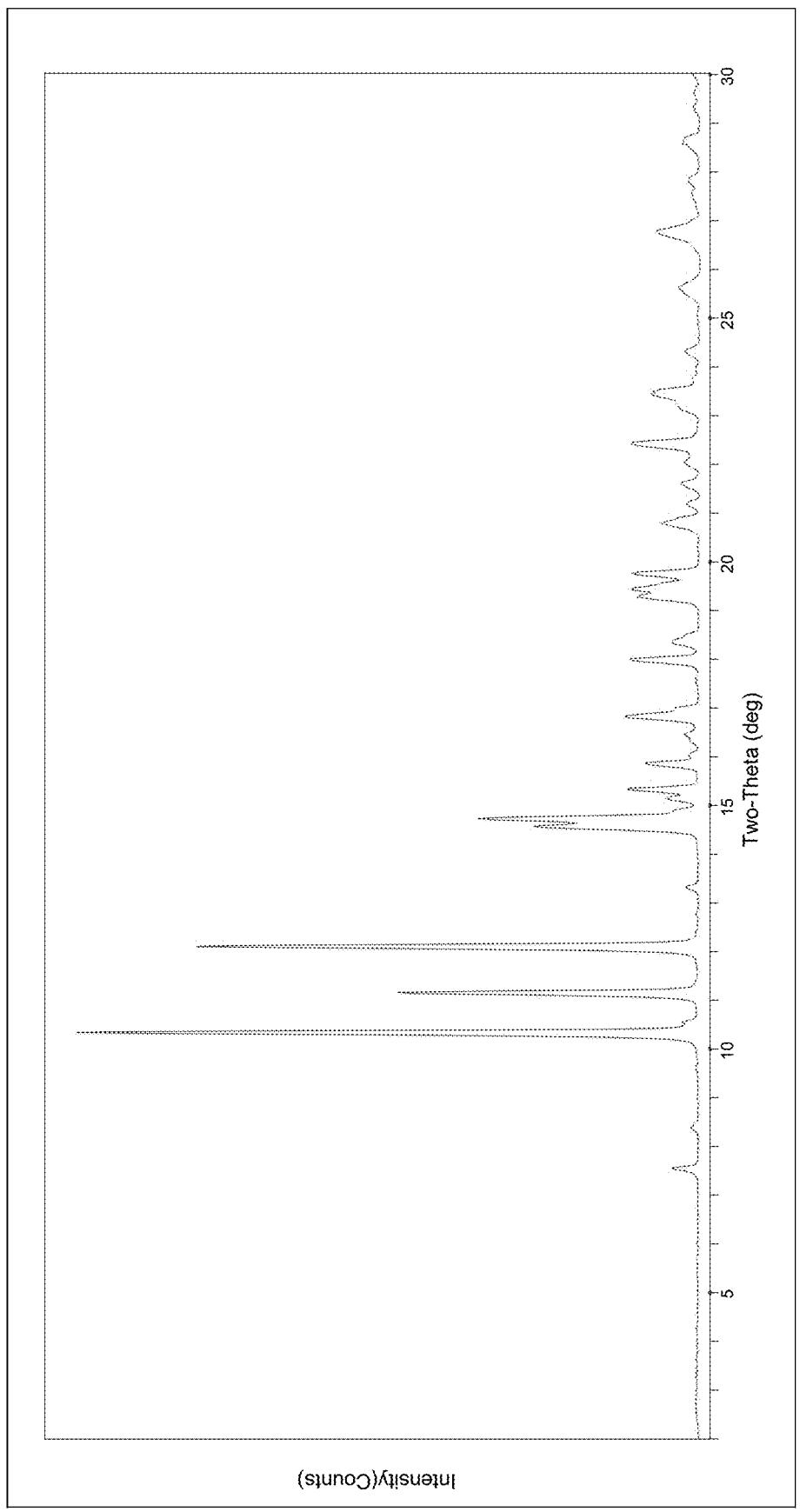
FIG. 56—PXRD patterns (2-30 °2θ) of RTA 408 Form B.
Figure 57:
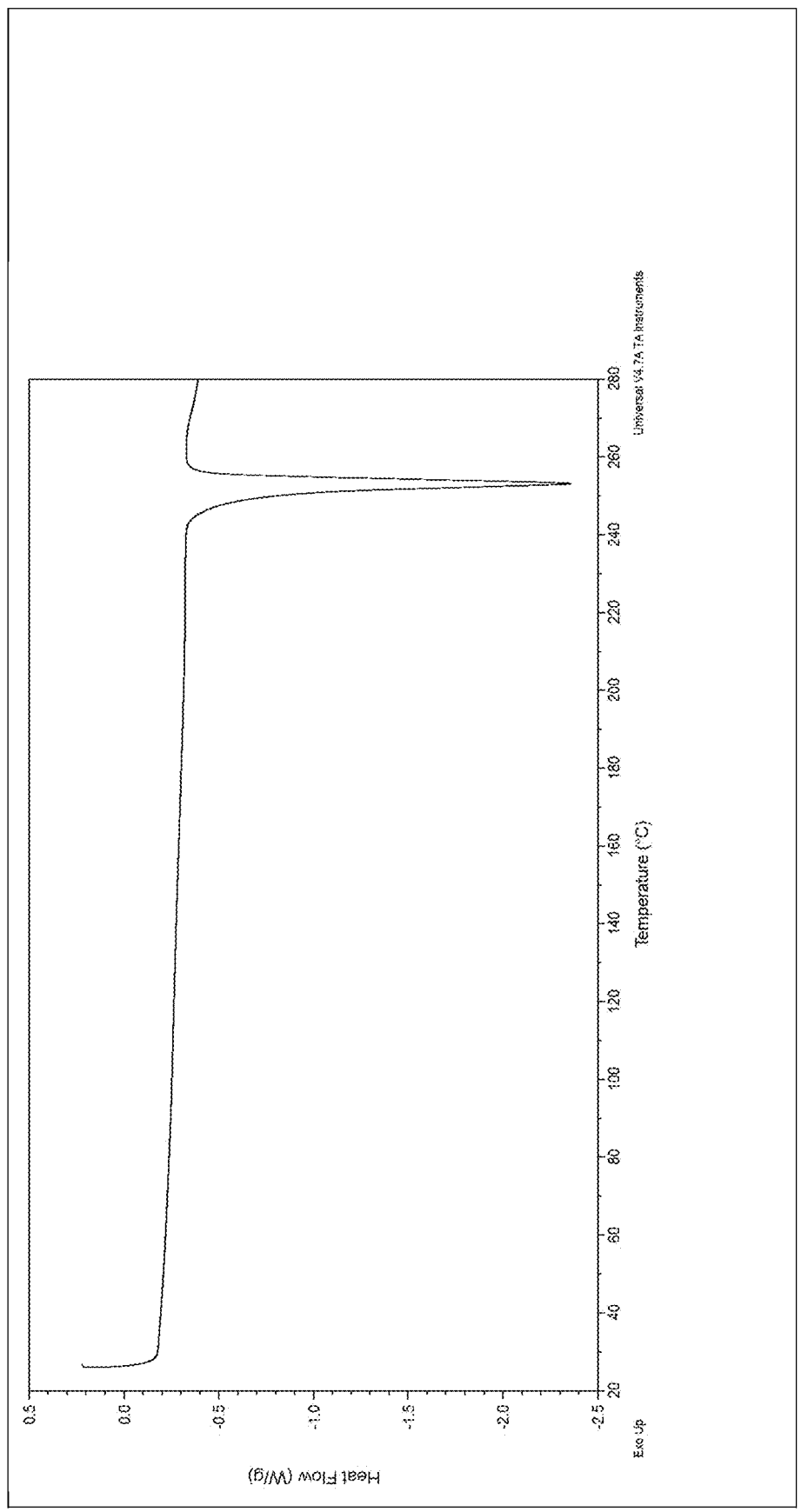
FIG. 57—DSC thermogram (25-280° C.) of RTA 408 Form B.

Powder X-ray diffraction (PXRD) pattern and peak listing with relative intensities are shown in FIG. 56 and Table 9, respectively. Differential scanning calorimetry (DSC) and thermogravimetric analysis with mass spectroscopy (TGA-MS) are shown in FIGS. 57 and 58, respectively.

The DSC of Form B indicated an essentially solvent free form with a melting point of 250.10° C. and enthalpy of fusion of 42.01 J/g. The TGA-MS of Form B shows the slight loss of ~0.2 wt.-% with traces of $H_2O$ between 25 and 200° C., indicating that RTA 408 Polymorphic Form B may be very slightly hygroscopic.

TABLE 9

Peak Listing of RTA 408 Form B

| Peak Position (°2θ) | Relative Intensity |
|---|---|
| 7.552 | 4.2 |
| 10.339 | 100.0 |
| 11.159 | 48.4 |
| 12.107 | 80.7 |
| 14.729 | 35.2 |
| 15.329 | 11.4 |
| 15.857 | 8.4 |
| 16.824 | 11.3 |
| 17.994 | 10.9 |
| 18.344 | 4.1 |
| 19.444 | 10.4 |
| 19.764 | 10.2 |

TABLE 9-continued

Peak Listing of RTA 408 Form B

| Peak Position (°2θ) | Relative Intensity |
|---|---|
| 20.801 | 5.7 |
| 22.414 | 10.1 |

J. Instrumental—Typical Measurement Conditions

Powder X-Ray Diffractometry (PXRD)

PXRD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromometer provided monochromatic radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 9.0.4, Materials Data, Inc., Livermore, Calif.). The sample was loaded onto an aluminum sample holder and leveled with a glass slide.

Thermo Gravimetric Analysis/Mass Spectrometry

The TGA was run with TA instruments, data were collected on a thermal balance (Q-5000, TA Instruments, New Castle, Del.) equipped with a data analyzer (Universal Analysis 2000, version 4.5A, TA Instruments, New Castle, Del.). During experiments, the furnace was purged with nitrogen at 60 mL/minute, while the balance chamber was purged at 40 mL/minute. Temperature of the TGA furnace was calibrated using curie points of aluminum and nickel. Sample size ranged from 2 to 20 mg, and a heating rate of 10° C./minute was used.

For TGA-MS, the thermogravimetric analysis part was the same as above. The mass of evolved gas was analyzed with PFEIFFER GSD 301 T3 ThermoStar (PFEIFFER Vacuum, Asslar, Germany). The instrument was operated and data evaluated with Software Quadstar 32-bit (V7.01, Inficon, LI-9496 Balzers, Liechtenstein).

Differential Scanning Calorimetery

A DSC (Q-2000, TA Instruments, New Castle, Del.) equipped with Universal Analysis 2000 software (Version 4.5A, TA Instruments, New Castle, Del.) was used to determine the DSC thermal traces. The temperature axis was calibrated with biphenyl, indium, and tin standards. The cell constant was calibrated with indium. Unless otherwise stated, the sample (2-5 mg) was encapsulated in a ventilated aluminum pan, and heated at a rate of 10° C./minute under a nitrogen gas flow of 50 mL/minute during the study.

Abbreviations

Methods:
AUC area under the curve analysis
DSC differential scanning calorimetry
$^1$H-NMR proton nuclear magnetic resonance spectroscopy
HPLC-MS high-performance liquid chromatography coupled to mass spectroscopy
LC/MS/MS liquid chromatography-tandem mass spectrometry
PXRD powder X-ray diffraction
TGA-MS thermogravimetric analysis coupled to mass spectroscopy Genes, Proteins, and Biological Parameters:
AIM antioxidant inflammation modulator
ARE antioxidant response element
ALP alkaline phosphatase
ALT alanine transaminase
ARE antioxidant response element
AST aspartate transaminase
AUC area under the curve
BAL bronchoalveolar lavage
BALF bronchoalveolar lavage fluid
COPD chronic obstructive pulmonary disease
COX-2 cyclooxygenase-2
Cr creatine
CYP450 cytochrome P450
Gclc glutamate-cysteine ligase, catalytic subunit
Gclm glutamate-cysteine ligase, modifier subunit
Glu glucose
GOT glutamic-oxaloacetic transaminase
GPT1 glutamic-pyruvate transaminase
GSH glutathione
GSR glutathione reductase
GST glutathione S-transferase
Gy Gray
H6PD hexose-6-phosphate dehydrogenase
hERG human ether a-go-go-related gene
HMOX1 heme oxygenase (decycling) 1
HO-1 heme oxygenase
IFN γ interferon-gamma
IL interleukin
iNOS inducible nitric oxide synthase
IκBα nuclear factor of kappa light polypeptide gene enhancer in B-cells inhibitor, alpha
KC mouse IL-8 related protein
Keap1 Kelch-like ECH associated protein-1
LPS lipopolysaccharide
ME1 malic enzyme 1
MPCE micronucleated polychromatic erythrocytes
Mrps multidrug resistance-related proteins
NADPH nicotinamide adenine dinucleotide phosphate, reduced
NF-κB nuclear factor of kappa-light-chain-enhancer of activated B cells
NO nitric oxide
NQO1 NAD(P)H quinone oxidoreductase 1
Nrf2 nuclear factor (erythroid-derived)-like 2
p-IκBα phosphorylated IκBα
PBMC peripheral blood mononuclear cell
PCE polychromatic erythrocytes
PGD phosphogluconate dehydrogenase
PMN polymorphonuclear
RANTES regulated and normal T cell expressed and secreted
SOD1 superoxide dismutase 1
SRXN1 sulfiredoxin-1
TG total glycerides
TKT transketolase TNFα tumor necrosis factor alpha
TXNRD1 thioredoxin reductase 1
Miscellaneous:
min minute(s)
m.p. melting point
Ph phenyl
T temperature
wt.-% weight percent K. Further Tables

TABLE 10

Figure 46:
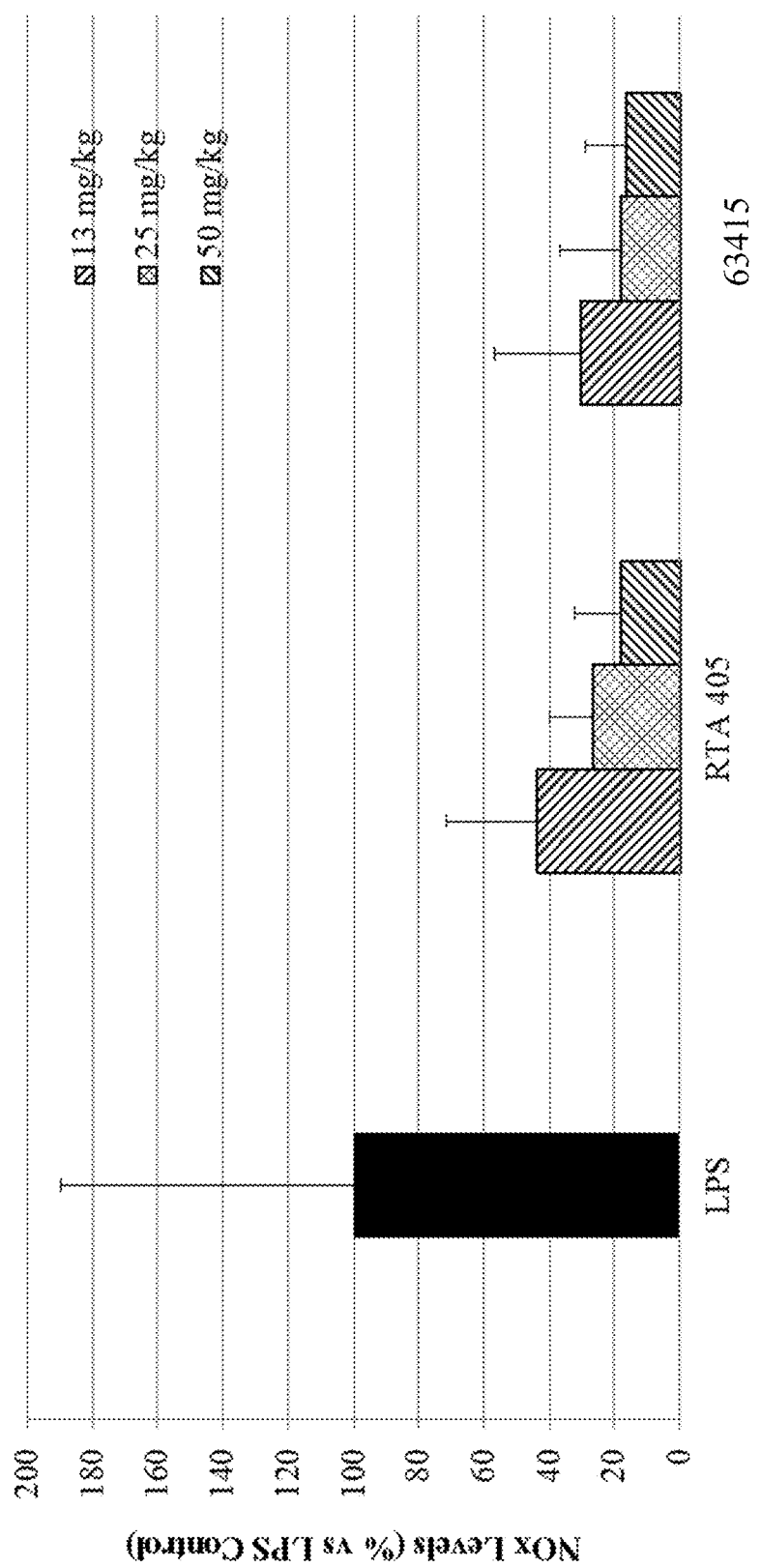
FIG. 46—RTA 408 (63415) dose-dependently suppresses NO in vivo. CD-1 mice (n=6) were dosed with dimethyl sulfoxide or AIM by oral gavage. LPS (5 mg/kg) was administered 24 h later. Twenty-four hours after LPS administration, whole blood was collected for NO assay. NO inhibition was determined by Griess Reaction from reduced, de-proteinated plasma.

Parameters of FIG. 46

| Compound | NOx Levels (% vs LPS Controls) | | |
|---|---|---|---|
| | 13 mg/kg | 25 mg/kg | 50 mg/kg |
| RTA 405 * | 44% | 26% | 18% |
| 63415 | 30% | 18% | 16% |

TABLE 11

63415: Primary In Vivi ADMET - Key
Primary ADMET Assays and Endpoints

| Assay | Key Endpoints |
|---|---|
| 14-day mouse toxicity | Tolerability, body weight, clinical chemistry<br>Tissue distribution<br>Nrf2 target gene mRNA expression & enzyme activation in liver |
| 14-day rat toxicity | Tolerability, body weight, clinical chemistry, & limited histopathology<br>Tissue distribution and plasma TK<br>Nrf2 target gene mRNA expression & enzyme activation in liver |
| 14-day monkey toxicity | Tolerability, body weight, clinical chemistry, & limited histopathology<br>Tissue distribution and plasma TK<br>Nrf2 target gene mRNA expression and enzyme activation in multiple tissues & PBMCs |

TABLE 12

Figure 49:
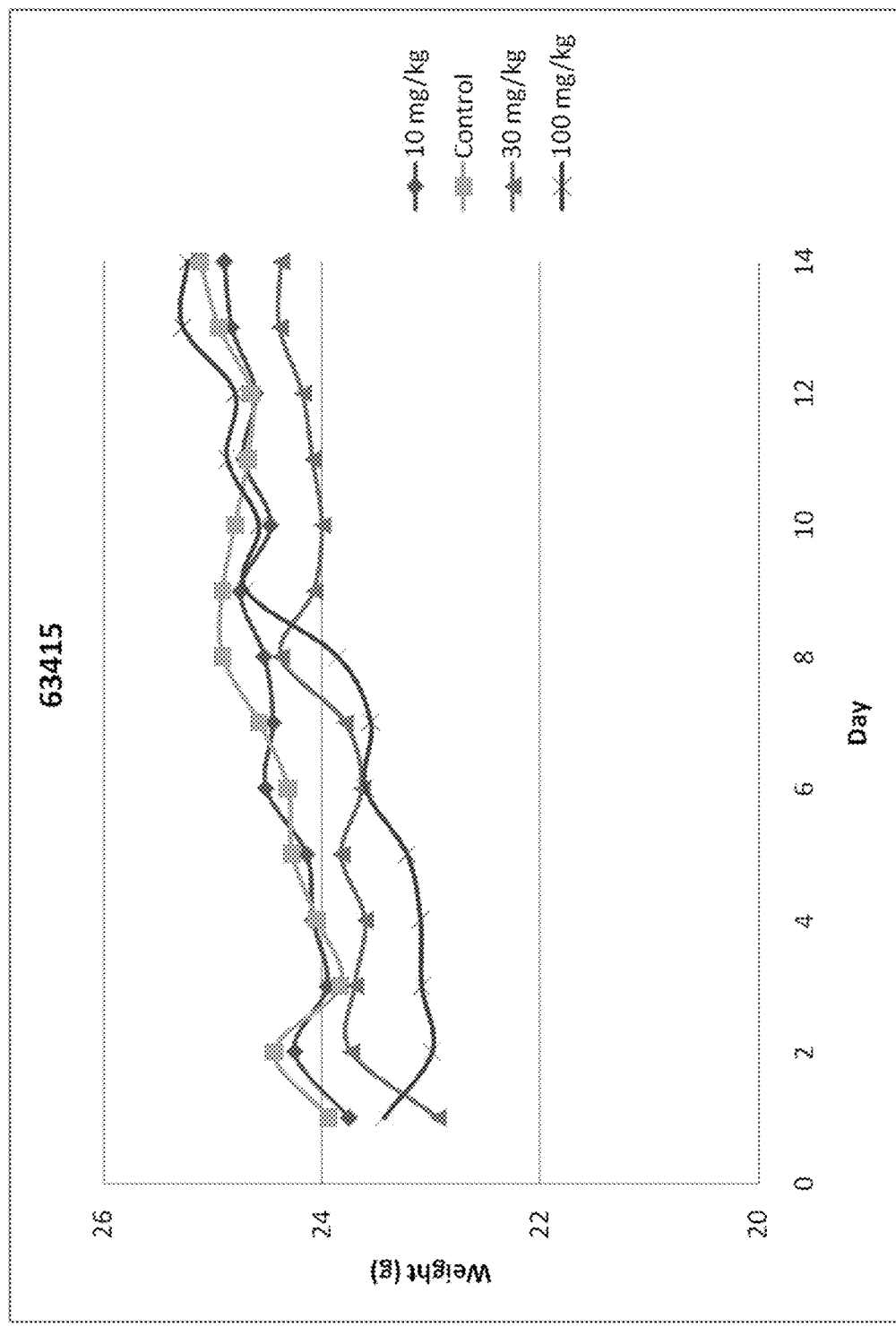
FIG. 49—Summary of RTA 408 (63415) 14-day mouse toxicity study. C57BL/6 mice were dosed PO QD×14. Endpoints included survival, weight, and clinical chemistries. All animals survived to day 14. No significant weight changes occurred compared to the vehicle group, and there was no evidence of toxicity at any dose based on clinical chemistries.
Figure 50:
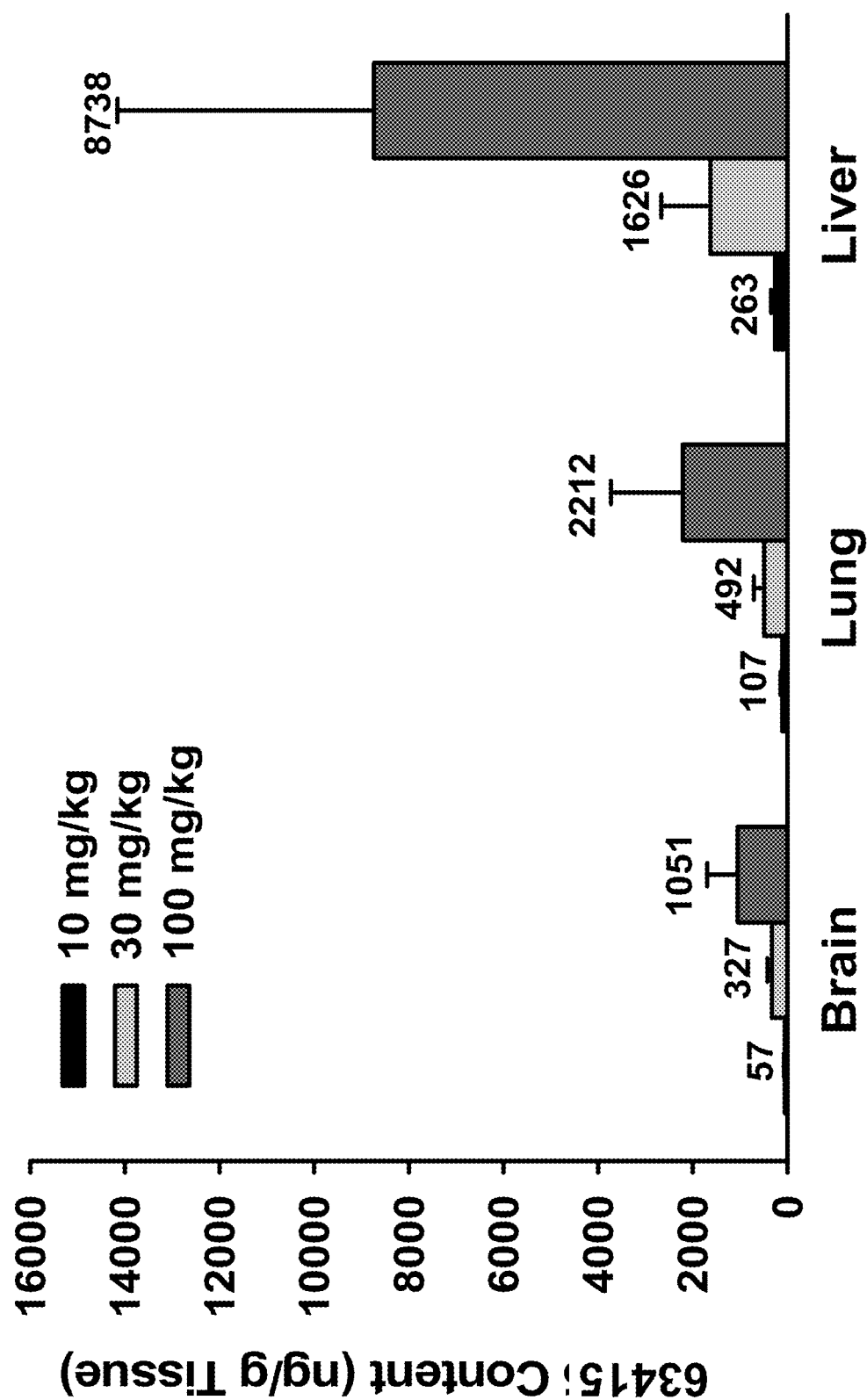
FIG. 50—Tissue distribution from RTA 408 (63415) 14-day mouse toxicity study in C57BL/6 mice. Brain, lung, and liver: Collected 4 hours after final dose, quantified for RTA 408 (63415) content using sensitive LC/MS/MS method. Exposures at 10 and 100 mg/kg: in lung exceeded in vitro $IC_{50}$ for NO induction by 55- and 1138-fold, respectively, and in brain exceeded in vitro $IC_{50}$ for NO induction by 29- and 541-fold, respectively.
Figure 51:
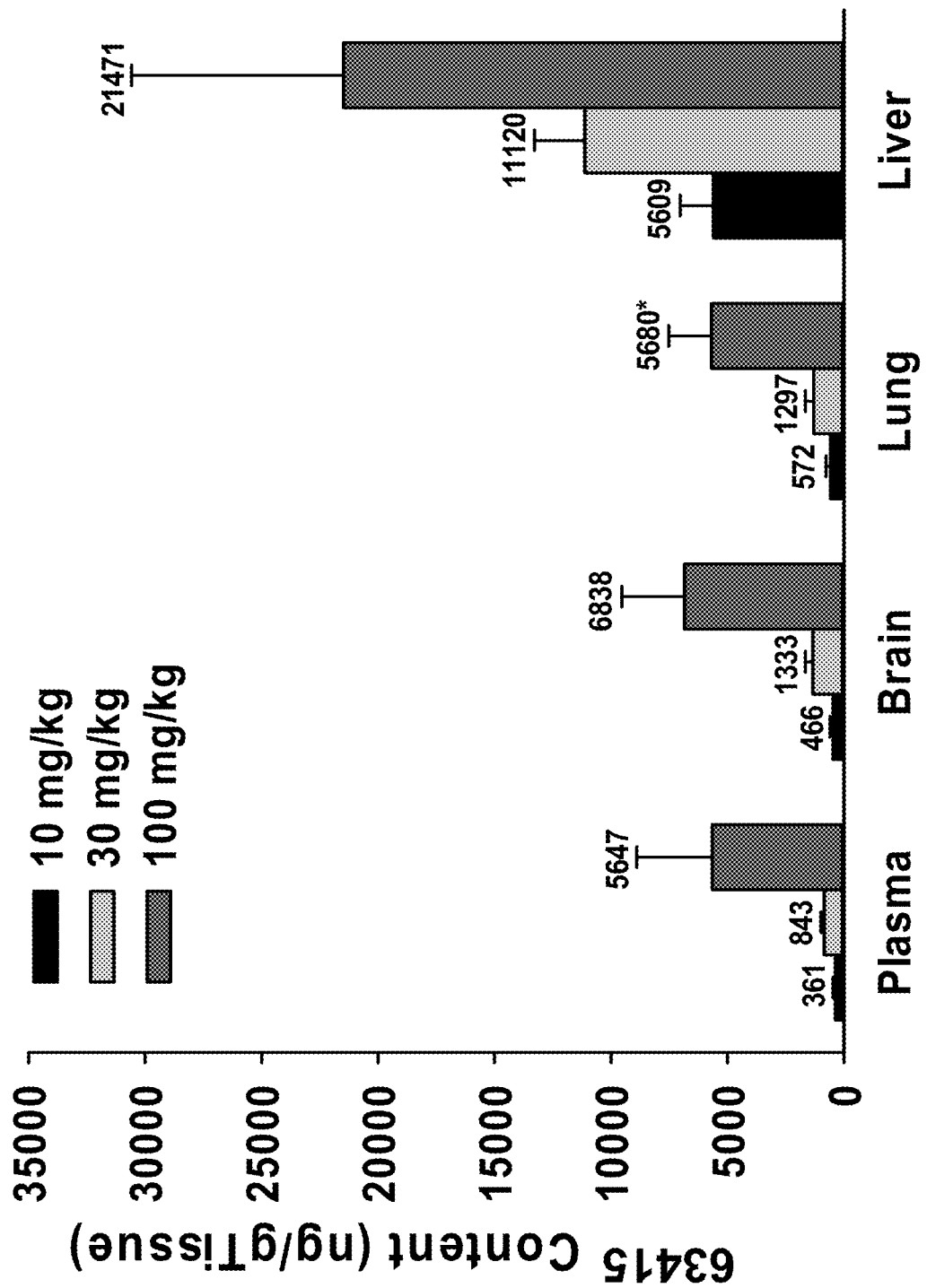
FIG. 51—RTA 408 (63415) tissue distribution in Sprague Dawley rats. RTA 408 (63415) distributes well into target tissues. Tissues were collected four hours after final dose on Day 14 or Day 6 (100 mg/kg), extracted, and quantified for RTA 408 (63415) content using a sensitive LC/MS/MS method. Exposures at 10 mg/kg in lung and brain exceed in vitro $IC_{50}$ for NO inhibition by 294- and 240-fold, respectively.
Figure 52:
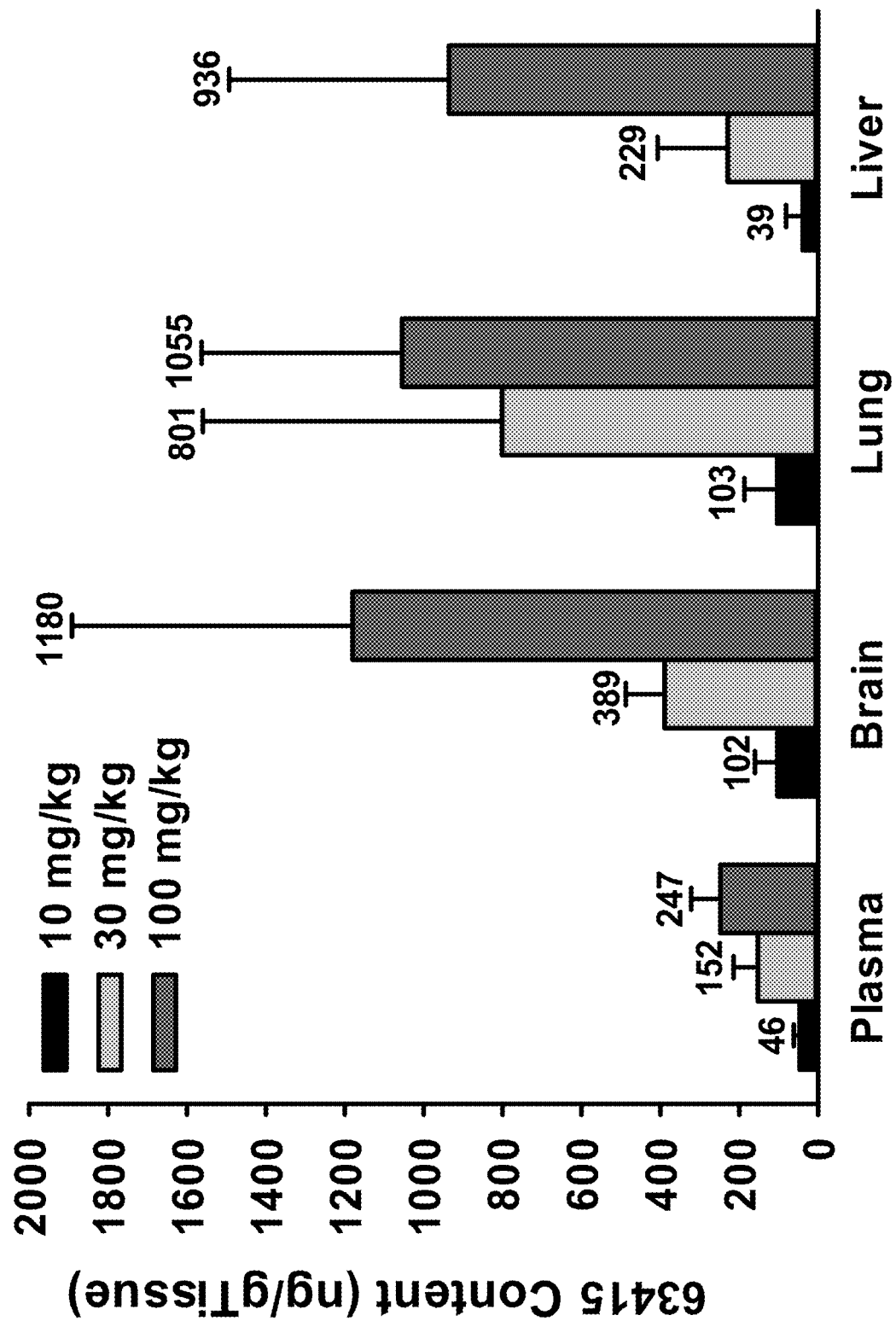
FIG. 52—RTA 408 (63415) target tissue distribution in cynomolgus monkeys. Tissues were collected four hours after final dose on Day 14. RTA 408 (63415) content was extracted and quantified using a sensitive LC/MS/MS method.

Parameters of FIG. 49

| | Vehicle | 63415 | | |
|---|---|---|---|---|
| Dose (mg/kg) | 0 | 10 | 30 | 100 |
| ALT (U/L) | 100 | 39 | 63 | 91 |
| AST (U/L) | 156 | 98 | 147 | 167 |
| ALP (U/L) | 120 | 131 | 110 | 98 |
| Tot Bil (mg/dL) | <0.2 | <0.2 | <0.2 | <0.2 |
| BUN (mg/dL) | 17 | 15 | 15 | 15 |
| Cr (mg/dL) | <0.2 | <0.2 | <0.2 | <0.2 |
| Glu (mg/dL) | 288 | 307 | 285 | 273 |

TABLE 13

63415 is Negative for Genotoxicity
in the In Vivo Micronucleus Study

| Treatment (n = 5/group) | PCE/Total Erythrocytes (Mean +/− SD) | Change from Control (%) | Number of MPCE/ 1000 PCE (Mean +/− SD) | Number of MPCE/ PCE Scored |
|---|---|---|---|---|
| 24-h timepoint | | | | |
| Sesame Oil | 0.588 ± 0.04 | — | 0.2 ± 0.27 | 2/10000 |
| 125 mg/kg | 0.543 ± 0.03 | −8 | 0.3 ± 0.27 | 3/10000 |
| 250 mg/kg | 0.520 ± 0.06 | −12 | 0.3 ± 0.27 | 3/10000 |
| 500 mg/kg | 0.426 ± 0.07 | −28 | 0.0 ± 0.00 | 0/10000 |
| 1000 mg/kg | 0.498 ± 0.05 | −15 | 0.2 ± 0.27 | 2/10000 |
| 1500 mg/kg | 0.499 ± 0.06 | −15 | 0.4 ± 0.22 | 4/10000 |
| 2000 mg/kg | 0.531 ± 0.05 | −10 | 0.2 ± 0.27 | 2/10000 |
| 48-h timepoint | | | | |
| Sesame Oil | 0.526 ± 0.05 | — | 0.3 ± 0.27 | 3/10000 |
| 125 mg/kg | 0.453 ± 0.03 | −14 | 0.2 ± 0.27 | 2/10000 |
| 250 mg/kg | 0.391 ± 0.02 | −26 | 0.2 ± 0.27 | 2/10000 |
| 500 mg/kg | 0.339 ± 0.05 | −36 | 0.3 ± 0.45 | 3/10000 |
| 1000 mg/kg | 0.344 ± 0.04 | −35 | 0.1 ± 0.22 | 1/10000 |
| 1500 mg/kg | 0.376 ± 0.05 | −39 | 0.4 ± 0.42 | 4/10000 |
| 2000 mg/kg | 0.360 ± 0.03 | −32 | 0.1 ± 0.22 | 1/10000 |

TABLE 14

Figure 32:
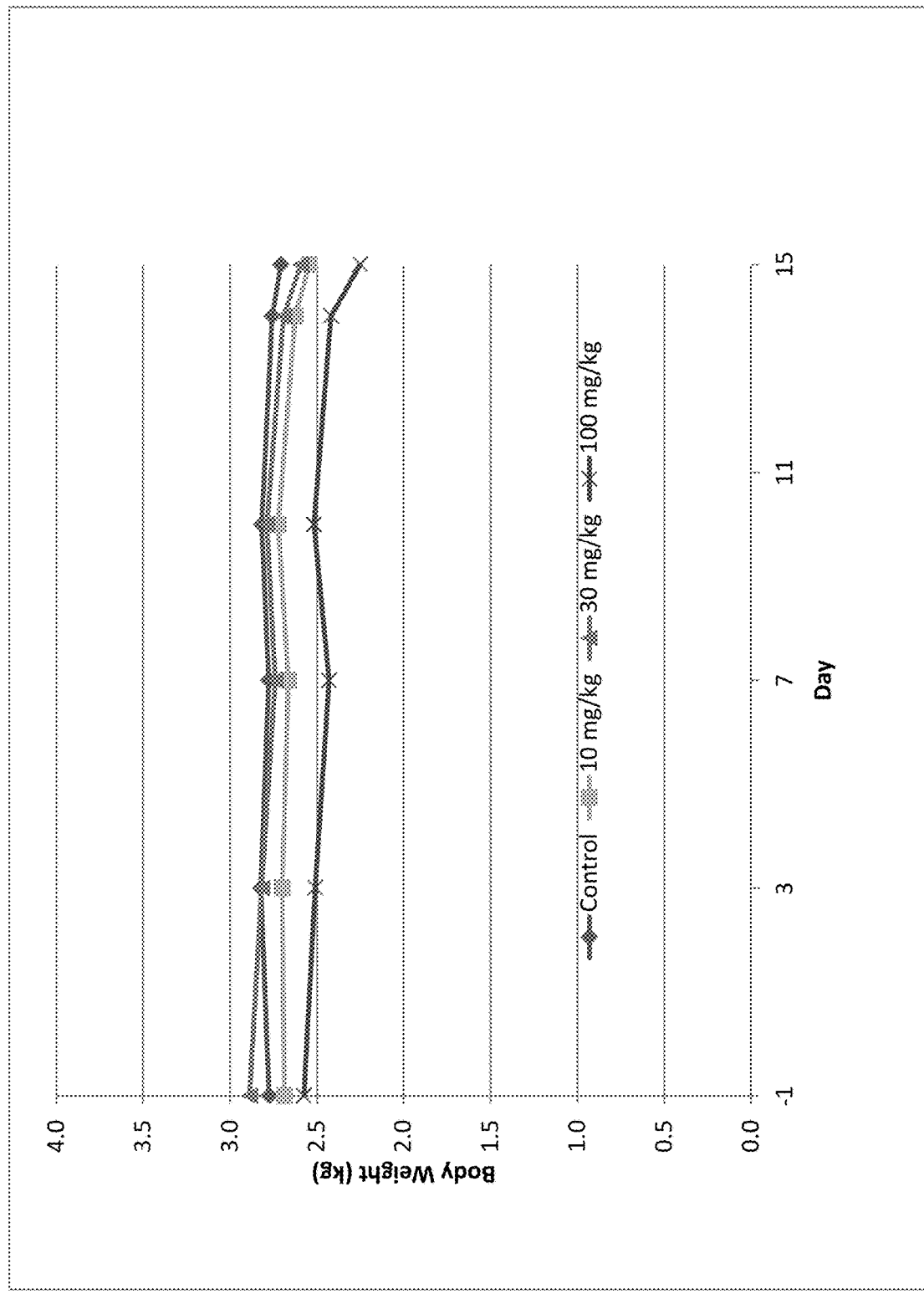
FIG. 32—Summary of RTA 408 (63415) 14-day monkey toxicity study. All doses were well-tolerated without adverse clinical signs. Clinical chemistry data suggested no obvious toxicity.

Parameters of FIG. 32

| Treatment | Day | ALT (U/L) | AST (U/L) | ALP (U/L) | Tot Bil (mg/dL) | BUN (mg/dL) | Cr (mg/dL) | Tot Prot (g/dL) | Albumin (g/dL) | Glucose (mg/dL) | Chol (mg/dL) | TG (mg/dL) |
|---|---|---|---|---|---|---|---|---|---|---|---|---|
| Vehicle | BL | 30 | 29 | 320 | 0.15 | 23 | 0.63 | 7.2 | 4.1 | 87 | 124 | 52 |
| | Day 14 | 37 | 37 | 345 | 0.23 | 18 | 0.63 | 6.9 | 4.1 | 63 | 130 | 64 |
| 10 mg/kg | BL | 46 | 32 | 351 | 0.18 | 35 | 0.78 | 7.4 | 4 | 74 | 146 | 51 |
| | Day 14 | 46 | 38 | 382 | 0.23 | 27 | 0.68 | 7.2 | 4 | 39 | 144 | 82 |
| 30 mg/kg | BL | 32 | 32 | 409 | 0.18 | 23 | 0.7 | 7.3 | 4.2 | 85 | 125 | 47 |
| | Day 14 | 47 | 43 | 416 | 0.2 | 20 | 0.58 | 7.2 | 4 | 53 | 122 | 64 |
| 100 mg/kg | BL | 32 | 35 | 381 | 0.15 | 24 | 0.7 | 6.9 | 4 | 96 | 137 | 37 |
| | Day 14 | 43 | 37 | 390 | 0.18 | 24 | 0.55 | 6 | 3.2 | 32 | 93 | 61 |

TABLE 15

In Vitro Activity of 63415 and 63355

|  | 63415 | 63355 |
|---|---|---|
| NO IC50 (nM), RAW264.7 | 4.0 ± 1 | 0.63 ± 0.06 |
| WST-1 IC50 (nM), RAW264.7 | 125 | 150 |
| NQO1-ARE (fold at 62.5 nM in HuH7) | 5.3 ± 1.0 | 6.5 ± 0.9 |

TABLE 16

Figure 47:
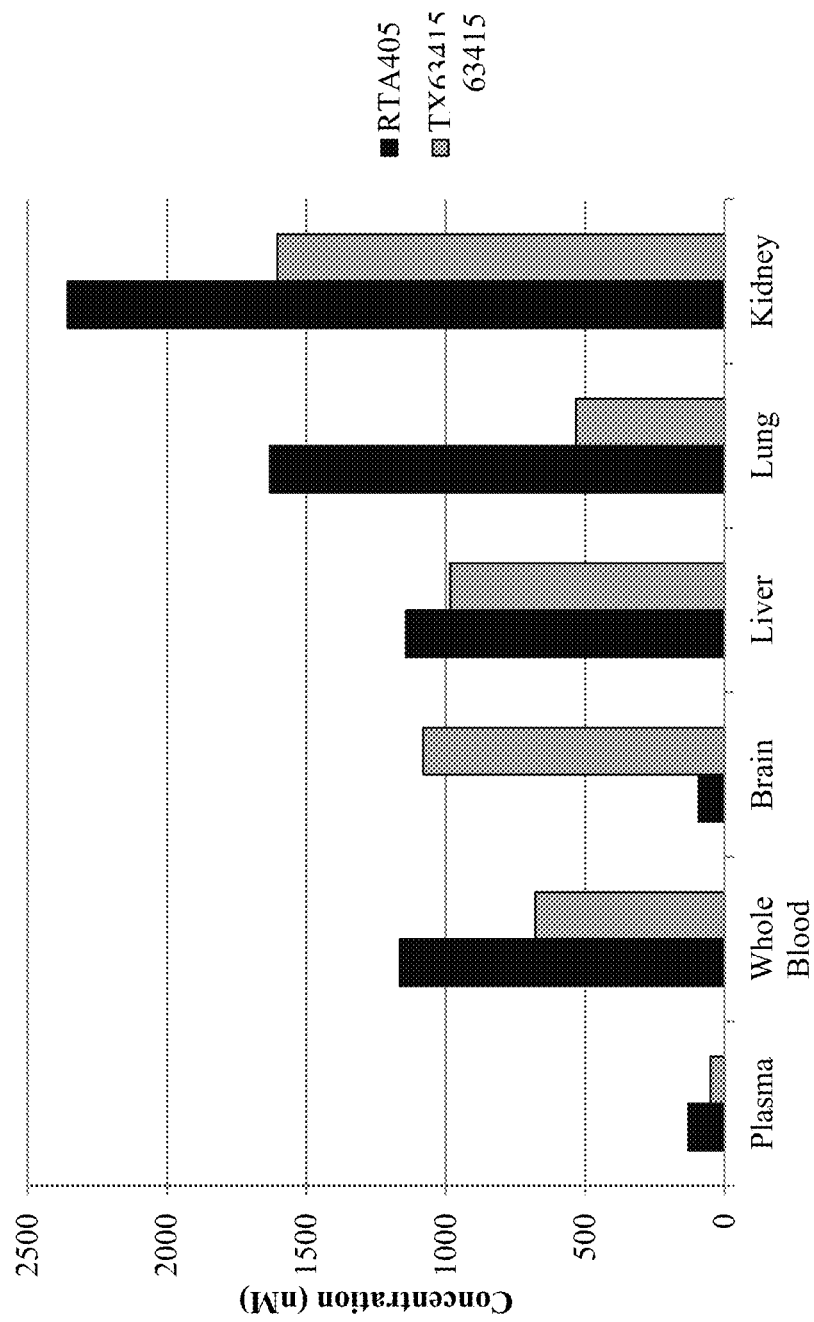
FIG. 47—RTA 408 (63415) distributes extensively into mouse tissues. Mice were dosed with 25 mg/kg PO QD×3 of either RTA 408 (63415) or RTA 405. Blood (plasma and whole blood) and tissues (brain, liver, lung, and kidney) were collected 6 hours after the last dose. Semi-quantitative analysis of drug content was performed. Notable levels were observed in the CNS.

Parameters of FIG. 47

| Compound | Plasma | Whole Blood | Brain | Liver | Lung | Kidney |
|---|---|---|---|---|---|---|
| RTA 405 (nM) | 130 | 1165 | 93 | 1143 | 1631 | 2357 |
| 63415 (nM) | 51 | 679 | 1081 | 985 | 533 | 1604 |

TABLE 17

Figure 48:
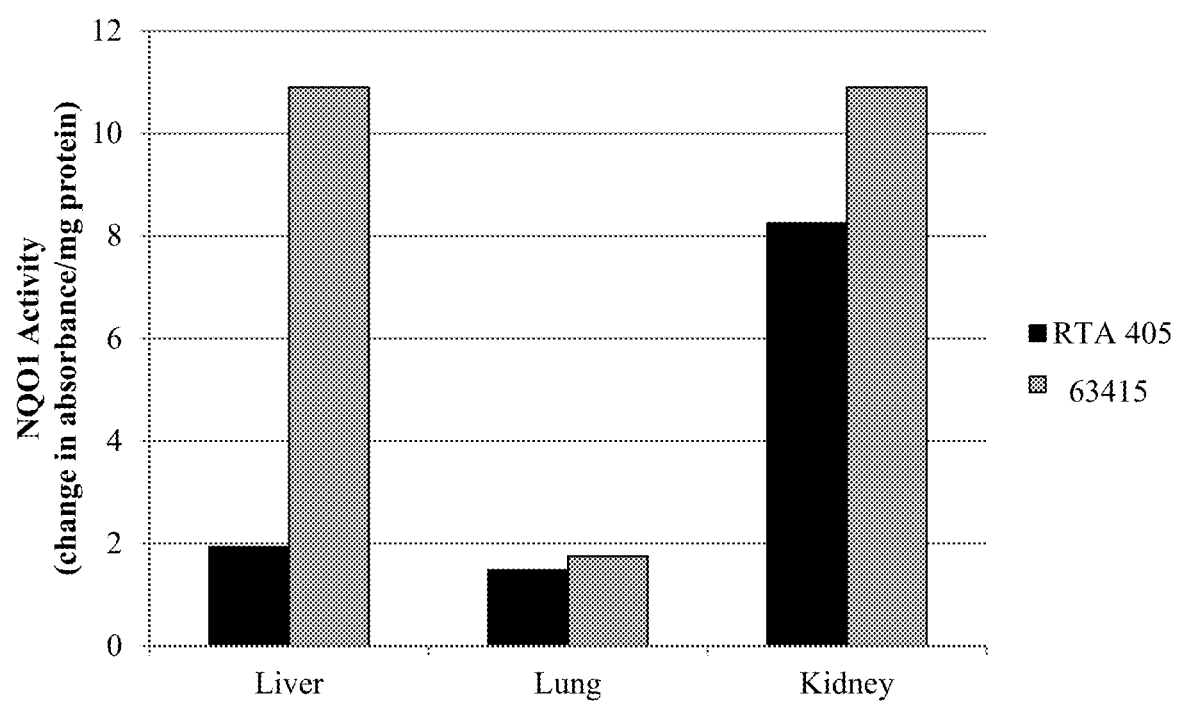
FIG. 48—RTA 408 (63415) induces NQO1 activity in mouse liver, lung, and kidney. Mice were dosed with 25 mg/kg PO QD×3, tissues were collected 6 hours after the last dose, and analysis of NQO1 activity was performed. Meaningful activation of NQO1 was observed in multiple tissues.

Parameters of FIG. 48

| Compound | Liver | Lung | Kidney |
|---|---|---|---|
| RTA 405 | 1.93 | 1.48 | 8.25 |
| 63415 | 10.9 | 1.75 | 10.9 |

All of the compounds, polymorphs, formulations, and methods disclosed and claimed herein can be made and executed without undue experimentation in light of the present disclosure. While the compounds, polymorphs, formulations, and methods of this invention have been described in terms of preferred embodiments, it will be apparent to those of skill in the art that variations may be applied to the compounds, polymorphs, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Abraham and Kappas, *Free Radical Biol. Med*, 39:1-25, 2005.
Ahmad, et. al., *Cancer Res.*, 68:2920-2926, 2008.
Ahmad, et. al., *J. Biol. Chem.*, 281:35764-9, 2006.
Akiyama et al., *Alzheimer Dis. Assoc. Disord.*, 14(1): S47-53, 35 2000.
Angulo et al., *Eur. J. Immunol.*, 30:1263-1271, 2000.
Araujo, et. al., *J. Immunol.*, 171(3):1572-1580, 2003.
Arend and Dayer, *Arthritis Rheum.*, 38:151-160, 1995.
Arend et al., *Annu. Rev. Immunol.*, 16:27-55, 1998.
Autenrieth et al., *Infect. Immun.*, 62:2590-2599, 1994.
Bach, *Hum. Immunol.*, 67(6):430-432, 2006.
Bagasra et al., *Proc. Natl. Acad. Sci. USA*, 92:12041-12045, 1995.
Ball, *Ann. Rheum. Dis.*, 30:213-223, 1971.
Beal, *Curr. Opin. Neurobiol.*, 6:661-666, 1996.
Blumberg et al., *Arthritis Rheum.*, 7:93-97, 1964.
Botoman et al., *Am. Fam. Physician*, 57(1):57-68, 1998.
Brandt et al., *Arthritis Rheum.*, 43:1346-1352, 2000.
Braun et al., *Arthritis Rheum.*, 42:2039-2044, 1999.
Brewerton et al., *Lancet.*, 1:904-907, 1973a.
Brewerton et al., *Lancet.*, 1:956-957, 1973b.
Bronte et al., *Trends Immunol.*, 24:302-306, 2003.
Brown and DuBois, *J. Clin. Oncol.*, 23:2840-2855, 2005.
Brynskov et al., *N. Engl. J. Med*, 321(13):845-850, 1989.
Burger and Dayer, Neurology, 45(6S-6):$39-43, 1995.
Cai et al., *Nat. Med*, 11(2): 183-190, 2005.
Calin and Taurog, In: *The Spondylarthritides*, Calin et al. (Eds.), Oxford, UK. Oxford University Press, 179, 1998.
Cann et al., *Gut.*, 24(12):1135-1140, 1983.
Chauhan and Chauhan, *Pathophysiology*, 13(3):171-181. 2006.
Chomarat et al., *ArthritisRheum.*, 38:1046-1054, 1995. 65.
Coyle and Puttfarcken, *Science*, 262:689-695, 1993.
Crowell et al., *Mol. Cancer. Ther.*, 2:815-823, 2003.
Dickerson, et. al., *Prog Neuropsychopharmacol Biol. Psychiatry*, Mar. 6, 2007.
de Waal et al., *J. Exp. Med.*, 174:1209-1220, 1991.
Dinarello, *Int. Rev. Immunol.*, 16:457-499, 1998.
Dinkova-Kostova, et. al., *Proc. Natl. Acad. Sci. USA*, 102 (12):4584-4589, 2005.
Dionne et al., *Clin. Exp. Immunol.*, 112(3):435-442, 1998.
Doran et al., *J. Rheumatol.*, 30(2):316-320, 2003.
Drossman et al., *Dig. Dis. Sci.*, 38(9):1569-1580, 1993.
Drossman et al., *Gastroenterol.*, 112(6):2120-2137, 1997.
Dudhgaonkar, et al., *Eur. J. Pain*, 10(7):573-9, 2006.
Eastgate, et al., *Lancet*, 2(8613): 706-9, 1988.
Eikelenboom et al., *Glia*, 40(2):232-239, 2002.
Ettehadi et al., *Clin. Exp. Immunol.*, 96(1):146-151, 1994.
Everhart et al., *Gastroenterol.*, 100(4):998-1005, 1991.
Fearon and Locksley, *Science*, 272(5258):50-53, 1996.
Feldtkeller et al., *Rheumatol. Int.*, 23(2):61-66, 2003.
Firestein et al., *Arthritis Rheum.*, 37:644-652, 1994.
Forstermann, *Biol. Chem.*, 387:1521, 2006.
Fujikawa et al., *Ann. Rheum. Dis.*, 54:318-320, 1995.
Funakoshi et al., *Digestion*, 59(1):73-78, 1998.
Galley and Webster, *Br. J. Anaesth.*, 77:11-16, 1996.
Gehrmann et al., *Glia*, 15(2):141-151, 1995.
Genain and Nauser, *J. Mol. Med.*, 75:187-197, 1997.
Gladman et al., *Br. J. Rheumatol.*, 22:675-679, 1995.
Gladman et al., *J. Med.*, 62:127-141, 1987.
Gladman, *Rheum. Dis. Clin. North Am.*, 18:247-256, 1992.
Goodman et al., *Kidney Int.*, 72(8):945-953, 2007.
Graeber et al., *Glia*, 40(2):252-259, 2002.
Greten et al., *Cell*, 118:285-296, 2004.
Griffin et al., *Proc. Natl. Acad. Sci. USA*, 86(19):7611-7615, 1989.
Guilherme et al., *Nat. Rev. Mol. Cell. Biol.*, 9(5):367-77, 2008.
Gwee et al., *Gut.*, 44(3):400-406, 1999.
Hahn and Tsao, In: *Dubois' Lupus Erythematosus*, $4^h$ Ed, Wallace and Hahn (Eds.), Lea and Febiger, Philadelphia, 195-201, 1993.
*Handbook of Pharmaceutical Salts: Properties, and Use*, Stahl and Wermuth Eds.), Verlag Helvetica Chimica Acta, 2002.
Hannum et al., *Nature*, 343:336-340, 1990.
Hanson et al., *BMC Medical Genetics*, 6(7), 2005.
Hansson et al., *Annu. Rev. Pathol. Mech. Dis.*, 1:297-329, 2006.
Harrison et al., *J. Rheumatol.*, 25(12):2324-2330, 1998.
Hart et al., *Immunology*, 84:536-542, 1995.

Honda, et. al. *Bioorg. Med Chem. Lett.*, 12:1027-1030, 2002.
Honda, et. al., *Bioorg. Med Chem. Lett.*, 7:1623-1628, 1997.
Honda, et. al., *Bioorg. Med Chem. Lett.*, 8(19):2711-2714, 1998.
Honda, et. al., *Bioorg. Med Chem. Lett.*, 9(24):3429-3434, 1999.
Honda, et. al., *J. Med Chem.*, 43:4233-4246, 2000a.
Honda, et. al., *J. Med Chem.*, 43:1866-1877, 2000b.
Horwitz and Fisher, *N. Engl. J. Med*, 344(24):1846-1850, 2001.
Hotamisligil, *Nature*, 444(7121):860-7, 2006.
Ishikawa et al., *Circulation*, 104(15): 1831-1836, 2001.
Ishizawa and Dickson, *J. Neuropathol. Exp. Neurol.*, 60(6): 647-657, 2001.
Jacob et al., *Proc. Natl. Acad. Sci. USA*, 87:1233-1237, 1990.
Jailwala et al., *Ann. Intern. Med.*, 133(2): 136-147, 2000.
Jarvis, *Curr. Opin. Rheumatol.*, 10(5):459-467, 1998.
Jarvis, *Pediatr. Ann.*, 31(7):437-446, 2002.
Jones et al., *Br. J. Rheumatol.*, 33(9):834-839, 1994.
Jonsson et al., *Br. J. Rheumatol.*, 32(7):578-581 1993.
Jonsson et al., *Oral Dis.*, 8(3): 130-140, 2002.
Jonsson et al., *Trends Immunol.*, 22(12):653-654, 2001.
Kahle et al., *Ann. Rheum. Dis.*, 51:731-734, 1992.
Kaltschmidt et al., *Proc. Natl. Acad. Sci. USA*, 94:2642-2647, 1997.
Kawakami et al., *Brain Dev.*, 28(4):243-246, 2006.
Kellow and Phillips, *Gastroenterol.*, 92(6): 1885-1893, 1987.
Kendall-Tackett, *Trauma Violence Abuse*, 8(2): 117-126, 2007.
Khan et al., *J. Neurochem.*, 71:78-87, 1998.
Khan et al., *Toxicol. AppliedPharmacol.*, 103:482-490, 1990.
Kortylewski et al., *Nat. Med.*, 11:1314-1321, 2005.
Kotake et al., *Infect. Immun.*, 67:2682-2686, 1999.
Kotzin and O'Dell, In: *Sampler's Immunologic Diseases*, 5th Ed., Frank et al. (Eds.), Little Brown & Co., Boston, 667-697, 1995.
Kotzin, *Cell*, 85:303-306, 1996.
Kruger et al., *J. Pharmacol. Exp. Ther.*, 319(3): 1144-1152, 2006.
Kuboyama, *KurumeMed. J*, 45(1):33-37, 1998.
Lahesmaa et al., *J. Immunol.*, 148:3079-3085, 1992.
Lee, et. al., *Glia.*, 55(7):712-22, 2007.
Lencz, et. al., *Mol. Psychiatry*, 12(6):572-80, 2007.
Liby, et. al., *Cancer Res.*, 65(11):4789-4798, 2005.
Liby, et. al., *Nat. Rev. Cancer*, 7(5):357-356, 2007.
Lipsky, In: *Harrison's Principles of Internal Medicine*, Fauci et al. (Eds.), 14th Ed., NY, McGraw-Hill, 1880-1888, 1998.
Liu, et. al., *FASEB J.*, 20(2):207-216, 2006.
Lo et al., *Curr. Dir. Autoimmun.*, 1:226-246, 1999.
Lugering et al., *Ital. J. Gastroenterol. Hepatol.*, 30(3):338-344, 1998.
Lynn and Friedman, *N. Engl. J. Med.*, 329(26):1940-1945, 1993.
Macatonia et al., *J. Immunol.*, 150:3755-3765, 1993.
*March's Advanced Organic Chemistry: Reactions*, Mechanisms, and Structure, 2007.
Marsal et al., *Rheumatology*, 38:332-337, 1999.
Mazur et al., *Cell Microbiol.*, 9(7): 1683-94, 2007.
Mazzoni et al., *J. Immunol.*, 168:689-695, 2002.
McAlindon et al., *Gut*, 42(2):214-219, 1998.
McGeer and McGeer, *Brain Res. Brain Res. Rev.*, 21:195-218, 1995.
McGeer et al., *Neurology*, 19:331-338, 1996.
McGonagle et al., *Arthritis Rheum.*, 41: 694-700, 1998.
McGonagle et al., *Curr. Opin. Rheumatol.*, 11:244-250, 1999.
McIver et al., *Pain*, 120(1-2):161-9, 2005.
Mease et al., *Lancet*, 356:385-390, 2000.
Merrill and Benvenist, *Trends Neurosci.*, 19:331-338, 1996.
Mertz et al., *Gastroenterol.*, 118(5):842-848, 2000.
Moll and Wright, *Ann. Rheum. Dis.*, 32:181-201, 1973.
Moll and Wright, *Semin. Arthritis Rheum.*, 3:55-78, 1973.
McIver, et. al., *Pain*, 120(1-2):161-9, 2005.
Morris, et. al., *J. Mol. Med*, 80(2):96-104, 2002.
Morse and Choi, *Am. J. Respir. Crit. Care Med*, 172(6):660-670, 2005.
Morse and Choi, *Am. J. Respir. Crit. Care Med*, 27(1):8-16, 2002.
Nath et al., *Neurology*, 66(1):149-150, 2006.
Neal et al., *BMJ.*, 314(7083):779-782, 1997.
Nichols, *Drug News Perspect.*, 17(2):99-104, 2004.
Nielen et al., *Arthritis Rheum.*, 50(2):380-386, 2004.
Ohnishi et al., *Int. Immunol.*, 6:817-830, 1994.
Pall, *Med Hypoth.*, 69:821-825, 2007.
Partsch et al., *Br. J. Rheumatol.*, 24:518-523, 1997.
Pica et al., *AntimicrobAgents Chemother.*, 44(1):200-4, 2000.
Pergola, et. al., *N Engl J Med* 365:327-336, 2011.
Pimentel et al., *Am. J. Gastroenterol.*, 95(12):3503-3506, 2000.
Prieur et al., *Lancet*, 2:1240-1242, 1987.
Place, et. al., *Clin. Cancer Res.*, 9(7):2798-806, 2003.
Rajakariar, et. al., *Proc. Natl. Acad Sci. USA*, 104(52): 20979-84, 2007.
Rantapaa-Dahlqvist et al., *Arthritis Rheum.*, 48(10):2741-2749, 2003.
Reimund et al., *Eur. J. Clin. Invest.*, 28(2):145-150, 1998.
Ribbens et al., *Eur. Cytokine Netw.*, 11:669-676, 2000.
Rogers et al., *NeurobiolAging*, 9(4):339-349, 1988.
Rogler and Andus, *WorldJ. Surg.*, 22(4):382-389, 1998.
Rooney et al., *RheumatolInt.*, 10:217-219, 1990.
Ross, et. al., *Am. J. Clin. Pathol.*, 120(Suppl):S53-71, 2003.
Ross, et. al., *Expert Rev. Mol. Diagn.*, 3(5):573-585, 2003.
Rostom et al., *Ann. Intern. Med.*, 146, 376-389, 2007.
Rothstein, *Med. Clin. North Am.*, 84(5): 1247-1257, 2000.
Ruster, et. al., *Scand. J. Rheumatol.*, 34(6):460-3, 2005.
Sacerdoti, et. al., *Curr Neurovasc Res.* 2(2): 103-111, 2005.
Saha, et. al., *J Biol Chem* 285:40581-92, 2010.
Saiki et al., *Scand. J. Gastroenterol.*, 33(6):616-622, 1998.
Salomonsson and Jonsson, *Arthritis Rheum.*, 48(11):3187-3201, 2003.
Salomonsson et al., *Scand. J. Immunol.*, 55(4):336-342, 2002.
Salvarani et al., *Curr. Opin. Rheumatol.* 1998; 10:299-305, 25 1998.
Salvemini et al., *J. Clin. Invest.*, 93:1940-1947, 1994.
Sandler, *Gastroenterol.*, 99(2):409-415, 1990.
Salvemini, et. al., *J. Clin. Invest.*, 93(5):1940-1947, 1994.
Sarchielli, et. al., *Cephalalgia*, 26(9):1071-1079, 2006.
Satoh, et. al., *Proc. Natl. Acad. Sci. USA*, 103(3):768-773, 2006.
Schlaak et al., *Clin. Exp. Rheumatol.*, 14:155-162, 1996.
Schlaak et al., *Eur. J. Immunol.*, 22:2771-2776, 1992.
Schlosstein et al., *NE J. Medicine*, 288:704-706, 1973.
Schreiber, *Neth. J. Med.*, 53(6):S24-31, 1998.
Schulz et al., *Antioxid. Redox. Sig.*, 10:115, 2008.
Shishodia, et. al., *Clin Cancer Res* 12:1828-38, 2006.
Sieper and Braun, *Arthritis Rheum.*, 38:1547-1554, 1995.
Simon et al., *Clin. Exp. Immunol.*, 94:122-126, 1993.

Simon et al., *Proc. Natl. Acad. Sci. USA*, 91:8562-85666, 1994.
Simonian and Coyle, *Annu. Rev. Pharmacol. Toxicol.*, 36:83-106, 1996.
Sinha et al., *CancerRes.*, 67:4507-4513, 2007.
Stack et al., *Lancet*, 349(9051):521-524, 1997.
Stewart et al., *Neurology*, 48:626-632, 1997.
Strejan, et. al., *J. Neuroimmunol.*, 7:27, 1984.
Suh, et. al., *Cancer Res.*, 58:717-723, 1998.
Suh, et. al., *Cancer Res.*, 59(2):336-341, 1999.
Szabo, et. al., *Nature Rev. Drug Disc.*, 6:662-680, 2007.
Takahashi, et. al., *Cancer Res.*, 57:1233-1237, 1997.
Talley et al., *Gastroenterol.*, 109(6): 1736-1741, 1995.
Tamir and Tannenbaum, *Biochim. Biophys. Acta.*, 1288:F31-F36, 1996.
Targan et al., *N. Engl. J. Med.*, 337(15):1029-1035, 1997.
Touzani et al., *J. Neuroimmunol.*, 100(1-2):203-215, 1999.
Tumlin et al., *Am. J. Cardiol.*, 98(6A): 14K-20K, 2006.
van den Berg, *Semin. Arthritis Rheum.*, 30(5S-2):7-16, 2001.
van Dullemen et al., *Gastroenterol.*, 109(1):129-135, 1995.
van Hogezand and Verspaget, *Drugs*, 56(3):299-305, 1998.
Vazquez et al., *J. Virol.*, 79(7):4479-91, 2005.
Vodovotz et al., In; *Handbook of Experimental Immunology*, Volumes I-IV, 1996.
Wardle, *Nephrol. Dial, Transplant.*, 16(9): 1764-8, 2001.
Warrington et al., *Arthritis and Rheumatism*, 44:13-20, 2001.
Weyand and Goronzy, *Ann. NY Acad. Sci.*, 987:140-149, 2003.
Whitehead et al., *Gastroenterol.*, 98(5 Pt 1): 1187-1192, 1990.
Williams et al., *Clin. Neurosci.*, 2(3-4):229-245, 1994.
Wordsworth, In: *Genes and Arthritis*, Brit. Medical Bulletin, 51:249-266, 1995.
Wright, *Ann. Rheum. Dis.*, 15:348-356, 1956.
Wright, *Clin. Orthop. Related Res.*, 143:8-14, 1979.
Xanthou et al., *Arthritis Rheum.*, 44(2):408-418, 2001.
Yin et al., *Arthritis Rheum.*, 40:1788-1797, 1997.
Yin et al., *Rheumatology*, 38:1058-1067, 1999.
Yoh et al., *Kidney Int.*, 60(4): 1343-1353, 2001.
Yore, et. al., *Mol Cancer Ther* 5:3232-9, 2006.
Yu et al., *Nat. Rev. Immunol.*, 7:41-51, 2007.
Zhou et al., *Am. J. Pathol.*, 166(1):27-37, 2005.
Zhou et al., *Cancer Sci.*, 98:882-889, 2007.
Zingarelli et al., *J. Immunol.*, 171(12):6827-6837, 2003.

What is claimed is:

1. A method of treating a condition associated with inflammation or oxidative stress in a patient in need thereof, comprising administering to the patient a therapeutically effective amount of the pharmaceutical composition comprising an active ingredient comprising a polymorphic form of a compound having the formula:

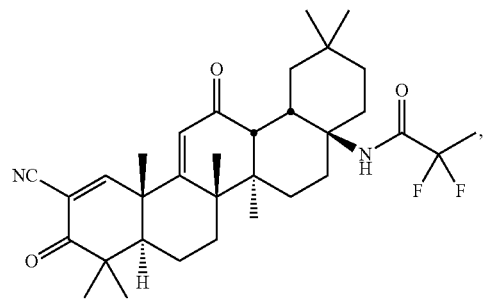

wherein the polymorphic form is crystalline, having an X-ray powder diffraction pattern (CuKα) comprising peaks at about (a) 10.601, 11.638, 12.121, 13.021, 13,435, 15.418, 15.760, 17.830, 18.753, and 19.671 °2θ, or (b) 7.552, 10.339, 11.159, 12.107, 14.729, 15.329, 15.857, 16.824, 17.994, 18.344, 19.444, 19.764, 20.801, and 22.414 °2θ; and a pharmaceutically acceptable carrier, wherein the condition is an eye disorder selected from the group consisting of uveitis, macular degeneration, glaucoma, diabetic macular edema, blepharitis, diabetic retinopathy, post-surgical inflammation, dry eye, ocular inflammation, and conjunctivitis.

2. The method of claim 1, wherein the eye disorder is macular degeneration.

3. The method of claim 2, wherein the macular degeneration is the dry form.

4. The method of claim 2, wherein the macular degeneration is the wet form.

5. The method of claim 1, wherein the pharmaceutical composition is administered in a single dose per day.

6. The method of claim 1, wherein the pharmaceutical composition is administered in more than one dose per day.

7. The method of claim 1, wherein the pharmaceutical composition is administered topically.

8. The method of claim 7, wherein the topical administration is administered to the eye.

9. The method of claim 1, wherein the pharmaceutical composition is administered intraocularly.

10. The method of claim 1, wherein the patient is a human.

11. The method of claim 1, wherein the patient is a non-human animal.

12. The method of claim 1, wherein the pharmaceutical formulation further comprises an agent that enhances solubility and dispersibility.

13. The method of claim 1, wherein the polymorphic form is suspended in sesame oil.

14. The method of claim 1, wherein the amount of the active ingredient is from 0.01% to 3% by weight.

15. The method of claim 1, wherein the conjunctivitis is allergic conjunctivitis.

* * * * *